(12) United States Patent
Yoo et al.

(10) Patent No.: US 10,042,983 B2
(45) Date of Patent: Aug. 7, 2018

(54) APPARATUS FOR CANCER DIAGNOSIS

(71) Applicant: National Cancer Center, Gyeonggi-do (KR)

(72) Inventors: Byong Chul Yoo, Gyeonggi-do (KR); Kyung Hee Kim, Seocho-gu (KR); Dae Yong Kim, Gyeonggi-do (KR); In Hoo Kim, Gyeonggi-do (KR); Ji Won Park, Gyeonggi-do (KR); Jae Hwan Oh, Seoul (KR); Jun Hwa Lee, Gyeonggi-do (KR); Eun Sook Lee, Gyeonggi-do (KR)

(73) Assignee: NATIONAL CANCER CENTER (KR)

( * ) Notice: Subject to any disclaimer, the term of this patent is extended or adjusted under 35 U.S.C. 154(b) by 681 days.

(21) Appl. No.: 13/690,252

(22) Filed: Nov. 30, 2012

(65) Prior Publication Data
US 2013/0231869 A1 Sep. 5, 2013

(30) Foreign Application Priority Data

| Jan. 3, 2012 | (KR) | 10-2012-0000729 |
| Jan. 3, 2012 | (KR) | 10-2012-0000730 |
| Jan. 3, 2012 | (KR) | 10-2012-0000745 |
| Nov. 15, 2012 | (KR) | 10-2012-0129390 |

(51) Int. Cl.
*G01N 33/48* (2006.01)
*G06F 19/00* (2018.01)
*G01N 33/68* (2006.01)
*G06F 19/24* (2011.01)
*G06G 7/58* (2006.01)

(52) U.S. Cl.
CPC ......... *G06F 19/34* (2013.01); *G01N 33/6848* (2013.01); *G06F 19/24* (2013.01)

(58) Field of Classification Search
CPC .................................................. G01N 33/6848
See application file for complete search history.

(56) References Cited

U.S. PATENT DOCUMENTS

| 7,439,118 B2 | 10/2008 | Kanno |
| 7,601,579 B2 | 10/2009 | Kanno |
| 7,864,161 B2 | 1/2011 | Hollemans et al. |
| 8,466,893 B2 | 6/2013 | Hollemans et al. |
| 2008/0046224 A1 | 2/2008 | Moon |
| 2009/0002328 A1 | 1/2009 | Ullrich et al. |
| 2011/0315871 A1 | 12/2011 | Komatsu et al. |

FOREIGN PATENT DOCUMENTS

| EP | 1426766 A1 | 6/2004 |
| JP | 05265636 A | 10/1993 |
| JP | 09022325 A | 1/1997 |
| JP | 09091080 A | 4/1997 |
| JP | 2007244554 A | 9/2007 |
| JP | 2009110248 A | 5/2009 |
| KR | 100234990 B1 | 9/1999 |
| KR | 1020080042560 A | 5/2008 |
| WO | 2004102190 A2 | 11/2004 |
| WO | 2007112082 A2 | 10/2007 |
| WO | 2007127011 A2 | 11/2007 |
| WO | 2008020699 A1 | 2/2008 |

OTHER PUBLICATIONS

Notice of Preliminary Rejection issued in corresponding Korean Patent Application 10-2012-0129390 dated Apr. 30, 2013.
Notice of Allowance issued in corresponding Korean Patent Application 10-2012-0129390 dated Nov. 3, 2014.
Office Action issued in corresponding European Patent Application No. 12195348.3 dated Oct. 9, 2014.
Davis et al. "Cancer biomarker discovery via low molecular weight serum preteome profiling—Where is the tumor?" Proteomics Clin. Appl. 2007, 1: 1545-1558.
Yoo et al. "Identification of hypoxanthine as a urine marker for non-Hodgkin lymphoma by low-mass-ion profiling." BMC Cancer 2010, 10(55): 1-9.
Ward et al. "Proteomic profiling of urine for the detection of colon cancer." Proteome Science 2008, 6(19): 1-15.
Preliminary Notice of Reasons for Rejection of JP2012-023045, dated Jun. 11, 2013.
Notice of Preliminary Rejection, KR10-2011-0110623, dated Apr. 24, 2013.
Notice of Allowance, KR10-2011-0087225, dated Mar. 29, 2013.
Notice of Allowance, KR10-2011-0110619, dated Apr. 24, 2013.
Notice of Allowance, KR10-2011-0110621, dated Apr. 24, 2013.
Notice of Allowance, KR10-2011-0106314, dated Apr. 24, 2013.

*Primary Examiner* — Eric S Dejong
(74) *Attorney, Agent, or Firm* — Porzio Bromberg & Newman P.C.

(57) ABSTRACT

The present invention provides an apparatus for screening cancer, which reads low-mass ion mass spectrum for diagnosing cancer based on biostatistical analysis with respect to low-mass ions extracted from biological materials, and diagnoses cancer using the low-mass ion spectrum. An apparatus for cancer diagnosis, including a low-mass ion detecting unit which detects mass spectra of low-mass ions of biological materials; a cancer diagnosing unit which compares and analyzes patterns of mass spectra and diagnoses cancer; a display unit which displays cancer diagnosis information from the cancer diagnosing unit.

26 Claims, 55 Drawing Sheets

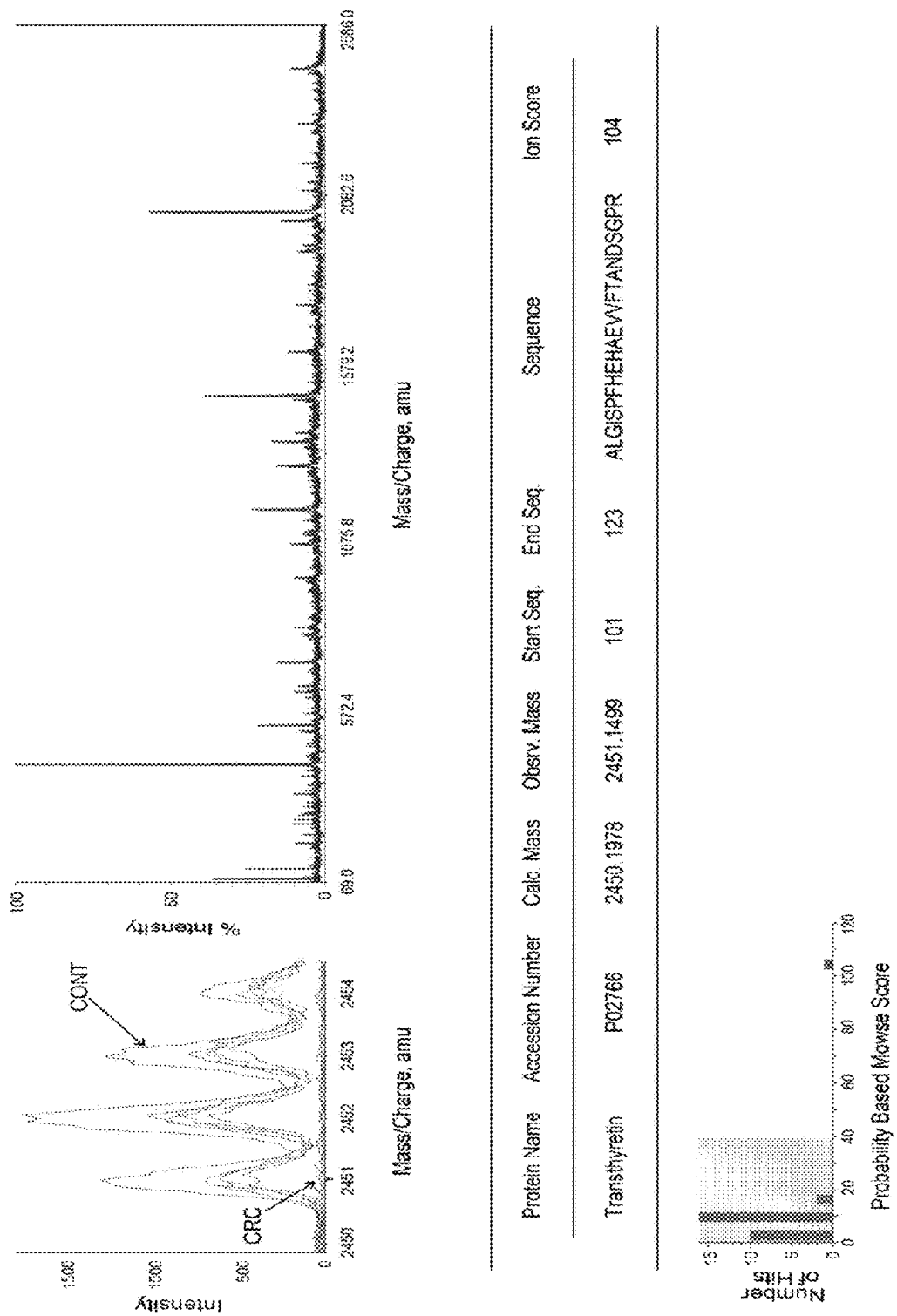

▲ BRC / ■ CONT / ● CRC / ◆ GC / ★ NHL

APPARATUS FOR CANCER DIAGNOSIS

CROSS-REFERENCE TO RELATED APPLICATIONS

This application claims priority from Korean Patent Application Nos. 10-2012-0000729, 10-2012-0000730, 10-2012-0000745 and 10-2012-0129390, respectively filed on Jan. 3, 2012, Jan. 3, 2012, Jan. 3, 2012 and Nov. 15, 2012, in the Korean Intellectual Property Office, the disclosure of which is incorporated herein by reference in its entirety.

BACKGROUND

Field of the Invention

The present invention relates to an apparatus for screening cancer, and more particularly, to an apparatus for screening cancer which is capable of diagnosing cancer by confirming mass spectra of low-mass ions for cancer diagnosis based on biostatistical analysis on low-mass ions extracted from biological materials and utilizing the low-mass ion mass spectra.

Description of the Related Art

Cancer is a disease that involves indefinite proliferation of cells, and examples thereof notably include lung cancer, gastric cancer (GC), breast cancer (BRC) or colorectal cancer (CRC). However, cancer can practically develop into any place of the body. In the early stage of cancer diagnosis, focus was on the external change of biological tissue that occurred in accordance with the growth of cancer cells. Recently, attempts are made to develop a diagnosis and detection of cancer by utilizing trace amounts of biological molecules present in the biological tissue or cells, blood, glycol chain, DNA, etc. However, the most widely used way of diagnosing cancer is based on tissue sample taken by biopsy and imaging.

The biopsy has shortcomings including tremendous pain, expensive cost and lengthy time until the diagnosis. If a patient suspected of cancer indeed has cancer, there is a possibility that the cancer spreads during biopsy. Further, for specific sites of a body where biopsy is limited, diagnosing is often not available until suspicious tissues are extracted by surgical operation.

The imaging-based diagnosis basically determines the cancer based on the X-ray image, the nuclear magnetic resonance (NMR) images, or the like, using contrast agent to which disease-targeting substance is attached. The shortcomings of the imaging-based diagnosis include possibility of misdiagnosis depending on expertise of clinician or personnel who reads the data, and high dependency on the precision of the image-acquisition devices. Furthermore, even the device with the upmost precision is not able to detect a tumor under several mm in size, which means that early detection is unlikely. Further, in the process of image acquisition, as a patient is exposed to high energy electromagnetic wave which itself can induce mutation of genes, there is possibility that another disease may be induced and the number of diagnosis by imaging is limited.

Presence and absence of disease in gastric system is generally determined by observation by naked eyes with the use of endoscope. The process is painful and even when abnormality is observed during this examination, biopsy is still required to accurately determine whether the cancer is malignant/benign tumor, polypus, etc.

Colorectal cancer (CRC) is the third most commonly diagnosed cancer in the world and the cure thereof hugely depends on the stages of cancer development. That is, CRC is highly curable when detected at an early stage by screening. While early detection is very important, symptoms of this cancer are not palpable until the patient perceives the possibility from changed color of excretion due to presence of blood therein. Generally, a patient or a person suspected of CRC first goes thorough endoscopic examination of large intestines and then necessarily takes biopsy to accurately determine specific disease. That is, for CRC, early detection is critical, but since endoscopic examination of large intestines and biopsy take tremendous time and cost and also are inconvenient and painful, a diagnosis method is necessary, which can considerably reduce the number of subjects of the endoscopic examination and biopsy which can be unnecessary.

Accordingly, by providing CRC screening at an early stage based on new molecular approach, patients will be benefited. The genomics, proteomics and molecular pathology have provided various biomarker candidates with clinical potentials. It will be possible to improve treatment effect by actively utilizing the biomarker candidates in the customized treatment of cancers according to stages and patients, and therefore, many researches are necessary to apply the above in the actual clinical treatment.

The recent CRC screening test includes determination of gross abnormality by endoscopic examination of large intestines, or fecal occult blood test (FOBT) which detects blood in feces. The endoscopic examination of large intestines has been utilized as a standard way of examination in the CRC screening, but due to invasiveness thereof, patients who can receive the examination are limited. Accordingly, many attempts have been focused on the examination of feces, for advantages such as noninvasiveness, no need for colonic irrigation, and transferability of the sample. The fecal marker may include feces oozing, excreted or exfoliated from the tumor. For example, hemoglobin in traditional FOBT was perceived as the oozing type of the marker in the large scale screening program. However, the markers known so far, including the above, have not met the satisfaction.

Meanwhile, it is possible to extract spectra of mass ions within blood using the matrix-assisted laser desorption/ionization-time of flight (MALDI-TOF) mass spectrometer. The mass spectrometry, generally used in the researches on proteins, mainly categorizes 800 to 2500 m/s mass range as the target of analysis, because the specific range corresponds to the mass value region of peptide when the protein is dissociated by trypsin. It is also possible to extract the mass spectra of los-mass ions by using MALDI-TOF mass spectrometer. However, for the low-mass region below approximately 800 m/z where the matrix mass ions coexist, research has not been active on this particular region.

The extracted low-mass ion mass spectra can be analyzed by the conventional software, MarkerView™ (version 1.2). The inventors of the present invention analyzed mass spectra of the low-mass ions extracted from the serums of CRC patient group and normal group (control, CONT) using MarkerView™ in a manner that will be explained in detail below with reference to FIG. 1.

The low-mass ion mass spectra in T2D file format was imported with MarkerView™ from the set ($A_1$) of samples of serums collected from 133 CRC patients of Table 101 and 153 normal controls of Table 102 (A11).

TABLE 101

| CRC | Sex | Age year | Stage | Location | Cell Type | CEA ng/mL |
|---|---|---|---|---|---|---|
| CRC-A1 | M | 77 | I | A-colon | AC | 1.8 |
| CRC-A2 | M | 50 | I | Rectum | AC | 1.9 |
| CRC-A3 | F | 47 | I | S-colon | AC | 0.7 |
| CRC-A4 | F | 56 | III | S-colon | AC | 1.2 |
| CRC-A5 | F | 82 | I | A-colon | AC | 1.1 |
| CRC-A6 | M | 59 | I | Rectum | AC | 1.9 |
| CRC-A7 | M | 73 | I | Rectum | AC | 3.6 |
| CRC-A8 | M | 71 | I | S-colon | AC | 3.6 |
| CRC-A9 | M | 50 | I | S-colon | AC | 2.5 |
| CRC-A10 | M | 56 | I | S-colon | AC | 7.3 |
| CRC-A11 | M | 61 | I | Rectum | AC | 7.7 |
| CRC-A12 | F | 78 | I | Rectum | AC | 2.6 |
| CRC-A13 | M | 64 | I | S-colon | AC | 1.8 |
| CRC-A14 | F | 50 | I | Rectum | AC | 1.6 |
| CRC-A15 | F | 59 | I | Rectum | AC | 1.6 |
| CRC-A16 | M | 73 | I | Rectum | AC | 1.9 |
| CRC-A17 | M | 65 | I | S-colon | AC | 14.0 |
| CRC-A18 | M | 72 | I | S-colon | AC | 4.6 |
| CRC-A19 | M | 82 | I | Rectum | AC | 3.2 |
| CRC-A20 | M | 52 | III | S-colon | AC | 3.2 |
| CRC-A21 | F | 59 | III | S-colon | AC | 1.7 |
| CRC-A22 | F | 73 | III | S-colon | AC | 5.7 |
| CRC-A23 | M | 70 | III | S-colon | AC | 3.6 |
| CRC-A24 | M | 75 | II | A-colon | AC | 2.1 |
| CRC-A25 | F | 81 | II | S-colon | AC | 4.1 |
| CRC-A26 | F | 76 | II | Rectum | AC | 25.3 |
| CRC-A27 | F | 71 | II | A-colon | AC | 1.6 |
| CRC-A28 | M | 72 | II | A-colon | AC | 3.8 |
| CRC-A29 | F | 82 | II | S-colon | AC | 1.8 |
| CRC-A30 | F | 68 | II | D-colon | AC | 1.7 |
| CRC-A31 | M | 71 | II | S-colon | AC | 3.6 |
| CRC-A32 | F | 67 | II | A-colon | AC | 1.9 |
| CRC-A33 | M | 45 | II | D-colon | MAC | 3.3 |
| CRC-A34 | M | 60 | II | S-colon | AC | 2.8 |
| CRC-A35 | M | 74 | II | S-colon | AC | 5.3 |
| CRC-A36 | M | 57 | II | Rectum | AC | 7.3 |
| CRC-A37 | F | 65 | II | S-colon | AC | 2.1 |
| CRC-A38 | M | 77 | II | A-colon | AC | 1.5 |
| CRC-A39 | M | 71 | II | D-colon | AC | 4.1 |
| CRC-A40 | F | 66 | II | Rectum | AC | 4.3 |
| CRC-A41 | F | 49 | II | A-colon | AC | 1.6 |
| CRC-A42 | F | 79 | II | A-colon | AC | 2.9 |
| CRC-A43 | M | 69 | II | S-colon | AC | 4.2 |
| CRC-A44 | M | 66 | II | S-colon | AC | 12.0 |
| CRC-A45 | M | 74 | II | A-colon | AC | 1.5 |
| CRC-A46 | M | 69 | II | T-colon | AC | 1.2 |
| CRC-A47 | M | 43 | II | S-colon | AC | 2.2 |
| CRC-A48 | F | 67 | II | A-colon | AC | 1.4 |
| CRC-A49 | M | 72 | II | A-colon | AC | 4.9 |
| CRC-A50 | F | 67 | II | A-colon | AC | 7.3 |
| CRC-A51 | F | 75 | II | Rectum | AC | 12.6 |
| CRC-A52 | M | 68 | II | D-colon | AC | 4.7 |
| CRC-A53 | F | 60 | II | S-colon | AC | 3.3 |
| CRC-A54 | M | 74 | II | S-colon | AC | 9.0 |
| CRC-A55 | M | 68 | III | A-colon | AC | 9.2 |
| CRC-A56 | F | 55 | III | Rectum | AC | 2.1 |
| CRC-A57 | F | 61 | III | A-colon | AC | 12.7 |
| CRC-A58 | F | 59 | III | S-colon | AC | 2.7 |
| CRC-A59 | M | 67 | III | Rectum | AC | 9.5 |
| CRC-A60 | M | 48 | III | S-colon | AC | 1.3 |
| CRC-A61 | M | 58 | III | Rectum | AC | 1.7 |
| CRC-A62 | F | 50 | III | S-colon | AC | 4.8 |
| CRC-A63 | F | 51 | III | S-colon | AC | 7.0 |
| CRC-A64 | F | 74 | III | T-colon | AC | 2.5 |
| CRC-A65 | M | 60 | III | Rectum | AC | 3.5 |
| CRC-A66 | M | 52 | III | S-colon | AC | 2.5 |
| CRC-A67 | M | 54 | III | A-colon | AC | 5.3 |
| CRC-A68 | M | 82 | III | S-colon | AC | 2.4 |
| CRC-A69 | M | 54 | III | S-colon | AC | 5.3 |
| CRC-A70 | F | 79 | III | Rectum | AC | 14.1 |
| CRC-A71 | F | 44 | III | S-colon | AC | 1.4 |
| CRC-A72 | F | 66 | III | Rectum | AC | 1.2 |
| CRC-A73 | M | 53 | III | A-colon | AC | 4.2 |
| CRC-A74 | M | 64 | III | T-colon | AC | 1.8 |
| CRC-A75 | F | 42 | III | S-colon | AC | 0.8 |
| CRC-A76 | M | 49 | III | Rectum | AC | 2.7 |
| CRC-A77 | M | 68 | III | Rectum | AC | 3.9 |
| CRC-A78 | M | 51 | III | S-colon | AC | 5.2 |
| CRC-A79 | M | 64 | III | Rectum | AC | 7.7 |
| CRC-A80 | M | 42 | III | S-colon | AC | 2.8 |
| CRC-A81 | F | 43 | III | A-colon | AC | 4.7 |
| CRC-A82 | M | 66 | III | S-colon | AC | 9.1 |
| CRC-A83 | M | 37 | III | Rectum | AC | 3.7 |
| CRC-A84 | F | 81 | III | Rectum | AC | 8.4 |
| CRC-A85 | F | 73 | III | S-colon | AC | 1.7 |
| CRC-A86 | M | 54 | III | Rectum | AC | 6.4 |
| CRC-A87 | F | 58 | III | Rectum | AC | 21.3 |
| CRC-A88 | F | 42 | III | Rectum | AC | 0.7 |
| CRC-A89 | F | 50 | III | D-colon | AC | 6.4 |
| CRC-A90 | M | 56 | III | S-colon | AC | 7.3 |
| CRC-A91 | F | 58 | III | S-colon | AC | 2.1 |
| CRC-A92 | F | 70 | IV | Rectum | AC | 3.9 |
| CRC-A93 | M | 68 | IV | Rectum | AC | 6.0 |
| CRC-A94 | M | 53 | IV | Rectum | AC | 54.7 |
| CRC-A95 | F | 63 | IV | D-colon | AC | 12.3 |
| CRC-A96 | F | 63 | IV | A-colon | AC | 1.4 |
| CRC-A97 | M | 63 | II | D-colon | AC | 4.9 |
| CRC-A98 | F | 66 | II | S-colon | AC | 4.2 |
| CRC-A99 | M | 48 | II | Rectum | AC | 28.4 |
| CRC-A100 | M | 68 | II | S-colon | AC | 2.3 |
| CRC-A101 | M | 48 | II | S-colon | AC | 4.8 |
| CRC-A102 | F | 81 | II | S-colon | AC | 2.4 |
| CRC-A103 | M | 56 | II | A-colon | AC | 34.6 |
| CRC-A104 | M | 71 | III | Rectum | AC | 16.5 |
| CRC-A105 | M | 66 | III | S-colon | AC | 689.8 |
| CRC-A106 | M | 65 | III | D-colon | AC | 3.4 |
| CRC-A107 | F | 65 | III | S-colon | MAC | 2.7 |
| CRC-A108 | F | 51 | III | Rectum | AC | 1.4 |
| CRC-A109 | M | 58 | III | S-colon | AC | 2.8 |
| CRC-A110 | F | 48 | III | A-colon | AC | 0.9 |
| CRC-A111 | M | 71 | III | S-colon | AC | 6.0 |
| CRC-A112 | M | 68 | III | A-colon | AC | 2.7 |
| CRC-A113 | F | 54 | III | A-colon | AC | 1.7 |
| CRC-A114 | M | 66 | IV | S-colon | AC | 6.4 |
| CRC-A115 | F | 72 | IV | A-colon | AC | 73.4 |
| CRC-A116 | F | 69 | IV | A-colon | AC | 49.0 |
| CRC-A117 | M | 75 | IV | S-colon | AC | 16.7 |
| CRC-A118 | F | 49 | III | S-colon | AC | 1.0 |
| CRC-A119 | F | 63 | III | A-colon | AC | 58.2 |
| CRC-A120 | M | 74 | III | A-colon | AC | 2.8 |
| CRC-A121 | F | 54 | III | T-colon | AC | 2.2 |
| CRC-A122 | M | 68 | III | Rectum | AC | 22.5 |
| CRC-A123 | M | 66 | III | Rectum | MAC | 1.2 |
| CRC-A124 | M | 72 | IV | Rectum | SC | 8.2 |
| CRC-A125 | M | 73 | IV | Rectum | AC | 52.2 |
| CRC-A126 | M | 54 | IV | A-colon | AC | 2.0 |
| CRC-A127 | F | 54 | IV | S-colon | AC | 29.8 |
| CRC-A128 | M | 43 | IV | Rectum | AC | 36.4 |
| CRC-A129 | F | 52 | IV | A-colon | MAC | 9.0 |
| CRC-A130 | M | 48 | IV | S-colon | AC | 15.9 |
| CRC-A131 | M | 62 | IV | Rectum | AC | 6.3 |
| CRC-A132 | M | 77 | I | D-colon | AC | 6.4 |
| CRC-A133 | M | 78 | I | Rectum | AC | 2.7 |

AC: Adenocarcinoma
CEA: Carcinoembryonic antigen
MAC: Mucinous adenocarcinoma

TABLE 102

| Control | Sex | Age year | CEA ng/mL |
|---|---|---|---|
| CONT-A1 | M | 39 | 1.3 |
| CONT-A2 | F | 70 | 1.2 |
| CONT-A3 | M | 66 | 1.3 |
| CONT-A4 | M | 53 | 0.8 |
| CONT-A5 | F | 69 | 1.0 |
| CONT-A6 | F | 68 | 1.8 |
| CONT-A7 | M | 35 | 1.7 |
| CONT-A8 | M | 62 | 3.7 |
| CONT-A9 | M | 62 | 1.1 |

TABLE 102-continued

| Control | Sex | Age year | CEA ng/mL |
|---|---|---|---|
| CONT-A10 | M | 48 | 5.3 |
| CONT-A11 | M | 48 | 1.8 |
| CONT-A12 | M | 66 | 1.6 |
| CONT-A13 | M | 66 | 1.4 |
| CONT-A14 | M | 66 | 4.2 |
| CONT-A15 | M | 54 | 1.4 |
| CONT-A16 | M | 54 | 1.0 |
| CONT-A17 | M | 62 | 2.0 |
| CONT-A18 | F | 45 | 0.7 |
| CONT-A19 | M | 39 | 3.2 |
| CONT-A20 | M | 67 | 1.8 |
| CONT-A21 | M | 63 | 5.5 |
| CONT-A22 | M | 48 | 2.8 |
| CONT-A23 | M | 66 | 3.2 |
| CONT-A24 | M | 55 | 5.0 |
| CONT-A25 | M | 55 | 1.0 |
| CONT-A26 | M | 62 | 7.0 |
| CONT-A27 | F | 57 | 1.2 |
| CONT-A28 | M | 61 | 0.9 |
| CONT-A29 | M | 50 | 1.9 |
| CONT-A30 | M | 46 | 1.5 |
| CONT-A31 | M | 51 | 4.0 |
| CONT-A32 | F | 68 | 1.8 |
| CONT-A33 | F | 68 | 1.4 |
| CONT-A34 | M | 64 | 1.7 |
| CONT-A35 | M | 30 | 0.7 |
| CONT-A36 | F | 52 | 2.1 |
| CONT-A37 | F | 59 | 1.2 |
| CONT-A38 | M | 53 | 1.6 |
| CONT-A39 | F | 69 | 1.2 |
| CONT-A40 | F | 68 | 1.0 |
| CONT-A41 | F | 65 | 3.1 |
| CONT-A42 | M | 31 | 1.2 |
| CONT-A43 | F | 59 | 0.7 |
| CONT-A44 | M | 43 | 1.4 |
| CONT-A45 | M | 66 | 2.3 |
| CONT-A46 | M | 48 | 4.2 |
| CONT-A47 | F | 41 | 2.1 |
| CONT-A48 | F | 65 | 3.8 |
| CONT-A49 | F | 67 | 1.5 |
| CONT-A50 | F | 45 | 0.6 |
| CONT-A51 | M | 30 | 1.0 |
| CONT-A52 | M | 55 | 1.2 |
| CONT-A53 | M | 54 | 2.1 |
| CONT-A54 | M | 69 | 2.8 |
| CONT-A55 | M | 53 | 1.8 |
| CONT-A56 | F | 47 | 1.7 |
| CONT-A57 | M | 31 | 1.7 |
| CONT-A58 | M | 53 | 3.2 |
| CONT-A59 | F | 49 | 1.4 |
| CONT-A60 | M | 62 | 1.7 |
| CONT-A61 | M | 31 | 2.3 |
| CONT-A62 | M | 40 | 0.8 |
| CONT-A63 | F | 49 | 1.4 |
| CONT-A64 | F | 33 | 1.7 |
| CONT-A65 | M | 51 | 3.4 |
| CONT-A66 | M | 52 | 2.0 |
| CONT-A67 | F | 66 | 1.3 |
| CONT-A68 | M | 56 | 1.9 |
| CONT-A69 | F | 65 | 1.4 |
| CONT-A70 | M | 50 | 1.4 |
| CONT-A71 | M | 54 | 1.3 |
| CONT-A72 | M | 68 | 1.6 |
| CONT-A73 | M | 59 | 2.5 |
| CONT-A74 | F | 51 | 2.1 |
| CONT-A75 | F | 39 | 0.8 |
| CONT-A76 | F | 40 | 1.5 |
| CONT-A77 | F | 50 | 1.9 |
| CONT-A78 | F | 64 | 2.9 |
| CONT-A79 | F | 52 | 1.9 |
| CONT-A80 | F | 37 | 2.1 |
| CONT-A81 | F | 49 | 2.6 |
| CONT-A82 | F | 48 | 1.5 |
| CONT-A83 | F | 30 | <0.5 |
| CONT-A84 | F | 56 | 1.4 |
| CONT-A85 | F | 50 | 1.2 |
| CONT-A86 | F | 49 | 2.1 |
| CONT-A87 | F | 38 | 0.6 |
| CONT-A88 | F | 59 | 1.6 |
| CONT-A89 | F | 51 | 1.0 |
| CONT-A90 | F | 41 | 1.8 |
| CONT-A91 | F | 48 | 1.2 |
| CONT-A92 | F | 39 | 0.5 |
| CONT-A93 | F | 51 | 1.1 |
| CONT-A94 | F | 44 | 1.5 |
| CONT-A95 | F | 38 | 1.5 |
| CONT-A96 | F | 48 | 1.9 |
| CONT-A97 | F | 70 | 4.8 |
| CONT-A98 | F | 54 | 2.8 |
| CONT-A99 | F | 38 | 2.8 |
| CONT-A100 | F | 50 | 1.1 |
| CONT-A101 | F | 54 | 1.8 |
| CONT-A102 | M | 49 | 1.2 |
| CONT-A103 | F | 38 | 0.9 |
| CONT-A104 | F | 44 | — |
| CONT-A105 | M | 52 | — |
| CONT-A106 | F | 45 | — |
| CONT-A107 | F | 54 | — |
| CONT-A108 | F | 51 | 3.1 |
| CONT-A109 | M | 54 | 6.4 |
| CONT-A110 | M | 46 | 1.1 |
| CONT-A111 | M | 47 | 1.8 |
| CONT-A112 | M | 49 | 1.7 |
| CONT-A113 | F | 55 | <0.5 |
| CONT-A114 | M | 36 | 0.7 |
| CONT-A115 | M | 59 | 0.8 |
| CONT-A116 | M | 46 | 3.7 |
| CONT-A117 | F | 46 | <0.5 |
| CONT-A118 | F | 50 | 0.9 |
| CONT-A119 | M | 58 | — |
| CONT-A120 | M | 34 | 1.7 |
| CONT-A121 | M | 53 | 2.9 |
| CONT-A122 | M | 45 | 3.7 |
| CONT-A123 | M | 47 | 4.5 |
| CONT-A124 | F | 34 | 0.6 |
| CONT-A125 | F | 58 | 1.5 |
| CONT-A126 | F | 54 | — |
| CONT-A127 | M | 35 | 1.8 |
| CONT-A128 | M | 49 | 1.4 |
| CONT-A129 | M | 48 | 3.2 |
| CONT-A130 | F | 34 | <0.5 |
| CONT-A131 | M | 45 | 4.4 |
| CONT-A132 | F | 45 | 0.8 |
| CONT-A133 | M | 52 | — |
| CONT-A134 | F | 44 | — |
| CONT-A135 | F | 46 | — |
| CONT-A136 | M | 58 | — |
| CONT-A137 | M | 45 | 4.3 |
| CONT-A138 | M | 61 | 1.4 |
| CONT-A139 | M | 42 | 2.7 |
| CONT-A140 | M | 48 | 3.0 |
| CONT-A141 | M | 53 | 1.9 |
| CONT-A142 | F | 54 | 2.3 |
| CONT-A143 | F | 39 | 1.3 |
| CONT-A144 | F | 55 | 1.3 |
| CONT-A145 | M | 53 | — |
| CONT-A146 | F | 46 | — |
| CONT-A147 | F | 45 | — |
| CONT-A148 | F | 63 | — |
| CONT-A149 | F | 51 | — |
| CONT-A150 | M | 51 | — |
| CONT-A151 | F | 52 | — |

TABLE 102-continued

| Control | Sex | Age year | CEA ng/mL |
|---|---|---|---|
| CONT-A152 | F | 52 | — |
| CONT-A153 | F | 70 | — |

The conditions of Table 103 were used for import.

TABLE 103

| | |
|---|---|
| Mass tolerance | 100 ppm |
| Minimum required response | 10.0 |
| Maximum number of peaks | 10000 |

The imported peak intensities were then normalized (A12). MarkerView™ has a plurality of normalization methods, and among these, "Normalization Using Total Area Sums" was employed for the normalization. According to the method, partial sums of the intensities of the respective samples were obtained and averaged, and then each peak intensity was multiplied by a scaling factor so that the sums of the respective samples were in agreement with the averages. As a result, the partial sums of the intensities of the respective samples became identical after the normalization.

Next, the normalized peak intensities were Pareto-scaled (A13). That is, the peak intensities were Pareto-scaled by subtracting the averages of the respective mass ions from the respective normalized peak intensities, and dividing the same by the square root of the standard deviation.

Next, with respect to the Pareto-scaled peak intensities, discriminant scores (DS) were computed by performing the principal component analysis-based linear discriminant analysis (PCA-DA) (A14). The PCA-DA was performed by two stages, to obtain factor loading, which are the weighting factors of the respective mass ions, and the Pareto-scaled intensities were multiplied by the factor loading. The resultant values were summed, to compute the discriminant scores of the respective samples. The import condition of Table 103 includes maximum 10,000 peaks with sufficient samples imported, so that there were 10,000 factor loading computed, and one DS was computed by summing 10,000 terms.

Next, it was determined whether the computed DS was positive number or not (A15), and if so, determined positive (A16), and if not, determined negative (A17). In other words, when implemented on CRC, the positive number was interpreted as CRC patient group, while negative number was interpreted as normal control group.

FIG. 2 illustrates distribution of DS which were computed by the method of FIG. 1 with respect to the set consisting of 133 clinically CRC-diagnosed patients and 153 non-cancer subjects. Reorganizing the interpretation results according to DS of FIG. 2 using confusion matrix will give:

TABLE 104

| Set A$_1$ | True CRC | True CONT |
|---|---|---|
| Predicted CRC | 131 | 2 |
| Predicted CONT | 2 | 151 |
| Sensitivity | | 98.50% |
| Specificity | | 98.69% |
| PPV | | 98.50% |
| NPV | | 98.69% |

Referring to FIG. 2 and Table 104, excellent discrimination result was obtained with all of the sensitivity, specificity, positive predictive value (PPV) and negative predictive value (NPV) exceeding 98% by the conventional PCA-DA of the MarkerView™.

However, the robustness of the formula must be verified for clinical use. That is, even the mass spectra that were additionally measured by a number of times with respect to the dataset that was measured once and constituted discriminant formula, are required to maintain good discrimination results, and the discrimination result based on the same discriminant also has to be sound with respect to new CRC patient groups and non-cancer subjects that were not taken into consideration in the designing of the discriminant. The process of repeatedly measuring mass spectra may include the process of freezing and thawing serums and mixing the serum newly with methanol/chloroform to obtain extract. These processes are considered the disturbances in the statistic analysis with respect to the mass spectra, and clinical implementation is only possible when the discriminant is least influenced by the disturbances.

The conventional PCA-DA explained above with reference to FIGS. 1 and 2 and Table 104 sometimes exhibit good discrimination result if applied individually to the set of specific samples, i.e., to individual training set. However, the discrimination result was unsatisfactory when applied with respect to the validation set (Tables 124, 126). It appears that the discriminant exhibiting very good discrimination result with respect to the training set, is not so robust because the 10,000 mass ions constituting the discriminant include a considerable amount of mass ions which may be at least unnecessary for the discrimination between CRC patients and non-cancer subjects and although not entirely problematic in the discrimination of training set, which can potentially cause confusion in the discrimination result in the discrimination of the validation set. Accordingly, a process is necessary, which exclusively locates mass ions that are absolutely necessary to obtain good and robust discrimination result, by actively removing mass ions which are at least unnecessary or which can potentially confuse discrimination result.

The incidence rate and prevalence rate of breast cancer (BRC) rapidly grew, following the thyroid cancer. Compared to the high incidence rate, BRC also has high cure rate following the thyroid cancer, for reasons mainly include development of effective drugs and change in public's awareness and also advancement of mammograpy which enables early detection of BRC. Like other carcinomas, BRC survival rate can be increased if detected and treated at an early stage. The survival rate is reported as high as 90% in the case of small-size BRC with no lymph node metastasis. However, the survival rate drops to 10% when BRC is detected after metastasis into another area. In order to discover BRC as early as possible, doctor's diagnosis and radiologic breast checkup as well as self test are prerequisite. However, sensitivity of mammography stays at a low level of 60-70%, and the diagnosis rate considerably decreases in the case of dense breasts which are more commonly found in young women. These women are generally advised to take breast ultrasonic test, but this test has a shortcoming of high dependency on the skill of the sonographer. Additionally, breast magnetic resonance imaging (MRI) is used in the diagnosis of BRC, but high cost thereof makes MRI unsuitable option for the BRC diagnosis and further, the false positive rate is high.

Accordingly, the patients will be benefited if it is possible to apply new molecular approach to screen BRC at an early stage. The genomics, proteomics and molecular pathology have provided many biomarkers with potential clinical value. The treatment effect would be improved by actively utilize these markers via customization with stages of the cancer and the patients. However, researchers have a long way to go until they would finally be able to implement these for clinical treatment.

Meanwhile, it is possible to extract spectra of mass ions within blood using the matrix-assisted laser desorption/ionization-time of flight (MALDI-TOF) mass spectrometer. The mass spectrometry, generally used in the researches on proteins, mainly categorizes 800 to 2500 m/s mass range as the target of analysis, because the specific range corresponds to the mass value region of peptide when the protein is dissociated by trypsin. It is also possible to extract the mass spectra of los-mass ions by using MALDI-TOF mass spectrometer. However, for the low-mass region below approximately 800 m/z where the matrix mass ions coexist, research has not been active on this particular region.

The extracted low-mass ion mass spectra can be analyzed by the conventional software, MarkerView™ (version 1.2). The inventors of the present invention analyzed mass spectra of the low-mass ions extracted from the serums of BRC patient group and normal group (control, CONT) using MarkerView™ in a manner that will be explained in detail below with reference to FIG. 3.

The low-mass ion mass spectrum in T2D file format was imported with MarkerView™ from the set ($C_1$) of samples of serums collected from 54 BRC patients of Table 201 and 202 normal controls of Table 202 (B11).

TABLE 201

| BRC | Sex | Age year | Node | ER | ER % | PR | PR % | HER2 | Tumor Size cm |
|---|---|---|---|---|---|---|---|---|---|
| BRC-C1 | F | 48 | —[a] | 5 | 33-66% | 6 | 33-66% | 2 | — |
| BRC-C2 | F | 35 | — | 6 | 33-66% | 6 | 33-66% | 1 | — |
| BRC-C3 | F | 45 | pN1a | 5 | 33-66% | 5 | 33-66% | 0 | 1.5 |
| BRC-C4 | F | 61 | — | 0 | 0% | 0 | 0% | 2 | — |
| BRC-C5 | F | 70 | pN0(sn) | 0 | 0% | 0 | 0% | 1 | <0.1 |
| BRC-C6 | F | 58 | ypN0 | 3 | <10% | 3 | 10-33% | 3 | 0.5 |
| BRC-C7 | F | 49 | ypN0(i+) | 0 | 0% | 0 | 0% | 2 | 1.9 |
| BRC-C8 | F | 49 | ypN2a | 0 | 0% | 0 | 0% | 1 | 2.5 |
| BRC-C9 | F | 39 | pN1a | 6 | 33-66% | 7 | >66% | 1 | 2.2 |
| BRC-C10 | F | 48 | ypN2a | 6 | 33-66% | 4 | <10% | 3 | 5.8 |
| BRC-C11 | F | 39 | — | 0 | 0% | 0 | 0% | 1 | — |
| BRC-C12 | F | 56 | pN1a | 6 | 33-66% | 6 | 33-66% | 0 | 2.8 |
| BRC-C13 | F | 59 | pN0(sn) | 6 | 33-66% | 2 | <10% | 1 | 2.3 |
| BRC-C14 | F | 31 | pN1a | 5 | 33-66% | 4 | 10-33% | 1 | 2.2 |
| BRC-C15 | F | 46 | pN3a | 6 | 33-66% | 6 | 33-66% | 1 | 3.5 |
| BRC-C16 | F | 56 | — | 7 | >66% | 4 | 10-33% | 1 | — |
| BRC-C17 | F | 55 | — | 0 | 0% | 0 | 0% | 2 | — |
| BRC-C18 | F | 46 | pN0 | 0 | 0% | 0 | 0% | 0 | 1.5 |
| BRC-C19 | F | 60 | ypN0 | 0 | 0% | 0 | 0% | 3 | 1.9 |
| BRC-C20 | F | 49 | pN0(sn) | 5 | 33-66% | 2 | <10% | 2 | 1.5 |
| BRC-C21 | F | 55 | pN1mi | 0 | 0% | 0 | 0% | 3 | 1.8 |
| BRC-C22 | F | 65 | pN0 | 6 | 33-66% | 6 | 33-66% | 0 | 1.7 |
| BRC-C23 | F | 35 | ypN2a | 6 | 66% | 4 | 10-33% | 2 | 2.6 |
| BRC-C24 | F | 46 | pN1a | 6 | 33-66% | 6 | 33-66% | 3 | 2.5 |
| BRC-C25 | F | 45 | pN0(sn) | 6 | 33-66% | 6 | 33-66% | 1 | 0.8 |
| BRC-C26 | F | 42 | pN0(sn) | 3 | 10-33% | 6 | 33-66% | 0 | 1 |
| BRC-C27 | F | 58 | pN0(sn) | 6 | 33-66% | 6 | 33-66% | 1 | 1.5 |
| BRC-C28 | F | 62 | pN1a | 0 | 0% | 0 | 0% | 2 | 2.2 |
| BRC-C29 | F | 61 | — | 0 | 0% | 0 | 0% | 1 | — |
| BRC-C30 | F | 60 | — | — | — | — | — | — | — |
| BRC-C31 | F | 51 | — | — | — | — | — | — | — |
| BRC-C32 | F | 42 | pN0 | 7 | >66% | 7 | >66% | 2 | — |
| BRC-C33 | F | 43 | pN0(sn) | 3 | 10-33% | 4 | 10-33% | 0 | 2.3 |
| BRC-C34 | F | 60 | pN0(sn) | 0 | 0% | 0 | 0% | 1 | 2.3 |
| BRC-C35 | F | 61 | — | 6 | 33-66% | 0 | 0% | 2 | — |
| BRC-C36 | F | 61 | pN0(sn) | 0 | 0% | 2 | <10% | 2 | 1.8 |
| BRC-C37 | F | 49 | — | — | — | — | — | — | — |
| BRC-C38 | F | 45 | ypN0 | 0 | 0% | 0 | 0% | 0 | 0.9 |
| BRC-C39 | F | 59 | pN0 | 0 | 0% | 0 | 0% | 3 | 1.1 |
| BRC-C40 | F | 43 | pN1 | 0 | 0% | 0 | 0% | 0 | 1.5 |
| BRC-C41 | F | 46 | pN1 | 8 | 100% | 8 | 100% | 0 | 1.3 |
| BRC-C42 | F | 48 | pN0 | 6 | 50-60% | 5 | 10-20% | 3 | 1.3 |
| BRC-C43 | F | 39 | pN0 | 0 | 0% | 0 | 0% | 0 | 2.2 |
| BRC-C44 | F | 66 | pN0 | 8 | 95% | 8 | 95% | 0 | 1.7 |
| BRC-C45 | F | 39 | ypN0 | 0 | 0% | 0 | 0% | 0 | DCIS |
| BRC-C46 | F | 37 | pN0 | 7 | 70-80% | 8 | 80% | 3 | 1.5 |
| BRC-C47 | F | 64 | pN0 | 8 | 95% | 8 | 95% | 0 | 0.5 |
| BRC-C48 | F | 44 | ypN1 | 7 | 90% | 8 | 95% | 0 | 2 |
| BRC-C49 | F | 50 | pN2 | 8 | 95% | 8 | 100% | 0 | 1.1 |
| BRC-C50 | F | 47 | pN0 | 7 | 70% | 7 | 50-60% | 1 | 0.5 |
| BRC-C51 | F | 44 | pN1 | 8 | 90% | 8 | 95% | 1 | 0.6 |
| BRC-C52 | F | 50 | pN0 | 0 | 0% | 0 | 0% | 2 | 2.2 |
| BRC-C53 | F | 53 | pN0 | 7 | 95% | 8 | 95% | 0 | 1.1 |
| BRC-C54 | F | 65 | pN0 | 8 | 95% | 7 | 40% | 0 | 1.5 |

TABLE 202

| Control | Sex | Age year | CEA ng/mL |
|---|---|---|---|
| CONT-C1 | F | 70 | 1.2 |
| CONT-C2 | F | 69 | 1 |
| CONT-C3 | F | 68 | 1.8 |
| CONT-C4 | F | 45 | 0.7 |
| CONT-C5 | F | 57 | 1.2 |
| CONT-C6 | F | 68 | 1.8 |
| CONT-C7 | F | 68 | 1.4 |
| CONT-C8 | F | 52 | 2.1 |
| CONT-C9 | F | 59 | 1.2 |
| CONT-C10 | F | 68 | 1 |
| CONT-C11 | F | 65 | 3.1 |
| CONT-C12 | F | 59 | 0.7 |
| CONT-C13 | F | 41 | 2.1 |
| CONT-C14 | F | 65 | 3.8 |
| CONT-C15 | F | 67 | 1.5 |
| CONT-C16 | F | 45 | 0.6 |
| CONT-C17 | F | 47 | 1.7 |
| CONT-C18 | F | 49 | 1.4 |
| CONT-C19 | F | 49 | 1.4 |
| CONT-C20 | F | 33 | 1.7 |
| CONT-C21 | F | 66 | 1.3 |
| CONT-C22 | F | 65 | 1.4 |
| CONT-C23 | F | 51 | 2.1 |
| CONT-C24 | F | 39 | 0.8 |
| CONT-C25 | F | 66 | 1.6 |
| CONT-C26 | F | 50 | 2.6 |
| CONT-C27 | F | 53 | 2.6 |
| CONT-C28 | F | 60 | 3.7 |
| CONT-C29 | F | 66 | 1.1 |
| CONT-C30 | F | 68 | 5.5 |
| CONT-C31 | F | 56 | 1.3 |
| CONT-C32 | F | 51 | 1.9 |
| CONT-C33 | F | 51 | 1.6 |
| CONT-C34 | F | 52 | 1.4 |
| CONT-C35 | F | 56 | 1.7 |
| CONT-C36 | F | 52 | 1.7 |
| CONT-C37 | F | 60 | 1.8 |
| CONT-C38 | F | 58 | 0.7 |
| CONT-C39 | F | 58 | 3.1 |
| CONT-C40 | F | 54 | 1.6 |
| CONT-C41 | F | 60 | 1.1 |
| CONT-C42 | F | 43 | — |
| CONT-C43 | F | 40 | — |
| CONT-C44 | F | 60 | — |
| CONT-C45 | F | 46 | — |
| CONT-C46 | F | 67 | — |
| CONT-C47 | F | 49 | — |
| CONT-C48 | F | 43 | — |
| CONT-C49 | F | 57 | — |

CEA: Carcinoembryonic antigen

The conditions of Table 203 were used for import.

TABLE 203

| Mass tolerance | 100 ppm |
|---|---|
| Minimum required response | 10.0 |
| Maximum number of peaks | 10000 |

The imported peak intensities were then normalized (A12). MarkerView™ has a plurality of normalization methods, and among these, "Normalization Using Total Area Sums" was employed for the normalization. According to the method, partial sums of the intensities of the respective samples were obtained and averaged, and then each peak intensity was multiplied by a scaling factor so that the partial sums of the respective samples were in agreement with the averages. As a result, the partial sums of the intensities of the respective samples became identical after the normalization.

Next, the normalized peak intensities were Pareto-scaled (B13). That is, the peak intensities were Pareto-scaled by subtracting the averages of the respective mass ions from the respective normalized peak intensities, and dividing the same by the square root of the standard deviation.

Next, with respect to the Pareto-scaled peak intensities, discriminant scores (DS) were computed by performing the principal component analysis-based linear discriminant analysis (PCA-DA) (B14). The PCA-DA was performed by two stages, to obtain factor loading, which are the weighting factors of the respective mass ions, and the Pareto-scaled intensities were multiplied by the factor loading. The resultant values were summed, to compute the discriminant scores of the respective samples. The import condition of Table 103 includes maximum 10,000 peaks with sufficient samples imported, so that there were 10,000 factor loading computed, and one DS was computed by summing 10,000 terms.

Next, it was determined whether the computed DS was positive number or not (B15), and if so, determined positive (B16), and if not, determined negative (B17). In other words, when implemented on BRC, the positive number was interpreted as BRC patient group, while negative number was interpreted as normal control group.

FIG. 4 illustrates distribution of DS which were computed by the method of FIG. 3 with respect to the set consisting of 54 clinically BRC-diagnosed patients and 49 non-cancer subjects. Reorganizing the interpretation results according to DS of FIG. 4 using confusion matrix will give:

TABLE 204

| Set $A_1$ | True BRC | True CONT |
|---|---|---|
| Predicted BRC | 54 | 0 |
| Predicted CONT | 0 | 49 |
| Sensitivity | 100.0% | |
| Specificity | 100.0% | |
| PPV | 100.0% | |
| NPV | 100.0% | |

Referring to FIG. 4 and Table 204, perfect discrimination result was obtained with all of the sensitivity, specificity, positive predictive value (PPV) and negative predictive value (NPV) reaching 100% by the conventional PCA-DA of the MarkerView™.

However, the robustness of the formula must be verified for clinical use. That is, even the mass spectra that were additionally measured by a number of times with respect to the dataset that was measured once and constituted discriminant formula, are required to maintain good discrimination results, and the discrimination result based on the same discriminant also has to be sound with respect to new BRC patient groups and non-cancer subjects that were not taken into consideration in the designing of the discriminant. The process of repeatedly measuring mass spectra may include the process of freezing and thawing serums and mixing the serum newly with methanol/chloroform to obtain extract. These processes are considered the disturbances in the statistic analysis with respect to the mass spectra, and clinical implementation is only possible when the discriminant is least influenced by the disturbances.

The conventional PCA-DA explained above with reference to FIGS. 3 and 4 and Table 204 sometimes exhibit good discrimination result if applied individually to the set of specific samples, i.e., to individual training set. However, the discrimination result was unsatisfactory when applied with respect to the validation set (Tables 224, 226). It appears that the discriminant exhibiting very good discrimination result with respect to the training set, is not so robust because the 10,000 mass ions constituting the discriminant include a considerable amount of mass ions which may be at least unnecessary for the discrimination between BRC patients and non-cancer subjects and although not entirely problematic in the discrimination of training set, which can potentially cause confusion in the discrimination result in the discrimination of the validation set. Accordingly, a process is necessary, which exclusively locates mass ions that are absolutely necessary to obtain good and robust discrimination result, by actively removing mass ions which are at least unnecessary, or which can potentially confuse discrimination result.

Meanwhile, gastric cancer (GC) is the most-commonly diagnosed cancer in South Korea (18.3%), with the incidence frequency recording highest among men, and third-highest among women following BRC and thyroid cancer (Major carcinoma incidence rates, 2003-2005, National Statistical Office). Although the rate of early detection is increasing thanks to endoscopic examination on general public and change in the public awareness, the death rate of this particular cancer still records highest frequency (22%) following lung cancer and liver cancer (2006. Statistical Year Book of Cause of Death. National Statistical Office).

Surgical treatment is the basic measure for complete recovery and the frequency of early GC is approximately 50% recently with the complete recovery rate exceeding 90%. However, unlike the early GC, metastatic or recurrent GC shows quite undesirable prognosis, in which the median survival time is as short as 1 year or shorter. The five year survival rate is also very low around 5% or below.

The palliative chemotherapy is accepted as a standard treatment of metastatic or recurrent GC, based on the researches that confirmed effect of prolonged survival period in 3 phrase study compared with the best supportive care and also the effect of improved life quality.

Since 1990, treatment with 5-fluorouracil (5-FU) and platinum have been most widely used as the treatment for metastatic GC, and irinotecan, oxaliplatin, paclitaxel, docetaxel, capecitabine have been used in various combinations for clinical study to develop new drugs with improved efficacy and minimized side effects. No particular research has been reported so far, which confirmed markedly increased performance than 5-FU based chemotherapy. While ECF (epirubicin, cisplatin and 5-fluorouracil) provides good effect, this is accompanied with side effect of high toxicity.

Various studies are conducted to overcome the limitations mentioned above, and among these, efforts to discover biomarker are at the center. The biomarkers can be used in the early diagnosis of cancer, and also used as a target for the treatment of metastatic carcinoma. Combined use of marker with the existent anticancer agents exhibit efficacy in the CRC, lung cancer, BRC and pancreatic cancer, and many efforts are necessary to develop and research use in GC.

Accordingly, by providing GC screening at an early stage based on new molecular approach, patients will be benefited. The genomics, proteomics and molecular pathology have provided various biomarker candidates with clinical potentials. It will be possible to improve treatment effect by actively utilizing the biomarker candidates in the customized treatment of cancers according to stages and patients, and therefore, many researches are necessary to apply the above in the actual clinical treatment.

The recent GC screening test includes determination of gross abnormality by endoscopic examination of large intestines, or fecal occult blood test (FOBT) which detects blood in feces. The endoscopic examination of large intestines has been utilized as a standard way of examination in the GC screening, but due to invasiveness thereof, patients who can receive the examination are limited. Accordingly, many attempts have been focused on the examination of feces, for advantages such as noninvasiveness, no need for colonic irrigation, and transferability of the sample. The fecal marker may include feces oozing, excreted or exfoliated from the tumor. For example, hemoglobin in traditional FOBT was perceived as the oozing type of the marker in the large scale screening program. However, the markers known so far, including the above, have not met the satisfaction.

Meanwhile, it is possible to extract spectra of mass ions within blood using the matrix-assisted laser desorption/ionization-time of flight (MALDI-TOF) mass spectrometer. The mass spectrometry, generally used in the researches on proteins, mainly categorizes 800 to 2500 m/s mass range as the target of analysis, because the specific range corresponds to the mass value region of peptide when the protein is dissociated by trypsin. It is also possible to extract the mass spectra of los-mass ions by using MALDI-TOF mass spectrometer. However, for the low-mass region below approximately 800 m/z where the matrix mass ions coexist, research has not been active on this particular region.

The extracted low-mass ion mass spectra can be analyzed by the conventional software, MarkerView™ (version 1.2). The inventors of the present invention analyzed mass spectra of the low-mass ions extracted from the serums of GC patient group and normal group (control, CONT) using MarkerView™ in a manner that will be explained in detail below with reference to FIG. 1.

The low-mass ion mass spectra in T2D file format was imported with MarkerView™ from the set $(A_1)$ of samples of serums collected from 49 GC patients of Table 301 and 84 normal controls of Table 302 (C11).

TABLE 301

| GC | Sex | Age year | CEA ng/mL | Stage |
|---|---|---|---|---|
| GC-E1 | M | 62 | 5.41 | I |
| GC-E2 | M | 58 | — | I |
| GC-E3 | M | 62 | 1.34 | I |
| GC-E4 | M | 48 | — | I |
| GC-E5 | M | 51 | — | I |
| GC-E6 | M | 44 | — | I |
| GC-E7 | F | 44 | — | I |
| GC-E8 | M | 61 | — | I |
| GC-E9 | M | 76 | — | I |
| GC-E10 | M | 51 | — | I |
| GC-E11 | F | 60 | 1.2 | II |
| GC-E12 | M | 73 | — | II |
| GC-E13 | F | 57 | — | II |
| GC-E14 | M | 78 | — | II |
| GC-E15 | M | 75 | — | II |
| GC-E16 | F | 67 | — | II |
| GC-E17 | M | 50 | — | II |
| GC-E18 | F | 60 | — | II |
| GC-E19 | F | 47 | — | II |
| GC-E20 | F | 62 | 8.3 | III |
| GC-E21 | M | 64 | — | III |
| GC-E22 | M | 58 | 6.89 | III |
| GC-E23 | F | 47 | 2.86 | III |
| GC-E24 | F | 55 | — | III |
| GC-E25 | F | 46 | — | III |
| GC-E26 | M | 64 | — | III |
| GC-E27 | M | 53 | — | III |
| GC-E28 | M | 61 | — | III |
| GC-E29 | F | 52 | 3.36 | IV |
| GC-E30 | M | 65 | 0.99 | IV |
| GC-E31 | M | 41 | —[a] | IV |

TABLE 301-continued

| GC | Sex | Age year | CEA ng/mL | Stage |
|---|---|---|---|---|
| GC-E32 | M | 78 | 4.93 | IV |
| GC-E33 | M | 79 | 1.11 | IV |
| GC-E34 | M | 76 | 2.37 | IV |
| GC-E35 | M | 54 | 117.13 | IV |
| GC-E36 | M | 58 | 2.24 | IV |
| GC-E37 | M | 67 | >1500 | IV |
| GC-E38 | F | 71 | 1.92 | IV |
| GC-E39 | M | 34 | 3.57 | IV |
| GC-E40 | M | 69 | 1.39 | IV |
| GC-E41 | M | 49 | 1.67 | IV |
| GC-E42 | F | 34 | 13.44 | IV |
| GC-E43 | M | 50 | — | IV |
| GC-E44 | M | 55 | — | IV |
| GC-E45 | M | 66 | — | IV |
| GC-E46 | F | 40 | — | IV |
| GC-E47 | M | 61 | — | IV |
| GC-E48 | M | 70 | — | IV |
| GC-E49 | M | 39 | — | IV |

CEA: Carcinoembryonic antigen

TABLE 302

| Control | Sex | Age year | CEA ng/mL |
|---|---|---|---|
| CONT-E1 | M | 39 | 1.3 |
| CONT-E2 | F | 70 | 1.2 |
| CONT-E3 | M | 66 | 1.3 |
| CONT-E4 | M | 53 | 0.8 |
| CONT-E5 | F | 69 | 1 |
| CONT-E6 | F | 68 | 1.8 |
| CONT-E7 | M | 35 | 1.7 |
| CONT-E8 | M | 62 | 3.7 |
| CONT-E9 | M | 62 | 1.1 |
| CONT-E10 | M | 48 | 5.3 |
| CONT-E11 | M | 48 | 1.8 |
| CONT-E12 | M | 66 | 1.6 |
| CONT-E13 | M | 66 | 1.4 |
| CONT-E14 | M | 66 | 4.2 |
| CONT-E15 | M | 54 | 1.4 |
| CONT-E16 | M | 54 | 1 |
| CONT-E17 | M | 62 | 2 |
| CONT-E18 | F | 45 | 0.7 |
| CONT-E19 | M | 39 | 3.2 |
| CONT-E20 | M | 67 | 1.8 |
| CONT-E21 | M | 63 | 5.5 |
| CONT-E22 | M | 48 | 2.8 |
| CONT-E23 | M | 55 | 5 |
| CONT-E24 | M | 55 | 1 |
| CONT-E25 | M | 62 | 7 |
| CONT-E26 | F | 57 | 1.2 |
| CONT-E27 | M | 61 | 0.9 |
| CONT-E28 | M | 50 | 1.9 |
| CONT-E29 | M | 46 | 1.5 |
| CONT-E30 | M | 51 | 4 |
| CONT-E31 | F | 68 | 1.8 |
| CONT-E32 | F | 68 | 1.4 |
| CONT-E33 | M | 64 | 1.7 |
| CONT-E34 | F | 52 | 2.1 |
| CONT-E35 | F | 59 | 1.2 |
| CONT-E36 | M | 53 | 1.6 |
| CONT-E37 | F | 68 | 1 |
| CONT-E38 | F | 65 | 3.1 |
| CONT-E39 | M | 31 | 1.2 |
| CONT-E40 | F | 59 | 0.7 |
| CONT-E41 | M | 43 | 1.4 |
| CONT-E42 | M | 66 | 2.3 |
| CONT-E43 | M | 48 | 4.2 |
| CONT-E44 | F | 41 | 2.1 |
| CONT-E45 | F | 65 | 3.8 |
| CONT-E46 | M | 64 | 2.4 |
| CONT-E47 | M | 53 | 3.3 |
| CONT-E48 | M | 63 | 0.9 |
| CONT-E49 | M | 57 | 1.5 |

TABLE 302-continued

| Control | Sex | Age year | CEA ng/mL |
|---|---|---|---|
| CONT-E50 | F | 66 | 1.6 |
| CONT-E51 | M | 60 | 1.5 |
| CONT-E52 | M | 57 | 2.2 |
| CONT-E53 | M | 53 | 1.9 |
| CONT-E54 | M | 60 | 0.8 |
| CONT-E55 | F | 50 | 2.6 |
| CONT-E56 | F | 53 | 2.6 |
| CONT-E57 | M | 64 | 1.5 |
| CONT-E58 | F | 60 | 3.7 |
| CONT-E59 | M | 58 | 1.2 |
| CONT-E60 | F | 66 | 1.1 |
| CONT-E61 | M | 57 | 2.9 |
| CONT-E62 | F | 68 | 5.5 |
| CONT-E63 | M | 56 | 1.7 |
| CONT-E64 | M | 51 | 3.4 |
| CONT-E65 | F | 56 | 1.3 |
| CONT-E66 | M | 57 | 1.5 |
| CONT-E67 | M | 61 | 4.2 |
| CONT-E68 | F | 51 | 1.9 |
| CONT-E69 | F | 51 | 1.6 |
| CONT-E70 | F | 52 | 1.4 |
| CONT-E71 | F | 56 | 1.7 |
| CONT-E72 | F | 52 | 1.7 |
| CONT-E73 | M | 63 | 1 |
| CONT-E74 | F | 60 | 1.8 |
| CONT-E75 | F | 58 | 0.7 |
| CONT-E76 | M | 65 | 4.1 |
| CONT-E77 | M | 52 | 2.2 |
| CONT-E78 | M | 50 | —[a] |
| CONT-E79 | F | 72 | — |
| CONT-E80 | F | 57 | — |
| CONT-E81 | M | 50 | — |
| CONT-E82 | F | 70 | — |
| CONT-E83 | F | 42 | — |
| CONT-E84 | F | 51 | — |

The conditions of Table 203 were used for import.

TABLE 303

| Mass tolerance | 100 ppm |
|---|---|
| Minimum required response | 10.0 |
| Maximum number of peaks | 10000 |

The imported peak intensities were then normalized (C12). MarkerView™ has a plurality of normalization methods, and among these, "Normalization Using Total Area Sums" was employed for the normalization. According to the method, partial sums of the intensities of the respective samples were obtained and averaged, and then each peak intensity was multiplied by a scaling factor so that the partial sums of the respective samples were in agreement with the averages. As a result, the partial sums of the intensities of the respective samples became identical after the normalization.

Next, the normalized peak intensities were Pareto-scaled (C13). That is, the peak intensities were Pareto-scaled by subtracting the averages of the respective mass ions from the respective normalized peak intensities, and dividing the same by the square root of the standard deviation.

Next, with respect to the Pareto-scaled peak intensities, discriminant scores (DS) were computed by performing the principal component analysis-based linear discriminant analysis (PCA-DA) (C14). The PCA-DA was performed by two stages, to obtain factor loading, which are the weighting factors of the respective mass ions, and the Pareto-scaled intensities were multiplied by the factor loading. The resultant values were summed, to compute the discriminant scores of the respective samples. The import condition of Table 103 includes maximum 10,000 peaks with sufficient samples imported, so that there were 10,000 factor loading computed, and one DS was computed by summing 10,000 terms.

Next, it was determined whether the computed DS was positive number or not (C15), and if so, determined positive (C16), and if not, determined negative (C17). In other words, when implemented on GC, the positive number was interpreted as GC patient group, while negative number was interpreted as normal control group.

FIG. 6 illustrates distribution of DS which were computed by the method of FIG. 5 with respect to the set consisting of 49 clinically GC-diagnosed patients and 84 non-cancer subjects. Reorganizing the interpretation results according to DS of FIG. 6 using confusion matrix will give:

TABLE 304

| Set $E_1$ | True GC | True CONT |
|---|---|---|
| Predicted GC | 48 | 0 |
| Predicted CONT | 1 | 84 |
| Sensitivity | | 97.96% |
| Specificity | | 100.0% |
| PPV | | 100.0% |
| NPV | | 98.82% |

Referring to FIG. 6 and Table 304, perfect discrimination result was obtained with all of the sensitivity, specificity, positive predictive value (PPV) and negative predictive value (NPV) exceeding 97% by the conventional PCA-DA of the MarkerView™.

However, the robustness of the formula must be verified for clinical use. That is, even the mass spectra that were additionally measured by a number of times with respect to the dataset that was measured once and constituted discriminant formula, are required to maintain good discrimination results, and the discrimination result based on the same discriminant also has to be sound with respect to new GC patient groups and non-cancer subjects that were not taken into consideration in the designing of the discriminant. The process of repeatedly measuring mass spectra may include the process of freezing and thawing serums and mixing the serum newly with methanol/chloroform to obtain extract. These processes are considered the disturbances in the statistic analysis with respect to the mass spectra, and clinical implementation is only possible when the discriminant is least influenced by the disturbances.

The conventional PCA-DA explained above with reference to FIGS. 5 and 6 and Table 304 sometimes exhibit good discrimination result if applied individually to the set of specific samples, i.e., to individual training set. However, the discrimination result was unsatisfactory when applied with respect to the validation set (Tables 329, 331). It appears that the discriminant exhibiting very good discrimination result with respect to the training set, is not so robust because the 10,000 mass ions constituting the discriminant include a considerable amount of mass ions which may be at least unnecessary for the discrimination between GC patients and non-cancer subjects and although not entirely problematic in the discrimination of training set, which can potentially cause confusion in the discrimination result in the discrimination of the validation set. Accordingly, a process is necessary, which exclusively locates mass ions that are absolutely necessary to obtain good and robust discrimination result, by actively removing mass ions which are at least unnecessary, or which can potentially confuse discrimination result.

SUMMARY OF THE INVENTION

Problems to Solve

The present invention provides an apparatus for screening cancer, which reads low-mass ion mass spectrum for diagnosing cancer based on biostatistical analysis with respect to low-mass ions extracted from biological materials, and diagnoses cancer using the low-mass ion spectrum.

The present invention provides a discriminant which provides robust discrimination result with respect to CRC patent samples and non-cancer subject samples, by providing a discriminant that results in all the sensitivity, specificity, positive predictability and negative predictability exceeding 85% with respect to the mass spectrum additionally and repeatedly measured on new CRC patient samples and normal patent samples as well as the mass spectrum additionally and repeatedly measured on the CRC patient samples and normal patent samples from which the discriminant is obtained, and an apparatus for screening cancer which diagnoses CRC by analyzing the constituent low-mass ions.

The present invention provides a discriminant which provides robust discrimination result with respect to BRC patent samples and non-cancer subject samples, by providing a discriminant that results in all the sensitivity, specificity, positive predictability and negative predictability exceeding 85% with respect to the mass spectrum additionally and repeatedly measured on new BRC patient samples and normal patent samples as well as the mass spectrum additionally and repeatedly measured on the BRC patient samples and normal patent samples from which the discriminant is obtained, and an apparatus for screening cancer which diagnoses BRC by analyzing the constituent low-mass ions.

The present invention provides a discriminant which provides robust discrimination result with respect to GC patent samples and non-cancer subject samples, by providing a discriminant that results in all the sensitivity, specificity, positive predictability and negative predictability exceeding approximately 80~90% with respect to the mass spectrum additionally and repeatedly measured on new GC patient samples and normal patent samples as well as the mass spectrum additionally and repeatedly measured on the GC patient samples and normal patent samples from which the discriminant is obtained, and an apparatus for screening cancer which diagnoses GC by analyzing the constituent low-mass ions.

Effect of the Invention

The apparatus for screening cancer according to the present invention provides advantages including economic analysis cost in the case of CRC diagnosis, short analysis time and large-scale analysis. To describe the procedure briefly, mass spectrum of the low-mass ion in blood is measured, peak intensities corresponding to the masses of the low-mass ions for CRC diagnosis are extracted, and through simple calculation, CRC positive/negative information can be provided.

Further, sound and robust discrimination performance is provided, so that with CRC as a target, it is confirmed that all the sensitivity, specificity, positive predictability and negative predictability exceed 85% with respect to not only training set, but also validation set. Further, by changing the CRC patient and non-cancer subject sets to patients with other diseases and non-cancer subjects, it is possible to advantageously implement the present invention for other various diseases.

Further, in terms of CRC target, compared to the comparison of FOBT with the feces as the analyte, the present invention can use blood as analyte, and thus can be co-conducted with the other analysis. Accordingly, the present invention provides more convenient and efficient CRC information. Compared to the conventional FOBT discrimination performance, the present invention using low-mass ions for the diagnosis of CRC exhibits comparable specificity and markedly increased sensitivity.

The apparatus for screening cancer according to the present invention provides advantages including economic analysis cost in the case of BRC diagnosis, short analysis time and large-scale analysis. To describe the procedure briefly, mass spectrum of the low-mass ion in blood is measured, peak intensities corresponding to the masses of the low-mass ions for BRC diagnosis are extracted, and through simple calculation, BRC positive/negative information can be provided.

Further, sound and robust discrimination performance is provided, so that with BRC as a target, it is confirmed that all the sensitivity, specificity, positive predictability and negative predictability exceed 85% with respect to not only training set, but also validation set. Further, by changing the BRC patient and non-cancer subject sets to patients with other diseases and non-cancer subjects, it is possible to advantageously implement the present invention for other various diseases.

The apparatus for screening cancer according to the present invention provides advantages including economic analysis cost in the case of GC diagnosis, short analysis time and large-scale analysis. To describe the procedure briefly, mass spectrum of the low-mass ion in blood is measured, peak intensities corresponding to the masses of the low-mass ions for GC diagnosis are extracted, and through simple calculation, BRC positive/negative information can be provided.

Further, sound and robust discrimination performance is provided, so that with GC as a target, it is confirmed that all the sensitivity, specificity, positive predictability and negative predictability exceed approximately 80-90% with respect to not only training set, but also validation set. Further, by changing the GC patient and non-cancer subject sets to patients with other diseases and non-cancer subjects, it is possible to advantageously implement the present invention for other various diseases.

BRIEF DESCRIPTION OF THE DRAWINGS

FIGS. 1 to 6 are provided to explain a conventional art, in which

FIG. 1 is a flowchart provided to explain a process of determining CRC using low-mass ion mass spectrum according to a conventional art;

FIG. 2 is a graph illustrating a result of interpretation made according to a conventional art with respect to a set consisting of 133 CRC patients and 153 normal controls;

FIG. 3 is a flowchart provided to explain a process of determining BRC using low-mass ion mass spectrum according to a conventional art;

FIG. 4 is a graph illustrating a result of interpretation made according to a conventional art with respect to a set consisting of 54 BRC patients and 49 normal controls;

FIG. 5 is a flowchart provided to explain a process of determining GC using low-mass ion mass spectrum according to a conventional art;

FIG. 6 is a graph illustrating a result of interpretation made according to a conventional art with respect to a set consisting of 49 GC patients and 84 normal controls;

FIGS. 7 to 13 are views provided to explain an apparatus for screening cancer according to a preferred embodiment of the present invention, in which FIG. 7 is a block diagram of an apparatus for screening cancer according to a preferred embodiment of the present invention;

FIG. 8 is a detailed block diagram of the cancer diagnosing unit of FIG. 7;

FIG. 9 is a detailed block diagram of the first discriminant score computing means of FIG. 8;

FIG. 10 is a detailed block diagram of the second discriminant score computing means of FIG. 8;

FIG. 11 is a detailed block diagram of the cancer-diagnosing ion selecting means of FIG. 8;

FIG. 12 is a detailed block diagram of the candidate ion set selecting means of FIG. 11;

FIG. 13 is a detailed block diagram of the final ion set selecting means of FIG. 11;

FIGS. 14 to 25 are views provided to explain an apparatus for screening cancer diagnosing CRC according to a preferred embodiment of the present invention, in which FIG. 14 is a detailed block diagram of the cancer diagnosing unit of FIG. 7 diagnosing CRC according to an embodiment;

FIG. 15 is a flowchart provided to explain a process of selecting a first training set ($A_0$) with predetermined sensitivity and specificity and calculating a weighting per mass ions, according to an embodiment of the present invention;

FIG. 16 is a flowchart provided to explain a process of applying a discriminant to an analyte;

FIG. 17 is a graph illustrating a result of determining a set $A_1$ with the weighting per mass ions computed based on the first training set $A_{01}$;

FIG. 18 is a graph illustrating a result of determining a set $A_1$ with the weighting per mass ions computed based on the first training set $A_{02}$;

FIG. 19 is a flowchart provided to explain a process of constructing a preliminary discriminant according to an embodiment, FIG. 20 is a graph illustrating a result of determining set $A_1$ with the first type of preliminary discriminant;

FIG. 21 is a graph presenting the result of discriminating set $A_1$ with the second type preliminary discriminant;

FIG. 22 is a flowchart provided to explain the process of constructing the final discriminant according to an embodiment of the present invention;

FIG. 23 is a graph presenting a discrimination result obtained by computing discriminant score (DS) according to the final discriminate with respect to the mass spectrum repeatedly measured five times with respect to set A and obtaining mean DS, according to an embodiment;

FIG. 24 is a graph presenting a discrimination result obtained by computing discriminant score (DS) according to the final discriminate with respect to the mass spectrum repeatedly measured five times with respect to set B and obtaining mean DS, according to an embodiment;

FIG. 25b is a graph presenting a characterization result of 2450.9701 m/z from among the first type CRC-diagnosing low-mass ion masses as confirmed, according to an embodiment;

FIGS. 26 to 37 are views provided to explain an apparatus for screening cancer which diagnoses BRC according to an embodiment, in which FIG. 26 is a detailed block diagram of the cancer diagnosing unit of FIG. 7 to diagnose BRC according to an embodiment;

FIG. 27 is a flowchart provided to explain a process of selecting a first training set $C_0$ with predetermined sensitivity and specificity and computing weightings per mass ions, according to an embodiment;

FIG. 28 is a flowchart provided to explain a process of applying a discriminant with respect to the biological materials for screening;

FIG. 29 is a graph presenting a discrimination result of set $C_1$ obtained by applying the weightings per mass ions computed from the first training set $C_{01}$;

FIG. 30 is a graph presenting a discrimination result of set $C_1$ obtained by applying the weightings per mass ions computed from the first training set $C_{03}$;

FIG. 31 is a flowchart provided to explain a process of constructing a preliminary discriminant according to an embodiment;

FIG. 32 is a graph presenting a discrimination result of set $C_1$ with a first type preliminary discriminant;

FIG. 33 is a graph presenting a discrimination result of set $C_1$ with a second type preliminary discriminant;

FIG. 34 is a graph presenting a discrimination result of set $C_1$ with a fourth type preliminary discriminant;

FIG. 35 is a flowchart provided to explain a process of constructing a final discriminant according to an embodiment;

FIG. 36 is a graph presenting a discrimination result obtained by computing DS according to the first, or second and third final discriminants with respect to the mass spectra repeatedly measured with respect to set C five times and obtaining a mean DS, according to an embodiment;

FIG. 37 is a graph presenting a discrimination result obtained by computing mean DS according to the first, or second and third final discriminants, and discriminating set D which is repeatedly measured five times, according to an embodiment;

FIGS. 38 to 54 are views provided to explain an apparatus for screening GC according to an embodiment, in which FIG. 38 is a detailed block diagram of the cancer diagnosing unit of FIG. 7 to diagnose GC according to an embodiment;

FIG. 39 is a flowchart provided to explain a process of selecting a first training set $E_0$ with predetermined sensitivity and specificity and computing weightings per mass ions, according to an embodiment;

FIG. 40 is a flowchart provided to explain a process of applying a discriminant with respect to the biological materials for screening;

FIG. 41 is a graph presenting a discrimination result of set $E_1$ obtained by applying the weightings per mass ions computed from the first training set $E_{01}$;

FIG. 42 is a graph presenting a discrimination result of set $E_1$ obtained by applying the weightings per mass ions computed from the first training set $E_{03}$;

FIG. 43 is a graph presenting a discrimination result of set $E_1$ with weightings per mass ions computed from the first training set $E_{03}$;

FIG. 44 is a graph presenting a discrimination result of set $E_1$ with weightings per mass ions computed from the first training set $E_{04}$;

FIG. 45 is a graph presenting a discrimination result of set $E_1$ with weightings per mass ions computed from the first training set $E_{05}$;

FIG. 46 is a flowchart provided to explain a process of constructing a preliminary discriminant according to an embodiment;

FIG. 47 is a graph presenting a discrimination result of set $E_1$ by the first type preliminary discriminant;

FIG. 48 is a graph presenting a discrimination result of set $E_1$ by the second type preliminary discriminant;

FIG. 49 is a graph presenting a discrimination result of set $E_1$ by the third type preliminary discriminant;

FIG. 50 is a graph presenting a discrimination result of set $E_1$ by the fourth type preliminary discriminant;

FIG. 51 is a graph presenting a discrimination result of set $E_1$ by the fifth type preliminary discriminant;

FIG. 52 is a flowchart provided to explain a process of constructing a final discriminant according to an embodiment;

FIG. 53 is a graph presenting a discrimination result obtained by computing DS according to the first and fifth final discriminants with respect to the mass spectra repeatedly measured with respect to set E five times and obtaining a mean DS, according to an embodiment;

FIG. 54 is a graph presenting a discrimination result obtained by computing mean DS according to the first and fifth final discriminants, and discriminating set F which is repeatedly measured five times, according to an embodiment;

DETAILED DESCRIPTION OF THE INVENTION

1. Definitions

Figure 1:
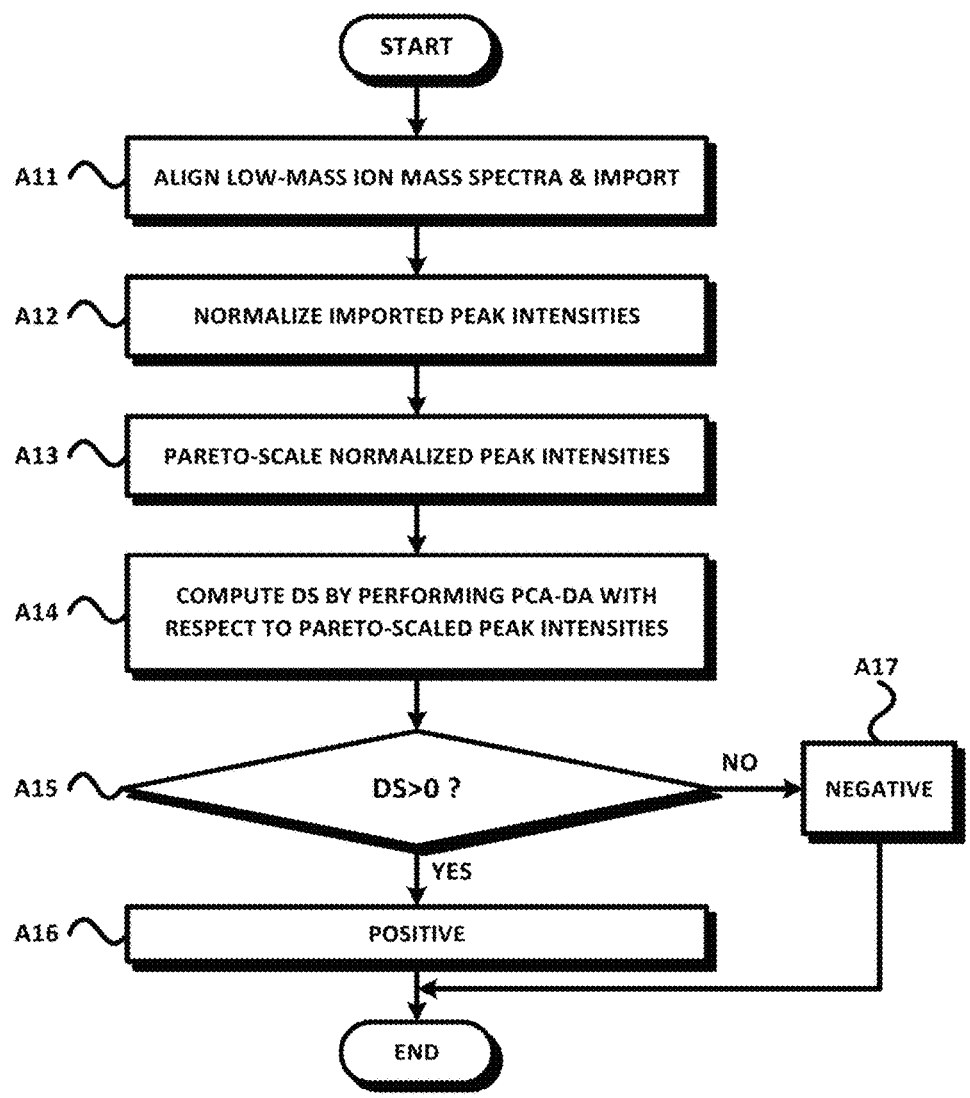

As used herein, the expression "biological material" encompasses whole blood, serum, plasma, urine, feces, sputum, saliva, tissue, cells, cell extract, or in vitro cell culture, but not limited thereto. In the Examples provided below, the biological materials of serums from patients or non-cancer subjects are used.

As used herein, the expression "peak intensity" refers to values obtained by the MALDI-TOF mass spectrometer, and have correlativity with the amount of mass ions corresponding to the peaks.

As used herein, the expression "normalization" refers to the process of brining data range to agreement with each other or brining data distribution to similar state, in which the normalization may be performed using mean or median, but not limited thereto. That is, various known methods may be adequately implemented. In one embodiment, the normalization involves obtaining partial sums of the peak intensities of the respective samples and averaging the partial sums of the samples, and multiplying the respective peak intensities by the scaling factors of the respective samples so that the partial sums of the peak intensities of the respective samples are brought into agreement with the average. As a result, the partial sums of the peak intensities of the respective samples are identical after the normalization.

As used herein, the "Pareto scaling" refers to the process of subtracting averages of the respective mass ions from the normalized peak intensities and dividing by the square root of the standard deviation. The Pareto-scaling has the advantage because it is possible to avoid amplification of noise by partially maintaining the data size information instead of applying more general method such as autoscaling which completely offsets the data size information by standard deviation.

As used herein, the "weighting factor" refers to a factor which adjusts the numeric data size after multiplication by weighting factor to a proportional relationship with the importance from the statistical viewpoint. One example of the weighting factor includes a factor loading which is obtained as a result of PCA-DA in the Examples provided below.

As used herein, the term "low-mass ion" refers to ions having mass within 1500 m/z as obtained using MALDI-TOF mass spectrometer, or the like. Although some of the low-mass ions for CRC diagnosis may have mass exceeding the above limit, considering the most low-mass ions are within this limit, all the ions will be collectively called "low-mass ions". Accordingly, the limit as 1500 m/z will be understood as approximate value rather than definite one.

The mass measured by the MALDI-TOF mass spectrometer includes an error range of "±0.05 m/z", considering a slight error that may be generated in the mass measure depending on the environment of experiment. Y way of example, the mass of 1467.5969 m/z as indicated in the appended claims is indeed understood to be within a range between 1467.5469 m/z and 1467.6469 m/z. The error range may be "±0.1 m/z" depending on the environment of experiment.

In one embodiment, the mass measured by the MALDI-TOF mass spectrometry may be acquired in positive mode of the MALDI-TOF mass spectrometry.

In one embodiment, the code of the weighting vector is determined to be positive if the discriminant score is positive number, while it is determined to be negative if the discriminant score is negative number. The factor loading vector in the PCA-DA mathematically corresponds to eigenvector, of which code may be determined arbitrarily. That is, mathematically, the values are considered equal according to the eigenvalue problem, even when the computed factor loading per mass ions are multiplied by −1 and thus change code. However, the negative value of discriminant score is considered to indicate positivity, while the positive value of the discriminant score is considered to indicate negativity. Although the positive discriminant score indicates negativity and the negative discriminant score indicates positivity, the scope of the invention is not limited to the specific example.

Further, as used herein, the term "discriminant score" refers to a value computed by a biostatistical analysis with respect to mass spectrum extracted from a biological material, based on which cancer positivity or negativity may be determined. Simple method of determining whether the computed discriminant score exceeds a specific reference value or not may be implemented, and a function may be used, according to which the computed discriminant score is input and a result of interpretation is output.

Although the specific term "discriminant score" is used in the embodiments of the present invention, the term is not limiting. Accordingly, various other forms of terms such as discriminant level, discriminant value or the like may be adequately used. Accordingly, the term "discriminant score" is not limited to the definition in the dictionary, but rather understood as a term that encompasses various terms such as discriminant level, value or any other similar terms that can indicate the discriminant score as defined by the invention.

Further, as used herein, the term "discrimination performance" refers to numeric representation of the index including, for example, sensitivity, specificity, positive predictability, negative predictability or accuracy. The term "discrimination performance" may also refer to a value computed by the functions of the indexes. For example, sensitivity, specificity, positive predictability, negative predictability and accuracy may each be used as the discrimination performance, or alternatively, the sum of two or more indexes, e.g., the sum of sensitivity and specificity, the sum of sensitivity and positive predictability, or the sum of negative predictability and accuracy, may be used as the discrimination performance.

The invention will be explained in greater detail below with reference to Examples. However, the Examples are given only for illustrative purpose, and accordingly, the scope of the present invention should not be construed as limited by any of specific Examples.

FIGS. 7 to 13 are views provided to explain an apparatus for screening cancer according to a preferred embodiment.

Figure 7:
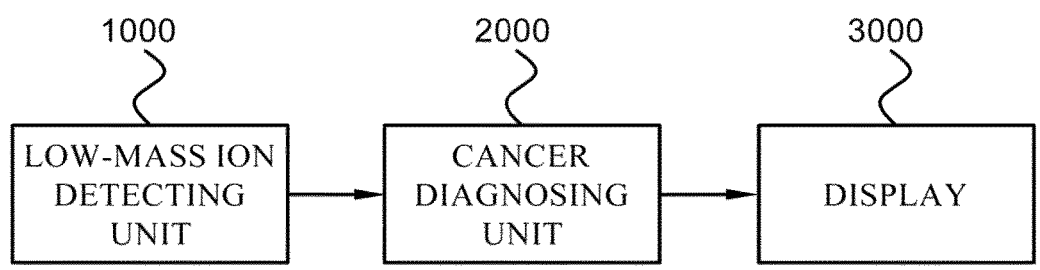

First, FIG. 7 is a block diagram of an apparatus for screening cancer according to a preferred embodiment. Referring to FIG. 7, the apparatus for screening cancer according to one embodiment includes a low-mass ion detector 1000 which detects a mass spectrum of low-mass ions from a plurality of cancer patients and normal cases, a cancer diagnosing unit 2000 which determines cancer diagnosis information by compare-analyzing the mass spectrum of the low-mass ions, and a display 3000 which converts the cancer diagnosis information determined at the cancer diagnosing unit 2000 into a form suitable for output and displays the result.

The low-mass ion detecting unit 1000 may extract the mass spectrum of the low-mass ions by detecting peak intensity of the low-mass ions from the biological material. Further, the low-mass ion detecting unit 1000 may include a mass spectrometer.

The display 3000 may convert the cancer diagnosis information as determined into various forms including text, numbers, or figures and displays the resultant converted information on a device such as monitor screen, or LCD of mobile terminal, or the like.

Figure 8:
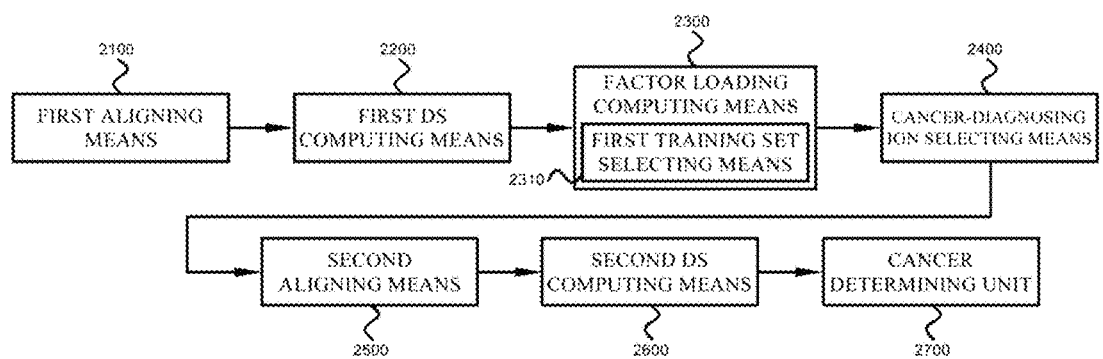

FIG. 8 is a detailed block diagram of the cancer diagnosing unit of FIG. 7. Referring to FIG. 8, the cancer diagnosing unit 2000 may include a first aligning means 2100 which aligns the low-mass ion mass spectra of the cancer patient and non-cancer patient cases as a training candidate set, a first discriminant score (DS) computing means 2200 which computes DS by performing biostatistical analysis with respect to the aligned mass spectra, a factor loading computing means 2300 which computes sensitivity and specificity according to DS, selects a first training set based on the result, and computes factor loading per low-mass ions, a cancer-diagnosing ion selecting means 2400 which selects low-mass ions for the purpose of cancer diagnosis based on the discrimination performance of the candidate low-mass ions that meets condition of candidates, a second aligning means which aligns the low-mass ion mass spectra of the biological biological materials for screening to the first training set, a second DS computing means 2600 which computes peak intensity of the low-mass ion of interest and DS based on the factor loading, and a cancer determining means 2700 which determines the object of analysis to be cancer positive or negative depending on the DS.

The factor loading computing means 2300 may perform biostatistical analysis with respect to the aligned mass spectra and may include a first training set selecting means 2310 which selects a first raining set based on the training cases that meet condition of training based on the biostatistical analysis among the cancer and non-cancer cases. The factor loading computing means 2300 may compute a factor loading based on the first training set.

The first training set selecting means 2310 may set the cancer and non-cancer cases to be the first training set, if the sensitivity according to the result of biostatistical analysis exceeds a threshold $N_1$, and the specificity exceeds a threshold $N_2$. The thresholds $N_1$ and $N_2$ may preferably be 1.

The cancer determining means 2700 may determine the subject of interest to be cancer positive or negative depending on the discriminant score, and may determine the subject of interest to be positive if the DS exceeds a reference value S, or negative if the DSC does not exceed the reference value S. The reference value S may preferably be 0.

The cancer determining means 2700 may determine the cancer information of the subjects of interest based on the ge of a plurality of DS which are computed with respect to a plurality of low-mass ion mass spectra detected by repetitive measure of a biological materials for cancer screening.

Figure 9:
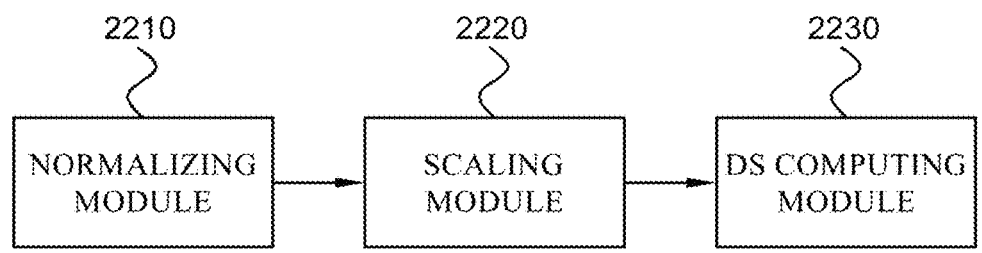

FIG. 9 is a detailed block diagram of the first DS computing means of FIG. 8. Referring to FIG. 9, the first DS computing means 2200 may include a normalizing module 2210 which normalizes the peak intensities of the low-mass ion mass spectra of the training candidate set, a scaling module 2200 which scales the normalized peak intensities, and a DS calculating module 2230 which computes the DS by performing the biostatistical analysis with respect to the scaled peak intensities.

The scaling module 2200 may perform Pareto-scaling. The DS calculating module 2230 may perform the biostatistical analysis using PCA-DA. The DS calculating module 2230 may compute the DS using the factor loading acquired as a result of PCA-DA and the scaled peak intensities.

Figure 10:
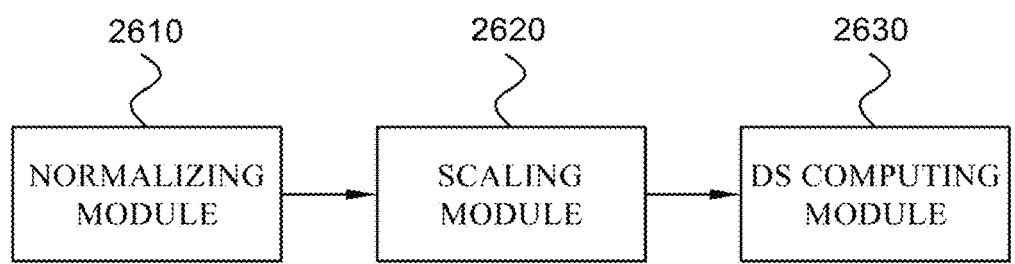

FIG. 10 is a detailed block diagram of the second DS computing means of FIG. 8. Referring to FIG. 10, the second DS computing means 2600 may include a normalizing module 2610 which normalizes the peak intensities of the low-mass ion mass spectra of the subjects of interest, a scaling module 2620 which scales the normalized peak intensities, and a DS calculating module 2630 which computes the DS based on the scaled peak intensities and the factor loading.

The scaling module 2620 may perform Pareto-scaling. The DS calculating module 2630 may compute the DS based on the scaled peak intensities of the low-mass ions for cancer diagnosis and the factor loading.

Figure 11:
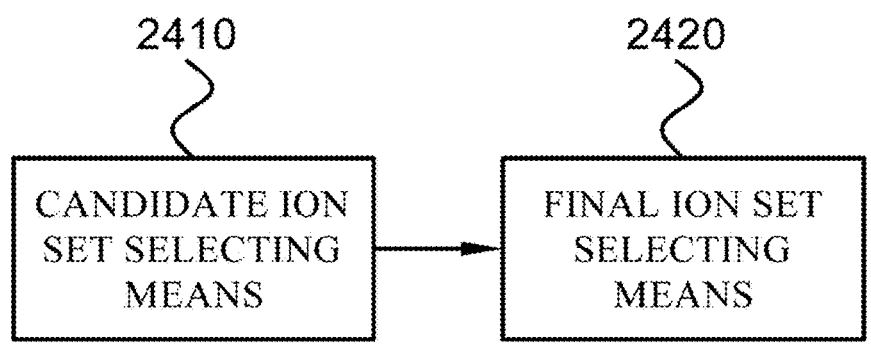

FIG. 11 is a detailed block diagram of the cancer-diagnosing ion selecting means of FIG. 8. Referring to FIG. 11, the cancer-diagnosing ion selecting means 2400 may include a candidate ion set selecting means 2410 which selects a candidate ion set based on candidate low-mass ions that meet condition of candidates from the selected first training set, and a final ion set selecting means 2420 which selects a final ion set with the cancer-diagnosing low-mass ions based on the individual or combinational discrimination performance of the candidate low-mass ions of the selected candidate ion set.

The criterion for evaluating the discrimination performance implementable at the final ion set selecting means 2420 may include a first criterion according to which ions, from among the candidate low-mass ions, that have sums of sensitivity and specificity greater than a reference are selected, or a combination of ions, from among the combinations of the candidate low-mass ions, that has a sum of sensitivity and specificity greater than the counterpart combinations is selected.

The criterion for evaluating the discrimination performance at the final ion set selecting means 2420 may additionally include a second criterion according to which a combination of the ions, from among the combinations of the candidate low-mass ions, that has the least number of the candidate low-mass ions among the counterpart combinations.

The criterion for evaluating the discrimination performance implementable at the final ion set selecting means 2420 may additionally include a third criterion according to which a combination of the candidate low-mass ions, from among the combinations of the candidate low-mass ions, that has the greatest difference between the maximum DS of the true positive case and the maximum DS of the true negative case, in which the DS may be computed based on the scaled peak intensities and the factor loading of the candidate low-mass ions, and indicate cancer positive or negative.

The final ion set selecting means 2420 may perform the operation of selecting low-mass ions with respect to a training set consisting of the first training set added with a second training set, independent from the first training set.

Figure 12:
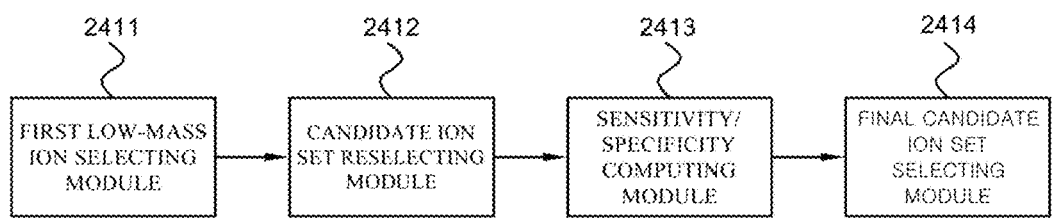

FIG. 12 is a detailed block diagram of the candidate ion set selecting means of FIG. 11. Referring to FIG. 12, the candidate ion set selecting means 2410 may include a first low-mass ion selecting module 2411 which selects the first low-mass ions for the respective training cases, in which, as illustrated in FIG. 12, an absolute product of multiplying the peak intensities of the low-mass ions of the respective training cases by the factor loading per low-mass ions obtained through the biostatistical analysis does not exceed a threshold $T_1$. The threshold $T_1$ may preferably be 0.1.

The candidate ion set selecting means 2410 may include a candidate ion set preselecting module 2412 which selects the candidate ion set with the second low-mass ions which are present commonly in the training cases of the first low-mass ions that exceed the threshold percentage $T_2$. The threshold percentage $T_2$ may preferably be 50%.

The candidate ion set selecting means 2410 may include a sensitivity/specificity calculating module 2413 which computes DS representing cancer positive or negative with respect to each training case using the second low-mass ions, and computes sensitivity and specificity based on the DS, and a candidate ion set final selecting module 2414 which changes at least one of $T_1$ and $T_2$ and selects the candidate ion set by repeating the above operations, if the sensitivity is less than the threshold $N_3$ or if the specificity is less than threshold $N_4$. The thresholds $N_3$ and $N_4$ may preferably be 0.9.

Figure 13:
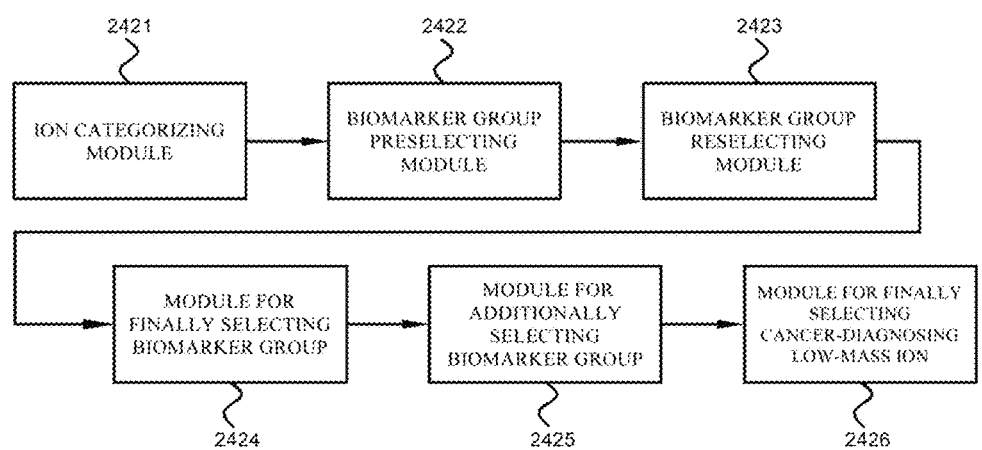

FIG. 13 is a detailed block diagram of the final ion set selecting means of FIG. 11. Referring to FIG. 13, the final ion set selecting means 2420 may include an ion dividing module 2421 which divides the candidate low-mass ions included in the candidate ion set into high sensitivity sets $\{Sns_1, Sns_2, Sns_3 \ldots Sns_I\}$ consisting of high sensitivity low-mass ions having greater sensitivity than the specificity in which the high sensitivity low-mass ions are sorted in descending order based on the sum of the sensitivity and the specificity, and high specificity sets $\{Spc_1, Spc_2, Spc_3 \ldots Spc_J\}$ having high specificity low-mass ions with greater specificity than sensitivity in which the high specificity low-mass ions are sorted in a descending order based on the sum of the sensitivity and the specificity; a biomarker group preselecting module 2422 which selects a biomarker group based on combinations that are selected according to the discrimination performance based on at least one of the first, the second and the third criteria from among the candidate combinations consisting of two or more low-mass ions of top L high sensitivity low-mass ions {$Sns_1$, $Sns_2$, $Sns_3$ ... $Sns_L$} and top L high specificity low-mass ions {$Spc_1$, $Spc_2$, $Spc_3$ ... $Spc_L$}; and a biomarker group re-selecting module 2424 which re-selects the biomarker group with a combination which is selected according to the criteria of the discrimination performance by at least one of the first, the second and third criteria, from among candidate combinations consisting of the biomarker group added with second top M high sensitivity low-mass ions of the high sensitivity set and second top M high specificity low-mass ions of the high specificity set; and a biomarker group final selecting module 2424 which repeats the re-selecting until there is no second top low-mass ions left in the high sensitivity set and the high specificity set and finally selects the biomarker group.

The final ion set selecting means 2420 may include a biomarker group additional selecting module 2425 which repeats the selecting operation of the three biomarker groups with respect to remaining candidate ion set of the candidate ion set except for the low-mass ions in the combinations selected as the biomarker group at the biomarker group final selecting module 2424 to thereby additionally select a biomarker group, and continues additionally selecting the biomarker group as far as there are more than L mass ions left in the high sensitivity set or the high specificity set; and a cancer-diagnosing low-mass ion final selecting module 2426 which selects the low-mass ions in the combination of top K biomarker groups as the low-mass ions for cancer diagnosis in terms of accuracy in determining true positivity or true negativity. The value L may be 2, and M may be 1, and K may be 1, 2 or 3.

The plurality of cancer patent cases may include any of CRC, BRC or GC patient cases.

2. Examples of Apparatus for Screening CRC

Figure 14:
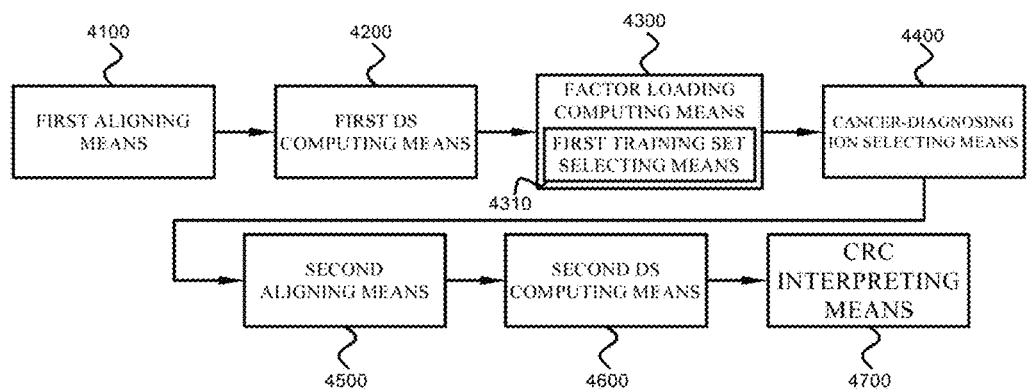

FIG. 14 is a detailed block diagram of the cancer diagnosing unit of FIG. 7 for the diagnosis of CRC according to an embodiment.

Referring to FIG. 14, the cancer diagnosing unit according to one embodiment may include a first aligning means 4100 which aligns a low-mass ion mass spectrum of a candidate training set consisting of the CRC patient and non-CRC cases; a first DS computing means 4200 which computes DS by conducting biostatistical analysis with respect to the aligned mass spectrum; a factor loading computing means 4300 which computes sensitivity and specificity according to DS and selects a first training set based on the computed result, and computes factor loadings per low-mass ions; a CRC diagnosing ion selecting means 4400 which selects low-mass ions for the purpose of diagnosing CRC in terms of the discrimination performance from among the candidate low-mass ions that meet candidate condition; a second aligning means which aligns the low-mass ion mass spectrum of a biological materials for screening to the first training set; a second DS computing means 4600 which computes DS based on peak intensities of the low-mass ions of interest and the factor loadings; and a CRC determining means 4700 which determines the subject of interest to be CRC positive or negative depending on the DS. The CRC diagnosing ion selecting means 4400 may divide the plurality of CRC patient and non-CRC cases into a first type discrimination case consisting of a plurality of CRC patient cases and a plurality of normal cases, a second type discrimination case consisting of the plurality of CRC patient cases and a plurality of cancer patient cases with cancers other than CRC, and executed with respect to the first and second discrimination cases, respectively, to divide the CRC-diagnosing low-mass ions into first type CRC diagnosing low-mass ions with respect to the first type discrimination case and second type CRC-diagnosing low-mass ions with respect to the second type discrimination case.

To the above-mentioned purpose, the low-mass ion detecting unit 1000 extracts mass spectrum of the low-mass ion by detecting peak intensity of the low-mass ions using mass spectrometer with respect to biological materials of a plurality of CRC patient and non-CRC cases.

The detailed components of the cancer diagnosing unit to diagnose the CRC are identical to those of the apparatus for screening cancer explained above with reference to FIGS. 9 to 13. Accordingly, the like elements will not be explained in detail below for the sake of brevity.

Referring to FIG. 14, the apparatus for screening cancer according to one embodiment may be implemented in a hardware level, or alternatively, in a software level via program structure, and the example of implementation in the software level will be explained below with reference to the flowcharts accompanied hereto, to explain diagnosing CRC with an apparatus for screening cancer according to an embodiment.

(2-1) Sample Preparation—Collecting Serums

Serums were collected from 133 CRC patients (Table 101), 153 normal controls (Table 102), 111 BRC patients (Table 105), 36 non-Hodgkin lymphoma (NHL) patients (Table 106) and 29 GC patients (Table 107), respectively.

TABLE 105

| BRC | Sex | Age year | Node | ER | ER % | PR | PR % | HER2 | Tumor Size cm |
|---|---|---|---|---|---|---|---|---|---|
| BRC-A1 | F | 48 | — | 5 | 33-66% | 6 | 33-66% | 2 | — |
| BRC-A2 | F | 35 | — | 6 | 33-66% | 6 | 33-66% | 1 | — |
| BRC-A3 | F | 45 | pN1a | 5 | 33-66% | 5 | 33-66% | 0 | 1.5 |
| BRC-A4 | F | 61 | — | 0 | 0% | 0 | 0% | 2 | — |
| BRC-A5 | F | 70 | pN0(sn) | 0 | 0% | 0 | 0% | 1 | <0.1 |
| BRC-A6 | F | 58 | ypN0 | 3 | <10% | 3 | 10-33% | 3 | 0.5 |
| BRC-A7 | F | 49 | ypN0(i+) | 0 | 0% | 0 | 0% | 2 | 1.9 |
| BRC-A8 | F | 49 | ypN2a | 0 | 0% | 0 | 0% | 1 | 2.5 |
| BRC-A9 | F | 39 | pN1a | 6 | 33-66% | 7 | >66% | 1 | 2.2 |
| BRC-A10 | F | 48 | ypN2a | 6 | 33-66% | 4 | <10% | 3 | 5.8 |
| BRC-A11 | F | 39 | — | 0 | 0% | 0 | 0% | 1 | — |
| BRC-A12 | F | 56 | pN1a | 6 | 33-66% | 6 | 33-66% | 0 | 2.8 |

TABLE 105-continued

| BRC | Sex | Age year | Node | ER | ER % | PR | PR % | HER2 | Tumor Size cm |
|---|---|---|---|---|---|---|---|---|---|
| BRC-A13 | F | 59 | pN0(sn) | 6 | 33-66% | 2 | <10% | 1 | 2.3 |
| BRC-A14 | F | 31 | pN1a | 5 | 33-66% | 4 | 10-33% | 1 | 2.2 |
| BRC-A15 | F | 46 | pN3a | 6 | 33-66% | 6 | 33-66% | 1 | 3.5 |
| BRC-A16 | F | 56 | — | 7 | >66% | 4 | 10-33% | 1 | — |
| BRC-A17 | F | 55 | — | 0 | 0% | 0 | 0% | 2 | — |
| BRC-A18 | F | 46 | pN0 | 0 | 0% | 0 | 0% | 0 | 1.5 |
| BRC-A19 | F | 60 | ypN0 | 0 | 0% | 0 | 0% | 3 | 1.9 |
| BRC-A20 | F | 49 | pN0(sn) | 5 | 33-66% | 2 | <10% | 2 | 1.5 |
| BRC-A21 | F | 55 | pN1mi | 0 | 0% | 0 | 0% | 3 | 1.8 |
| BRC-A22 | F | 65 | pN0 | 6 | 33-66% | 6 | 33-66% | 0 | 1.7 |
| BRC-A23 | F | 35 | ypN2a | 6 | 66% | 4 | 10-33% | 2 | 2.6 |
| BRC-A24 | F | 46 | pN1a | 6 | 33-66% | 6 | 33-66% | 3 | 2.5 |
| BRC-A25 | F | 45 | pN0(sn) | 6 | 33-66% | 6 | 33-66% | 1 | 0.8 |
| BRC-A26 | F | 42 | pN0(sn) | 3 | 10-33% | 6 | 33-66% | 0 | 1 |
| BRC-A27 | F | 58 | pN0(sn) | 6 | 33-66% | 6 | 33-66% | 1 | 1.5 |
| BRC-A28 | F | 62 | pN1a | 0 | 0% | 0 | 0% | 2 | 2.2 |
| BRC-A29 | F | 61 | — | 0 | 0% | 0 | 0% | 1 | — |
| BRC-A30 | F | 60 | — | — | — | — | — | — | — |
| BRC-A31 | F | 51 | — | — | — | — | — | — | — |
| BRC-A32 | F | 42 | pN0 | 7 | >66% | 7 | >66% | 2 | — |
| BRC-A33 | F | 43 | pN0(sn) | 3 | 10-33% | 4 | 10-33% | 0 | 2.3 |
| BRC-A34 | F | 60 | pN0(sn) | 0 | 0% | 0 | 0% | 1 | 2.3 |
| BRC-A35 | F | 61 | — | 6 | 33-66% | 0 | 0% | 2 | — |
| BRC-A36 | F | 61 | pN0(sn) | 0 | 0% | 2 | <10% | 2 | 1.8 |
| BRC-A37 | F | 49 | — | — | — | — | — | — | — |
| BRC-A38 | F | 44 | pN0 | 6 | 33-66% | 7 | >66% | 1 | 1.2 |
| BRC-A39 | F | 72 | pN0(sn) | 0 | 0% | 0 | 0% | 0 | 1.8 |
| BRC-A40 | F | 48 | pN0(sn) | 5 | 33-66% | 4 | 10-33% | 1 | 0.8 |
| BRC-A41 | F | 44 | pN0 | 5 | 33-66% | 7 | >66% | 1 | 2 |
| BRC-A42 | F | 41 | pN2a | 5 | 33-66% | 6 | 33-66% | 1 | 4 |
| BRC-A43 | F | 58 | pN0 | 6 | 33-66% | 0 | 0% | 2 | <0.1 |
| BRC-A44 | F | 42 | — | 5 | 33-66% | 6 | 33-66% | 2 | — |
| BRC-A45 | F | 44 | pN1a | 4 | 10-33% | 2 | <10% | 2 | 5.5 |
| BRC-A46 | F | 62 | pN0(sn) | 7 | >66% | 0 | 0% | 0 | 2 |
| BRC-A47 | F | 47 | pN0 | 6 | 33-66% | 6 | 33-66% | 2 | 2.4 |
| BRC-A48 | F | 52 | pN1a | 6 | 33-66% | 0 | 0% | 3 | 1.8 |
| BRC-A49 | F | 44 | pN0(sn) | 6 | 33-66% | 0 | 0% | 0 | 2 |
| BRC-A50 | F | 49 | pN0(sn) | 2 | <10% | 2 | <10% | 3 | 0.4 |
| BRC-A51 | F | 46 | pN0(sn) | 6 | 33-66% | 5 | 33-66% | 1 | 0.7 |
| BRC-A52 | F | 58 | pN0(sn) | 7 | >66% | 5 | 33-66% | 1 | 2.3 |
| BRC-A53 | F | 64 | pN1a | 6 | 33-66% | 7 | >66% | 1 | 2 |
| BRC-A54 | F | 47 | — | 6 | 33-66% | 6 | 33-66% | 2 | — |
| BRC-A55 | F | 74 | pN1a | 6 | 33-66% | 6 | 33-66% | 1 | 1.8 |
| BRC-A56 | F | 64 | pN0(sn) | 0 | 0% | 0 | 0% | 1 | 2.2 |
| BRC-A57 | F | 40 | ypN1a | 6 | 33-66% | 6 | 33-66% | 1 | 3.5 |
| BRC-A58 | F | 43 | pN0 | 6 | 33-66% | 6 | 33-66% | 2 | 2.5 |
| BRC-A59 | F | 43 | ypN0 | 0 | 0% | 0 | 0% | 2 | — |
| BRC-A60 | F | 42 | pN0 | 0 | 0% | 0 | 0% | 0 | 2.3 |
| BRC-A61 | F | 37 | pN0(i+) | 6 | 33-66% | 6 | 33-66% | 1 | 1 |
| BRC-A62 | F | 50 | pN1a | 6 | 33-66% | 6 | 33-66% | 1 | 1 |
| BRC-A63 | F | 57 | pN0(sn) | 6 | 33-66% | 96 | 33-66% | 1 | 1.4 |
| BRC-A64 | F | 38 | ypN0 | 0 | 0% | 0 | 0% | 1 | 2 |
| BRC-A65 | F | 67 | — | 6 | 33-66% | 2 | <10% | 1 | — |
| BRC-A66 | F | 42 | pN0(sn) | 6 | 33-66% | 6 | 33-66% | 2 | 0.5 |
| BRC-A67 | F | 46 | pN0(sn) | 6 | 33-66% | 6 | 33-66% | 1 | 1 |
| BRC-A68 | F | 48 | pN2a | 4 | 10-33% | 4 | 10-33% | 3 | 2.5 |
| BRC-A69 | F | 58 | pN0 | 2 | <10% | 0 | 0 | 1 | 0.5 |
| BRC-A70 | F | 53 | pN0(sn) | 0 | 0% | 0 | 0% | 3 | <0.1 |
| BRC-A71 | F | 56 | — | 0 | 0% | 0 | 0% | 0 | — |
| BRC-A72 | F | 45 | pN0(sn) | 6 | 33-66% | 6 | 33-66% | 2 | <0.1 |
| BRC-A73 | F | 59 | pN0(sn) | 5 | 33-66% | 0 | 0% | 2 | 1.4 |
| BRC-A74 | F | 40 | ypN1a | 2 | <10% | 0 | 0% | 0 | 0.3 |
| BRC-A75 | F | 34 | pN0(sn) | 2 | <10% | 0 | 0% | 2 | 2 |
| BRC-A76 | F | 69 | — | 6 | 33-66% | 6 | 33-66% | 1 | — |
| BRC-A77 | F | 52 | — | — | — | — | — | — | — |
| BRC-A78 | F | 67 | — | — | — | — | — | — | — |
| BRC-A79 | F | 61 | — | 6 | 33-66% | 2 | <10% | 0 | — |
| BRC-A80 | F | 38 | pN1a | 6 | 33-66% | 5 | 33-66% | 1 | — |
| BRC-A81 | F | 60 | pN0 | 6 | 33-66% | 3 | 10-33% | 1 | 1 |
| BRC-A82 | F | 55 | pN2a | 5 | 33-66% | 0 | 0% | 2 | 2.2 |
| BRC-A83 | F | 46 | ypN0 | 5 | 33-66% | 2 | <10% | 1 | 1.5 |
| BRC-A84 | F | 67 | pN0 | 6 | 33-66% | 6 | 33-66% | 1 | 2.8 |
| BRC-A85 | F | 46 | pN1a | 6 | 33-66% | 6 | 33-66% | 2 | 0.7 |
| BRC-A86 | F | 39 | pN1mi | 6 | 33-66% | 6 | 33-66% | 2 | 2.5 |
| BRC-A87 | F | 50 | pN0(sn) | 4 | 10-33% | 5 | 33-66% | 0 | 1 |
| BRC-A88 | F | 31 | pN1mi (sn) | 6 | 33-66% | 6 | 33-66% | 1 | 1 |
| BRC-A89 | F | 46 | pN0 | 6 | 33-66% | 7 | >66% | 1 | 1.2 |

TABLE 105-continued

| BRC | Sex | Age year | Node | ER | ER % | PR | PR % | HER2 | Tumor Size cm |
|---|---|---|---|---|---|---|---|---|---|
| BRC-A90 | F | 44 | pN0(sn) | 6 | 33-66% | 7 | >66% | 1 | 2.5 |
| BRC-A91 | F | 40 | pN0 | 0 | 0% | 0 | 0% | 0 | — |
| BRC-A92 | F | 40 | — | 6 | 33-66% | 6 | 33-66% | 1 | — |
| BRC-A93 | F | 56 | — | 7 | >66% | 0 | 0 | 0 | 0.6 |
| BRC-A94 | F | 48 | pN1a | 0 | 0% | 0 | 0% | 0 | 3 |
| BRC-A95 | F | 39 | pN0(sn) | 6 | 33-66% | 6 | 33-66% | 1 | 3.5 |
| BRC-A96 | F | 40 | ypN1a | 6 | 33-66% | 4 | 10-33% | 2 | 3 |
| BRC-A97 | F | 48 | pN0(sn) | 6 | 33-66% | 6 | 33-66% | 0 | 2.5 |
| BRC-A98 | F | 59 | — | 7 | >66% | 2 | <10% | 1 | — |
| BRC-A99 | F | 46 | — | 0 | 0% | 0 | 0% | 2 | — |
| BRC-A100 | F | 37 | pN3a | 6 | 33-66% | 6 | 33-66% | 2 | 0.6 |
| BRC-A101 | F | 38 | pN0(sn) | 6 | 33-66% | 6 | 33-66% | 2 | 0.3 |
| BRC-A102 | F | 66 | pN1a | 6 | 33-66% | 6 | 33-66% | 0 | 1.5 |
| BRC-A103 | F | 58 | pN0(sn) | 0 | 0% | 0 | 0% | 2 | 1.7 |
| BRC-A104 | F | 42 | pN3a | 5 | 33-66% | 6 | 33-66% | 0 | 1.8 |
| BRC-A105 | F | 52 | pN0 | 6 | 33-66% | 6 | 33-66% | 0 | 0.7 |
| BRC-A106 | F | 46 | pN0(sn) | 0 | 0% | 2 | <10% | 1 | 1.5 |
| BRC-A107 | F | 42 | pN0(sn) | 4 | 10-33% | 6 | 33-66% | 1 | 0.6 |
| BRC-A108 | F | 48 | — | — | — | — | — | — | — |
| BRC-A109 | F | 47 | pN0 | 6 | 33-66% | 2 | <10% | 2 | 3 |
| BRC-A110 | F | 59 | pN1a | 6 | 33-66% | 4 | 10-33% | 1 | 1.8 |
| BRC-A111 | F | 56 | — | 0 | 0% | 0 | 0% | 3 | — |

TABLE 106

| NHL | Sex | Age year | Stage | Involved Site | Subtype | IPI |
|---|---|---|---|---|---|---|
| NHL-A1 | M | 65 | 3 | multiple | DLBL | 3 |
| NHL-A2 | M | 63 | 2 | stomach | DLBL | 1 |
| NHL-A3 | M | 65 | 3 | multiple | DLBL | 3 |
| NHL-A4 | M | 65 | 3 | multiple | Follicular L | 2 |
| NHL-A5 | M | 64 | 2 | stomach | DLBL | 2 |
| NHL-A6 | M | 52 | 3 | multiple | DLBL | 2 |
| NHL-A7 | M | 52 | 2 | spleen, pancreatic LN | DLBL | 1 |
| NHL-A8 | M | 52 | 3 | multiple | DLBL | 2 |
| NHL-A9 | M | 42 | 2 | multiple | DLBL | 2 |
| NHL-A10 | M | 44 | 1 | stomach | DLBL | 1 |
| NHL-A11 | M | 44 | 2 | cervical LN, tonsil | DLBL | 0 |
| NHL-A12 | M | 40 | 4 | multiple | DLBL | 3 |
| NHL-A13 | M | 39 | 1 | nasal cavity | NK/T cell L | 1 |
| NHL-A14 | M | 41 | 1 | inguinal LN | ALCL | 0 |
| NHL-A15 | F | 57 | 4 | multiple | DLBL | 3 |
| NHL-A16 | F | 38 | 2 | tonsil, neck LN | DLBL | 0 |
| NHL-A17 | F | 56 | 1 | breast | DLBL | 0 |
| NHL-A18 | M | 71 | 4 | multiple | Mantle cell L | 3 |
| NHL-A19 | M | 70 | 2 | neck area LN | DLBL | 1 |
| NHL-A20 | M | 80 | 2 | stomach | PTCL | 1 |
| NHL-A21 | F | 39 | 2 | tonsil, neck LN | DLBL | 0 |
| NHL-A22 | F | 38 | 4 | multiple | DLBL | 3 |
| NHL-A23 | F | 38 | 1 | stomach | DLBL | 0 |
| NHL-A24 | M | 67 | 4 | multiple | DLBL | 2 |
| NHL-A25 | M | 67 | 3 | multiple | Burkitt's L | 3 |
| NHL-A26 | F | 73 | 1 | nasal cavity | DLBL | 2 |
| NHL-A27 | F | 73 | 3 | multiple | DLBL | 2 |
| NHL-A28 | F | 41 | 1 | 0 | DLBL | 0 |
| NHL-A29 | M | 49 | 3 | multiple | DLBL | 3 |
| NHL-A30 | M | 31 | 2 | neck | DLBL | 0 |
| NHL-A31 | M | 46 | 2 | nasopharynx, tonsil | DLBL | 0 |
| NHL-A32 | M | 71 | — | stomach | r/o Lymphoma | — |
| NHL-A33 | M | 73 | 1 | nasal cavity | DLBL | 1 |
| NHL-A34 | M | 73 | 4 | tibia, leg(skin) | DLBL | 3 |
| NHL-A35 | M | 72 | 2 | stomach | DLBL | 1 |
| NHL-A36 | M | 79 | 1 | nasal cavity | malignant L | 2 |

TABLE 107

| GC | Sex | Age year | CEA ng/mL | Stage |
|---|---|---|---|---|
| GC-A1 | F | 52 | 3.36 | IV |
| GC-A2 | M | 65 | 0.99 | IV |
| GC-A3 | M | 41 | —[a] | IV |
| GC-A4 | M | 78 | 4.93 | IV |
| GC-A5 | M | 79 | 1.11 | IV |
| GC-A6 | M | 76 | 2.37 | IV |
| GC-A7 | M | 54 | 117.13 | IV |
| GC-A8 | M | 58 | 2.24 | IV |
| GC-A9 | M | 67 | >1500 | IV |
| GC-A10 | F | 71 | 1.92 | IV |
| GC-A11 | F | 42 | <0.4 | IV |
| GC-A12 | M | 49 | 104.73 | IV |
| GC-A13 | M | 65 | 1.69 | IV |
| GC-A14 | F | 57 | 6.98 | IV |
| GC-A15 | M | 55 | 2.03 | IV |
| GC-A16 | F | 51 | 0.51 | IV |
| GC-A17 | M | 63 | 27.18 | IV |
| GC-A18 | M | 51 | 1.93 | IV |
| GC-A19 | M | 64 | 2.41 | IV |
| GC-A20 | M | 62 | 2.72 | IV |
| GC-A21 | M | 71 | 8.46 | IV |
| GC-A22 | M | 46 | 2.67 | IV |
| GC-A23 | M | 68 | 24.93 | IV |
| GC-A24 | M | 68 | 3.23 | IV |
| GC-A25 | M | 57 | 41.32 | IV |
| GC-A26 | M | 71 | 2.8 | IV |
| GC-A27 | F | 43 | 1.62 | IV |
| GC-A28 | M | 58 | 6.6 | IV |
| GC-A29 | M | 73 | — | IV |

With respect to set $A_1$ consisting of 462 cases, subset $A_0$ was constructed into the first training set. The weightings (factor loadings) per mass ions were computed by the biostatistical analysis, and the preliminary discriminant was acquired. Further, the training set was enlarged to include the second training set $A_2$ consisting of the 144 CRC patients of Table 108, 50 normal controls of Table 109, 25 BRC patients of Table 110, 15 NHL patients of Table 111 and 57 GC patients of Table 112. That is, to analyze CRC-diagnosing low-mass ions according to the method explained below with respect to the preliminary candidate groups of the low-mass ions constructing the preliminary discriminant, the set A, i.e., union of set $A_1$ and set $A_2$, which are independent from each other, was used as the training set.

TABLE 108

| CRC | Sex | Age year | Stage | Location | Cell Type | CEA ng/mL |
|---|---|---|---|---|---|---|
| CRC-A134 | M | 49 | I | Rectum | AC | 6.6 |
| CRC-A135 | F | 60 | III | A-colon | AC | 30.4 |
| CRC-A136 | M | 69 | IV | A-colon | AC | 33.5 |
| CRC-A137 | M | 43 | III | A-colon | MAC | 77.6 |
| CRC-A138 | F | 69 | III | Rectum | AC | 1.0 |
| CRC-A139 | M | 72 | III | A-colon | AC | 2.4 |
| CRC-A140 | M | 54 | II | Rectum | AC | 4.6 |
| CRC-A141 | M | 58 | II | S-colon | AC | 2.9 |
| CRC-A142 | F | 52 | III | S-colon | AC | 9.2 |
| CRC-A143 | M | 52 | III | S-colon | AC | 3.2 |
| CRC-A144 | M | 78 | IV | Rectum | AC | 4.1 |
| CRC-A145 | F | 55 | III | Rectum | AC | 0.9 |
| CRC-A146 | M | 65 | II | S-colon | AC | 1.7 |
| CRC-A147 | F | 46 | I | S-colon | AC | 1.4 |
| CRC-A148 | M | 77 | III | S-colon | AC | 2.5 |
| CRC-A149 | F | 52 | II | S-colon | AC | <0.5 |
| CRC-A150 | F | 47 | III | S-colon | AC | 1.5 |
| CRC-A151 | M | 48 | III | S-colon | AC | 1.7 |
| CRC-A152 | F | 76 | II | S-colon | AC | 2.2 |
| CRC-A153 | M | 51 | II | S-colon | ASC | 8.6 |
| CRC-A154 | M | 61 | I | Rectum | AC | 1.4 |
| CRC-A155 | M | 56 | II | Rectum | AC | 3 |
| CRC-A156 | F | 70 | III | S-colon | MAC | 36.0 |
| CRC-A157 | M | 64 | III | A-colon | AC | 2.2 |
| CRC-A158 | F | 54 | III | Rectum | AC | 5.5 |
| CRC-A159 | F | 77 | II | Rectum | AC | 6.2 |
| CRC-A160 | M | 53 | III | Rectum | AC | 1.4 |
| CRC-A161 | M | 43 | I | Rectum | AC | 0.5 |
| CRC-A162 | M | 81 | III | A-colon | MAC | 10.9 |
| CRC-A163 | F | 52 | III | A-colon | AC | 1.2 |
| CRC-A164 | F | 71 | III | A-colon | AC | 2.8 |
| CRC-A165 | M | 84 | III | Rectum | AC | 15.0 |
| CRC-A166 | F | 33 | III | D-colon | AC | 4.7 |
| CRC-A167 | F | 68 | III | Rectum | AC | 3.3 |
| CRC-A168 | M | 69 | III | Rectum | AC | 3.5 |
| CRC-A169 | F | 61 | III | A-colon | AC | 2.8 |
| CRC-A170 | M | 44 | II | T-colon | AC | 1.8 |
| CRC-A171 | F | 82 | II | A-colon | AC | 2.8 |
| CRC-A172 | M | 38 | IV | Rectum | AC | 2.1 |
| CRC-A173 | M | 73 | III | Rectum | AC | 11.1 |
| CRC-A174 | M | 64 | III | D-colon | AC | 8.2 |
| CRC-A175 | M | 67 | II | A-colon | AC | 20.1 |
| CRC-A176 | M | 72 | II | A-colon | AC | 3.4 |
| CRC-A177 | M | 59 | II | S-colon | AC | 2.1 |
| CRC-A178 | M | 53 | I | Rectum | AC | 3.5 |
| CRC-A179 | M | 70 | II | Rectum | AC | 1.3 |
| CRC-A180 | M | 55 | II | Rectum | AC | 22.0 |
| CRC-A181 | M | 62 | II | Rectum | AC | 6.1 |
| CRC-A182 | M | 64 | III | Rectum | AC | 4.8 |
| CRC-A183 | M | 62 | IV | Rectum | AC | 25.3 |
| CRC-A184 | M | 51 | III | Rectum | AC | 149.3 |
| CRC-A185 | F | 45 | II | Rectum | AC | 2.7 |
| CRC-A186 | F | 49 | II | Rectum | AC | 2.1 |
| CRC-A187 | F | 45 | 0 | Rectum | AC | 0.9 |
| CRC-A188 | M | 62 | III | Rectum | AC | 2.4 |
| CRC-A189 | M | 54 | 0 | Rectum | AC | 6.9 |
| CRC-A190 | M | 45 | 0 | Rectum | AC | 7.4 |
| CRC-A191 | F | 54 | 0 | Rectum | AC | 3.6 |
| CRC-A192 | M | 69 | II | Rectum | AC | 24.0 |
| CRC-A193 | M | 51 | I | Rectum | AC | 2.7 |
| CRC-A194 | M | 45 | I | Rectum | AC | 3.2 |
| CRC-A195 | M | 67 | I | Rectum | AC | 2.9 |
| CRC-A196 | M | 60 | I | Rectum | AC | 1.5 |
| CRC-A197 | M | 49 | 0 | Rectum | AC | 0.8 |
| CRC-A198 | M | 71 | I | Rectum | AC | 9.8 |
| CRC-A199 | M | 62 | III | Rectum | AC | 2.5 |
| CRC-A200 | M | 54 | II | Rectum | AC | 4.6 |
| CRC-A201 | M | 56 | II | Rectum | AC | 3.0 |
| CRC-A202 | F | 71 | III | Rectum | AC | 6.7 |
| CRC-A203 | M | 73 | 0 | Rectum | AC | 61.5 |
| CRC-A204 | F | 50 | III | Rectum | AC | 2.2 |
| CRC-A205 | F | 49 | 0 | Rectum | AC | 1.6 |
| CRC-A206 | F | 42 | III | Rectum | AC | 9.9 |
| CRC-A207 | M | 61 | III | Rectum | AC | 68.1 |
| CRC-A208 | F | 72 | II | Rectum | AC | 8 |
| CRC-A209 | F | 69 | III | Rectum | AC | 11.3 |
| CRC-A210 | M | 58 | II | Rectum | AC | 5.3 |
| CRC-A211 | M | 56 | I | Rectum | AC | 24.8 |
| CRC-A212 | M | 72 | III | Rectum | AC | 1.4 |
| CRC-A213 | M | 62 | III | Rectum | AC | 1.6 |
| CRC-A214 | M | 55 | II | Rectum | AC | 2.4 |
| CRC-A215 | F | 71 | III | Rectum | AC | 1.3 |
| CRC-A216 | M | 59 | III | Rectum | AC | 2.8 |
| CRC-A217 | M | 52 | II | Rectum | AC | 4.0 |
| CRC-A218 | M | 47 | III | Rectum | AC | 2.3 |
| CRC-A219 | M | 58 | II | Rectum | AC | 1.1 |
| CRC-A220 | M | 60 | 0 | Rectum | AC | 2.0 |
| CRC-A221 | M | 64 | I | Rectum | AC | 2.0 |
| CRC-A222 | M | 41 | III | Rectum | AC | 1.6 |
| CRC-A223 | M | 48 | I | Rectum | AC | 0.8 |
| CRC-A224 | M | 58 | II | Rectum | AC | 1.1 |
| CRC-A225 | M | 61 | I | Rectum | AC | 2.6 |
| CRC-A226 | M | 63 | I | Rectum | AC | 1.3 |
| CRC-A227 | F | 52 | II | Rectum | AC | 1.6 |
| CRC-A228 | M | 53 | II | Rectum | AC | 2.0 |
| CRC-A229 | M | 64 | I | Rectum | AC | 2.0 |
| CRC-A230 | M | 73 | II | Rectum | AC | 5.6 |
| CRC-A231 | M | 41 | III | Rectum | AC | 1.6 |
| CRC-A232 | M | 57 | III | Rectum | AC | 2.0 |
| CRC-A233 | M | 48 | I | Rectum | AC | 0.8 |
| CRC-A234 | M | 72 | III | Rectum | AC | 6.1 |
| CRC-A235 | F | 67 | 0 | Rectum | AC | 4.4 |
| CRC-A236 | F | 66 | II | Rectum | AC | 4.8 |
| CRC-A237 | M | 47 | III | S-colon | AC | 3.7 |
| CRC-A238 | M | 40 | III | A-colon | AC | 1.2 |
| CRC-A239 | M | 55 | II | D-colon | AC | 6.0 |
| CRC-A240 | F | 73 | I | D-colon, T-colon | AC | 2.0 |
| CRC-A241 | F | 69 | I | A-colon | AC | 5.0 |
| CRC-A242 | F | 69 | I | A-colon | AC | 5.7 |
| CRC-A243 | F | 74 | II | D-colon | AC | 12.5 |
| CRC-A244 | M | 61 | II | S-colon | MAC | 1.9 |
| CRC-A245 | M | 37 | III | Rectum | AC | 6.0 |
| CRC-A246 | M | 60 | III | S-colon | AC | 5.4 |
| CRC-A247 | M | 70 | II | S-colon | AC | 2.6 |
| CRC-A248 | M | 68 | III | Rectum | AC | 13.2 |
| CRC-A249 | M | 73 | I | Rectum | AC | 1.7 |
| CRC-A250 | M | 82 | III | T-colon | AC | 2.1 |
| CRC-A251 | F | 75 | II | Rectum | AC | 0.9 |
| CRC-A252 | F | 57 | I | A-colon | AC | 1.5 |
| CRC-A253 | F | 62 | III | S-colon | AC | 4.4 |
| CRC-A254 | M | 73 | II | Rectum | AC | 15.5 |
| CRC-A255 | M | 59 | I | S-colon | AC | 1.1 |
| CRC-A256 | F | 74 | III | Rectum | AC | 31.0 |
| CRC-A257 | F | 70 | I | A-colon | AC | 2.5 |
| CRC-A258 | M | 74 | II | S-colon | AC | 15.4 |
| CRC-A259 | M | 69 | II | Rectum | AC | 2.1 |
| CRC-A260 | M | 61 | II | A-colon, T-colon | AC | 2.3 |
| CRC-A261 | M | 73 | I | Rectum | AC | 1.9 |
| CRC-A262 | M | 64 | I | Rectum | AC | 2.8 |
| CRC-A263 | M | 69 | II | D-colon | AC | 5.0 |
| CRC-A264 | M | 58 | III | Rectum | AC | 1.6 |
| CRC-A265 | M | 73 | II | T-colon | AC | 2.6 |
| CRC-A266 | M | 70 | II | A-colon | AC | 20.8 |
| CRC-A267 | M | 56 | IV | Rectum | AC | 29.9 |
| CRC-A268 | F | 70 | II | A-colon | AC | 5.9 |
| CRC-A269 | M | 71 | III | S-colon | AC | 110.1 |
| CRC-A270 | M | 47 | III | Rectum | AC | 13.7 |
| CRC-A271 | M | 61 | III | Rectum | AC | 2.8 |
| CRC-A272 | F | 77 | II | S-colon | AC | 1.5 |
| CRC-A273 | F | 62 | III | Rectum | AC | 13.7 |
| CRC-A274 | M | 61 | II | S-colon | AC | 2.3 |

TABLE 108-continued

| CRC | Sex | Age year | Stage | Location | Cell Type | CEA ng/mL |
|---|---|---|---|---|---|---|
| CRC-A275 | M | 66 | II | S-colon | AC | 1.7 |
| CRC-A276 | M | 64 | III | A-colon | AC | 1.0 |
| CRC-A277 | M | 69 | II | S-colon | AC | 23.0 |

ASC: Adenosquamous carcinoma

TABLE 109

| Control | Sex | Age year | CEA ng/mL |
|---|---|---|---|
| CONT-A154 | F | 51 | 1.7 |
| CONT-A155 | F | 62 | 1.3 |
| CONT-A156 | M | 54 | 4.2 |
| CONT-A157 | F | 63 | 1.6 |
| CONT-A158 | F | 60 | 1.9 |
| CONT-A159 | F | 68 | 1.4 |
| CONT-A160 | F | 62 | 1.9 |
| CONT-A161 | F | 68 | 5.6 |
| CONT-A162 | M | 63 | 4.5 |
| CONT-A163 | M | 50 | 2.1 |
| CONT-A164 | F | 53 | 2.3 |
| CONT-A165 | M | 60 | 3.3 |
| CONT-A166 | M | 64 | 1.8 |
| CONT-A167 | M | 63 | 3.4 |
| CONT-A168 | F | 63 | 1.1 |
| CONT-A169 | M | 53 | 2.0 |
| CONT-A170 | F | 51 | 2.0 |
| CONT-A171 | M | 57 | 3.3 |
| CONT-A172 | M | 61 | 2.8 |
| CONT-A173 | F | 68 | 1.4 |

TABLE 109-continued

| Control | Sex | Age year | CEA ng/mL |
|---|---|---|---|
| CONT-A174 | F | 52 | 1.5 |
| CONT-A175 | M | 60 | 4.6 |
| CONT-A176 | M | 55 | 2.2 |
| CONT-A177 | M | 55 | 1.8 |
| CONT-A178 | M | 56 | 2.2 |
| CONT-A179 | F | 63 | 1.8 |
| CONT-A180 | F | 65 | 1.1 |
| CONT-A181 | M | 64 | 1.4 |
| CONT-A182 | F | 55 | 4.8 |
| CONT-A183 | M | 63 | 2.6 |
| CONT-A184 | F | 52 | 4.1 |
| CONT-A185 | M | 51 | 4.0 |
| CONT-A186 | M | 59 | 2.0 |
| CONT-A187 | M | 68 | 4.6 |
| CONT-A188 | M | 50 | 5.0 |
| CONT-A189 | F | 64 | <0.5 |
| CONT-A190 | F | 63 | 2.2 |
| CONT-A191 | M | 64 | 1.7 |
| CONT-A192 | M | 51 | 2.3 |
| CONT-A193 | F | 62 | 1.1 |
| CONT-A194 | M | 54 | 2.5 |
| CONT-A195 | F | 53 | 0.7 |
| CONT-A196 | F | 65 | 3.8 |
| CONT-A197 | F | 64 | 1.5 |
| CONT-A198 | F | 53 | 1.0 |
| CONT-A199 | M | 50 | 1.1 |
| CONT-A200 | F | 66 | 1.7 |
| CONT-A201 | F | 50 | 1.0 |
| CONT-A202 | F | 50 | 1.9 |
| CONT-A203 | M | 61 | 1.5 |

TABLE 110

| BRC | Sex | Age year | Node | ER | ER % | PR | PR % | HER2 | Tumor Size cm |
|---|---|---|---|---|---|---|---|---|---|
| BRC-A112 | F | 61 | pN0(i + 0) | 7 | >95% | 0 | 0% | 0 | 4 |
| BRC-A113 | F | 53 | pN0 | 7 | 80% | 5 | 25% | 0 | 0.6 |
| BRC-A114 | F | 49 | pN0 | 3 | 20% | 7 | 60% | 0 | 0.3 |
| BRC-A115 | F | 57 | pN0 | 0 | 0% | 0 | 0% | 0 | 0.8 |
| BRC-A116 | F | 68 | pN0 | 0 | 0% | 3 | 1% | 3 | 1.2 |
| BRC-A117 | F | 58 | pN0 | 8 | 95% | 4 | 40% | 0 | 0.8 |
| BRC-A118 | F | 40 | — | 8 | 95% | 8 | 95% | 0 | — |
| BRC-A119 | F | 29 | pN0 | 8 | 95% | 8 | 95% | 1 | 1.2 |
| BRC-A120 | F | 40 | — | — | — | — | — | — | — |
| BRC-A121 | F | 61 | pN0(i + 0) | 7 | >95% | 0 | 0% | 0 | 4 |
| BRC-A122 | F | 40 | — | 8 | 95% | 8 | 95% | 0 | — |
| BRC-A123 | F | 43 | pN0 | 0 | 0% | 0 | 0% | 3 | 0.7 |
| BRC-A124 | F | 59 | pN0 | 8 | 95% | 8 | 95% | 0 | 1.2 |
| BRC-A125 | F | 45 | PN2 | 7 | 95% | 8 | 95% | 1 | 2.1 |
| BRC-A126 | F | 55 | pN0 | 0 | 0% | 0 | 0% | 3 | 1.8 |
| BRC-A127 | F | 52 | pN0 | 7 | 80-90% | 8 | 80-90% | 0 | 0.3 |
| BRC-A128 | F | 59 | pN0 | 8 | 95% | 5 | 2~3% | 1 | 1.3 |
| BRC-A129 | F | 39 | — | 7 | >95% | 7 | 70-80% | 0 | — |
| BRC-A130 | F | 39 | pN0 | 0 | 0% | 0 | 0% | 3 | 1.1 |
| BRC-A131 | F | 40 | pN0 | 5 | 50-60% | 5 | 20-30% | 0 | 0.8 |
| BRC-A132 | F | 46 | pN0 | 7 | 95% | 8 | 95% | 0 | 4.9 |
| BRC-A133 | F | 51 | pN0 | 0 | <1% | 0 | 0% | 0 | 0.9 |
| BRC-A134 | F | 61 | pN0 | 7 | 90% | 8 | 90% | 0 | 1.3 |
| BRC-A135 | F | 48 | pN0 | 0 | 0% | 0 | 0% | 0 | 0.6 |
| BRC-A136 | F | 47 | pN0 | 8 | >95% | 8 | 95% | 0 | 0.7 |

TABLE 111

| NHL | Sex | Age year | Stage | Involved Site | Subtype | IPI |
|---|---|---|---|---|---|---|
| NHL-A37 | F | 69 | 3 | multiple | ATCL | 3 |
| NHL-A38 | F | 72 | 1 | stomach | DLBL | 2 |
| NHL-A39 | M | 24 | 4 | multiple | DLBL | 3 |
| NHL-A40 | F | 41 | 2 | stomach | DLBL | 1 |
| NHL-A41 | F | 48 | 4 | multiple | DLBL | 3 |
| NHL-A42 | F | 66 | 2 | gum, submandibular | DLBL | 1 |
| NHL-A43 | F | 61 | 2 | stomach | DLBL | 3 |
| NHL-A44 | M | 38 | 4 | multiple | Hodgkin L | — |
| NHL-A45 | M | 70 | 4 | multiple | DLBL | 3 |
| NHL-A46 | M | 37 | 1 | cervical LN | DLBL | 0 |
| NHL-A47 | M | 64 | 4 | multiple | DLBL | 4 |
| NHL-A48 | F | 76 | 2 | stomach | DLBL | 1 |
| NHL-A49 | M | 34 | 2 | neck, SCN | DLBL | 1 |
| NHL-A50 | M | 25 | 4 | multiple | PTCL | 2 |
| NHL-A51 | M | 70 | 2 | stomach | DLBL | 1 |

TABLE 112

| GC | Sex | Age year | CEA ng/mL | Stage |
|---|---|---|---|---|
| GC-A30 | M | 70 | 1.26 | III |
| GC-A31 | M | 62 | 5.41 | I |
| GC-A32 | M | 58 | — | I |
| GC-A33 | M | 62 | 1.34 | I |
| GC-A34 | M | 32 | — | I |
| GC-A35 | M | 71 | 3.54 | I |
| GC-A36 | M | 56 | 2.83 | I |
| GC-A37 | M | 69 | 21.71 | II |
| GC-A38 | F | 62 | — | I |
| GC-A39 | M | 52 | 1.86 | I |
| GC-A40 | F | 64 | 4.16 | I |
| GC-A41 | M | 59 | — | II |
| GC-A42 | M | 61 | 10.41 | IV |
| GC-A43 | F | 68 | 5.56 | III |
| GC-A44 | M | 48 | 1.44 | III |
| GC-A45 | F | 80 | — | III |
| GC-A46 | M | 66 | — | IV |
| GC-A47 | F | 57 | 2.46 | IV |
| GC-A48 | M | 46 | 1.68 | III |
| GC-A49 | M | 79 | — | I |
| GC-A50 | M | 81 | — | I |
| GC-A51 | M | 52 | — | I |
| GC-A52 | M | 53 | — | I |
| GC-A53 | M | 67 | — | I |
| GC-A54 | M | 61 | — | I |
| GC-A55 | F | 77 | — | I |
| GC-A56 | F | 74 | — | I |
| GC-A57 | F | 81 | — | I |
| GC-A58 | F | 55 | — | I |
| GC-A59 | M | 62 | — | II |
| GC-A60 | M | 67 | — | II |
| GC-A61 | F | 64 | — | II |
| GC-A62 | F | 40 | — | II |
| GC-A63 | M | 64 | — | II |
| GC-A64 | M | 68 | — | II |
| GC-A65 | M | 54 | — | II |
| GC-A66 | F | 52 | — | II |
| GC-A67 | M | 59 | — | II |
| GC-A68 | F | 81 | — | II |
| GC-A69 | M | 46 | — | III |
| GC-A70 | M | 62 | — | III |
| GC-A71 | M | 51 | — | III |
| GC-A72 | M | 42 | — | III |
| GC-A73 | M | 81 | — | III |
| GC-A74 | F | 81 | — | III |
| GC-A75 | M | 70 | — | III |
| GC-A76 | M | 51 | — | III |
| GC-A77 | M | 68 | — | IV |
| GC-A78 | M | 68 | — | IV |
| GC-A79 | F | 33 | — | IV |
| GC-A80 | M | 31 | — | IV |
| GC-A81 | M | 52 | — | IV |
| GC-A82 | M | 59 | — | IV |
| GC-A83 | M | 56 | — | IV |
| GC-A84 | M | 82 | — | IV |
| GC-A85 | F | 52 | — | IV |
| GC-A86 | M | 82 | — | IV |

Further, validation set was constructed with set A and set B consisting of 143 CRC patients of Table 113, 50 normal controls of Table 114, 25 BRC patients of Table 115, 15 NHL patients of Table 116, 55 GC patents of Table 117, 25 ovarian cancer (OVC) patients of Table 118, 19 Tis or Advanced Adenoma (TA) patients of Table 119. The OVC patients and TA patients were not reflected at all when obtaining weighting per mass ions or investigating CRC-diagnosing low-mass ions, and included to see how these particular patient groups are discriminated with the discriminant constructed according to the present invention.

TABLE 113

| CRC | Sex | Age year | Stage | Location | Cell Type | CEA ng/mL |
|---|---|---|---|---|---|---|
| CRC-B1 | F | 51 | II | Rectum | AC | 6.7 |
| CRC-B2 | M | 71 | I | Rectum | AC | 9.8 |
| CRC-B3 | F | 47 | I | Rectum | AC | 3.9 |
| CRC-B4 | F | 50 | IV | Rectum | AC | 62.0 |
| CRC-B5 | M | 79 | II | S-colon | AC | 6.2 |
| CRC-B6 | F | 54 | I | Rectum | AC | 1.6 |
| CRC-B7 | F | 52 | III | S-colon | AC | 22.1 |
| CRC-B8 | M | 61 | III | Rectum | AC | 128.1 |
| CRC-B9 | F | 47 | III | S-colon | AC | 1.2 |
| CRC-B10 | M | 73 | I | S-colon | AC | 7.1 |
| CRC-B11 | F | 74 | I | S-colon | AC | 2.3 |
| CRC-B12 | M | 71 | III | A-colon | AC | 8.2 |
| CRC-B13 | M | 57 | IV | Rectum | AC | 6.4 |
| CRC-B14 | M | 57 | IV | S-colon | AC | 41.7 |
| CRC-B15 | M | 52 | III | S-colon | AC | 4.1 |
| CRC-B16 | F | 64 | III | S-colon | AC | 6.8 |
| CRC-B17 | M | 48 | IV | A-colon | AC | 59.4 |
| CRC-B18 | F | 51 | III | S-colon | AC | 1.2 |
| CRC-B19 | M | 67 | IV | Rectum | AC | 16.2 |
| CRC-B20 | M | 71 | I | Rectum | AC | 83.7 |
| CRC-B21 | M | 59 | I | S-colon | AC | 3.0 |
| CRC-B22 | F | 66 | IV | S-colon | AC | 18.5 |
| CRC-B23 | F | 78 | IV | A-colon | AC | 12.6 |
| CRC-B24 | M | 55 | III | A-colon | AC | 1.2 |
| CRC-B25 | M | 62 | III | Rectum | AC | 2.5 |
| CRC-B26 | M | 38 | III | Rectum | AC | 6.1 |
| CRC-B27 | F | 65 | III | D-colon | AC | 3.5 |
| CRC-B28 | M | 49 | III | S-colon, T-colon | AC | 3.8 |
| CRC-B29 | F | 59 | II | A-colon | AC | 1 |
| CRC-B30 | M | 62 | II | S-colon | AC | — |
| CRC-B31 | F | 54 | IV | S-colon | AC | 27.9 |
| CRC-B32 | M | 66 | III | S-colon | AC | 10.7 |
| CRC-B33 | M | 84 | II | S-colon | AC | 11.3 |
| CRC-B34 | F | 54 | III | S-colon | AC | 8.8 |
| CRC-B35 | M | 68 | II | Rectum | AC | 5.8 |
| CRC-B36 | M | 54 | II | A-colon | AC | 1.1 |
| CRC-B37 | M | 62 | III | S-colon | AC | 10.8 |
| CRC-B38 | F | 60 | III | S-colon, A-colon | AC | 28.5 |
| CRC-B39 | F | 51 | II | D-colon | AC | 5.9 |
| CRC-B40 | M | 73 | III | Rectum | AC | 3.7 |
| CRC-B41 | F | 54 | III | D-colon | AC | 1122.2 |
| CRC-B42 | M | 64 | I | Rectum | AC | 2.5 |
| CRC-B43 | F | 69 | II | S-colon, A-colon | AC | 5.1 |
| CRC-B44 | M | 39 | II | S-colon | AC | 2.9 |
| CRC-B45 | M | 74 | II | Rectum | AC | 7.9 |
| CRC-B46 | F | 59 | III | Rectum | AC | 1.4 |

TABLE 113-continued

| CRC | Sex | Age year | Stage | Location | Cell Type | CEA ng/mL |
|---|---|---|---|---|---|---|
| CRC-B47 | M | 56 | I | Rectum | AC | 2.6 |
| CRC-B48 | M | 69 | II | Rectum | AC | 14.0 |
| CRC-B49 | M | 58 | II | Rectum | AC | 10.2 |
| CRC-B50 | F | 75 | II | Rectum | AC | 2.4 |
| CRC-B51 | M | 47 | II | Rectum | AC | 3.2 |
| CRC-B52 | F | 68 | II | Rectum | AC | 0.7 |
| CRC-B53 | M | 52 | III | Rectum | AC | 2.9 |
| CRC-B54 | M | 68 | I | Rectum | AC | 7.0 |
| CRC-B55 | M | 51 | II | Rectum | AC | 1.4 |
| CRC-B56 | M | 66 | 0 | Rectum | AC | 1.2 |
| CRC-B57 | M | 74 | 0 | Rectum | AC | 4.5 |
| CRC-B58 | M | 43 | II | Rectum | AC | 12.3 |
| CRC-B59 | M | 68 | III | Rectum | AC | 2.5 |
| CRC-B60 | M | 68 | III | Rectum | AC | 19.4 |
| CRC-B61 | F | 56 | I | Rectum | AC | 2.3 |
| CRC-B62 | M | 63 | 0 | Rectum | AC | 1.3 |
| CRC-B63 | M | 65 | II | Rectum | AC | 2.1 |
| CRC-B64 | M | 60 | II | Rectum | AC | 4.6 |
| CRC-B65 | M | 51 | II | Rectum | AC | 1.3 |
| CRC-B66 | M | 44 | 0 | Rectum | AC | 2.2 |
| CRC-B67 | M | 61 | II | Rectum | AC | 2.0 |
| CRC-B68 | M | 57 | III | Rectum | AC | 2.2 |
| CRC-B69 | M | 41 | II | Rectum | AC | 3.1 |
| CRC-B70 | M | 50 | I | Rectum | AC | 4.9 |
| CRC-B71 | F | 56 | III | Rectum | AC | 1.0 |
| CRC-B72 | M | 54 | III | Rectum | AC | 1.7 |
| CRC-B73 | F | 69 | I | Rectum | AC | 1.5 |
| CRC-B74 | M | 54 | I | Rectum | AC | 2.6 |
| CRC-B75 | M | 61 | II | Rectum | AC | 3.7 |
| CRC-B76 | M | 72 | III | Rectum | AC | 3.0 |
| CRC-B77 | F | 71 | II | Rectum | AC | 1.8 |
| CRC-B78 | M | 54 | II | Rectum | AC | 3.0 |
| CRC-B79 | M | 77 | II | Rectum | AC | 1.6 |
| CRC-B80 | M | 67 | III | Rectum | AC | 1.1 |
| CRC-B81 | M | 59 | II | Rectum | AC | 7.2 |
| CRC-B82 | M | 56 | III | Rectum | AC | 9.0 |
| CRC-B83 | F | 51 | I | Rectum | AC | 1.5 |
| CRC-B84 | F | 67 | III | Rectum | AC | 3.4 |
| CRC-B85 | F | 76 | III | Rectum | AC | 1.0 |
| CRC-B86 | F | 38 | III | Rectum | AC | 0.7 |
| CRC-B87 | M | 53 | II | Rectum | AC | 3.3 |
| CRC-B88 | M | 58 | III | Rectum | AC | 1.6 |
| CRC-B89 | M | 69 | III | Rectum | AC | 6.4 |
| CRC-B90 | F | 60 | I | Rectum | AC | 1.2 |
| CRC-B91 | M | 52 | II | Rectum | AC | 4.0 |
| CRC-B92 | M | 59 | III | Rectum | AC | 2.8 |
| CRC-B93 | F | 56 | III | Rectum | AC | 2.3 |
| CRC-B94 | F | 68 | I | Rectum | AC | 2.0 |
| CRC-B95 | M | 65 | I | Rectum | AC | 1.6 |
| CRC-B96 | M | 33 | II | Rectum | AC | 1.9 |
| CRC-B97 | M | 61 | III | Rectum | AC | 3.2 |
| CRC-B98 | F | 41 | III | Rectum | AC | 1.5 |
| CRC-B99 | M | 61 | I | Rectum | AC | 1.6 |
| CRC-B100 | F | 34 | III | Rectum | AC | 5.2 |
| CRC-B101 | M | 47 | III | Rectum | AC | 2.3 |
| CRC-B102 | F | 61 | III | A-colon | AC | 30.4 |
| CRC-B103 | M | 71 | IV | A-colon | AC | 33.5 |
| CRC-B104 | M | 44 | III | A-colon | MAC | 77.6 |
| CRC-B105 | F | 71 | III | A-colon | AC | 1.0 |
| CRC-B106 | M | 59 | II | S-colon | AC | 2.9 |
| CRC-B107 | M | 79 | IV | Rectum | AC | 4.1 |
| CRC-B108 | M | 66 | II | S-colon | AC | 1.7 |
| CRC-B109 | M | 78 | III | S-colon | AC | 2.5 |
| CRC-B110 | F | 53 | II | S-colon | AC | 1.3 |
| CRC-B111 | M | 50 | III | S-colon | AC | 1.7 |
| CRC-B112 | F | 77 | II | S-colon | AC | 2.2 |
| CRC-B113 | M | 53 | II | S-colon | ASC | 8.6 |
| CRC-B114 | M | 63 | I | Rectum | AC | 1.4 |
| CRC-B115 | F | 71 | III | S-colon | MAC | 36.0 |
| CRC-B116 | F | 79 | II | Rectum | AC | 6.2 |
| CRC-B117 | M | 83 | III | A-colon | MAC | 10.9 |
| CRC-B118 | F | 53 | III | A-colon | AC | 1.2 |
| CRC-B119 | F | 72 | III | A-colon | AC | 2.8 |
| CRC-B120 | F | 34 | III | D-colon | AC | 4.7 |
| CRC-B121 | M | 70 | III | Rectum | AC | 3.5 |
| CRC-B122 | F | 62 | III | A-colon | AC | 2.8 |
| CRC-B123 | M | 45 | II | T-colon | AC | 1.8 |
| CRC-B124 | F | 84 | II | A-colon | AC | 2.8 |
| CRC-B125 | M | 74 | III | Rectum | AC | 11.1 |
| CRC-B126 | M | 65 | III | D-colon | AC | 8.2 |
| CRC-B127 | M | 69 | II | A-colon | AC | 20.1 |
| CRC-B128 | M | 73 | II | A-colon | AC | 2.3 |
| CRC-B129 | M | 61 | II | S-colon | AC | 2.1 |
| CRC-B130 | F | 71 | II | S-colon | AC | 15.3 |
| CRC-B131 | F | 56 | I | S-colon | AC | 0.7 |
| CRC-B132 | F | 70 | II | S-colon | AC | 1.4 |
| CRC-B133 | F | 62 | III | Rectum | AC | 235.4 |
| CRC-B134 | M | 61 | III | S-colon | AC | 11.2 |
| CRC-B135 | F | 52 | III | S-colon | AC | 6.4 |
| CRC-B136 | M | 62 | II | S-colon | AC | 4.9 |
| CRC-B137 | F | 61 | III | T-colon | AC | 13.9 |
| CRC-B138 | F | 88 | II | A-colon | AC | 3.0 |
| CRC-B139 | M | 73 | II | S-colon | AC | 16.5 |
| CRC-B140 | M | 69 | III | A-colon | AC | 1.7 |
| CRC-B141 | M | 71 | III | A-colon | MAC | 2.4 |
| CRC-B142 | F | 45 | 0 | Rectum | AC | — |
| CRC-B143 | M | 66 | 0 | Rectum | AC | 58.4 |

TABLE 114

| Control | Sex | Age year | CEA ng/mL |
|---|---|---|---|
| CONT-B1 | M | 64 | 2.4 |
| CONT-B2 | M | 53 | 3.3 |
| CONT-B3 | M | 63 | 0.9 |
| CONT-B4 | M | 57 | 1.5 |
| CONT-B5 | F | 66 | 1.6 |
| CONT-B6 | M | 60 | 1.5 |
| CONT-B7 | M | 57 | 2.2 |
| CONT-B8 | M | 53 | 1.9 |
| CONT-B9 | M | 60 | 0.8 |
| CONT-B10 | F | 50 | 2.6 |
| CONT-B11 | F | 53 | 2.6 |
| CONT-B12 | M | 64 | 1.5 |
| CONT-B13 | F | 60 | 3.7 |
| CONT-B14 | M | 58 | 1.2 |
| CONT-B15 | F | 66 | 1.1 |
| CONT-B16 | M | 57 | 2.9 |
| CONT-B17 | F | 68 | 5.5 |
| CONT-B18 | M | 56 | 1.7 |
| CONT-B19 | M | 51 | 3.4 |
| CONT-B20 | F | 56 | 1.3 |
| CONT-B21 | M | 57 | 1.5 |
| CONT-B22 | M | 61 | 4.2 |
| CONT-B23 | F | 51 | 1.9 |
| CONT-B24 | F | 51 | 1.6 |
| CONT-B25 | F | 52 | 1.4 |
| CONT-B26 | F | 56 | 1.7 |
| CONT-B27 | F | 52 | 1.7 |
| CONT-B28 | M | 63 | 1.0 |
| CONT-B29 | F | 60 | 1.8 |
| CONT-B30 | F | 58 | 0.7 |
| CONT-B31 | M | 65 | 4.1 |
| CONT-B32 | M | 52 | 2.2 |
| CONT-B33 | F | 58 | 3.1 |
| CONT-B34 | M | 65 | 2.8 |
| CONT-B35 | M | 66 | 0.8 |
| CONT-B36 | M | 69 | 2.1 |
| CONT-B37 | F | 54 | 1.6 |
| CONT-B38 | M | 50 | 1.9 |
| CONT-B39 | F | 60 | 1.1 |
| CONT-B40 | F | 55 | 8.8 |
| CONT-B41 | M | 62 | 0.9 |
| CONT-B42 | F | 51 | 2.0 |
| CONT-B43 | M | 65 | 2.3 |
| CONT-B44 | M | 52 | 2.4 |
| CONT-B45 | F | 64 | 1.7 |
| CONT-B46 | M | 57 | 0.8 |
| CONT-B47 | F | 54 | <0.5 |
| CONT-B48 | F | 59 | 0.8 |

TABLE 114-continued

| Control | Sex | Age year | CEA ng/mL |
|---|---|---|---|
| CONT-B49 | F | 65 | 1.6 |
| CONT-B50 | F | 68 | 1.6 |

TABLE 115

| BRC | Sex | Age year | Node | ER | ER % | PR | PR % | HER2 | Tumor Size cm |
|---|---|---|---|---|---|---|---|---|---|
| BRC-B1 | F | 45 | ypN0 | 0 | 0% | 0 | 0% | 0 | 0.9 |
| BRC-B2 | F | 59 | pN0 | 0 | 0% | 0 | 0% | 3 | 1.1 |
| BRC-B3 | F | 43 | pN1 | 0 | 0% | 0 | 0% | 0 | 1.5 |
| BRC-B4 | F | 46 | pN1 | 8 | 100% | 8 | 100% | 0 | 1.3 |
| BRC-B5 | F | 48 | pN0 | 6 | 50-60% | 5 | 10-20% | 3 | 1.3 |
| BRC-B6 | F | 39 | pN0 | 0 | 0% | 0 | 0% | 0 | 2.2 |
| BRC-B7 | F | 66 | pN0 | 8 | 95% | 8 | 95% | 0 | 1.7 |
| BRC-B8 | F | 39 | ypN0 | 0 | 0% | 0 | 0% | 0 | DCIS |
| BRC-B9 | F | 37 | pN0 | 7 | 70-80% | 8 | 80% | 3 | 1.5 |
| BRC-B10 | F | 64 | pN0 | 8 | 95% | 8 | 95% | 0 | 0.5 |
| BRC-B11 | F | 44 | ypN1 | 7 | 90% | 8 | 95% | 0 | 2 |
| BRC-B12 | F | 50 | pN2 | 8 | 95% | 8 | 100% | 0 | 1.1 |
| BRC-B13 | F | 47 | pN0 | 7 | 70% | 7 | 50-60% | 1 | 0.5 |
| BRC-B14 | F | 44 | pN1 | 8 | 90% | 8 | 95% | 1 | 0.6 |
| BRC-B15 | F | 50 | pN0 | 0 | 0% | 0 | 0% | 2 | 2.2 |
| BRC-B16 | F | 53 | pN0 | 7 | 95% | 8 | 95% | 0 | 1.1 |
| BRC-B17 | F | 65 | pN0 | 8 | 95% | 7 | 40% | 0 | 1.5 |
| BRC-B18 | F | 39 | pN1 | 7 | >95% | 3 | <10% | 0 | 2.2 |
| BRC-B19 | F | 54 | pN0(i+) | 7 | 95% | 5 | 10-30% | 1 | 1.7 |
| BRC-B20 | F | 48 | pN3a | 7 | 90% | 8 | 90% | 0 | 3.2 |
| BRC-B21 | F | 54 | pN0 | 0 | 0% | 0 | 0% | 0 | 3 |
| BRC-B22 | F | 43 | pN0 | 7 | 50-60% | 7 | 50-60% | 3 | 2.3 |
| BRC-B23 | F | 61 | pN0 | 8 | 95% | 8 | 95% | 0 | 1.6 |
| BRC-B24 | F | 54 | — | 0 | 0% | 0 | 0% | 3 | — |
| BRC-B25 | F | 46 | pN0 | 7 | 80% | 8 | 95% | 0 | 2.2 |

TABLE 116

| NHL | Sex | Age year | Stage | Involved Site | Subtype | IPI |
|---|---|---|---|---|---|---|
| NHL-B1 | M | 58 | 3 | multiple | DLBL | 2 |
| NHL-B2 | F | 24 | 4 | multiple | DLBL | 4 |
| NHL-B3 | M | 56 | 4 | multiple | DLBL | 3 |
| NHL-B4 | M | 54 | 2 | stomach | DLBL | 1 |
| NHL-B5 | F | 76 | 4 | multiple | DLBL | 3 |
| NHL-B6 | F | 69 | 4 | multiple | Mantle cell L | 4 |
| NHL-B7 | F | 49 | 1 | mandibular area | DLBL | 0 |
| NHL-B8 | F | 64 | 4 | multiple | DLBL | 5 |
| NHL-B9 | M | 44 | 4 | multiple | DLBL | 2 |
| NHL-B10 | F | 70 | 4 | multiple | DLBL | 3 |
| NHL-B11 | M | 25 | 4 | multiple | NK/T cell L | 3 |
| NHL-B12 | F | 48 | 1 | neck, submandibular | DLBL | 0 |
| NHL-B13 | F | 48 | 1 | breast | DLBL | 1 |
| NHL-B14 | M | 48 | 4 | multiple | DLBL | 3 |
| NHL-B15 | M | 67 | 4 | multiple | MZBCL | 2 |

TABLE 117

| GC | Sex | Age year | CEA ng/mL | Stage |
|---|---|---|---|---|
| GC-B1 | F | 62 | 8.30 | III |
| GC-B2 | M | 64 | — | III |
| GC-B3 | M | 58 | 6.89 | III |
| GC-B4 | M | 34 | 3.57 | IV |
| GC-B5 | M | 69 | 1.39 | IV |
| GC-B6 | M | 49 | 1.67 | IV |
| GC-B7 | F | 34 | 13.44 | IV |
| GC-B8 | F | 47 | 2.86 | III |
| GC-B9 | F | 40 | 0.64 | IV |
| GC-B10 | F | 60 | 1.20 | II |
| GC-B11 | M | 66 | 11.68 | IV |
| GC-B12 | M | 73 | — | II |
| GC-B13 | M | 53 | 1.00 | III |
| GC-B14 | M | 51 | 5.60 | IV |
| GC-B15 | M | 42 | 0.69 | III |
| GC-B16 | M | 81 | — | III |
| GC-B17 | M | 72 | — | II |
| GC-B18 | M | 66 | 1.22 | IV |
| GC-B19 | F | 49 | — | II |
| GC-B20 | M | 48 | — | I |
| GC-B21 | M | 51 | — | I |
| GC-B22 | M | 44 | — | I |
| GC-B23 | F | 44 | — | I |
| GC-B24 | M | 61 | — | I |
| GC-B25 | M | 76 | — | I |
| GC-B26 | M | 51 | — | I |
| GC-B27 | F | 40 | — | I |
| GC-B28 | M | 62 | — | I |
| GC-B29 | F | 57 | — | II |
| GC-B30 | M | 78 | — | II |
| GC-B31 | M | 75 | — | II |
| GC-B32 | F | 67 | — | II |
| GC-B33 | M | 50 | — | II |
| GC-B34 | F | 60 | — | II |
| GC-B35 | F | 47 | — | II |
| GC-B36 | M | 69 | — | II |
| GC-B37 | M | 72 | — | II |
| GC-B38 | F | 49 | — | II |
| GC-B39 | F | 55 | — | III |
| GC-B40 | F | 46 | — | III |
| GC-B41 | M | 64 | — | III |
| GC-B42 | M | 53 | — | III |
| GC-B43 | M | 61 | — | III |

TABLE 117-continued

| GC | Sex | Age year | CEA ng/mL | Stage |
|---|---|---|---|---|
| GC-B44 | F | 81 | — | III |
| GC-B45 | F | 36 | — | III |
| GC-B46 | M | 50 | — | IV |
| GC-B47 | M | 55 | — | IV |
| GC-B48 | M | 66 | — | IV |
| GC-B49 | F | 40 | — | IV |
| GC-B50 | M | 61 | — | IV |
| GC-B51 | M | 70 | — | IV |
| GC-B52 | M | 39 | — | IV |
| GC-B53 | M | 70 | — | IV |
| GC-B54 | F | 71 | — | IV |
| GC-B55 | F | 52 | — | IV |

TABLE 118

| OVC | Age year | Stage | Histology |
|---|---|---|---|
| OVC-B1 | 56 | IIIc | Clear cell carcinoma |
| OVC-B2 | 52 | IIa | Endometrioid adenocarcinoma |
| OVC-B3 | 63 | IV | Papillary serous adenocarcinoma |
| OVC-B4 | 55 | Ia | Malignant Brenner tumor |
| OVC-B5 | 47 | IIIc | Papillary serous adenocarcinoma |
| OVC-B6 | 50 | Ic | Clear cell carcinoma |
| OVC-B7 | 68 | Ib | Serous adenocarcinoma |
| OVC-B8 | 74 | IIIc | Papillary serous adenocarcinoma |
| OVC-B9 | 43 | Ic | Mucinous adenocarcinoma |
| OVC-B10 | 44 | IIIc | Papillary serous adenocarcinoma |
| OVC-B11 | 54 | IIIc | Papillary serous adenocarcinoma |
| OVC-B12 | 55 | IV | Serous adenocarcinoma |
| OVC-B13 | 72 | IIIc | Serous adenocarcinoma |
| OVC-B14 | 58 | IIIc | Mucinous adenocarcinoma |
| OVC-B15 | 44 | IIIc | Papillary serous adenocarcinoma |
| OVC-B16 | 57 | IV | Serous adenocarcinoma |
| OVC-B17 | 54 | IIIc | Papillary serous adenocarcinoma |
| OVC-B18 | 73 | IIIc | Serous adenocarcinoma |
| OVC-B19 | 47 | IIIc | Papillary serous adenocarcinoma |
| OVC-B20 | 40 | Ic | Papillary serous adenocarcinoma |
| OVC-B21 | 74 | IIb | Transitional cell carcinoma |
| OVC-B22 | 65 | IIIc | Papillary serous adenocarcinoma |
| OVC-B23 | 47 | IV | Serous adenocarcinoma |
| OVC-B24 | 58 | IIc | Serous adenocarcinoma |
| OVC-B25 | 57 | Ib | Mixed cell adenocarcinoma |

TABLE 119

| TA | Sex | Age year | FOBT | CEA ng/mL |
|---|---|---|---|---|
| TA-B1 | M | 70 | Negative | 2.0 |
| TA-B2 | M | 58 | Negative | 2.0 |
| TA-B3 | M | 52 | Negative | 0.6 |
| TA-B4 | M | 48 | —[a] | 2.6 |
| TA-B5 | F | 59 | Negative | 5.8 |
| TA-B6 | M | 77 | Negative | 5.1 |
| TA-B7 | F | 53 | Negative | 3.2 |
| TA-B8 | M | 63 | Negative | — |
| TA-B9 | F | 68 | — | — |
| TA-B10 | M | 54 | Negative | 79.4 |
| TA-B11 | M | 69 | — | 1.1 |
| TA-B12 | M | 56 | — | 0.5 |
| TA-B13 | M | 53 | — | 2.0 |
| TA-B14 | F | 76 | Negative | 2.7 |
| TA-B15 | M | 63 | Positive | 3.2 |
| TA-B16 | F | 54 | Negative | 0.7 |
| TA-B17 | F | 62 | — | 1.1 |
| TA-B18 | F | 64 | Negative | 1.6 |
| TA-B19 | F | 46 | Positive | 1.2 |

(2-2) Sample Preparation—Preparing Serum and Measuring Mass Spectrum

4× volume of methanol/chloroform (2:1, v/v) was mixed with 25 μl serum violently and incubated at room temperature for 10 min. The mixture was centrifuged at 4° C., 10 min, 6000×g. The supernatant was completely dried for 1 h in the concentrator, and dissolved in the vortexer in 300 of 50% acetonitrile/0.1% trifluoroacetic acid (TFA).

Methanol/chloroform extract was mixed with a-cyano-4-hydroxycinnamic acid solution in 50% acetonitrile/0.1% TFA (1:12, v/v), and 1 μl mixture was placed on MALDI-target plate. The mass spectra of the serum extracts from the CRC patients and normal subjects were measured using the Proteomics Analyzer (Applied Biosystems, Foster City, Calif., USA).

The mass spectrum data for one sample is extracted based on the average of spectrum which was repeatedly measured 20 times. The mass region of the entire individual samples was adjusted so that the maximum mass was set at approximately 2500 m/z. To minimize experimental error, various factors including focus mass, laser intensity, target plate, data acquisition time were taken into consideration.

The focus mass and the laser intensity were fixed at preferable levels, i.e., 500 m/z and 5000, respectively. In addition to the fixed focus mass and the laser intensity, the entire samples were repeatedly measured at least five times under viewpoint of other extraction and other data collection. The set $A_1$, from which weightings per mass ions were computed, was measured one more time.

Accordingly, the low-mass ion detecting means 4000 extracted the low-mass ion mass spectrum from the serum sample via the processes explained above, using the MALDI-TOF.

(2-3) Discrimination Strategy

In order for the constructed discriminant to be CRC specific, the discriminant is required to discriminate the CRC patient group from not only the normal control, but also the patient groups with other cancer types. In one embodiment, the patient groups with other cancer types include BRC patients, NHL patients and GC patients. Table 120 provides the result of implementing the conventional PCA-DA to investigate whether one discriminant can discriminate the CRC patient group from the non-CRC group (normal controls, BRC patient group, NHL patient group and GC patient group). To be specific, the specificity of the normal controls is as low as 69.28%. This reveals the fact that one discriminant cannot discriminate the CRC patient group from all the non-CRC groups.

TABLE 120

| | True | True Non-CRC | | | |
|---|---|---|---|---|---|
| Set $A_1$ | CRC | CONT | BRC | NHL | GC |
| Predicted CRC | 132 | 47 | 3 | 1 | 0 |
| Predicted Non-CRC | 1 | 106 | 108 | 35 | 29 |
| Sensitivity | | | | 99.25% | |
| Specificity | | CONT | | 69.28% | |
| | | BRC | | 97.30% | |
| | | NHL | | 97.22% | |
| | | GC | | 100.0% | |

Figure 2:
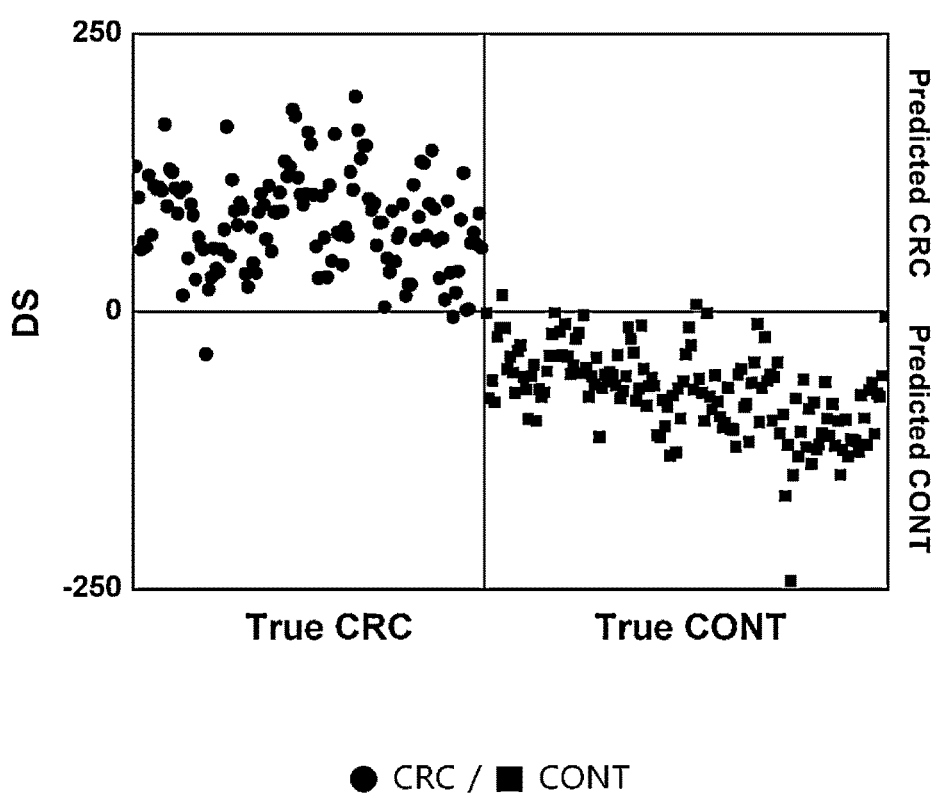
Figure 3:
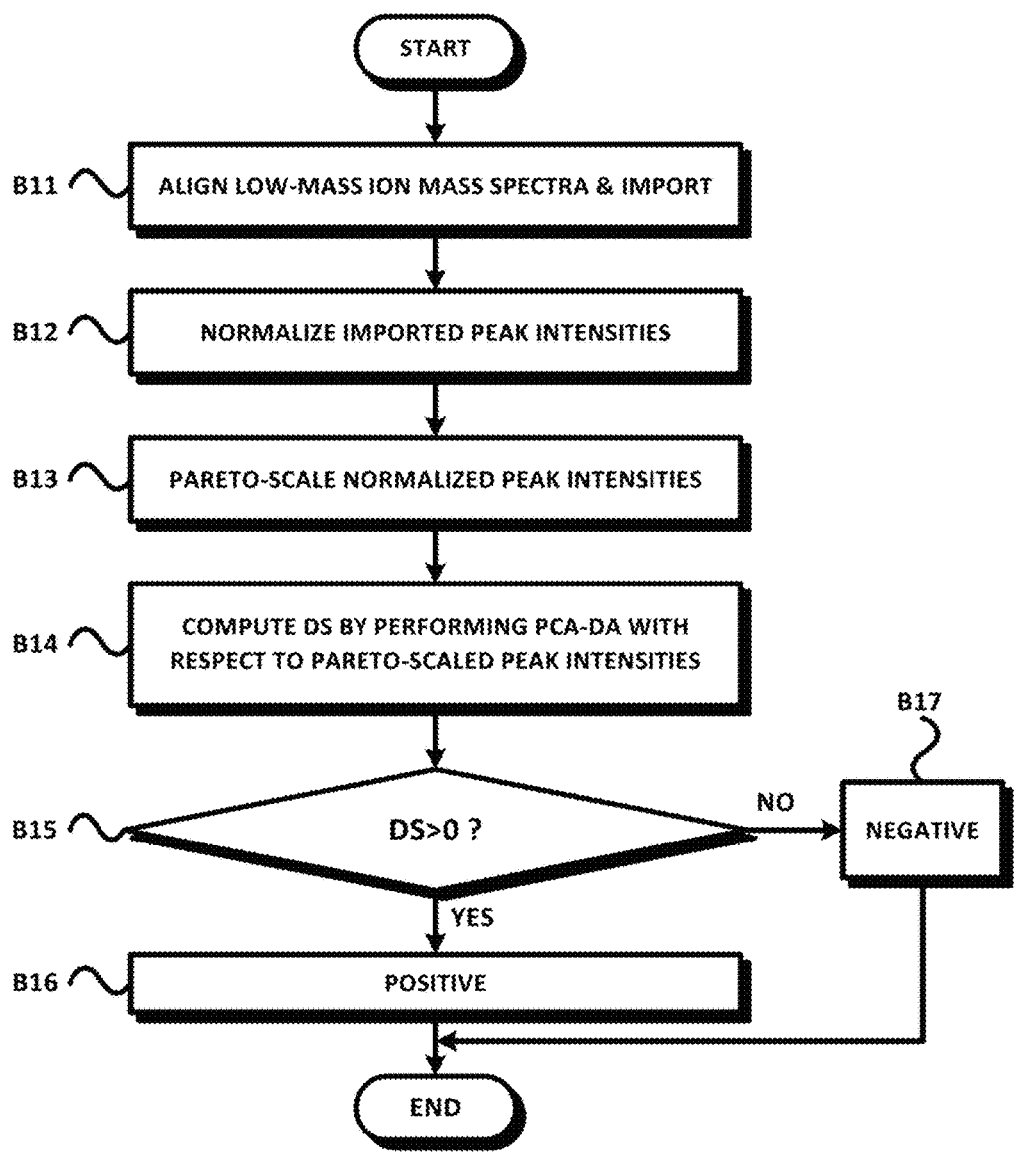

Referring to FIG. 2 and Table 104, considering the superior discrimination result of the CRC patient group from the normal controls, it was also investigated if the CRC patient group was discriminated from the patient groups with other cancer types, and the result is provided by Table 121. Except for the specificity (83.33%) of the NHL patient group which is relatively lower than the other cancer groups, the result is good overall.

TABLE 121

| Set $A_1$ | True CRC | True Non-CRC | | |
|---|---|---|---|---|
| | | BRC | NHL | GC |
| Predicted CRC | 132 | 1 | 6 | 1 |
| Predicted Non-CRC | 1 | 110 | 30 | 28 |
| Sensitivity | | | 99.25% | |
| Specificity | BRC | | 99.10% | |
| | NHL | | 83.33% | |
| | GC | | 96.55% | |
| | Total | | 95.45% | |

Accordingly, discriminating the CRC patient group from the non-CRC patient groups may include implementing a first type discriminant to discriminate CRC patient group from normal controls and a second discriminant to discriminate CRC patient group from the patient groups with other cancer types, in which the CRC patient is determined if both the discriminants indicate CRC, while the non-CRC patient is determined if any of the two discriminants indicates non-CRC patient.

(2-4) Selecting First Training Set $A_0$ and Computing Weightings Per Mass Ions

Although the result of discrimination of Tables 104 and 121 are good, the sensitivity and the specificity are not always 100%. In one embodiment of the present invention, the first training set $A_0$ with predetermined sensitivity and specificity is selected, and weightings per mass ions of the first training set $A_0$ were computed, in which the predetermined sensitivity and specificity were both 100%.

Figure 15:
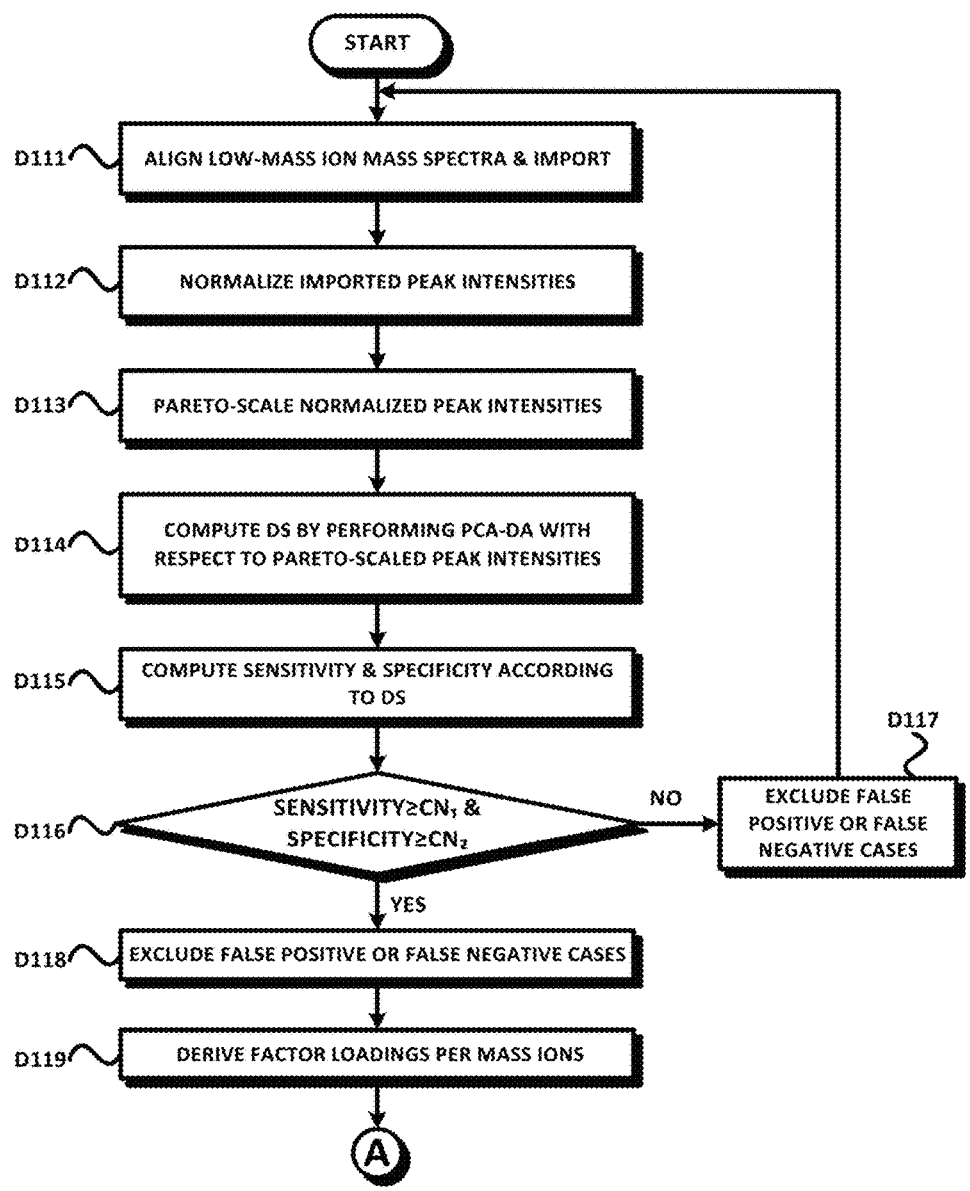

A method for selecting the first training set $A_0$ with the predetermined sensitivity and specificity will be explained below with reference to FIG. 15.

The first DS computing means 4200 aligned and imported the low-mass ion mass spectra of the CRC patient group and the normal control group of set $A_1$ (D111), normalized the imported peak intensities (D112), Pareto-scaled the normalized peak intensities (D113), and computed DS by performing biostatistical analysis with respect to the Pareto-scaled peak intensities (D114).

Among a variety of biostatistical analyzing methods that can be implemented to compute DS, in one embodiment, the PCA-DA was performed. Sensitivity and specificity were computed based on the DS (D115) and the result is shown in FIG. 2 and Table 104.

Next, sensitivity threshold $CN_1$ and specificity threshold $CN_2$ were set (D116), and false positive or false negative cases were excluded when the sensitivity or the specificity was less than the corresponding threshold (D117).

In one embodiment, both the sensitivity threshold $CN_1$ and the specificity threshold $CN_2$ were set to 1, to thus find the first training set $A_0$ with both the sensitivity and the specificity being 100%. That is, steps D111 to D115 were performed again with respect to the set from which two false positive cases and two false negative cases in Table 104 were excluded. The sensitivity and the specificity did not directly reach 100% when the steps D111 to D115 were repeated with respect to the set excluding the false positive and false negative cases. That is, the first training set $A_0$ with both the sensitivity and the specificity being 100% was found after the steps D111 to D117 were repeated predetermined number of times (D118).

The first type discriminant to discriminate CRC patient group from the normal controls reached discrimination result with 100% sensitivity and specificity when 8 false negative and 9 false positive cases were excluded, and the second type discriminant reached discrimination result with 100% sensitivity and specificity when 5 false negative and 10 false positive cases (1 BRC, 8 NHL, and 1 GC) were excluded. Through this process, it is possible to derive factor loadings per mass ions which provide discrimination result with both 100% sensitivity and specificity (D119).

The series of the processes explained above may be performed at the factor loading computing means 4300.

(2-5) Implementing a Discriminant

The process of implementing the constructed discriminant on the sample of interest will be explained below.

First, MarkerView™ supports the function that can be used for the similar purpose. That is, it is possible to apply the PCA-DA on only the part of the imported sample data, and discriminate the rest samples using the discriminant constructed as a result. According to this function, it is possible to select only the first training set after the import of the first training set and the other samples for analysis so that only the first training set undergoes the PCA-DA to show how the samples for analysis are interpreted.

Meanwhile, the peak alignment function to align the peaks is performed in the import process of MarkerView™. Because there is no function to align the peaks of the samples of interest based on the first training set, the peak table (matrix of m/z rows and rows of peak intensities per samples) obtained when only the first training set is imported, does not match the first training set of the peak table which is generated when the first training set is imported together with the samples of interest. The peak intensity matrices are difference, and the m/z values corresponding to the same peak intensity column also do not always appear the same. Accordingly, in order to compute DS by implementing the discriminant constructed from the first training set on the samples of interest, a realignment operation to realign the peak table, generated when the first training set is imported together with the samples of interest, to the peak table generated when only the first training set is imported.

The misalignment becomes more serious, if several samples of interests are imported together with the first training set. Accordingly, in one embodiment, with respect to the entire samples of interest, one sample of interest is added to the first training set to be imported, realigned, normalized and Pareto-scaled.

The embodiment will be explained in greater detail below with reference to FIG. 16.

First, the low-mass ion mass spectra of the samples of interest were aligned with the first training set and imported (D211).

Meanwhile, since MarkerView™ in one embodiment does not support the function of aligning and importing the sample of interest to the first training set, as explained above, a program may be designed to realign the peak table generated after importing the low-mass ion mass spectrum of the sample of interest together with the first training set to the peak table which is generated after importing the first training set only, so that the low-mass ion mess spectrum of the sample of interest aligned with the first training set is extracted. However, it is more preferable that the sample of interest is directly aligned and imported to the first training set without having realigning process and this is implementable by designing a program.

Next, the imported peak intensities were normalized (D212), and the normalized peak intensities were Pareto-scaled (D213).

Next, discriminant score was computed using the Pareto-scaled peak intensities of the low-mass ions and the factor loadings per mass ions acquired by the PCA-DA (D214).

It is determined whether or not the computed DS exceeds a reference CS (D215), and if so, it is interpreted positive (D216), while it is interpreted negative if the computed DS is less than the reference CS (D217). In one embodiment, the reference DS may preferably be 0.

The series of processes explained above may be performed at the second aligning means 4500, the second DS computing means 4600 and a CRC determining means 4700.

The DS was computed by applying factor loadings per mass ions computed at Clause (2-4) with respect to the 8 CRC patient samples and 9 normal control samples which were excluded when constructing the first training set $A_{01}$ from the set $A_1$ to construct the first type discriminant, and the 5 CRC patient samples, 1 BRC patient sample, 8 NHL patient samples and 1 GC patient sample which were excluded when constructing the first training set $A_{02}$ from the set $A_1$ to construct the second type discriminant Considering that the cases were excluded when constructing the first training sets $A_{01}$ and $A_{02}$, it was expected that the cases would be discriminated to be false positive or false negative, and they were discriminated to be false positive or false negative as expected when the computation was done. The result of discrimination of the set $A_1$ by applying the factor loadings per mass ions computed at Clause (2-4) is presented in FIGS. 17 and 18, in which FIG. 17 shows the result of the first type discriminant and FIG. 18 shows the result of the second discriminant.

(2-6) Constructing Preliminary Discriminant

Conventionally, DS is computed using the entire mass ions that are taken into consideration in the PCA-DA and the CRC patient was determined according to the computed DS. In one embodiment of the present invention, a preliminary discriminant is constructed, which uses only the mass ions that contribute considerably to the DS, in order to derive a discriminant with robust discrimination performance. As used herein, the term "preliminary discriminant" refers to an intermediate form of a discriminant which is obtained before the final discriminant is obtained, and the low-mass ions constructing the discriminant are the "preliminary candidate group" of the CRC-diagnosing low-mass ions to construct the final discriminant.

Figure 17:
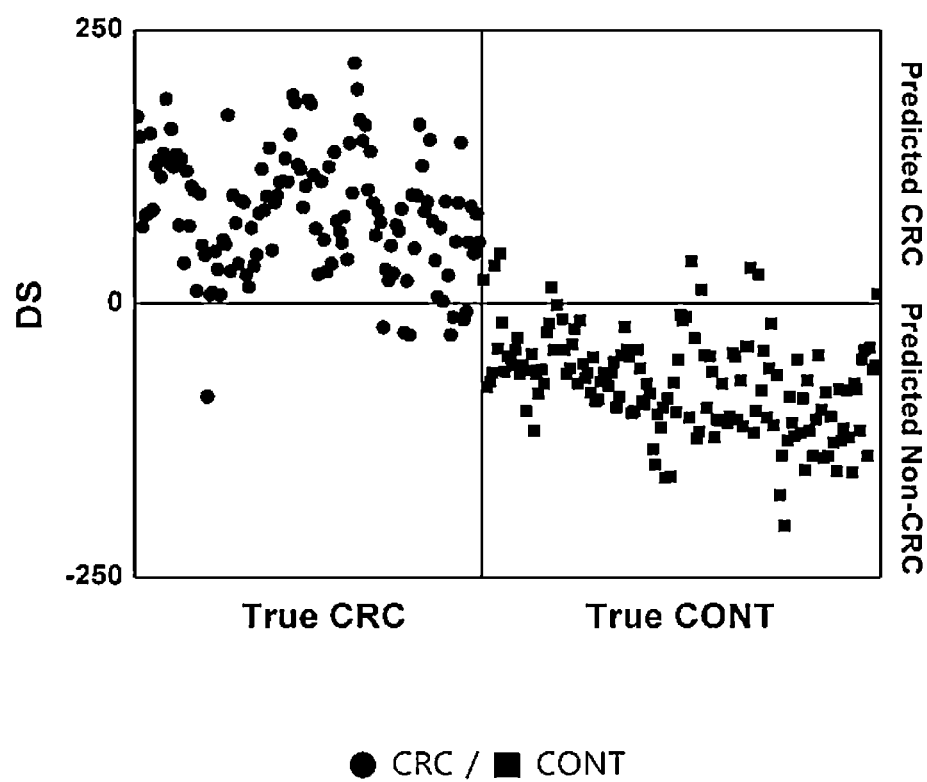
Figure 18:
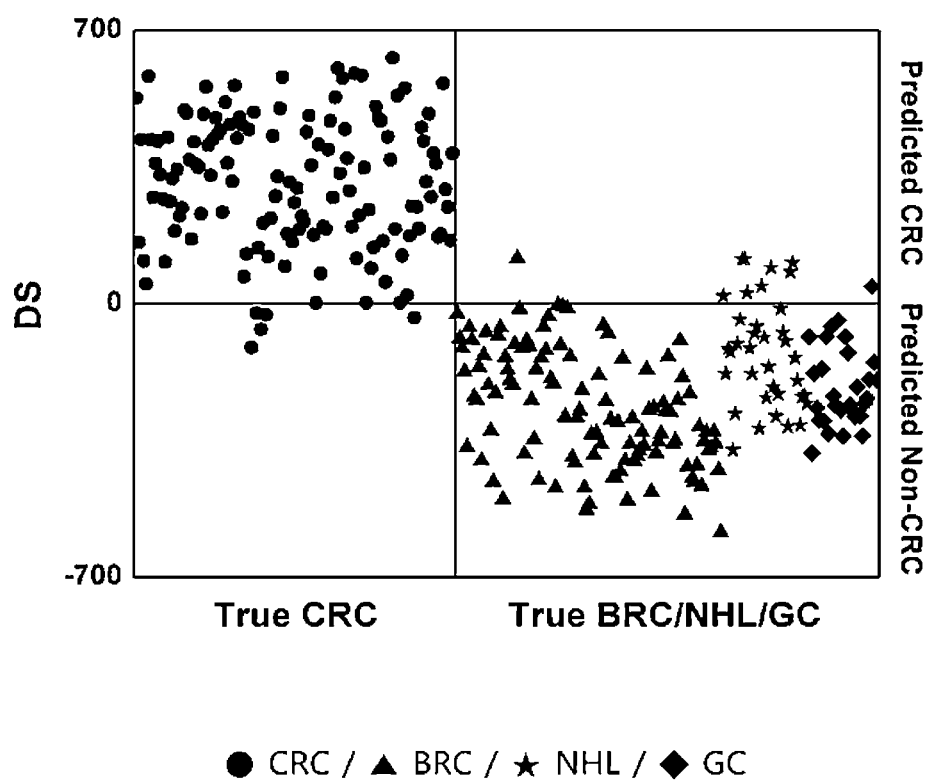

Through the process of FIG. 17, predetermined mass ions were selected, which give considerable influence on the DS, from among 10,000 mass ions. In one embodiment, 278 mass ions were selected by the first type discriminant, while 383 mass ions were selected by the second discriminant.

Figure 19:
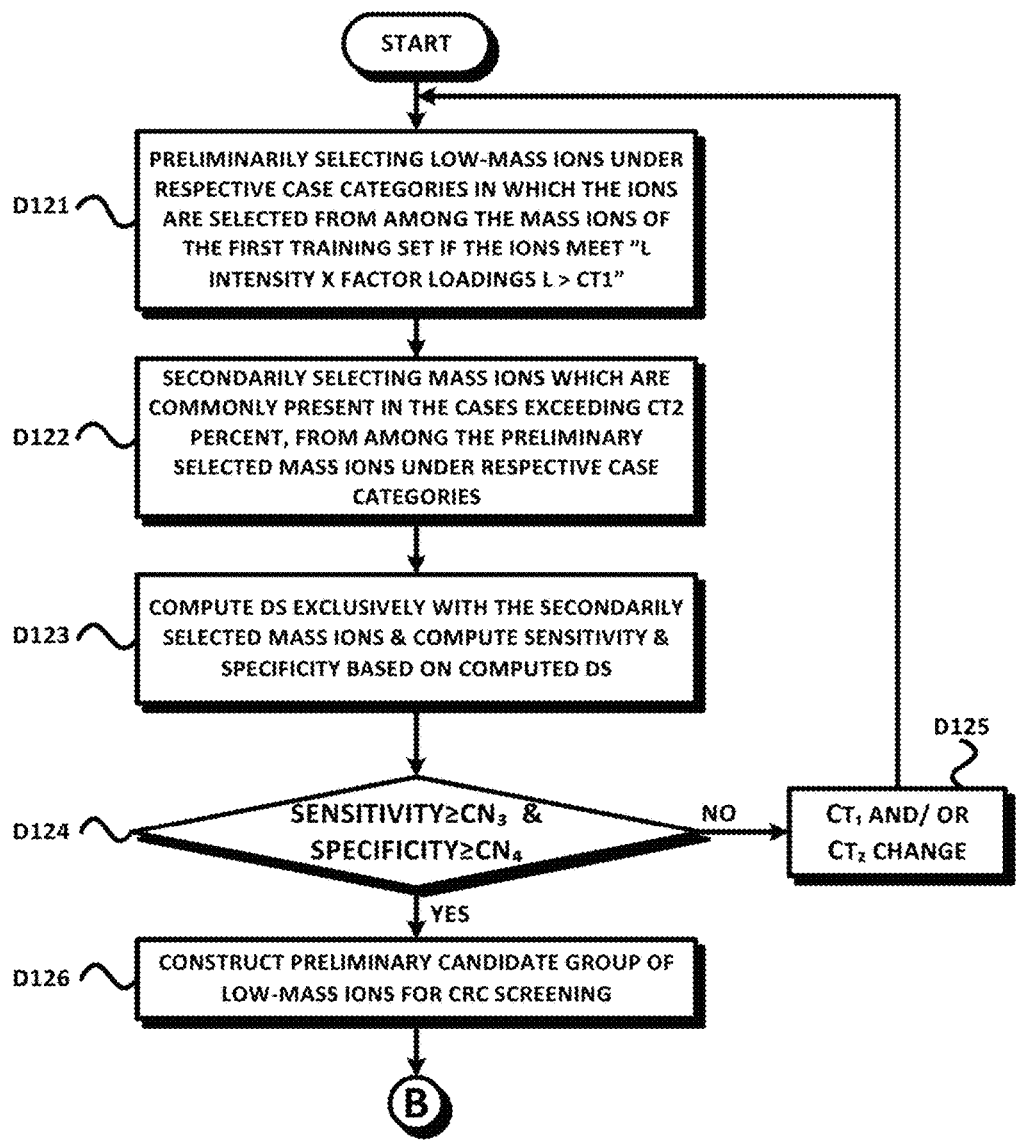

As explained above with reference to Table 103, because the maximum number of the peaks under the import condition is set to 10,000 and sufficient samples are imported, the discriminant constructed by the PCA-DA of MarkerView™ consists of 10,000 terms. However, not all the 10,000 terms have the equal importance particularly in distinguishing CRC patients and non-CRC patients. Accordingly, the mass ions that give considerable influence on the DS were selected from among the 10,000 mass ions by two steps according to the process of FIG. 19. This particular step is employed to remove unnecessary mass ions in distinguishing CRC patients from non-CRC patients from the 10,000 mass ions.

The mass ions were preliminarily selected under corresponding case categories, if the absolute product obtained by multiplying the peak intensities by the factor loadings per mass ions exceeds the threshold $CT_1$ (D121). In one embodiment, the threshold $CT_1$ may preferably be 0.1.

Next, the mass ions were again selected from among the preliminarily-selected mass ions under each case category, if the mass ions appear commonly in the cases exceeding the threshold percentage $CT_2$ (D122). In one embodiment, the threshold percentage $CT_2$ may preferably be 50. That is, take the first type discriminant for example, only the mass ions that appear commonly in at least 135 cases from among the 269 cases of the first training set were used to construct the preliminary discriminant.

The DS was again computed exclusively with the mass ions that were selected as explained above, and the sensitivity and the specificity were computed accordingly (D123). Again, the sensitivity threshold $CN_3$ and the specificity threshold $CN_4$ were set (D124), so that if the sensitivity or the specificity is less than the corresponding threshold, the threshold $CT_1$ used at step D121 and/or the threshold $CT_2$ used at step D122 was changed (D125) and the steps from D121 to D124 were repeated. In one embodiment, the sensitivity threshold $CN_3$ and the specificity threshold $CN_4$ may preferably be 0.9, respectively.

The preliminary candidate group of the CRC-diagnosing low-mass ions was constructed with the mass ions that were selected as explained above (D126), and in one embodiment, 278 mass ions were selected by the first type discriminant or 383 mass ions were selected by the second type discriminant from among the 10,000 mass ions. Tables 122 and 123 provides the results of discriminating the first training sets $A_{01}$ and $A_{02}$ with the first and second type preliminary discriminants, according to which the discrimination performance including the sensitivity and the specificity was slightly degraded from 100%, but still the result of computing with less than 3~4% of the total mass ions was certainly as good as the result obtained by using the entire mass ions.

Figure 20:
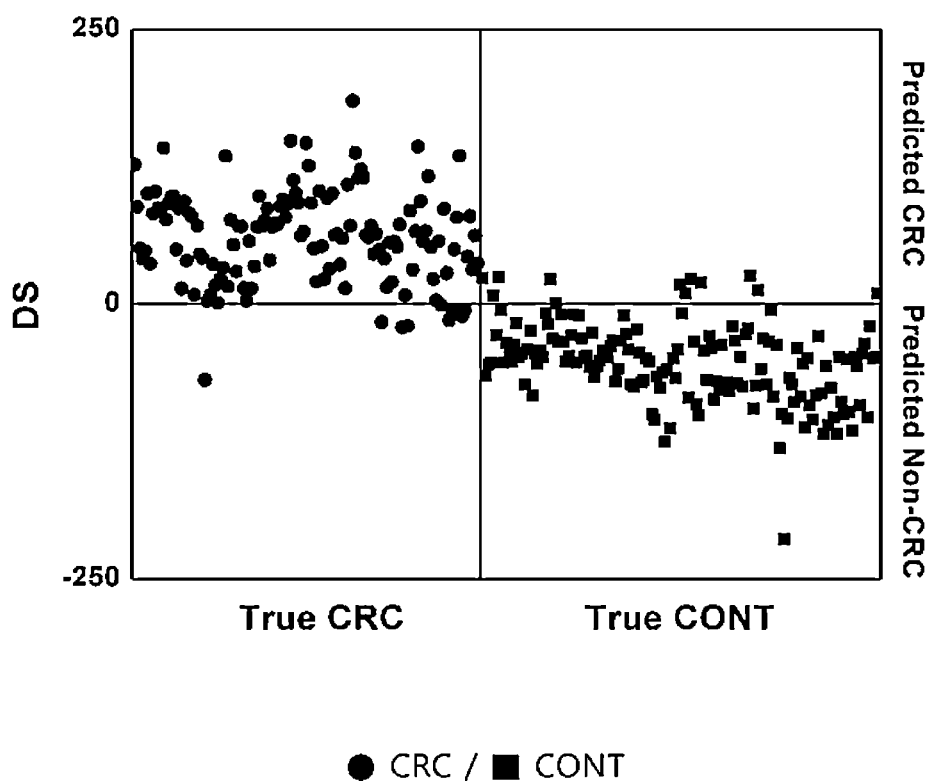
Figure 21:
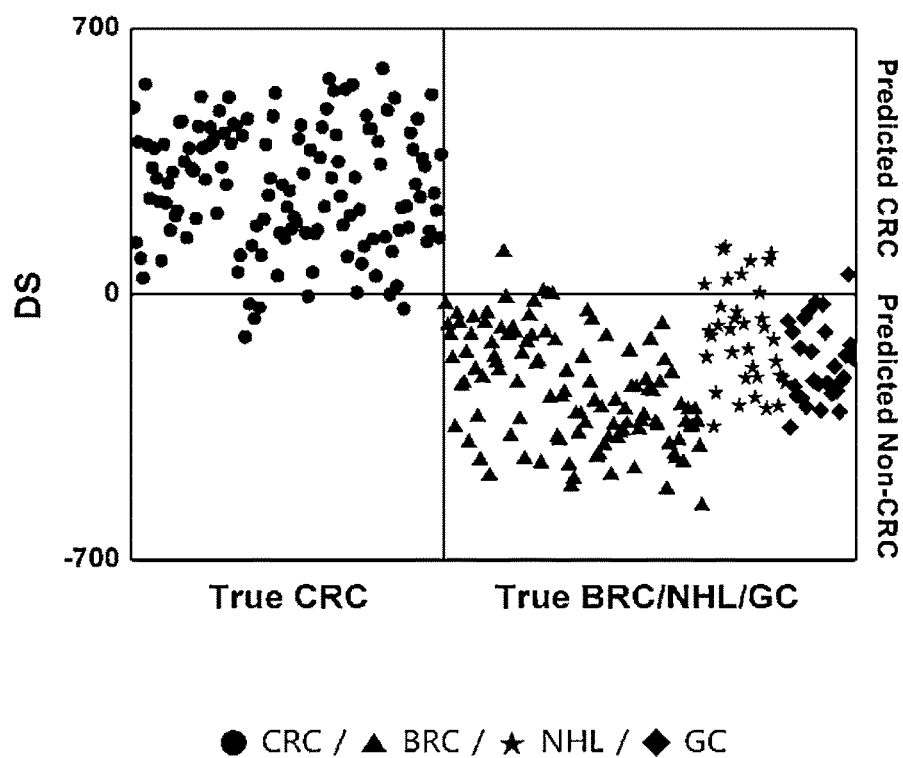

Further, FIGS. 20 and 21 provide the result of discriminating the set $A_1$ with the preliminary discriminant, in which FIG. 20 shows the result by the first type preliminary discriminant and FIG. 21 shows the result by the second type discriminant Compared to the sharp reduction in the number of mass ions used for the computation, the range of DS was not so influenced. This suggests that not all 10,000 mass ions are necessary to distinguish CRC patients from non-CRC patients.

TABLE 122

| Set $A_{01}$ | True CRC | True CONT |
|---|---|---|
| Predicted CRC | 124 | 3 |
| Predicted CONT | 1 | 141 |
| Sensitivity | | 99.20% |
| Specificity | | 97.92% |
| PPV | | 97.64% |
| NPV | | 99.30% |

TABLE 123

| Set $A_{02}$ | True CRC | True Non-CRC BRC | NHL | GC |
|---|---|---|---|---|
| Predicted CRC | 126 | 2 | 1 | 0 |
| Predicted Non-CRC | 2 | 108 | 27 | 28 |

|  |  |
|---|---|
| Sensitivity | 98.44% |
| Specificity | 98.19% |
| PPV | 97.67% |
| NPV | 98.79% |

The series of processes explained above may be performed at the CRC-diagnosing ion selecting means 4400 which includes the candidate ion set selecting means.

(2-7) Constructing a Final Discriminant

The mass ions were extracted from among the 10,000 mass ions imported in the process of constructing the preliminary discriminant, as those that contribute considerably to the numerical aspect of the DS. Considering that the selected mass ions include the mass ions that do not generate a problem in the first training set $A_0$, but can potentially deteriorate the discrimination performance in the discrimination with the mass spectrum that was re-measured with respect to the same CRC patient samples and non-CRC samples or in the discrimination of new CRC patient group and non-CRC patient group, additional step is necessary, which can actively remove the presence of such mass ions. The process of constructing a final discriminant includes such step before finally determining CRC-diagnosing low-mass ions.

To validate robustness of a discriminant, repeated measure experiment was conducted with respect to the set $A_1$ 5 times, and the repeated measure experiment was also performed 5 times with respect to the sets $A_2$ and B which were independent from the set $A_1$ and also independent from each other. It is hardly possible to confirm that the repeated measure of the mass spectrum is always conducted under the exactly same conditions in the processes like vaporization using laser beam, desorption, ionization, or the like, in addition to the process of freezing and thawing the serums and mixing the serums with methanol/chloroform to obtain extract, and it is also hard to rule out introduction of disturbances due to various causes. In other words, the DS with respect to the repeatedly-measured individual mass spectrum may have a predetermined deviation, and considering this, interpretation in one embodiment was made by computing an average DS with respect to the sample which was repeatedly measured 5 times.

Table 124 provides the result of discriminating the sets A and B with the discriminant of 10,000 terms as a result of the conventional technology, i.e., PCA-DA by MarkerView™, and Table 125 shows the result of discriminating the sets A and B with the first type preliminary discriminant with 278 terms and the second type preliminary discriminant with 383 terms. Referring to the table, CRC LOME 1 (colorectal cancer low mass ion discriminant equation) refers to the first type discriminant, and CRC LOME 2 refers to the second type discriminant, and the following numbers indicate the number of low-mass ions included in the discriminant. Further, Table 126 shows the discrimination performance with respect to the validation set only, i.e., to the set B, in which the numbers in parenthesis refers to the discrimination performance when TA patient group is included in the CRC patient group. Considering that TA patients have high risk of developing CRC, discriminating the TA patient group is considered to be rather advantageous result for the purpose of early detection of the diagnosis.

TABLE 124

| | CRC LOME 1-10000 | | | | | | CRC LOME 1-10000 | | | | | | |
|---|---|---|---|---|---|---|---|---|---|---|---|---|---|
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 131 | 18 | 26 | 36 | 36 | Predicted CRC | 68 | 0 | 7 | 4 | 23 | 6 | 13 |
| Predicted Non-CRC | 146 | 185 | 110 | 15 | 50 | Predicted Non-CRC | 75 | 50 | 18 | 11 | 32 | 19 | 6 |
| | CRC LOME 2-10000 | | | | | | CRC LOME 2-10000 | | | | | | |
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 109 | 120 | 21 | 3 | 2 | Predicted CRC | 43 | 0 | 4 | 0 | 0 | 0 | 9 |
| Predicted Non-CRC | 168 | 83 | 115 | 48 | 84 | Predicted Non-CRC | 100 | 50 | 21 | 15 | 55 | 25 | 10 |
| | CRC LOMEs 1 & 2 | | | | | | CRC LOMEs 1 & 2 | | | | | | |
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 80 | 17 | 3 | 3 | 1 | Predicted CRC | 39 | 0 | 1 | 0 | 0 | 0 | 8 |
| Predicted Non-CRC | 197 | 186 | 133 | 48 | 85 | Predicted Non-CRC | 104 | 50 | 24 | 15 | 55 | 25 | 11 |

TABLE 125

| | CRC LOME 1-278 | | | | | | CRC LOME 1-278 | | | | | | |
|---|---|---|---|---|---|---|---|---|---|---|---|---|---|
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 136 | 14 | 26 | 36 | 35 | Predicted CRC | 70 | 0 | 5 | 4 | 24 | 7 | 13 |
| Predicted Non-CRC | 141 | 189 | 110 | 15 | 51 | Predicted Non-CRC | 73 | 50 | 20 | 11 | 31 | 18 | 6 |
| | CRC LOME 2-383 | | | | | | CRC LOME 2-383 | | | | | | |
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 106 | 121 | 21 | 3 | 4 | Predicted CRC | 43 | 0 | 3 | 0 | 0 | 0 | 9 |
| Predicted Non-CRC | 171 | 82 | 115 | 48 | 82 | Predicted Non-CRC | 100 | 50 | 22 | 15 | 55 | 25 | 10 |
| | CRC LOMEs 1 & 2 | | | | | | CRC LOMEs 1 & 2 | | | | | | |
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 75 | 13 | 3 | 3 | 1 | Predicted CRC | 39 | 0 | 1 | 0 | 0 | 0 | 8 |
| Predicted Non-CRC | 202 | 190 | 133 | 48 | 85 | Predicted Non-CRC | 104 | 50 | 24 | 15 | 55 | 25 | 11 |

TABLE 126

| Set B | Sensitivity (%) | Specificity (%) | PPV (%) | NPV (%) |
|---|---|---|---|---|
| CRC LOME 1-10000 & CRC LOME 2-10000 | 27.27 (29.01) | 95.24 (99.41) | 81.25 (97.92) | 63.38 (59.51) |
| CRC LOME 1-278 & CRC LOME 2-383 | 27.27 (29.01) | 95.24 (99.41) | 81.25 (97.92) | 63.38 (59.51) |
| CRC LOME 1-104 & CRC LOME 2-23 | 94.41 (93.21) | 88.36 (96.47) | 85.99 (96.18) | 95.43 (93.71) |

The discriminant consisting of 10,000 mass ions exhibits perfect discrimination performance with respect to the first training set $A_0$, but with reference to Table 126, the sensitivity is particularly low with respect to set B. Both the first and second preliminary discriminants exhibited very good discrimination performance (Tables 122, 123) with respect to the first training set $A_0$, but the discrimination result with respect to set B is far from satisfaction.

Figure 22:
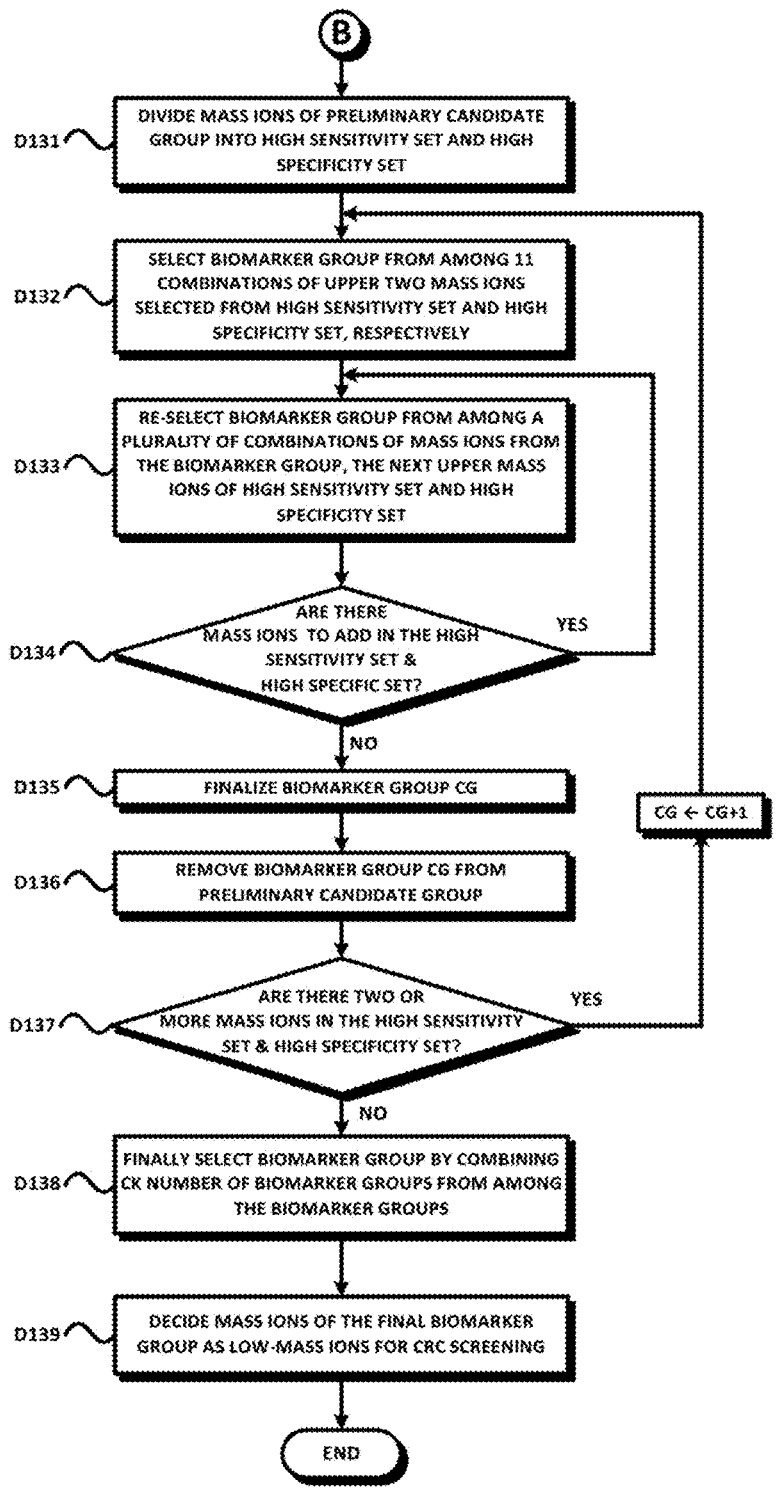

Accordingly, in one embodiment of the present invention, steps illustrated in FIG. 22 were performed to improve the preliminary discriminant to more robust discriminant.

First, the mass ions of the preliminary candidate group were divided into high sensitivity set and high specificity set (D131). As used herein, the mass ions of the high sensitivity set have higher sensitivity per mass ions than specificity, while the mass ions of the high specificity set have higher specificity per mass ions than sensitivity.

Next, the mass ions of the high sensitivity set and the mass ions of the high specificity set were sorted in a descending order $\{Sns_1, Sns_2, Sns_3 \ldots Sns_j\}$ $\{Spc_1, Spc_2, Spc_3 \ldots Spc_j\}$ in terms of the sum of the sensitivity and specificity per mass ions, and two top mass ions of the respective sets were taken $\{Sns_1, Sns_2, Spc_1, Spc_2\}$, and a biomarker group was selected with a combination of the best performance from among 11 combinations that are possibly made with the two or more mass ions of the four mass ions (D132).

The criteria to determine whether a combination has the best performance or not may be selected objectively and universally from among the following criteria which are listed in the order of importance:

Criterion 1) The combination with greater sum of sensitivity and specificity has better performance;

Criterion 2) The combination with less mass ions has better performance; and Criterion 3) The combination with a greater difference between minimum DS of the true positive case and the maximum DS of true negative case has better performance.

Next, one more mass ion, i.e., the second top mass ion $\{Sns_3, Spc_3\}$ was additionally taken from each of the high sensitivity set and the high specificity, so that a set with the best performance was re-selected as a biomarker group from among the four sets {biomarker group}, {biomarker group, $Sns_3$}, {biomarker group, $Spc_3$}, {biomarker group, $Sns_3$, $Spc_3$} which are the combinations of the additionally-taken mass ions $\{Sns_3, Spc_3\}$ (D133).

The process repeated until the high sensitivity set and the high specificity set had no further mass ion to add (D134).

In other words, the process (D133) repeats as long as both the high sensitivity set and the high specificity set have mass ions to add, and when any of the high sensitivity set and the high specificity set has no further mass ion left to add, the next top mass ion $\{Sns_i \text{ or } Spc_j\}$ in the set having mass ions is additionally taken, so that a biomarker group is selected with a set of the best performance among the two sets {biomarker group}, {biomarker group, $Sns_i$ or $Spc_j$} which are combinations of the additionally-taken mass ion $\{Sns_i$ or $Spc_j\}$.

The process repeats as long as the high sensitivity set or the high specificity set is out of the mass ion, and the biomarker group that is selected when there is no mass ion left in the high sensitivity set and high specificity set becomes the biomarker group 1 (CG) (D135).

The biomarker group 1 (CG) was removed from the preliminary candidate group (D136), the high sensitivity set and the high specificity set were constructed with the remaining mass ions, and the above-explained process repeats. The process repeats until any of the high sensitivity set and the high specificity has less than two mass ions therein (D137).

CK number of biomarker groups were combined with the biomarker groups 1, 2, . . . which were obtained by the repeated process explained above, in the order of accuracy, to form a final biomarker group. As used herein, the "accuracy" refers to a proportion of true positive and true negative cases in the entire cases. In one embodiment, CK may preferably be 1, 2, or 3 (D138).

Accordingly, the mass ions of the final biomarker group were determined to be the CRC-diagnosing low-mass ions (D139).

The preliminary candidate group of the mass ions was selected from the set $A_1$, and more specifically, from the subset $A_0$, and to avoid overfitting problem, the set $A_2$ which was independent from the set $A_1$ was added to enlarge the training set when the final biomarker group was determined from the preliminary candidate group.

As a result of performing the process explained above with respect to the samples to distinguish CRC patient group from the normal controls, 104 mass ions were selected as the first type CRC-diagnosing low-mass ions. Further, as a result of performing the process explained above with respect to the samples to distinguish CRC patient group from the patient group with other cancer types, 23 mass ions were selected as the second type CRC-diagnosing low-mass ions. The masses of the first and second type CRC-diagnosing low-mass ions are listed in Tables 127 and 128. The low-mass ions explained above are referred to as the "first type CRC-diagnosing low-mass ions" and the "second type CRC-diagnosing low-mass ions", and the discriminant according to the present invention which is finally obtained using the same are referred to as the "first type CRC-diagnosing final discriminant" and the "second type CRC-diagnosing final discriminant", respectively.

TABLE 127

| |
|---|
| 18.0260 |
| 22.9797 |
| 74.0948 |
| 76.0763 |
| 102.0916 |
| 105.1078 |
| 106.0899 |
| 107.0477 |
| 118.0822 |
| 123.0395 |
| 137.0423 |
| 137.0729 |
| 147.0573 |
| 147.1058 |
| 169.0653 |
| 181.0656 |
| 190.0849 |
| 191.0848 |
| 191.3324 |
| 195.0785 |
| 212.3195 |
| 231.0667 |
| 235.0053 |
| 256.0939 |
| 266.9557 |
| 267.9501 |
| 288.2033 |
| 291.0997 |
| 295.0663 |

TABLE 127-continued

| |
|---|
| 300.1297 |
| 301.1269 |
| 316.2288 |
| 317.2311 |
| 335.1862 |
| 340.2241 |
| 343.2451 |
| 345.2583 |
| 357.0666 |
| 357.2784 |
| 366.2310 |
| 368.2551 |
| 369.3302 |
| 377.0570 |
| 379.1438 |
| 379.4765 |
| 383.0529 |
| 384.1745 |
| 388.2688 |
| 401.0531 |
| 423.0313 |
| 428.1878 |
| 454.2090 |
| 465.3014 |
| 466.1923 |
| 468.1851 |
| 469.2831 |
| 477.1721 |
| 478.1678 |
| 480.1715 |
| 482.3220 |
| 483.3258 |
| 496.8683 |
| 497.7636 |
| 503.8719 |
| 508.3407 |
| 510.3265 |
| 512.3119 |
| 513.3177 |
| 518.2931 |
| 518.8555 |
| 519.2967 |
| 519.8598 |
| 525.3449 |
| 534.2739 |
| 537.2800 |
| 538.3306 |
| 540.2629 |
| 540.8144 |
| 542.8457 |
| 544.8692 |
| 548.2856 |
| 566.8375 |
| 581.1957 |
| 582.1888 |
| 583.2242 |
| 656.0270 |
| 667.3291 |
| 709.3519 |
| 710.3581 |
| 711.3617 |
| 712.3683 |
| 713.3798 |
| 991.6196 |
| 992.6209 |
| 1016.6113 |
| 1020.4817 |
| 1206.5305 |
| 1207.5571 |
| 1465.6184 |
| 1466.6096 |
| 1467.5969 |
| 2450.9701 |
| 2451.9662 |
| 2452.9546 |

Referring to Table 127, 1465.6184, 1466.6096, 1467.5969, 2450.9701, 2451.9662, 2452.9546 m/z were characterized into fibrinogen alpha chain and transthyretin.

TABLE 128

| |
|---|
| 60.0476 |
| 138.0540 |
| 172.6653 |
| 173.1158 |
| 179.1451 |
| 191.1277 |
| 279.0855 |
| 280.0895 |
| 280.2642 |
| 281.1440 |
| 296.2574 |
| 312.3248 |
| 332.3224 |
| 333.3324 |
| 369.3406 |
| 465.3161 |
| 486.6356 |
| 488.6882 |
| 544.8908 |
| 551.3287 |
| 566.8737 |
| 707.3475 |
| 733.3569 |

The series of the processes explained above may be performed at the CRC-diagnosing ion selecting means 4400 which includes the final ion set selecting means.

(2-8) Implementation of the Final Discriminant & Analysis

Figure 16:
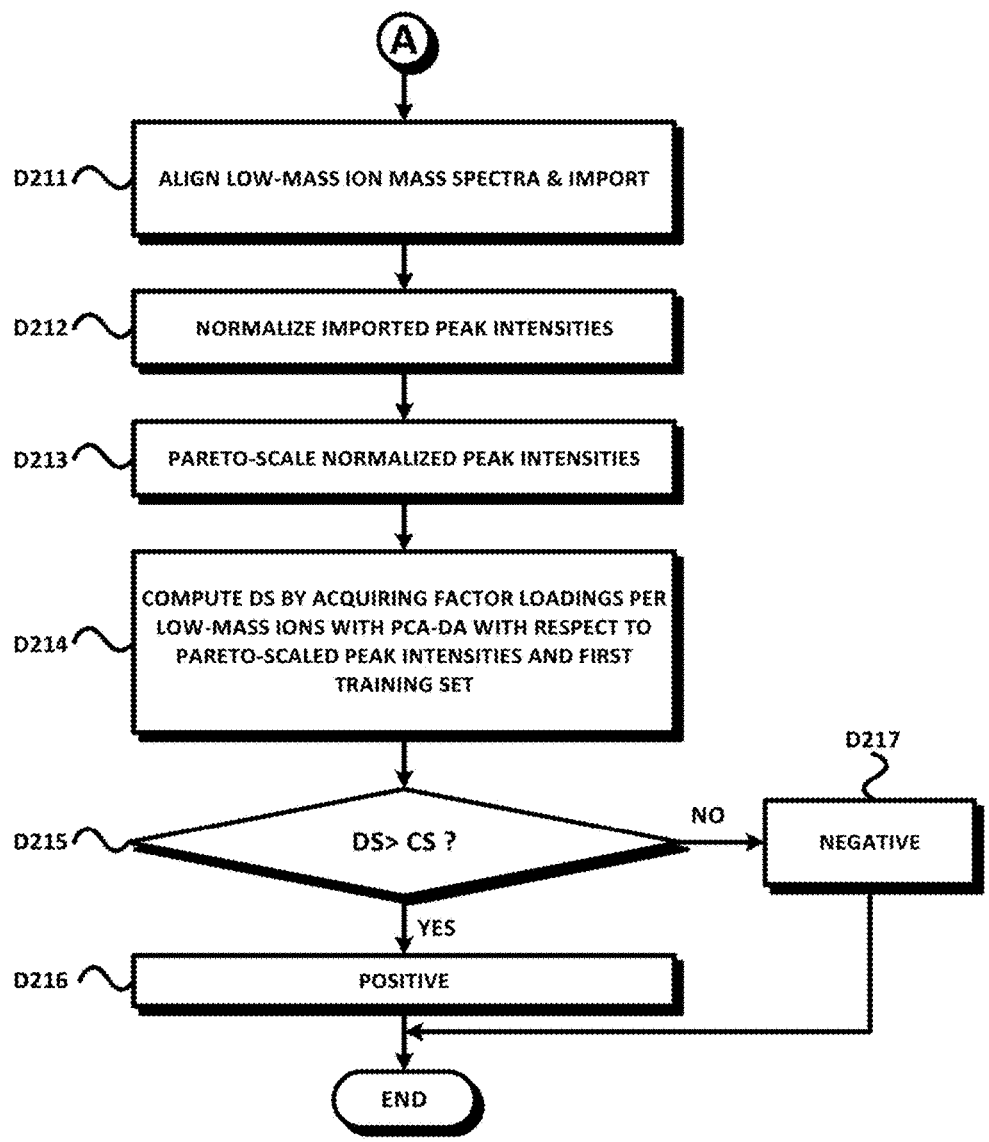

The interpretation is available when the first and second type CRC-diagnosing final discriminants using the first and second type CRC-diagnosing low-mass ions are implemented on the set B according to the method of FIG. 16.

Figure 23:
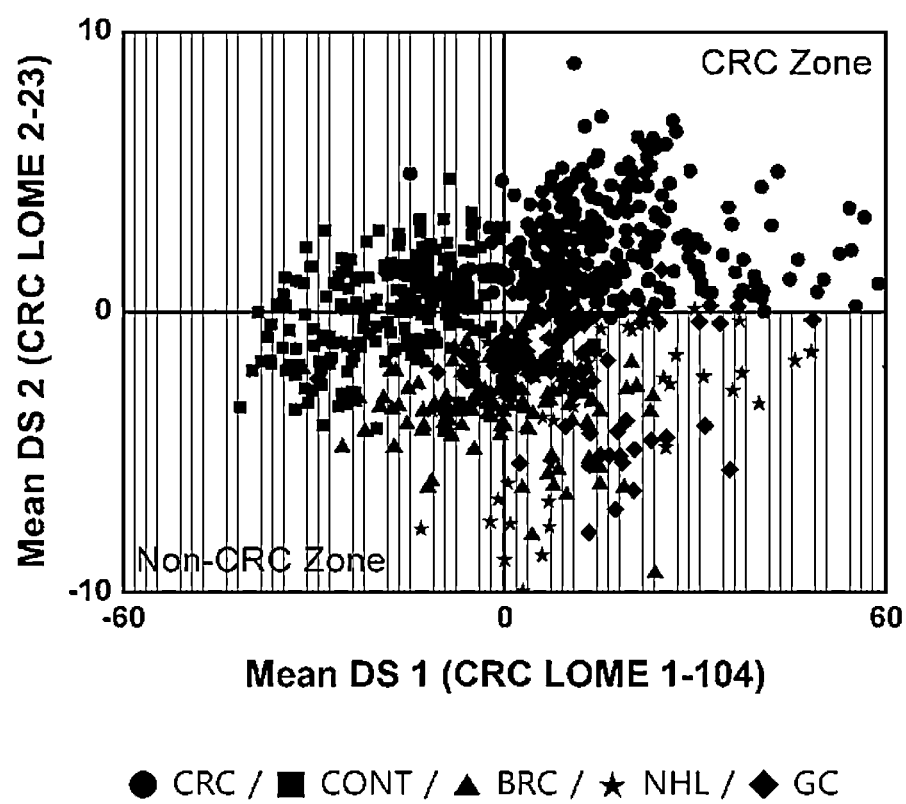
Figure 24:
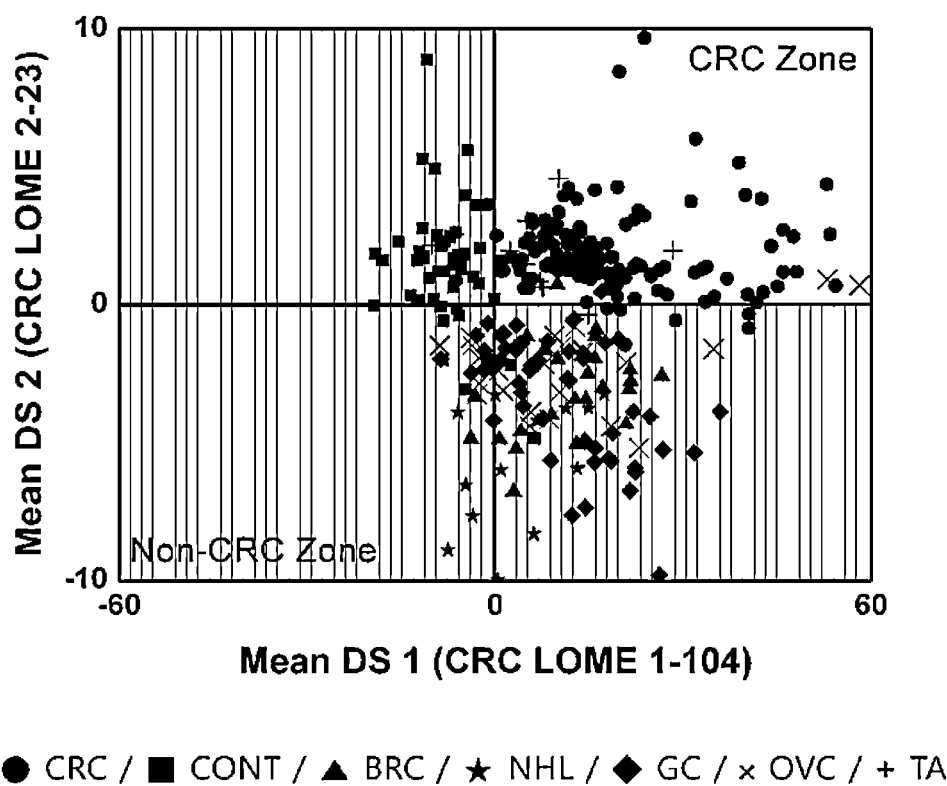

The result of interpretation obtained by the final discriminant is shown in FIGS. 23 and 24 and Tables 126 and 129. FIGS. 23 and 24 illustrate the result of interpretation based on the average DS of the DS of five rounds, in which FIG. 23 shows the result of interpretation on set A and FIG. 24 shows the result of interpretation on set B.

The validation set (set B) exhibits all the sensitivity, specificity, positive predictability and negative predictability exceeding 85%. Further, if TA patient group is added into CRC patient group, the discrimination performance exceeds 90% which is quite satisfactory.

Table 130 shows the discrimination performance of the conventional FOBT conducted with respect to the analyte, in comparison with the discrimination performance according to the present invention. Among the validation sets, the FOBT result exhibits 100% of specificity, but low sensitivity at 50% with respect to the 96 CRC patient samples and 49 normal control samples.

The sensitivity is less than 60~85% which is generally accepted sensitivity of the FOBT. That is, in comparison with the discrimination performance of the general conventional FOBT, the present invention provides comparable performance in terms of the specificity, and provides distinguishing result in terms of the sensitivity. Therefore, the present invention provides superior discrimination performance. The similar result is displayed in the training set. Table 131 lists the results of discrimination by FOBT and the present invention with respect to both the training set and the validation set.

TABLE 130

| Set B | CRC LOME 1-104 | | CRC LOME 1-104 & CRC LOME 2-23 | | FOBT | |
|---|---|---|---|---|---|---|
| | True CRC | True CONT | True CRC | True CONT | True CRC | True CONT |
| Predicted CRC | 94 | 3 | 91 | 1 | 48 | 0 |

TABLE 129

| | CRC CRC LOME 1-104 | | | | | | CRC LOME 1-104 | | | | | | |
|---|---|---|---|---|---|---|---|---|---|---|---|---|---|
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 258 | 2 | 67 | 44 | 69 | Predicted CRC | 141 | 3 | 23 | 10 | 45 | 19 | 17 |
| Predicted Non-CRC | 19 | 201 | 69 | 7 | 17 | Predicted Non-CRC | 2 | 47 | 2 | 5 | 10 | 6 | 2 |
| | CRC CRC LOME 2-23 | | | | | | CRC LOME 2-23 | | | | | | |
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 273 | 113 | 0 | 2 | 7 | Predicted CRC | 137 | 39 | 1 | 0 | 2 | 2 | 18 |
| Predicted Non-CRC | 4 | 90 | 136 | 49 | 79 | Predicted Non-CRC | 6 | 11 | 24 | 15 | 53 | 23 | 1 |
| | CRC LOMEs 1 & 2 | | | | | | CRC LOMEs 1 & 2 | | | | | | |
| | True | True Non-CRC | | | | | True | True Non-CRC | | | | | |
| Set A | CRC | CONT | BRC | NHL | GC | Set B | CRC | CONT | BRC | NHL | GC | OVC | TA |
| Predicted CRC | 254 | 0 | 0 | 2 | 5 | Predicted CRC | 135 | 1 | 1 | 0 | 2 | 2 | 16 |
| Predicted Non-CRC | 23 | 203 | 136 | 49 | 81 | Predicted Non-CRC | 8 | 49 | 24 | 15 | 53 | 23 | 3 |

TABLE 130-continued

| Set B | Sensitivity (%) | Specificity (%) | PPV (%) | NPV (%) |
|---|---|---|---|---|
| Predicted Non-CRC | 2 | 46 | 5 | 48 | 48 | 49 |
| CRC LOME 1-104 | 97.92 | 93.88 | 96.91 | 95.83 |
| CRC LOME 1-104 & CRC LOME 2-23 | 94.79 | 97.96 | 98.91 | 90.57 |
| FOBT | 50.00 | 100.0 | 100.0 | 50.52 |

TABLE 131

| Control | FOBT | Prediction | | Control | FOBT | Prediction | |
|---|---|---|---|---|---|---|---|
| CRC-B61 | Positive | CRC CRC LOME 1-104 | CRC CRC LOME 1-104 & CRC LOME 2-23 | CRC-B133 | — | CRC CRC LOME 1-104 | CRC CRC LOME 1-104 & CRC LOME 2-23 |
| CRC-A68 | Negative | CRC | CRC | CRC-A207 | Positive | CRC | CRC |
| CONT-A1 | — | Non-CRC | Non-CRC | CONT-A103 | Negative | Non-CRC | Non-CRC |
| CRC-B62 | Positive | CRC | CRC | CRC-B134 | Positive | CRC | CRC |
| CONT-A2 | Negative | Non-CRC | Non-CRC | CONT-A104 | — | Non-CRC | Non-CRC |
| CRC-A69 | Positive | CRC | CRC | CRC-A208 | Negative | CRC | CRC |
| CONT-A3 | Negative | Non-CRC | Non-CRC | CONT-A105 | Negative | Non-CRC | Non-CRC |
| CRC-B63 | Negative | CRC | CRC | CRC-B135 | — | CRC | CRC |
| CONT-A4 | Negative | Non-CRC | Non-CRC | CONT-A106 | — | Non-CRC | Non-CRC |
| CRC-A70 | Positive | CRC | CRC | CRC-A209 | — | CRC | CRC |
| CONT-A5 | Negative | Non-CRC | Non-CRC | CONT-A107 | Negative | Non-CRC | Non-CRC |
| CRC-B64 | Negative | CRC | CRC | CRC-B136 | — | CRC | CRC |
| CONT-A6 | Negative | Non-CRC | Non-CRC | CONT-A108 | Negative | Non-CRC | Non-CRC |
| CRC-A71 | Positive | CRC | CRC | CRC-A210 | Negative | CRC | CRC |
| CONT-A7 | Negative | Non-CRC | Non-CRC | CONT-A109 | Negative | Non-CRC | Non-CRC |
| CRC-B65 | Negative | CRC | CRC | CRC-B137 | Positive | CRC | CRC |
| CONT-A8 | Negative | Non-CRC | Non-CRC | CONT-A110 | Negative | Non-CRC | Non-CRC |
| CRC-A72 | Positive | Non-CRC | Non-CRC | CRC-A211 | — | CRC | CRC |
| CONT-A9 | Negative | Non-CRC | Non-CRC | CONT-A111 | Negative | Non-CRC | Non-CRC |
| CRC-B66 | Positive | CRC | CRC | CRC-B138 | Positive | CRC | CRC |
| CONT-A10 | Negative | Non-CRC | Non-CRC | CONT-A112 | Negative | Non-CRC | Non-CRC |
| CRC-A73 | — | CRC | CRC | CRC-A212 | — | CRC | CRC |
| CONT-A11 | Negative | Non-CRC | Non-CRC | CONT-A113 | Negative | Non-CRC | Non-CRC |
| CRC-B67 | Negative | CRC | CRC | CRC-B139 | Positive | CRC | CRC |
| CONT-A12 | Negative | Non-CRC | Non-CRC | CONT-A114 | Negative | Non-CRC | Non-CRC |
| CRC-A74 | — | CRC | CRC | CRC-A213 | — | CRC | CRC |
| CONT-A13 | Negative | Non-CRC | Non-CRC | CONT-A115 | Negative | Non-CRC | Non-CRC |
| CRC-B68 | Negative | CRC | CRC | CRC-B140 | — | CRC | CRC |
| CONT-A14 | Negative | Non-CRC | Non-CRC | CONT-A116 | Negative | Non-CRC | Non-CRC |
| CRC-A75 | — | Non-CRC | Non-CRC | CRC-A214 | — | CRC | CRC |
| CONT-A15 | Negative | Non-CRC | Non-CRC | CONT-A117 | Negative | Non-CRC | Non-CRC |
| CRC-B69 | — | CRC | CRC | CRC-B141 | Negative | CRC | CRC |
| CONT-A16 | Negative | Non-CRC | Non-CRC | CONT-A118 | Negative | Non-CRC | Non-CRC |
| CRC-A76 | Positive | CRC | CRC | CRC-A215 | Negative | CRC | CRC |
| CONT-A17 | Negative | Non-CRC | Non-CRC | CONT-A119 | Negative | Non-CRC | Non-CRC |
| CRC-B70 | Positive | CRC | CRC | CRC-B142 | Positive | CRC | CRC |
| CONT-A18 | Negative | Non-CRC | Non-CRC | CONT-A120 | — | Non-CRC | Non-CRC |
| CRC-A77 | — | CRC | CRC | CRC-A216 | Positive | CRC | CRC |
| CONT-A19 | — | Non-CRC | Non-CRC | CONT-A121 | — | Non-CRC | Non-CRC |
| CRC-B71 | — | CRC | CRC | CRC-B143 | — | CRC | CRC |

TABLE 131-continued

| | | | | | | | |
|---|---|---|---|---|---|---|---|
| CONT-A20 | Negative | Non-CRC | Non-CRC | CONT-A122 | Negative | Non-CRC | Non-CRC |
| CRC-A78 | Positive | CRC | CRC | CRC-A217 | — | CRC | CRC |
| CONT-A21 | Negative | Non-CRC | Non-CRC | CONT-A123 | Negative | Non-CRC | Non-CRC |
| CRC-B72 | Negative | CRC | CRC | | | | |
| CONT-A22 | Negative | Non-CRC | Non-CRC | CONT-A124 | Negative | Non-CRC | Non-CRC |
| CRC-A79 | Positive | Non-CRC | Non-CRC | CRC-A218 | — | CRC | CRC |
| CONT-A23 | Negative | Non-CRC | Non-CRC | CONT-A125 | Negative | Non-CRC | Non-CRC |
| CONT-A24 | Negative | Non-CRC | Non-CRC | CONT-A126 | Negative | Non-CRC | Non-CRC |
| CRC-A80 | Positive | CRC | CRC | CRC-A219 | Negative | CRC | CRC |
| CONT-A25 | Negative | Non-CRC | Non-CRC | CONT-A127 | Negative | Non-CRC | Non-CRC |
| CONT-A26 | Negative | Non-CRC | Non-CRC | CONT-A128 | Negative | Non-CRC | Non-CRC |
| CRC-A81 | Positive | Non-CRC | Non-CRC | CRC-A220 | — | CRC | CRC |
| CONT-A27 | Negative | Non-CRC | Non-CRC | CONT-A129 | Negative | Non-CRC | Non-CRC |
| CONT-A28 | Negative | Non-CRC | Non-CRC | CONT-A130 | — | Non-CRC | Non-CRC |
| CRC-A82 | — | CRC | CRC | CRC-A221 | — | CRC | CRC |
| CONT-A29 | Negative | Non-CRC | Non-CRC | CONT-A131 | Negative | Non-CRC | Non-CRC |
| CONT-A30 | Negative | Non-CRC | Non-CRC | CONT-A132 | Negative | Non-CRC | Non-CRC |
| CONT-A31 | Negative | Non-CRC | Non-CRC | CONT-A133 | Negative | Non-CRC | Non-CRC |
| CRC-A83 | Positive | CRC | CRC | CRC-A222 | Negative | CRC | CRC |
| CONT-A32 | Negative | Non-CRC | Non-CRC | CONT-A134 | — | Non-CRC | Non-CRC |
| CONT-A33 | Negative | Non-CRC | Non-CRC | CONT-A135 | — | Non-CRC | Non-CRC |
| CRC-A84 | Positive | CRC | CRC | CRC-A223 | — | CRC | CRC |
| CONT-A34 | Negative | Non-CRC | Non-CRC | CONT-A136 | Negative | Non-CRC | Non-CRC |
| CONT-A35 | Negative | Non-CRC | Non-CRC | CONT-A137 | Negative | Non-CRC | Non-CRC |
| CRC-A85 | Positive | CRC | CRC | CRC-A224 | Negative | CRC | CRC |
| CONT-A36 | Negative | Non-CRC | Non-CRC | CONT-A138 | Negative | Non-CRC | Non-CRC |
| CONT-A37 | Negative | Non-CRC | Non-CRC | CONT-A139 | Negative | Non-CRC | Non-CRC |
| CRC-A86 | Positive | CRC | CRC | CRC-A225 | — | CRC | CRC |
| CONT-A38 | Negative | Non-CRC | Non-CRC | CONT-A140 | Negative | Non-CRC | Non-CRC |
| CONT-A39 | Negative | Non-CRC | Non-CRC | CONT-A141 | Negative | Non-CRC | Non-CRC |
| CRC-A87 | — | CRC | CRC | CRC-A226 | — | CRC | CRC |
| CONT-A40 | — | Non-CRC | Non-CRC | CONT-A142 | Negative | Non-CRC | Non-CRC |
| CONT-A41 | Negative | Non-CRC | Non-CRC | CONT-A143 | Negative | Non-CRC | Non-CRC |
| CRC-A88 | Negative | CRC | CRC | CRC-A227 | — | CRC | CRC |
| CONT-A42 | Negative | Non-CRC | Non-CRC | CONT-A144 | Negative | Non-CRC | Non-CRC |
| CONT-A43 | Negative | Non-CRC | Non-CRC | CONT-A145 | Negative | Non-CRC | Non-CRC |
| CRC-A89 | — | CRC | CRC | CRC-A228 | — | CRC | CRC |
| CONT-A44 | — | Non-CRC | Non-CRC | CONT-A146 | — | Non-CRC | Non-CRC |
| CONT-A45 | Negative | Non-CRC | Non-CRC | CONT-A147 | — | Non-CRC | Non-CRC |
| CRC-A90 | Positive | CRC | CRC | CRC-A229 | Positive | CRC | CRC |
| CONT-A46 | Negative | Non-CRC | Non-CRC | CONT-A148 | Negative | Non-CRC | Non-CRC |
| CONT-A47 | Negative | Non-CRC | Non-CRC | CONT-A149 | — | Non-CRC | Non-CRC |
| CRC-A91 | Negative | CRC | CRC | CRC-A230 | Negative | CRC | CRC |
| CONT-A48 | Negative | Non-CRC | Non-CRC | CONT-A150 | Negative | Non-CRC | Non-CRC |
| CONT-A49 | Negative | Non-CRC | Non-CRC | CONT-A151 | Negative | Non-CRC | Non-CRC |
| CRC-A92 | Positive | CRC | CRC | CRC-A231 | Negative | CRC | CRC |
| CONT-A50 | Negative | Non-CRC | Non-CRC | CONT-A152 | Negative | Non-CRC | Non-CRC |
| CONT-A51 | Negative | Non-CRC | Non-CRC | CONT-A153 | — | Non-CRC | Non-CRC |
| CRC-A93 | Negative | CRC | CRC | CRC-A232 | — | CRC | CRC |
| CONT-A52 | Negative | Non-CRC | Non-CRC | CONT-A154 | Negative | Non-CRC | Non-CRC |
| CONT-A53 | Negative | Non-CRC | Non-CRC | CONT-A155 | Negative | Non-CRC | Non-CRC |
| CRC-A94 | — | CRC | CRC | CRC-A233 | Positive | CRC | CRC |
| CONT-A54 | Negative | Non-CRC | Non-CRC | CONT-A156 | Negative | Non-CRC | Non-CRC |
| CONT-A55 | Negative | Non-CRC | Non-CRC | CONT-A157 | Positive | Non-CRC | Non-CRC |
| CRC-A95 | — | CRC | CRC | CRC-A234 | Positive | CRC | CRC |
| CONT-A56 | Negative | Non-CRC | Non-CRC | CONT-A158 | Negative | Non-CRC | Non-CRC |
| CONT-A57 | Negative | Non-CRC | Non-CRC | CONT-A159 | Negative | Non-CRC | Non-CRC |
| CRC-A96 | Positive | CRC | CRC | CRC-A235 | — | CRC | CRC |

TABLE 131-continued

| | | | | | | | |
|---|---|---|---|---|---|---|---|
| CONT-A58 | Negative | Non-CRC | Non-CRC | CONT-A160 | Negative | Non-CRC | Non-CRC |
| CONT-A59 | Negative | Non-CRC | Non-CRC | CONT-A161 | Negative | Non-CRC | Non-CRC |
| CRC-A97 | Positive | CRC | CRC | CRC-A236 | Positive | CRC | CRC |
| CONT-A60 | Negative | Non-CRC | Non-CRC | CONT-A162 | Negative | Non-CRC | Non-CRC |
| CONT-A61 | Negative | Non-CRC | Non-CRC | CONT-A163 | Negative | Non-CRC | Non-CRC |
| CRC-A98 | Positive | CRC | CRC | CRC-A237 | Positive | CRC | CRC |
| CONT-A62 | Negative | Non-CRC | Non-CRC | CONT-A164 | — | Non-CRC | Non-CRC |
| CONT-A63 | Negative | Non-CRC | Non-CRC | CONT-A165 | Negative | Non-CRC | Non-CRC |
| CRC-A99 | Positive | CRC | CRC | CRC-A238 | Negative | CRC | CRC |
| CONT-A64 | Negative | Non-CRC | Non-CRC | CONT-A166 | Negative | Non-CRC | Non-CRC |
| CONT-A65 | Negative | Non-CRC | Non-CRC | CONT-A167 | Negative | Non-CRC | Non-CRC |
| CRC-A100 | Negative | CRC | CRC | CRC-A239 | Negative | Non-CRC | Non-CRC |
| CONT-A66 | Negative | Non-CRC | Non-CRC | CONT-A168 | Negative | Non-CRC | Non-CRC |
| CONT-A67 | Negative | Non-CRC | Non-CRC | CONT-A169 | Negative | Non-CRC | Non-CRC |
| CRC-A101 | — | Non-CRC | Non-CRC | CRC-A240 | Negative | CRC | CRC |
| CONT-A68 | Negative | Non-CRC | Non-CRC | CONT-A170 | Negative | Non-CRC | Non-CRC |
| CONT-A69 | Negative | Non-CRC | Non-CRC | CONT-A171 | Negative | Non-CRC | Non-CRC |
| CRC-A102 | Negative | CRC | CRC | CRC-A241 | Negative | CRC | CRC |
| CONT-A70 | Negative | Non-CRC | Non-CRC | CONT-A172 | Negative | Non-CRC | Non-CRC |
| CONT-A71 | Negative | Non-CRC | Non-CRC | CONT-A173 | Negative | Non-CRC | Non-CRC |
| CRC-A103 | Positive | CRC | CRC | CRC-A242 | — | CRC | CRC |
| CONT-A72 | Negative | Non-CRC | Non-CRC | CONT-A174 | Negative | Non-CRC | Non-CRC |
| CONT-A73 | Negative | Non-CRC | Non-CRC | CONT-A175 | Negative | Non-CRC | Non-CRC |
| CRC-A104 | Positive | CRC | CRC | CRC-A243 | — | CRC | CRC |
| CONT-A74 | Negative | Non-CRC | Non-CRC | CONT-A176 | — | Non-CRC | Non-CRC |
| CONT-A75 | Negative | Non-CRC | Non-CRC | CONT-A177 | Negative | Non-CRC | Non-CRC |
| CRC-A105 | Positive | CRC | CRC | CRC-A244 | Positive | CRC | Non-CRC |
| CONT-A76 | Negative | Non-CRC | Non-CRC | CONT-A178 | Negative | Non-CRC | Non-CRC |
| CONT-A77 | Negative | Non-CRC | Non-CRC | CONT-A179 | Negative | Non-CRC | Non-CRC |
| CRC-A106 | Negative | CRC | CRC | CRC-A245 | — | CRC | CRC |
| CONT-A78 | Negative | Non-CRC | Non-CRC | CONT-A180 | Negative | Non-CRC | Non-CRC |
| CONT-A79 | Negative | Non-CRC | Non-CRC | CONT-A181 | Negative | Non-CRC | Non-CRC |
| CRC-A107 | Positive | CRC | CRC | CRC-A246 | — | CRC | CRC |
| CONT-A80 | Negative | Non-CRC | Non-CRC | CONT-A182 | Negative | Non-CRC | Non-CRC |
| CONT-A81 | Negative | Non-CRC | Non-CRC | CONT-A183 | Negative | Non-CRC | Non-CRC |
| CRC-A108 | Positive | CRC | CRC | CRC-A247 | Negative | CRC | CRC |
| CONT-A82 | Negative | Non-CRC | Non-CRC | CONT-A184 | Negative | Non-CRC | Non-CRC |
| CONT-A83 | Negative | CRC | Non-CRC | CONT-A185 | Negative | Non-CRC | Non-CRC |
| CRC-A109 | Positive | CRC | CRC | CRC-A248 | — | Non-CRC | Non-CRC |
| CONT-A84 | Negative | Non-CRC | Non-CRC | CONT-A186 | Negative | Non-CRC | Non-CRC |
| CONT-A85 | Negative | Non-CRC | Non-CRC | CONT-A187 | Negative | Non-CRC | Non-CRC |
| CRC-A110 | Positive | CRC | CRC | CRC-A249 | — | CRC | CRC |
| CONT-A86 | Negative | Non-CRC | Non-CRC | CONT-A188 | — | Non-CRC | Non-CRC |
| CONT-A87 | Negative | Non-CRC | Non-CRC | CONT-A189 | Negative | Non-CRC | Non-CRC |
| CRC-A111 | Positive | CRC | CRC | CRC-A250 | Negative | CRC | CRC |
| CONT-A88 | Negative | Non-CRC | Non-CRC | CONT-A190 | Negative | Non-CRC | Non-CRC |
| CONT-A89 | Negative | Non-CRC | Non-CRC | CONT-A191 | Negative | Non-CRC | Non-CRC |
| CRC-A112 | — | CRC | CRC | CRC-A251 | Positive | CRC | CRC |
| CONT-A90 | Negative | Non-CRC | Non-CRC | CONT-A192 | Negative | Non-CRC | Non-CRC |
| CONT-A91 | Negative | Non-CRC | Non-CRC | CONT-A193 | Negative | Non-CRC | Non-CRC |
| CRC-A113 | Positive | CRC | CRC | CRC-A252 | Negative | CRC | CRC |
| CONT-A92 | Negative | Non-CRC | Non-CRC | CONT-A194 | Negative | Non-CRC | Non-CRC |
| CONT-A93 | Negative | Non-CRC | Non-CRC | CONT-A195 | Negative | Non-CRC | Non-CRC |
| CRC-A114 | — | CRC | CRC | CRC-A253 | Positive | CRC | CRC |
| CONT-A94 | Negative | Non-CRC | Non-CRC | CONT-A196 | Negative | Non-CRC | Non-CRC |
| CONT-A95 | — | Non-CRC | Non-CRC | CONT-A197 | Negative | Non-CRC | Non-CRC |
| CRC-A115 | Positive | CRC | CRC | CRC-A254 | Positive | CRC | CRC |
| CONT-A96 | Negative | Non-CRC | Non-CRC | CONT-A198 | Negative | Non-CRC | Non-CRC |
| CONT-A97 | Negative | Non-CRC | Non-CRC | CONT-A199 | Negative | Non-CRC | Non-CRC |
| CRC-A116 | — | CRC | CRC | CRC-A255 | Negative | Non-CRC | Non-CRC |

TABLE 131-continued

| Sample | FOBT | CRC LOME 1-104 | CRC LOME 1-104 & CRC LOME 2-23 | Sample | FOBT | CRC LOME 1-104 | CRC LOME 1-104 & CRC LOME 2-23 |
|---|---|---|---|---|---|---|---|
| CONT-A98 | Negative | Non-CRC | Non-CRC | CONT-A200 | Negative | Non-CRC | Non-CRC |
| CONT-A99 | Negative | Non-CRC | Non-CRC | CONT-A201 | Negative | CRC | Non-CRC |
| CRC-A117 | Positive | CRC | CRC | CRC-A256 | Negative | Non-CRC | Non-CRC |
| CONT-A100 | Negative | Non-CRC | Non-CRC | CONT-A202 | Negative | Non-CRC | Non-CRC |
| CONT-A101 | Negative | Non-CRC | Non-CRC | CONT-A203 | Negative | Non-CRC | Non-CRC |
| CRC-A118 | Positive | CRC | CRC | CRC-A257 | Negative | CRC | CRC |
| CONT-A102 | Negative | Non-CRC | Non-CRC | | | | |
| CONT-B1 | Negative | Non-CRC | Non-CRC | CONT-B26 | Negative | Non-CRC | Non-CRC |
| CRC-A119 | Negative | CRC | CRC | CRC-A258 | Positive | CRC | CRC |
| CONT-B2 | Negative | Non-CRC | Non-CRC | CONT-B27 | Negative | Non-CRC | Non-CRC |
| CONT-B3 | Negative | Non-CRC | Non-CRC | CONT-B28 | Negative | Non-CRC | Non-CRC |
| CONT-B4 | Negative | Non-CRC | Non-CRC | CONT-B29 | Negative | Non-CRC | Non-CRC |
| CONT-B5 | Negative | Non-CRC | Non-CRC | CONT-B30 | Negative | Non-CRC | Non-CRC |
| CRC-A120 | — | CRC | CRC | CRC-A259 | Positive | CRC | CRC |
| CONT-B6 | Negative | Non-CRC | Non-CRC | CONT-B31 | Negative | Non-CRC | Non-CRC |
| CONT-B7 | Negative | Non-CRC | Non-CRC | CONT-B32 | — | Non-CRC | Non-CRC |
| CONT-B8 | Negative | Non-CRC | Non-CRC | CONT-B33 | Negative | CRC | CRC |
| CONT-B9 | Negative | Non-CRC | Non-CRC | CONT-B34 | Negative | CRC | Non-CRC |
| CONT-B10 | Negative | Non-CRC | Non-CRC | CONT-B35 | Negative | Non-CRC | Non-CRC |
| CRC-A121 | — | CRC | CRC | CRC-A260 | — | CRC | CRC |
| CONT-B11 | Negative | Non-CRC | Non-CRC | CONT-B36 | Negative | Non-CRC | Non-CRC |
| CONT-B12 | Negative | Non-CRC | Non-CRC | CONT-B37 | Negative | Non-CRC | Non-CRC |
| CONT-B13 | Negative | Non-CRC | Non-CRC | CONT-B38 | Negative | Non-CRC | Non-CRC |
| CONT-B14 | Negative | Non-CRC | Non-CRC | CONT-B39 | Negative | Non-CRC | Non-CRC |
| CRC-A122 | Positive | CRC | Non-CRC | CRC-A261 | Negative | Non-CRC | Non-CRC |
| CONT-B15 | Negative | Non-CRC | Non-CRC | CONT-B40 | Negative | Non-CRC | Non-CRC |
| CONT-B16 | Negative | Non-CRC | Non-CRC | CONT-B41 | Negative | Non-CRC | Non-CRC |
| CONT-B17 | Negative | Non-CRC | Non-CRC | CONT-B42 | Negative | Non-CRC | Non-CRC |
| CONT-B18 | Negative | Non-CRC | Non-CRC | CONT-B43 | Negative | Non-CRC | Non-CRC |
| CRC-A123 | Positive | CRC | CRC | CRC-A262 | Negative | Non-CRC | Non-CRC |
| CONT-B19 | Negative | Non-CRC | Non-CRC | CONT-B44 | Negative | Non-CRC | Non-CRC |
| CONT-B20 | Negative | Non-CRC | Non-CRC | CONT-B45 | Negative | Non-CRC | Non-CRC |
| CONT-B21 | Negative | Non-CRC | Non-CRC | CONT-B46 | Negative | Non-CRC | Non-CRC |
| CONT-B22 | Negative | Non-CRC | Non-CRC | CONT-B47 | Negative | Non-CRC | Non-CRC |
| CRC-A124 | Positive | CRC | CRC | CRC-A263 | Negative | Non-CRC | Non-CRC |
| CONT-B23 | Negative | CRC | Non-CRC | CONT-B48 | Negative | Non-CRC | Non-CRC |
| CONT-B24 | Negative | Non-CRC | Non-CRC | CONT-B49 | Negative | Non-CRC | Non-CRC |
| CONT-B25 | Negative | Non-CRC | Non-CRC | CONT-B50 | Negative | Non-CRC | Non-CRC |
| CRC-A125 | Positive | CRC | CRC | CRC-A264 | Positive | CRC | CRC |
| CRC-A126 | Negative | CRC | CRC | CRC-A265 | Positive | CRC | CRC |
| CRC-A1 | Negative | CRC | CRC | CRC-A140 | — | CRC | CRC |
| CRC-A127 | Positive | Non-CRC | Non-CRC | CRC-A266 | Positive | CRC | CRC |
| CRC-A2 | — | CRC | CRC | CRC-A141 | Positive | CRC | CRC |
| CRC-A128 | Positive | CRC | CRC | CRC-A267 | — | CRC | CRC |
| CRC-A3 | Negative | CRC | CRC | CRC-A142 | Negative | CRC | CRC |
| CRC-A129 | — | CRC | CRC | CRC-A268 | Positive | CRC | CRC |
| CRC-A4 | Negative | CRC | CRC | CRC-A143 | — | CRC | CRC |

To investigate the reproducibility of the discrimination result according to the present invention, the same process was repeated with respect to some of the validation sets, i.e., 13 normal controls, 35 CRC patients, 7 BRC patients, 14 GC patients, 7 OVC patients, and 5 TA patients and the result is shown in Table 132. TA patient group has most reversal of the interpretation. The clinical category of Tis of TA is sometimes confusing between cancer and non-cancer, and the discrimination result according to the present invention reflect such confusion. Except for the TA patent group, reproducibility exceeds 90% which is indicative of good discrimination performance of the present invention.

TABLE 132

| | Prediction after 1st 5 times repeated Low mass ion measurements CRC LOME 1-104 & CRC LOME 2-23 | Prediction after 2nd 5 times repeated Low mass ion measurements CRC LOME 1-104 & CRC LOME 2-23 | | Prediction after 1st 5 times repeated Low mass ion measurements CRC LOME 1-104 & CRC LOME 2-23 | Prediction after 2nd 5 times repeated Low mass ion measurements CRC LOME 1-104 & CRC LOME 2-23 |
|---|---|---|---|---|---|
| CONT-B1 | Non-CRC | Non-CRC | CRC-B1 | CRC | CRC |
| CONT-B5 | Non-CRC | Non-CRC | CRC-B2 | CRC | CRC |
| CONT-B9 | Non-CRC | Non-CRC | CRC-B3 | CRC | CRC |
| CONT-B13 | Non-CRC | Non-CRC | CRC-B4 | CRC | CRC |
| CONT-B17 | Non-CRC | Non-CRC | CRC-B5 | Non-CRC | Non-CRC |
| CONT-B21 | Non-CRC | Non-CRC | CRC-B7 | Non-CRC | CRC |
| CONT-B26 | Non-CRC | Non-CRC | CRC-B8 | CRC | CRC |
| CONT-B29 | Non-CRC | Non-CRC | CRC-B9 | CRC | CRC |
| CONT-B33 | CRC | Non-CRC | CRC-B10 | Non-CRC | CRC |
| CONT-B36 | Non-CRC | Non-CRC | CRC-B11 | CRC | CRC |
| CONT-B41 | Non-CRC | Non-CRC | CRC-B12 | CRC | CRC |
| CONT-B47 | Non-CRC | Non-CRC | CRC-B13 | CRC | CRC |
| CONT-B49 | Non-CRC | Non-CRC | CRC-B15 | CRC | CRC |
| BRC-B1 | Non-CRC | Non-CRC | CRC-B16 | CRC | CRC |
| BRC-B5 | Non-CRC | Non-CRC | CRC-B18 | CRC | CRC |
| BRC-B9 | Non-CRC | Non-CRC | CRC-B19 | Non-CRC | CRC |
| BRC-B13 | Non-CRC | Non-CRC | CRC-B20 | CRC | CRC |
| BRC-B17 | Non-CRC | Non-CRC | CRC-B22 | CRC | CRC |
| BRC-B21 | Non-CRC | Non-CRC | CRC-B24 | CRC | CRC |
| BRC-B25 | Non-CRC | Non-CRC | CRC-B25 | CRC | CRC |
| GC-B1 | Non-CRC | Non-CRC | CRC-B26 | CRC | CRC |
| GC-B5 | Non-CRC | Non-CRC | CRC-B28 | CRC | CRC |
| GC-B9 | Non-CRC | Non-CRC | CRC-B29 | CRC | CRC |
| GC-B13 | Non-CRC | Non-CRC | CRC-B32 | CRC | CRC |
| GC-B17 | Non-CRC | Non-CRC | CRC-B33 | CRC | CRC |
| GC-B21 | Non-CRC | Non-CRC | CRC-B34 | CRC | CRC |
| GC-B25 | CRC | Non-CRC | CRC-B35 | CRC | Non-CRC |
| GC-B29 | Non-CRC | Non-CRC | CRC-B36 | CRC | CRC |
| GC-B33 | Non-CRC | Non-CRC | CRC-B37 | CRC | CRC |
| GC-B37 | Non-CRC | Non-CRC | CRC-B38 | Non-CRC | Non-CRC |
| GC-B41 | Non-CRC | Non-CRC | CRC-B39 | CRC | CRC |
| GC-B45 | Non-CRC | Non-CRC | CRC-B40 | CRC | CRC |
| GC-B49 | Non-CRC | Non-CRC | CRC-B41 | Non-CRC | CRC |
| GC-B53 | Non-CRC | Non-CRC | CRC-B42 | CRC | CRC |
| OVC-B1 | Non-CRC | Non-CRC | CRC-B43 | CRC | CRC |
| OVC-B5 | Non-CRC | Non-CRC | TA-B1 | CRC | Non-CRC |
| OVC-B9 | CRC | CRC | TA-B5 | CRC | Non-CRC |
| OVC-B13 | Non-CRC | Non-CRC | TA-B8 | CRC | Non-CRC |
| OVC-B17 | Non-CRC | Non-CRC | TA-B14 | CRC | Non-CRC |
| OVC-B21 | Non-CRC | Non-CRC | TA-B18 | Non-CRC | Non-CRC |
| OVC-B25 | Non-CRC | Non-CRC | | Reproducibility 90.79% (86.42%, when TA was included) | |

Figure 25A:
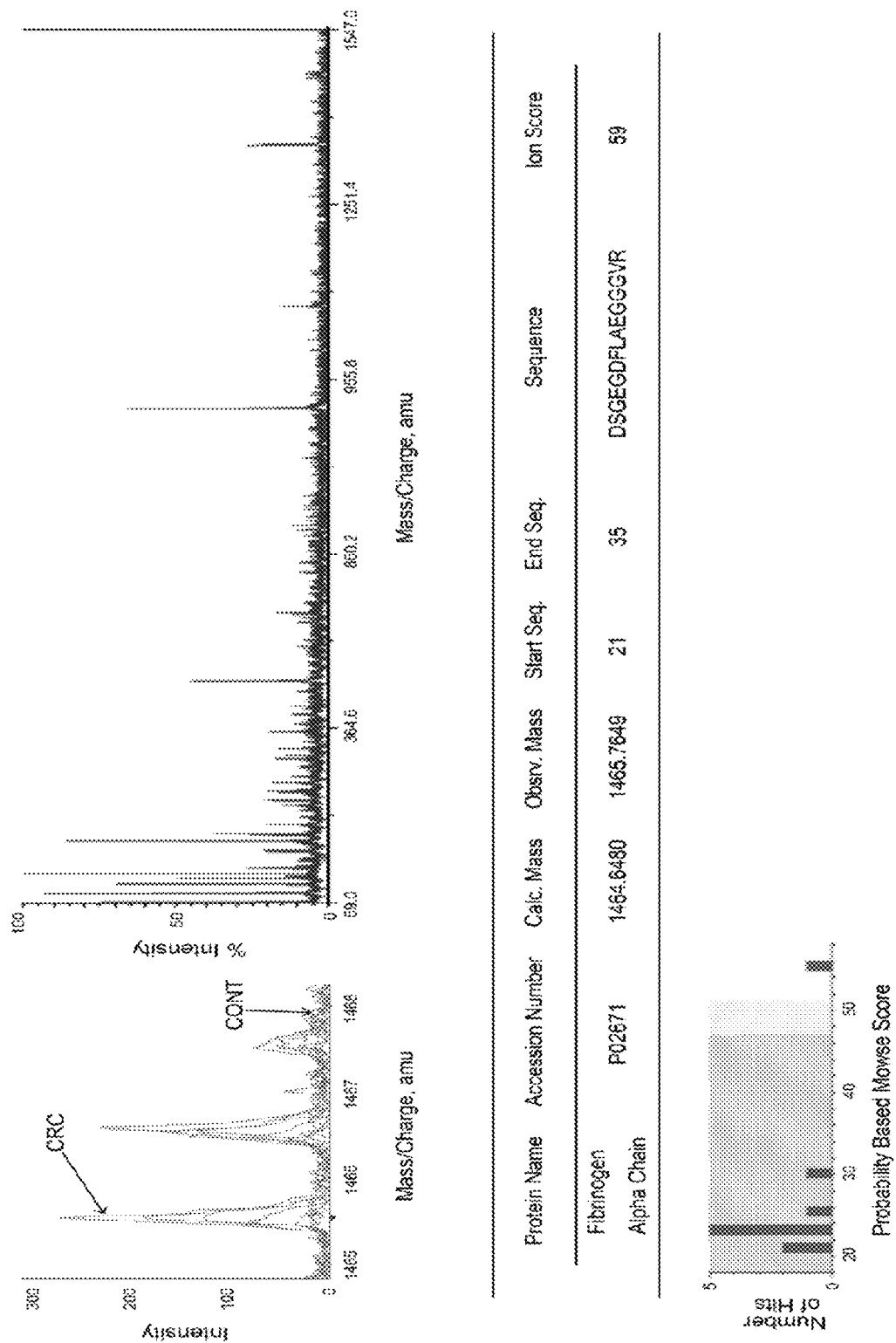
FIG. 25a is a graph presenting a characterization result of 1465.6184 m/z from among the first type CRC-diagnosing low-mass ion masses as confirmed, according to an embodiment.

FIGS. 25a and 25b present the result of characterizing 1465.6184 m/z and 2450.9701 m/z among the first type CRC-diagnosing low-mass ions. The two low-mass ions both exhibit the same material mass peak group which has a mass difference of approximately 1 m/z depending on the number of constituent isotopes. This is typical mass peaks of protein or peptide appearing in the mass spectrometer.

The left-upper sides of FIGS. 25a and 25b represent mass spectra of the two low-mass ions. The spectrum in red represents peak intensity of the CRC patient group serum extract, and the spectrum in blue represents the peak intensity of the normal control. 1465.6184 m/z shows higher peak intensity in CRC patient group, while, on the contrary, 2450.9701 m/z shows lower peak intensity in the CRC patient group. The right-upper parts of FIGS. 25a and 25b represent MS/MS spectra of the two low-mass ions, and the table of FIGS. 25a and 25b and left-lower parts thereof show that 1465.6184 m/z and 2450.9701 m/z ion materials are characterized by the MS/MS analysis into fibrinogen alpha chain and transthyretin, respectively.

Corresponding to the qualitative result that indicates higher peak intensity of the low-mass ion 1465.6184 m/z corresponding to the fibrinogen alpha chain in the CRC patient group, the quantitative measure indicates that the level of fibrinogen in blood of the CRC patient is higher than the normal counter part, and higher according to the progress of the stage (Table 133).

TABLE 133

| | Number | Plasma fibrinogen level (mg/dL), mean ± standard deviation | p-value |
|---|---|---|---|
| Healthy control | 37 | 274.51 ± 93.22 | <0.001 |
| Colorectal adenoma | 29 | 279.59 ± 58.03 | 1.000 |
| Stage I CRC | 148 | 298.93 ± 69.40 | 0.685 |
| Stage II CRC | 340 | 351.14 ± 96.65 | <0.001 |
| Stage III CRC | 507 | 345.19 ± 95.25 | <0.001 |
| Stage IV CRC | 57 | 365.33 ± 91.37 | <0.001 |

On the contrary, corresponding to the qualitative result that indicates lower peak intensity of the low-mass ion 2450.9701 m/z corresponding to transthyretin in the CRC patient group, the quantitative measure indicates that the level of transthyretin in blood of the CRC patient is lower than that of the normal counterpart (Table 134). To summarize in the form of average±standard deviation, the CRC patient group has 160.39±62.41 ng/mL, and the normal control indicates 171.19±30.86 ng/mL.

TABLE 134

| | Level of Transthyretin (ng/mL) |
|---|---|
| CRC-A134 | 194.4053871 |
| CRC-A135 | 160.3388216 |
| CRC-A137 | 45.31734887 |
| CRC-A139 | 154.2433081 |
| CRC-A140 | 201.5848401 |
| CRC-A141 | 181.6259276 |
| CRC-A142 | 181.8730938 |
| CRC-A143 | 209.4562651 |
| CRC-A144 | 204.9015183 |
| CRC-A145 | 204.8086556 |
| CRC-A146 | 151.7466189 |
| CRC-A147 | 155.5422654 |
| CRC-A148 | 241.4415416 |
| CRC-A149 | 232.1575272 |
| CRC-A150 | 178.8075456 |
| CRC-A151 | 150.5475887 |
| CRC-A152 | 150.3770739 |
| CRC-A153 | 140.3009368 |
| CRC-A154 | 146.5080959 |
| CRC-A155 | 20.11742957 |
| CRC-A156 | 148.9523525 |
| CRC-B2 | 107.8883621 |
| CRC-B4 | 176.2724527 |
| CRC-B5 | 39.91544623 |
| CRC-B6 | 156.5325266 |
| CRC-B7 | 199.4036008 |
| CRC-B10 | 145.7793662 |
| CRC-B11 | 181.4202125 |
| CRC-B12 | 158.8557207 |
| CRC-B13 | 176.0328979 |
| CRC-B14 | 209.6462481 |
| CRC-B16 | 142.1897289 |
| CRC-B18 | 224.0415149 |
| CRC-B19 | 212.08369 |
| CRC-B20 | 179.8236103 |
| CRC-B21 | 154.8387737 |
| CRC-B22 | 156.8521618 |
| CRC-B23 | 89.36660383 |
| CRC-B24 | 120.9443976 |
| CRC-B25 | 163.7544561 |
| CRC-B26 | 103.763308 |
| CRC-B27 | 272.5678515 |
| CRC-B28 | 146.0108407 |
| CRC-B29 | 157.6719758 |
| CRC-B30 | 34.24514756 |
| CRC-B32 | 209.2664543 |
| CRC-B33 | 14.23188743 |
| CRC-B34 | 170.7668514 |
| CRC-B35 | 240.8403292 |
| CRC-B46 | 314.1906603 |
| CRC-B47 | 24.56925637 |
| CRC-B48 | 201.2652628 |
| CONT-B2 | 131.7631966 |
| CONT-B3 | 185.5791386 |
| CONT-B4 | 118.2875787 |
| CONT-B5 | 134.204582 |
| CONT-B6 | 122.8785828 |
| CONT-B7 | 163.1616804 |
| CONT-B8 | 155.4717726 |
| CONT-B9 | 234.9631822 |
| CONT-B10 | 162.5710506 |
| CONT-B11 | 162.7922858 |
| CONT-B12 | 159.0358497 |
| CONT-B14 | 251.1537438 |
| CONT-B15 | 160.8484111 |
| CONT-B16 | 157.2437136 |
| CONT-B18 | 187.9070482 |
| CONT-B19 | 158.4960747 |
| CONT-B20 | 184.9911989 |
| CONT-B22 | 177.2741119 |

TABLE 134-continued

| | Level of Transthyretin (ng/mL) |
|---|---|
| CONT-B23 | 151.5403947 |
| CONT-B24 | 203.7437549 |
| CONT-B27 | 179.7828571 |
| CONT-B32 | 199.8560708 |
| CONT-B34 | 185.7895696 |
| CONT-B35 | 163.8658411 |
| CONT-B48 | 158.9637736 |
| CONT-B50 | 198.7268159 |

According to the present invention, it is possible to interpret the low-mass ion mass spectrum of the serum as CRC patient and non-CRC patent with high level of discrimination performance.

3. Example of an Apparatus for Screening Breast Cancer (BRC)

Figure 26:
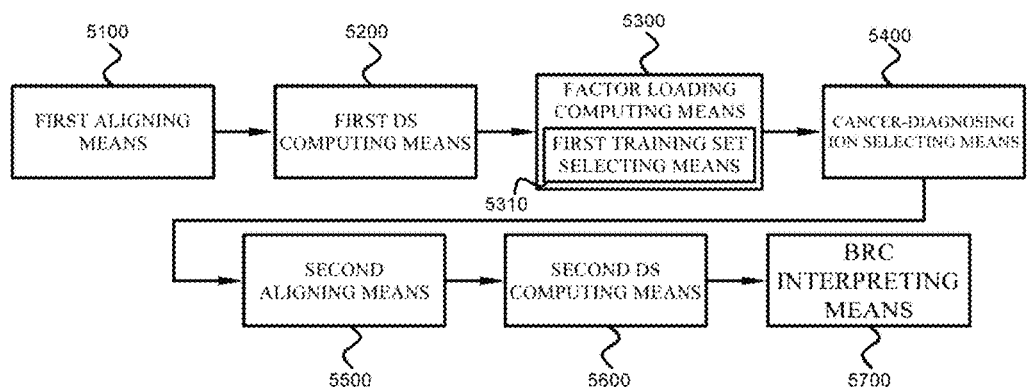

FIG. 26 is a detailed block diagram of the cancer diagnosing unit of FIG. 7 to diagnose BRC according to an embodiment of the present invention.

Referring to FIG. 26, the cancer diagnosing unit according to one embodiment may include a first aligning means 5100 which aligns a low-mass ion mass spectrum of a candidate training set consisting of the BRC patient and non-BRC cases; a first DS computing means 5200 which computes DS by conducting biostatistical analysis with respect to the aligned mass spectrum; a factor loading computing means 5300 which computes sensitivity and specificity according to DS and selects a first training set based on the computed result, and computes factor loadings per low-mass ions; a BRC diagnosing ion selecting means 5400 which selects low-mass ions for the purpose of diagnosing BRC in terms of the discrimination performance from among the candidate low-mass ions that meet candidate condition; a second aligning means which aligns the low-mass ion mass spectrum of a biological sample of interest to the first training set; a second DS computing means 5600 which computes DS based on peak intensities of the low-mass ions of interest and the factor loadings; and a BRC determining means 5700 which determines the subject of interest to be BRC positive or negative depending on the DS. The BRC diagnosing ion selecting means 5400 may divide the plurality of BRC patient and non-BRC cases into a first type discrimination case consisting of a plurality of BRC patient cases and a plurality of normal cases, a second type discrimination case consisting of the plurality of BRC patient cases and a plurality of cancer patient cases with cancers other than BRC, and executed with respect to the first and second discrimination cases, respectively, to divide the BRC-diagnosing low-mass ions into first type BRC diagnosing low-mass ions with respect to the first type discrimination case and second type BRC-diagnosing low-mass ions with respect to the second type discrimination case.

To the above-mentioned purpose, the low-mass ion detecting unit 1000 extracts mass spectrum of the low-mass ion by detecting peak intensity of the low-mass ions using mass spectrometer with respect to biological samples of a plurality of BRC patient and non-BRC cases.

The detailed components of the cancer diagnosing unit to diagnose the BRC are identical to those of the apparatus for screening cancer explained above with reference to FIGS. 9 to 13. Accordingly, the like elements will not be explained in detail below for the sake of brevity.

Referring to FIG. 26, the apparatus for screening cancer according to one embodiment may be implemented in a hardware level, or alternatively, in a software level via program structure, and the example of implementation in the software level will be explained below with reference to the flowcharts accompanied hereto, to explain diagnosing BRC with an apparatus for screening cancer according to an embodiment.

(3-1) Sample Preparation—Collecting Serums

Serums were collected from 54 BRC patients (Table 201), 49 normal controls (Table 202), 34 CRC patients (Table 205), 16 GC patients (Table 206), and 12 non-Hodgkin lymphoma (NHL) patients (Table 207) and, respectively.

TABLE 205

| CRC | Sex | Age year | Stage | Location | Cell Type | CEA ng/mL |
|---|---|---|---|---|---|---|
| CRC-C1 | F | 47 | I | S-colon | AC | 0.7 |
| CRC-C2 | F | 82 | I | A-colon | AC | 1.1 |
| CRC-C3 | F | 47 | I | Rectum | AC | 3.9 |
| CRC-C4 | F | 54 | I | Rectum | AC | 1.6 |
| CRC-C5 | F | 81 | II | S-colon | AC | 4.1 |
| CRC-C6 | F | 76 | II | Rectum | AC | 25.3 |
| CRC-C7 | F | 71 | II | A-colon | AC | 1.6 |
| CRC-C8 | F | 82 | II | S-colon | AC | 1.8 |
| CRC-C9 | F | 68 | II | D-colon | AC | 1.7 |
| CRC-C10 | F | 67 | II | A-colon | AC | 1.9 |
| CRC-C11 | F | 51 | II | Rectum | AC | 6.7 |
| CRC-C12 | F | 59 | II | A-colon | AC | 1 |
| CRC-C13 | F | 51 | II | D-colon | AC | 5.9 |
| CRC-C14 | F | 56 | III | S-colon | AC | 1.2 |
| CRC-C15 | F | 59 | III | S-colon | AC | 1.7 |
| CRC-C16 | F | 73 | III | S-colon | AC | 5.7 |
| CRC-C17 | F | 55 | III | Rectum | AC | 2.1 |
| CRC-C18 | F | 61 | III | A-colon | AC | 12.7 |
| CRC-C19 | F | 50 | III | S-colon | AC | 4.8 |
| CRC-C20 | F | 51 | III | S-colon | AC | 7 |
| CRC-C21 | F | 74 | III | T-colon | AC | 2.5 |
| CRC-C22 | F | 79 | III | Rectum | AC | 14.1 |
| CRC-C23 | F | 52 | III | S-colon | AC | 22.1 |
| CRC-C24 | F | 47 | III | S-colon | AC | 1.2 |
| CRC-C25 | F | 64 | III | S-colon | AC | 6.8 |
| CRC-C26 | F | 51 | III | S-colon | AC | 1.2 |
| CRC-C27 | F | 65 | III | D-colon | AC | 3.5 |
| CRC-C28 | F | 54 | III | S-colon | AC | 8.8 |
| CRC-C29 | F | 60 | III | S-colon, A-colon | AC | 28.5 |
| CRC-C30 | F | 70 | IV | Rectum | AC | 3.9 |
| CRC-C31 | F | 63 | IV | D-colon | AC | 12.3 |
| CRC-C32 | F | 63 | IV | A-colon | AC | 1.4 |
| CRC-C33 | F | 50 | IV | Rectum | AC | 62 |
| CRC-C34 | F | 66 | IV | S-colon | AC | 18.5 |

AC: Adenocarcinoma

TABLE 206

| GC | Sex | Age year | CEA ng/mL | Stage |
|---|---|---|---|---|
| GC-C1 | F | 62 | — | I |
| GC-C2 | F | 44 | — | I |
| GC-C3 | F | 40 | — | I |
| GC-C4 | F | 60 | 1.2 | II |
| GC-C5 | F | 57 | — | II |
| GC-C6 | F | 67 | — | II |
| GC-C7 | F | 60 | — | II |
| GC-C8 | F | 62 | 8.3 | III |
| GC-C9 | F | 47 | 2.86 | III |
| GC-C10 | F | 55 | — | III |
| GC-C11 | F | 46 | — | III |
| GC-C12 | F | 52 | 3.36 | IV |
| GC-C13 | F | 71 | 1.92 | IV |
| GC-C14 | F | 34 | 13.44 | IV |
| GC-C15 | F | 40 | — | IV |
| GC-C16 | F | 71 | — | IV |

TABLE 207

| NHL | Sex | Age year | Stage | Involved Site | Subtype | IPI |
|---|---|---|---|---|---|---|
| NHL-C1 | F | 56 | 1 | breast | DLBL | 0 |
| NHL-C2 | F | 38 | 1 | stomach | DLBL | 0 |
| NHL-C3 | F | 49 | 1 | mandibular area | DLBL | 0 |
| NHL-C4 | F | 48 | 1 | neck, submandibular | DLBL | 0 |
| NHL-C5 | F | 38 | 2 | tonsil, neck LN | DLBL | 0 |
| NHL-C6 | F | 41 | 2 | stomach | DLBL | 1 |
| NHL-C7 | F | 66 | 2 | gum, submandibular | DLBL | 1 |
| NHL-C8 | F | 73 | 3 | multiple | DLBL | 2 |
| NHL-C9 | F | 69 | 3 | multiple | ATCL | 3 |
| NHL-C10 | F | 57 | 4 | multiple | DLBL | 3 |
| NHL-C11 | F | 24 | 4 | multiple | DLBL | 4 |
| NHL-C12 | F | 76 | 4 | multiple | DLBL | 3 |

With respect to set $C_1$ consisting of 165 cases, subset $C_0$ was constructed into the first training set. The weightings (factor loadings) per mass ions were computed by the biostatistical analysis, and the preliminary discriminant was acquired. Further, the training set was enlarged to include the second training set $C_2$ consisting of the 54 BRC patients of Table 208, 46 normal controls of Table 209, 29 CRC patients of Table 210, 15 GC patients of Table 211 and 7 NHL patients of Table 212. That is, to analyze BRC-diagnosing low-mass ions according to the method explained below with respect to the preliminary candidate groups of the low-mass ions constructing the preliminary discriminant, the set C, i.e., union of set $C_1$ and set $C_2$, which are independent from each other, was used as the training set.

TABLE 208

| BRC | Sex | Age year | Node | ER | ER % | PR | PR % | HER2 | Tumor Size cm |
|---|---|---|---|---|---|---|---|---|---|
| BRC-C55 | F | 44 | pN0 | 6 | 33-66% | 7 | >66% | 1 | 1.2 |
| BRC-C56 | F | 72 | pN0(sn) | 0 | 0% | 0 | 0% | 0 | 1.8 |
| BRC-C57 | F | 48 | pN0(sn) | 5 | 33-66% | 4 | 10-33% | 1 | 0.8 |
| BRC-C58 | F | 44 | pN0 | 5 | 33-66% | 1 | >66% | 1 | 2 |
| BRC-C59 | F | 41 | pN2a | 5 | 33-66% | 6 | 33-66% | 1 | 4 |
| BRC-C60 | F | 58 | pN0 | 6 | 33-66% | 0 | 0% | 2 | <0.1 |
| BRC-C61 | F | 42 | — | 5 | 33-66% | 6 | 33-66% | 2 | — |
| BRC-C62 | F | 44 | pN1a | 4 | 10-33% | 2 | <10% | 2 | 5.5 |
| BRC-C63 | F | 62 | pN0(sn) | 7 | >66% | 0 | 0% | 0 | 2 |
| BRC-C64 | F | 47 | pN0 | 6 | 33-66% | 6 | 33-66% | 2 | 2.4 |
| BRC-C65 | F | 52 | pN1a | 6 | 33-66% | 0 | 0% | 3 | 1.8 |
| BRC-C66 | F | 44 | pN0(sn) | 6 | 33-66% | 0 | 0% | 0 | 2 |

TABLE 208-continued

| BRC | Sex | Age year | Node | ER | ER % | PR | PR % | HER2 | Tumor Size cm |
|---|---|---|---|---|---|---|---|---|---|
| BRC-C67 | F | 49 | pN0(sn) | 2 | <10% | 2 | <10% | 3 | 0.4 |
| BRC-C68 | F | 46 | pN0(sn) | 6 | 33-66% | 5 | 33-66% | 1 | 0.7 |
| BRC-C69 | F | 58 | pN0(sn) | 7 | >66% | 5 | 33-66% | 1 | 2.3 |
| BRC-C70 | F | 64 | pN1a | 6 | 33-66% | 7 | >66% | 1 | 2 |
| BRC-C71 | F | 47 | — | 6 | 33-66% | 6 | 33-66% | 2 | — |
| BRC-C72 | F | 74 | pN1a | 6 | 33-66% | 6 | 33-66% | 1 | 1.8 |
| BRC-C73 | F | 64 | pN0(sn) | 0 | 0% | 0 | 0% | 1 | 2.2 |
| BRC-C74 | F | 40 | ypN1a | 6 | 33-66% | 6 | 33-66% | 1 | 3.5 |
| BRC-C75 | F | 43 | pN0 | 6 | 33-66% | 6 | 33-66% | 2 | 2.5 |
| BRC-C76 | F | 43 | ypN0 | 0 | 0% | 0 | 0% | 2 | — |
| BRC-C77 | F | 42 | pN0 | 0 | 0% | 0 | 0% | 0 | 2.3 |
| BRC-C78 | F | 37 | pN0(i+) | 6 | 33-66% | 6 | 33-66% | 1 | 1 |
| BRC-C79 | F | 50 | pN1a | 6 | 33-66% | 6 | 33-66% | 1 | 1 |
| BRC-C80 | F | 57 | pN0(sn) | 6 | 33-66% | 96 | 33-66% | 1 | 1.4 |
| BRC-C81 | F | 38 | ypN0 | 0 | 0% | 0 | 0% | 1 | 2 |
| BRC-C82 | F | 67 | — | 6 | 33-66% | 2 | <10% | 1 | |
| BRC-C83 | F | 42 | pN0(sn) | 6 | 33-66% | 6 | 33-66% | 2 | 0.5 |
| BRC-C84 | F | 46 | pN0(sn) | 6 | 33-66% | 6 | 33-66% | 1 | 1 |
| BRC-C85 | F | 48 | pN2a | 4 | 10-33% | 4 | 10-33% | 3 | 2.5 |
| BRC-C86 | F | 58 | pN0 | 2 | <10% | 0 | 0 | 1 | 0.5 |
| BRC-C87 | F | 53 | pN0(sn) | 0 | 0% | 0 | 0% | 3 | <0.1 |
| BRC-C88 | F | 56 | — | 0 | 0% | 0 | 0% | 0 | — |
| BRC-C89 | F | 45 | pN0(sn) | 6 | 33-66% | 6 | 33-66% | 2 | <0.1 |
| BRC-C90 | F | 59 | pN0(sn) | 5 | 33-66% | 0 | 0% | 2 | 1.4 |
| BRC-C91 | F | 40 | ypN1a | 2 | <10% | 0 | 0% | 0 | 0.3 |
| BRC-C92 | F | 39 | pN1 | 7 | >95% | 3 | <10% | 0 | 2.2 |
| BRC-C93 | F | 54 | pN0(i+) | 7 | 95% | 5 | 10-30% | 1 | 1.7 |
| BRC-C94 | F | 48 | pN3a | 7 | 90% | 8 | 90% | 0 | 3.2 |
| BRC-C95 | F | 54 | pN0 | 0 | 0% | 0 | 0% | 0 | 3 |
| BRC-C96 | F | 43 | pN0 | 7 | 50-60% | 7 | 50-60% | 3 | 2.3 |
| BRC-C97 | F | 61 | pN0 | 8 | 95% | 8 | 95% | 0 | 1.6 |
| BRC-C98 | F | 54 | — | 0 | 0% | 0 | 0% | 3 | — |
| BRC-C99 | F | 46 | pN0 | 7 | 80% | 8 | 95% | 0 | 2.2 |
| BRC-C100 | F | 61 | pN0(i + 0) | 7 | >95% | 0 | 0% | 0 | 4 |
| BRC-C101 | F | 53 | pN0 | 7 | 80% | 5 | 25% | 0 | 0.6 |
| BRC-C102 | F | 49 | pN0 | 3 | 20% | 7 | 60% | 0 | 0.3 |
| BRC-C103 | F | 57 | pN0 | 0 | 0% | 0 | 0% | 0 | 0.8 |
| BRC-C104 | F | 68 | pN0 | 0 | 0% | 3 | 1% | 3 | 1.2 |
| BRC-C105 | F | 58 | pN0 | 8 | 95% | 4 | 40% | 0 | 0.8 |
| BRC-C106 | F | 40 | — | 8 | 95% | 8 | 95% | 0 | — |
| BRC-C107 | F | 29 | pN0 | 8 | 95% | 8 | 95% | 1 | 1.2 |
| BRC-C108 | F | 40 | — | — | — | — | — | — | — |

TABLE 209

| Control | Sex | Age year | CEA ng/mL |
|---|---|---|---|
| CONT-C50 | F | 40 | 1.5 |
| CONT-C51 | F | 50 | 1.9 |
| CONT-C52 | F | 64 | 2.9 |
| CONT-C53 | F | 52 | 1.9 |
| CONT-C54 | F | 37 | 2.1 |
| CONT-C55 | F | 49 | 2.6 |
| CONT-C56 | F | 30 | <0.5 |
| CONT-C57 | F | 50 | 1.2 |
| CONT-C58 | F | 49 | 2.1 |
| CONT-C59 | F | 38 | 0.6 |
| CONT-C60 | F | 59 | 1.6 |
| CONT-C61 | F | 41 | 1.8 |
| CONT-C62 | F | 48 | 1.2 |
| CONT-C63 | F | 39 | 0.5 |
| CONT-C64 | F | 51 | 1.1 |
| CONT-C65 | F | 44 | 1.5 |
| CONT-C66 | F | 38 | 1.5 |
| CONT-C67 | F | 48 | 1.9 |
| CONT-C68 | F | 70 | 4.8 |
| CONT-C69 | F | 38 | 2.8 |
| CONT-C70 | F | 50 | 1.1 |
| CONT-C71 | F | 54 | 1.8 |
| CONT-C72 | F | 38 | 0.9 |
| CONT-C73 | F | 55 | 8.8 |
| CONT-C74 | F | 51 | 2 |
| CONT-C75 | F | 64 | 1.7 |
| CONT-C76 | F | 54 | <0.5 |
| CONT-C77 | F | 59 | 0.8 |
| CONT-C78 | F | 65 | 1.6 |
| CONT-C79 | F | 68 | 1.6 |
| CONT-C80 | F | 51 | 1.7 |
| CONT-C81 | F | 62 | 1.3 |
| CONT-C82 | F | 63 | 1.6 |
| CONT-C83 | F | 60 | 1.9 |
| CONT-C84 | F | 68 | 1.4 |
| CONT-C85 | F | 62 | 1.9 |
| CONT-C86 | F | 68 | 5.6 |
| CONT-C87 | F | 53 | 2.3 |
| CONT-C88 | F | 63 | 1.1 |
| CONT-C89 | F | 46 | leiomyoma |
| CONT-C90 | F | 39 | myoma |
| CONT-C91 | F | 46 | leiomyoma |
| CONT-C92 | F | 46 | leiomyoma |
| CONT-C93 | F | 23 | leiomyoma |
| CONT-C94 | F | 38 | leiomyoma |
| CONT-C95 | F | 40 | leiomyoma |

TABLE 210

| CRC | Sex | Age year | Stage | Location | Cell Type | CEA ng/mL |
|---|---|---|---|---|---|---|
| CRC-C35 | F | 78 | I | Rectum | AC | 2.6 |
| CRC-C36 | F | 50 | I | Rectum | AC | 1.6 |
| CRC-C37 | F | 74 | I | S-colon | AC | 2.3 |
| CRC-C38 | F | 65 | II | S-colon | AC | 2.1 |
| CRC-C39 | F | 66 | II | Rectum | AC | 4.3 |
| CRC-C40 | F | 49 | II | A-colon | AC | 1.6 |
| CRC-C41 | F | 79 | II | A-colon | AC | 2.9 |
| CRC-C42 | F | 67 | II | A-colon | AC | 1.4 |
| CRC-C43 | F | 69 | II | S-colon, A-colon | AC | 5.1 |
| CRC-C44 | F | 52 | II | S-colon | AC | <0.5 |
| CRC-C45 | F | 76 | II | S-colon | AC | 2.2 |
| CRC-C46 | F | 44 | III | S-colon | AC | 1.4 |
| CRC-C47 | F | 42 | III | S-colon | AC | 0.8 |
| CRC-C48 | F | 43 | III | A-colon | AC | 4.7 |
| CRC-C49 | F | 81 | III | Rectum | AC | 8.4 |
| CRC-C50 | F | 73 | III | S-colon | AC | 1.7 |
| CRC-C51 | F | 58 | III | Rectum | AC | 21.3 |
| CRC-C52 | F | 42 | III | Rectum | AC | 0.7 |
| CRC-C53 | F | 50 | III | D-colon | AC | 6.4 |
| CRC-C54 | F | 73 | III | Rectum | AC | 3.7 |
| CRC-C55 | F | 54 | III | D-colon | AC | 1122.2 |
| CRC-C56 | F | 60 | III | A-colon | AC | 30.4 |
| CRC-C57 | F | 69 | III | Rectum | AC | 1 |
| CRC-C58 | F | 52 | III | S-colon | AC | 9.2 |
| CRC-C59 | F | 55 | III | Rectum | AC | 0.9 |
| CRC-C60 | F | 47 | III | S-colon | AC | 1.5 |
| CRC-C61 | F | 72 | IV | A-colon | AC | 73.4 |
| CRC-C62 | F | 69 | IV | A-colon | AC | 49 |
| CRC-C63 | F | 78 | IV | A-colon | AC | 12.6 |

TABLE 211

| GC | Sex | Age year | CEA ng/mL | Stage |
|---|---|---|---|---|
| GC-C17 | F | 64 | 4.16 | I |
| GC-C18 | F | 77 | — | I |
| GC-C19 | F | 74 | — | I |
| GC-C20 | F | 49 | — | II |
| GC-C21 | F | 47 | — | II |
| GC-C22 | F | 49 | — | II |
| GC-C23 | F | 64 | — | II |
| GC-C24 | F | 68 | 5.56 | III |
| GC-C25 | F | 81 | — | III |
| GC-C26 | F | 36 | — | III |
| GC-C27 | F | 42 | <0.4 | IV |
| GC-C28 | F | 57 | 6.98 | IV |
| GC-C29 | F | 40 | 0.64 | IV |
| GC-C30 | F | 52 | — | IV |
| GC-C31 | F | 33 | — | IV |

TABLE 212

| NHL | Sex | Age year | Stage | Involved Site | Subtype | IPI |
|---|---|---|---|---|---|---|
| NHL-C13 | F | 73 | 1 | nasal cavity | DLBL | 2 |
| NHL-C14 | F | 48 | 1 | breast | DLBL | 1 |
| NHL-C15 | F | 39 | 2 | tonsil, neck LN | DLBL | 0 |
| NHL-C16 | F | 61 | 2 | stomach | DLBL | 3 |
| NHL-C17 | F | 38 | 4 | multiple | DLBL | 3 |
| NHL-C18 | F | 69 | 4 | multiple | Mantle cell L | 4 |
| NHL-C19 | F | 64 | 4 | multiple | DLBL | 5 |

Further, validation set was constructed with set A and set B consisting of 53 BRC patients of Table 213, 46 normal controls of Table 214, 88 CRC patients of Table 215, 11 GC patients of Table 216, 5 NHL patents of Table 217, and 25 ovarian cancer (OVC) patients of Table 218. The OVC patients were not reflected at all when obtaining weighting per mass ions or investigating BRC-diagnosing low-mass ions, and included to see how these particular patient group IS discriminated with the discriminant constructed according to the present invention.

TABLE 213

| BRC | Sex | Age year | Node | ER | ER % | PR | PR % | HER2 | Tumor Size cm |
|---|---|---|---|---|---|---|---|---|---|
| BRC-D1 | F | 34 | pN0(sn) | 2 | <10% | 0 | 0% | 2 | 2 |
| BRC-D2 | F | 69 | — | 6 | 33-66% | 6 | 33-66% | 1 | — |
| BRC-D3 | F | 52 | — | — | — | — | — | — | — |
| BRC-D4 | F | 67 | — | — | — | — | — | — | — |
| BRC-D5 | F | 61 | — | 6 | 33-66% | 2 | <10% | 0 | — |
| BRC-D6 | F | 38 | pN1a | 6 | 33-66% | 5 | 33-66% | 1 | — |
| BRC-D7 | F | 60 | pN0 | 6 | 33-66% | 3 | 10-33% | 1 | 1 |
| BRC-D8 | F | 55 | pN2a | 5 | 33-66% | 0 | 0% | 2 | 2.2 |
| BRC-D9 | F | 46 | ypN0 | 5 | 33-66% | 2 | <10% | 1 | 1.5 |
| BRC-D10 | F | 67 | pN0 | 6 | 33-66% | 6 | 33-66% | 1 | 2.8 |
| BRC-D11 | F | 46 | pN1a | 6 | 33-66% | 6 | 33-66% | 2 | 0.7 |
| BRC-D12 | F | 39 | pN1mi | 6 | 33-66% | 6 | 33-66% | 2 | 2.5 |
| BRC-D13 | F | 50 | pN0(sn) | 4 | 10-33% | 5 | 33-66% | 0 | 1 |
| BRC-D14 | F | 31 | pN1mi(sn) | 6 | 33-66% | 6 | 33-66% | 1 | 1 |
| BRC-D15 | F | 46 | pN0 | 6 | 33-66% | 7 | >66% | 1 | 1.2 |
| BRC-D16 | F | 44 | pN0(sn) | 6 | 33-66% | 7 | >66% | 1 | 2.5 |
| BRC-D17 | F | 40 | pN0 | 0 | 0% | 0 | 0% | 0 | — |
| BRC-D18 | F | 40 | — | 6 | 33-66% | 6 | 33-66% | 1 | — |
| BRC-D19 | F | 56 | — | 7 | >66% | 0 | 0 | 0 | 0.6 |
| BRC-D20 | F | 48 | pN1a | 0 | 0% | 0 | 0% | 0 | 3 |
| BRC-D21 | F | 39 | pN0(sn) | 6 | 33-66% | 6 | 33-66% | 1 | 3.5 |
| BRC-D22 | F | 40 | ypN1a | 6 | 33-66% | 4 | 10-33% | 2 | 3 |
| BRC-D23 | F | 48 | pN0(sn) | 6 | 33-66% | 6 | 33-66% | 0 | 2.5 |
| BRC-D24 | F | 59 | — | 7 | >66% | 2 | <10% | 1 | — |
| BRC-D25 | F | 46 | — | 0 | 0% | 0 | 0% | 2 | — |
| BRC-D26 | F | 37 | pN3a | 6 | 33-66% | 6 | 33-66% | 2 | 0.6 |
| BRC-D27 | F | 38 | pN0(sn) | 6 | 33-66% | 6 | 33-66% | 2 | 0.3 |
| BRC-D28 | F | 66 | pN1a | 6 | 33-66% | 6 | 33-66% | 0 | 1.5 |

TABLE 213-continued

| BRC | Sex | Age year | Node | ER | ER % | PR | PR % | HER2 | Tumor Size cm |
|---|---|---|---|---|---|---|---|---|---|
| BRC-D29 | F | 58 | pN0(sn) | 0 | 0% | 0 | 0% | 2 | 1.7 |
| BRC-D30 | F | 42 | pN3a | 5 | 33-66% | 6 | 33-66% | 0 | 1.8 |
| BRC-D31 | F | 52 | pN0 | 6 | 33-66% | 6 | 33-66% | 0 | 0.7 |
| BRC-D32 | F | 46 | pN0(sn) | 0 | 0% | 2 | <10% | 1 | 1.5 |
| BRC-D33 | F | 42 | pN0(sn) | 4 | 10-33% | 6 | 33-66% | 1 | 0.6 |
| BRC-D34 | F | 48 | — | — | — | — | — | — | — |
| BRC-D35 | F | 47 | pN0 | 6 | 33-66% | 2 | <10% | 2 | 3 |
| BRC-D36 | F | 59 | pN1a | 6 | 33-66% | 4 | 10-33% | 1 | 1.8 |
| BRC-D37 | F | 56 | — | 0 | 0% | 0 | 0% | 3 | — |
| BRC-D38 | F | 61 | pN0(i + 0) | 7 | >95% | 0 | 0% | 0 | 4 |
| BRC-D39 | F | 40 | — | 8 | 95% | 8 | 95% | 0 | — |
| BRC-D40 | F | 43 | pN0 | 0 | 0% | 0 | 0% | 3 | 0.7 |
| BRC-D41 | F | 59 | pN0 | 8 | 95% | 8 | 95% | 0 | 1.2 |
| BRC-D42 | F | 45 | PN2 | 7 | 95% | 8 | 95% | 1 | 2.1 |
| BRC-D43 | F | 55 | pN0 | 0 | 0% | 0 | 0% | 3 | 1.8 |
| BRC-D44 | F | 52 | pN0 | 7 | 80-90% | 8 | 80-90% | 0 | 0.3 |
| BRC-D45 | F | 59 | pN0 | 8 | 95% | 5 | 2~3% | 1 | 1.3 |
| BRC-D46 | F | 39 | — | 7 | >95% | 7 | 70-80% | 0 | — |
| BRC-D47 | F | 39 | pN0 | 0 | 0% | 0 | 0% | 3 | 1.1 |
| BRC-D48 | F | 40 | pN0 | 5 | 50-60% | 5 | 20-30% | 0 | 0.8 |
| BRC-D49 | F | 46 | pN0 | 7 | 95% | 8 | 95% | 0 | 4.9 |
| BRC-D50 | F | 51 | pN0 | 0 | <1% | 0 | 0% | 0 | 0.9 |
| BRC-D51 | F | 61 | pN0 | 7 | 90% | 8 | 90% | 0 | 1.3 |
| BRC-D52 | F | 48 | pN0 | 0 | 0% | 0 | 0% | 0 | 0.6 |
| BRC-D53 | F | 47 | pN0 | 8 | >95% | 8 | 95% | 0 | 0.7 |

TABLE 214

| Control | Sex | Age year | CEA ng/mL |
|---|---|---|---|
| CONT-D1 | F | 44 | — |
| CONT-D2 | F | 45 | — |
| CONT-D3 | F | 54 | — |
| CONT-D4 | F | 51 | 3.1 |
| CONT-D5 | F | 55 | <0.5 |
| CONT-D6 | F | 46 | <0.5 |
| CONT-D7 | F | 34 | 0.6 |
| CONT-D8 | F | 58 | 1.5 |
| CONT-D9 | F | 54 | — |
| CONT-D10 | F | 34 | <0.5 |
| CONT-D11 | F | 45 | 0.8 |
| CONT-D12 | F | 44 | — |
| CONT-D13 | F | 46 | — |
| CONT-D14 | F | 54 | 2.3 |
| CONT-D15 | F | 39 | 1.3 |
| CONT-D16 | F | 55 | 1.3 |
| CONT-D17 | F | 46 | — |
| CONT-D18 | F | 45 | — |
| CONT-D19 | F | 63 | — |
| CONT-D20 | F | 51 | — |
| CONT-D21 | F | 52 | — |
| CONT-D22 | F | 52 | — |
| CONT-D23 | F | 70 | — |
| CONT-D24 | F | 51 | 2 |
| CONT-D25 | F | 68 | 1.4 |
| CONT-D26 | F | 52 | 1.5 |
| CONT-D27 | F | 63 | 1.8 |
| CONT-D28 | F | 65 | 1.1 |
| CONT-D29 | F | 55 | 4.8 |
| CONT-D30 | F | 52 | 4.1 |
| CONT-D31 | F | 64 | <0.5 |
| CONT-D32 | F | 63 | 2.2 |
| CONT-D33 | F | 62 | 1.1 |
| CONT-D34 | F | 53 | 0.7 |
| CONT-D35 | F | 65 | 3.8 |
| CONT-D36 | F | 64 | 1.5 |
| CONT-D37 | F | 53 | 1 |
| CONT-D38 | F | 66 | 1.7 |
| CONT-D39 | F | 50 | 1.9 |
| CONT-D40 | F | 70 | pelic organ prolapse |
| CONT-D41 | F | 44 | leiomyoma |
| CONT-D42 | F | 70 | pelic organ prolapse |
| CONT-D43 | F | 53 | leiomyoma |
| CONT-D44 | F | 34 | leiomyoma |
| CONT-D45 | F | 44 | leiomyoma |
| CONT-D46 | F | 41 | leiomyoma, adenomyosis |

TABLE 215

| CRC | Sex | Age year | Stage | Location | Cell Type | CEA ng/mL |
|---|---|---|---|---|---|---|
| CRC-D1 | F | 59 | I | Rectum | AC | 1.6 |
| CRC-D2 | F | 46 | I | S-colon | AC | 1.4 |
| CRC-D3 | F | 67 | II | A-colon | AC | 7.3 |
| CRC-D4 | F | 75 | II | Rectum | AC | 12.6 |
| CRC-D5 | F | 60 | II | S-colon | AC | 3.3 |
| CRC-D6 | F | 66 | II | S-colon | AC | 4.2 |
| CRC-D7 | F | 81 | II | S-colon | AC | 2.4 |
| CRC-D8 | F | 77 | II | Rectum | AC | 6.2 |
| CRC-D9 | F | 82 | II | A-colon | AC | 2.8 |
| CRC-D10 | F | 58 | III | S-colon | AC | 2.1 |
| CRC-D11 | F | 65 | III | S-colon | MAC | 2.7 |
| CRC-D12 | F | 51 | III | Rectum | AC | 1.4 |
| CRC-D13 | F | 48 | III | A-colon | AC | 0.9 |
| CRC-D14 | F | 54 | III | A-colon | AC | 1.7 |
| CRC-D15 | F | 49 | III | S-colon | AC | 1 |
| CRC-D16 | F | 63 | III | A-colon | AC | 58.2 |
| CRC-D17 | F | 54 | III | T-colon | AC | 2.2 |
| CRC-D18 | F | 70 | III | S-colon | MAC | 36 |
| CRC-D19 | F | 54 | III | Rectum | AC | 5.5 |
| CRC-D20 | F | 52 | III | A-colon | AC | 1.2 |
| CRC-D21 | F | 71 | III | A-colon | AC | 2.8 |
| CRC-D22 | F | 33 | III | D-colon | AC | 4.7 |
| CRC-D23 | F | 68 | III | Rectum | AC | 3.3 |
| CRC-D24 | F | 61 | III | A-colon | AC | 2.8 |
| CRC-D25 | F | 54 | IV | S-colon | AC | 29.8 |
| CRC-D26 | F | 52 | IV | A-colon | MAC | 9 |
| CRC-D27 | F | 54 | IV | S-colon | AC | 27.9 |
| CRC-D28 | F | 59 | III | Rectum | AC | 1.4 |
| CRC-D29 | F | 75 | II | Rectum | AC | 2.4 |

TABLE 215-continued

| CRC | Sex | Age year | Stage | Location | Cell Type | CEA ng/mL |
|---|---|---|---|---|---|---|
| CRC-D30 | F | 68 | II | Rectum | AC | 0.7 |
| CRC-D31 | F | 56 | I | Rectum | AC | 2.3 |
| CRC-D32 | F | 45 | II | Rectum | AC | 2.7 |
| CRC-D33 | F | 49 | II | Rectum | AC | 2.1 |
| CRC-D34 | F | 45 | 0 | Rectum | AC | 0.9 |
| CRC-D35 | F | 54 | 0 | Rectum | AC | 3.6 |
| CRC-D36 | F | 71 | III | Rectum | AC | 6.7 |
| CRC-D37 | F | 56 | III | Rectum | AC | 1 |
| CRC-D38 | F | 69 | I | Rectum | AC | 1.5 |
| CRC-D39 | F | 71 | III | Rectum | AC | 1.8 |
| CRC-D40 | F | 51 | I | Rectum | AC | 1.5 |
| CRC-D41 | F | 67 | III | Rectum | AC | 3.4 |
| CRC-D42 | F | 76 | III | Rectum | AC | 1 |
| CRC-D43 | F | 38 | III | Rectum | AC | 0.7 |
| CRC-D44 | F | 50 | III | Rectum | AC | 2.2 |
| CRC-D45 | F | 49 | 0 | Rectum | AC | 1.6 |
| CRC-D46 | F | 42 | III | Rectum | AC | 9.9 |
| CRC-D47 | F | 72 | II | Rectum | AC | 8 |
| CRC-D48 | F | 69 | III | Rectum | AC | 11.3 |
| CRC-D49 | F | 71 | III | Rectum | AC | 1.3 |
| CRC-D50 | F | 60 | — | Rectum | AC | 1.2 |
| CRC-D51 | F | 56 | III | Rectum | AC | 2.3 |
| CRC-D52 | F | 68 | — | Rectum | AC | 2 |
| CRC-D53 | F | 41 | III | Rectum | AC | 1.5 |
| CRC-D54 | F | 34 | III | Rectum | AC | 5.2 |
| CRC-D55 | F | 52 | II | Rectum | AC | 1.6 |
| CRC-D56 | F | 67 | 0 | Rectum | AC | 4.4 |
| CRC-D57 | F | 66 | II | Rectum | AC | 4.8 |
| CRC-D58 | F | 61 | III | A-colon | AC | 30.4 |
| CRC-D59 | F | 71 | III | Rectum | AC | 1 |
| CRC-D60 | F | 53 | II | S-colon | AC | 1.3 |
| CRC-D61 | F | 77 | II | S-colon | AC | 2.2 |
| CRC-D62 | F | 71 | III | S-colon | MAC | 36 |
| CRC-D63 | F | 79 | II | Rectum | AC | 6.2 |
| CRC-D64 | F | 53 | III | A-colon | AC | 1.2 |
| CRC-D65 | F | 72 | III | A-colon | AC | 2.8 |
| CRC-D66 | F | 34 | III | D-colon | AC | 4.7 |
| CRC-D67 | F | 62 | III | A-colon | AC | 2.8 |
| CRC-D68 | F | 84 | II | A-colon | AC | 2.8 |
| CRC-D69 | F | 71 | II | S-colon | AC | 15.3 |
| CRC-D70 | F | 56 | I | S-colon | AC | 0.7 |
| CRC-D71 | F | 70 | II | S-colon | AC | 1.4 |
| CRC-D72 | F | 62 | III | Rectum | AC | 235.4 |
| CRC-D73 | F | 52 | III | S-colon | AC | 6.4 |
| CRC-D74 | F | 61 | III | T-colon | AC | 13.9 |
| CRC-D75 | F | 88 | II | A-colon | AC | 3 |
| CRC-D76 | F | 73 | I | D-colon, T-colon | AC | 2 |
| CRC-D77 | F | 69 | I | A-colon | AC | 5 |
| CRC-D78 | F | 69 | I | A-colon | AC | 5.7 |
| CRC-D79 | F | 74 | II | D-colon | AC | 12.5 |
| CRC-D80 | F | 75 | II | Rectum | AC | 0.9 |
| CRC-D81 | F | 57 | I | A-colon | AC | 1.5 |
| CRC-D82 | F | 62 | III | S-colon | AC | 4.4 |
| CRC-D83 | F | 74 | III | Rectum | AC | 31 |
| CRC-D84 | F | 70 | I | A-colon | AC | 2.5 |
| CRC-D85 | F | 70 | II | A-colon | AC | 5.9 |
| CRC-D86 | F | 77 | II | S-colon | AC | 1.5 |
| CRC-D87 | F | 62 | III | Rectum | AC | 13.7 |
| CRC-D88 | F | 45 | 0 | Rectum | AC | — |

MAC: Mucinous adenocarcinoma

TABLE 216

| GC | Sex | Age year | CEA ng/mL | Stage |
|---|---|---|---|---|
| GC-D1 | F | 81 | — | I |
| GC-D2 | F | 55 | — | I |
| GC-D3 | F | 40 | — | II |
| GC-D4 | F | 52 | — | II |
| GC-D5 | F | 81 | — | II |
| GC-D6 | F | 80 | — | III |
| GC-D7 | F | 81 | — | III |
| GC-D8 | F | 51 | 0.51 | IV |
| GC-D9 | F | 43 | 1.62 | IV |
| GC-D10 | F | 57 | 2.46 | IV |
| GC-D11 | F | 52 | — | IV |

TABLE 217

| NHL | Sex | Age year | Stage | Involved Site | Subtype | IPI |
|---|---|---|---|---|---|---|
| NHL-D1 | F | 41 | 1 | 0 | DLBL | 0 |
| NHL-D2 | F | 72 | 1 | stomach | DLBL | 2 |
| NHL-D3 | F | 76 | 2 | stomach | DLBL | 1 |
| NHL-D4 | F | 70 | 4 | multiple | DLBL | 3 |
| NHL-D5 | F | 48 | 4 | multiple | DLBL | 3 |

TABLE 218

| OVC | Age year | Histology | Stage |
|---|---|---|---|
| OVC-D1 | 56 | IIIc | Clear cell carcinoma |
| OVC-D2 | 52 | IIa | Endometrioid adenocarcinoma |
| OVC-D3 | 63 | IV | Papillary serous adenocarcinoma |
| OVC-D4 | 55 | Ia | Malignant Brenner tumor |
| OVC-D5 | 47 | IIIc | Papillary serous adenocarcinoma |
| OVC-D6 | 50 | Ic | Clear cell carcinoma |
| OVC-D7 | 68 | Ib | Serous adenocarcinoma |
| OVC-D8 | 74 | IIIc | Papillary serous adenocarcinoma |
| OVC-D9 | 43 | Ic | Mucinous adenocarcinoma |
| OVC-D10 | 44 | IIIc | Papillary serous adenocarcinoma |
| OVC-D11 | 54 | IIIc | Papillary serous adenocarcinoma |
| OVC-D12 | 55 | IV | Serous adenocarcinoma |
| OVC-D13 | 72 | IIIc | Serous adenocarcinoma |
| OVC-D14 | 58 | IIIc | Mucinous adenocarcinoma |
| OVC-D15 | 44 | IIIc | Papillary serous adenocarcinoma |
| OVC-D16 | 57 | IV | Serous adenocarcinoma |
| OVC-D17 | 54 | IIIc | Papillary serous adenocarcinoma |
| OVC-D18 | 73 | IIIc | Serous adenocarcinoma |
| OVC-D19 | 47 | IIIc | Papillary serous adenocarcinoma |
| OVC-D20 | 40 | Ic | Papillary serous adenocarcinoma |
| OVC-D21 | 74 | IIb | Transitional cell carcinoma |
| OVC-D22 | 65 | IIIc | Papillary serous adenocarcinoma |
| OVC-D23 | 47 | IV | Serous adenocarcinoma |
| OVC-D24 | 58 | IIc | Serous adenocarcinoma |
| OVC-D25 | 57 | Ib | Mixed cell adenocarcinoma |

(3-2) Sample Preparation—Preparing Serum and Measuring Mass Spectrum

4× volume of methanol/chloroform (2:1, v/v) was mixed with 250 serum violently and incubated at room temperature for 10 min. The mixture was centrifuged at 4° C., 10 min, 6000×g. The supernatant was completely dried for 1 h in the concentrator, and dissolved in the vortexer in 30 μl of 50% acetonitrile/0.1% trifluoroacetic acid (TFA).

Methanol/chloroform extract was mixed with a-cyano-4-hydroxycinnamic acid solution in 50% acetonitrile/0.1% TFA (1:12, v/v), and 1 μl mixture was placed on MALDI-target plate. The mass spectra of the serum extracts from the BRC patients and normal subjects were measured using the Proteomics Analyzer (Applied Biosystems, Foster City, Calif., USA).

The mass spectrum data for one sample is extracted based on the average of spectrum which was repeatedly measured 20 times. The mass region of the entire individual samples was adjusted so that the maximum mass was set at approximately 2500 m/z. To minimize experimental error, various factors including focus mass, laser intensity, target plate, data acquisition time were taken into consideration.

The focus mass and the laser intensity were fixed at preferable levels, i.e., 500 m/z and 5000, respectively. In addition to the fixed focus mass and the laser intensity, the entire samples were repeatedly measured at least five times under viewpoint of other extraction and other data collection. The set $C_1$, from which weightings per mass ions were computed, was measured one more time.

Accordingly, the low-mass ion detecting means 5000 extracted the low-mass ion mass spectrum from the serum sample via the processes explained above, using the MALDI-TOF.

(3-3) Discrimination Strategy

In order for the constructed discriminant to be BRC specific, the discriminant is required to discriminate the BRC patient group from not only the normal control, but also the patient groups with other cancer types. In one embodiment, the patient groups with other cancer types include CRC patients, GC patients and NHL patients. Table 219 provides the result of implementing the conventional PCA-DA to investigate whether one discriminant can discriminate the BRC patient group from the non-BRC group (normal controls, CRC patient group, GC patient group and NHL patient group). Although the result of discrimination was not as perfect as that of Table 204, the discrimination performance was generally as high as 80% or above. This reveals the fact that one discriminant can discriminate the BRC patient group from all the non-BRC groups.

TABLE 219

| Set $C_1$ | True BRC | True Non-BRC | | | |
|---|---|---|---|---|---|
| | | CONT | CRC | GC | NHL |
| Predicted BRC | 54 | 5 | 3 | 2 | 2 |
| Predicted Non-BRC | 0 | 44 | 31 | 14 | 10 |
| Sensitivity | | | | 100.0% | |
| Specificity | | CONT | | 89.80% | |
| | | CRC | | 91.18% | |
| | | GC | | 87.50% | |
| | | NHL | | 83.33% | |

Figure 4:
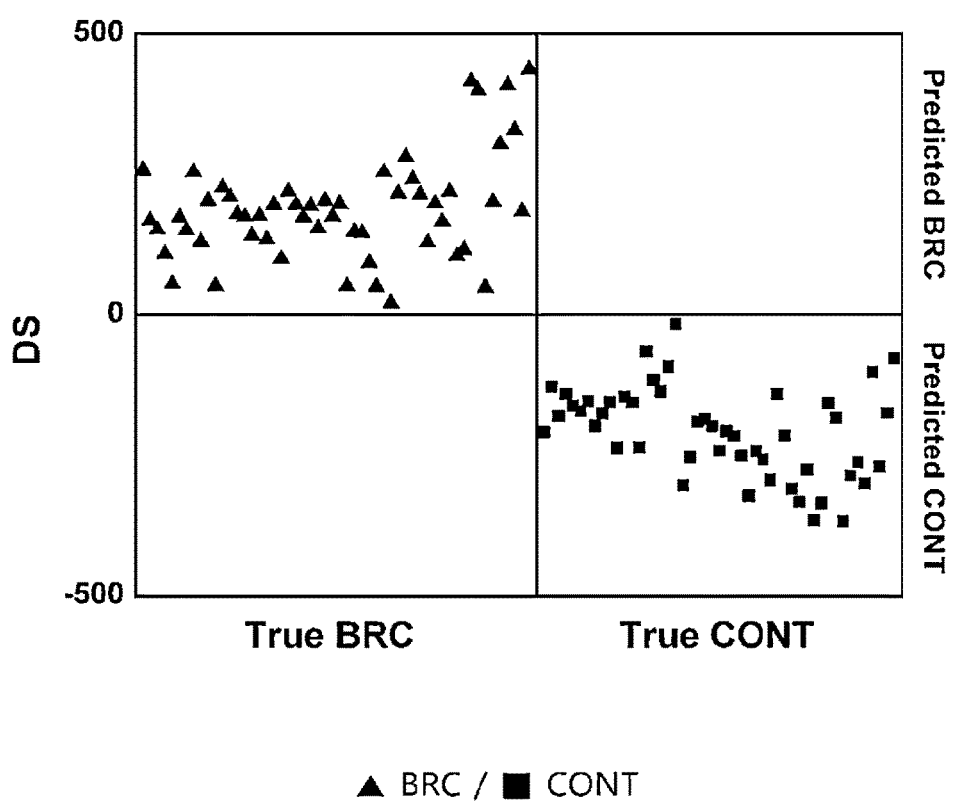
Figure 5:
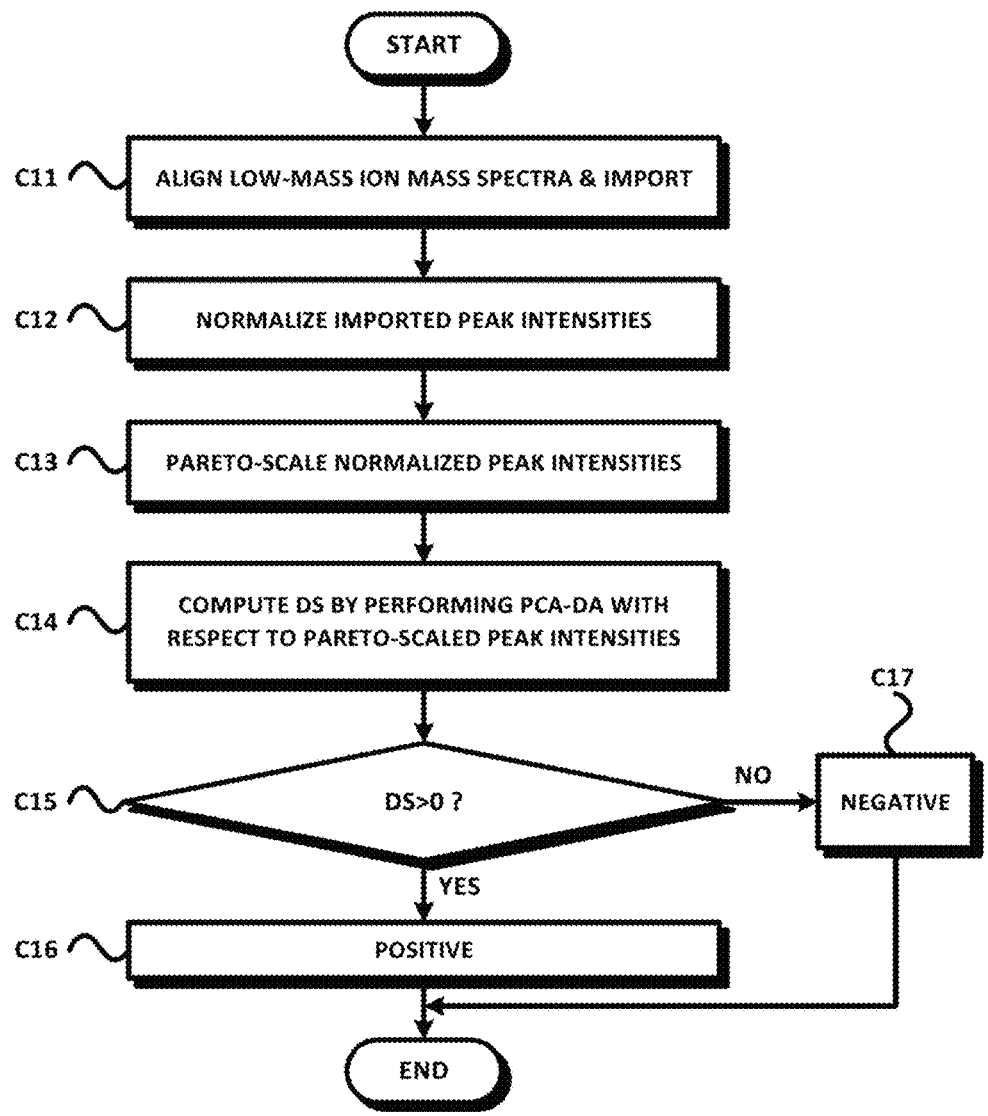

Referring to FIG. 4 and Table 204, considering the perfect discrimination result of the BRC patient group from the normal controls, it was also investigated if the BRC patient group was discriminated from the patient groups with other cancer types, and the result is provided by Table 220. The discrimination result was good overall, considering that no presence of false negative case and presence of only one false positive case.

TABLE 220

| Set $C_1$ | True BRC | True Non-BRC | | |
|---|---|---|---|---|
| | | CRC | GC | NHL |
| Predicted BRC | 54 | 0 | 1 | 0 |
| Predicted Non-BRC | 0 | 34 | 15 | 12 |

TABLE 220-continued

| Sensitivity | | 100.0% |
|---|---|---|
| Specificity | CRC | 100.0% |
| | GC | 93.75% |
| | NHL | 100.0% |
| | Total | 98.39% |

Accordingly, discriminating the BRC patient group from the non-BRC patient groups may implement one discriminant or two discriminants as explained detail in the Examples provided below. A first type discriminant may be used to discriminate BRC patient group from non-patient group. A second discriminant may be used to discriminate the BRC patient group from the normal controls, with a third discriminant which may be used to discriminate the BRC patient group from non-BRC patient groups with other types of cancers, in which the BRC patient is determined if both discriminants indicate BRC, while the non-BRC patient is determined if any of the two discriminants indicates non-BRC patient.

(3-4) Selecting First Training Set $C_0$ and Computing Weightings Per Mass Ions

Although the result of discrimination of Tables 219 and 220 are good, the sensitivity and the specificity are not always 100%. In one embodiment of the present invention, the first training set $C_0$ with predetermined sensitivity and specificity is selected, and weightings per mass ions of the first training set $C_0$ were computed, in which the predetermined sensitivity and specificity were both 100%.

Figure 27:
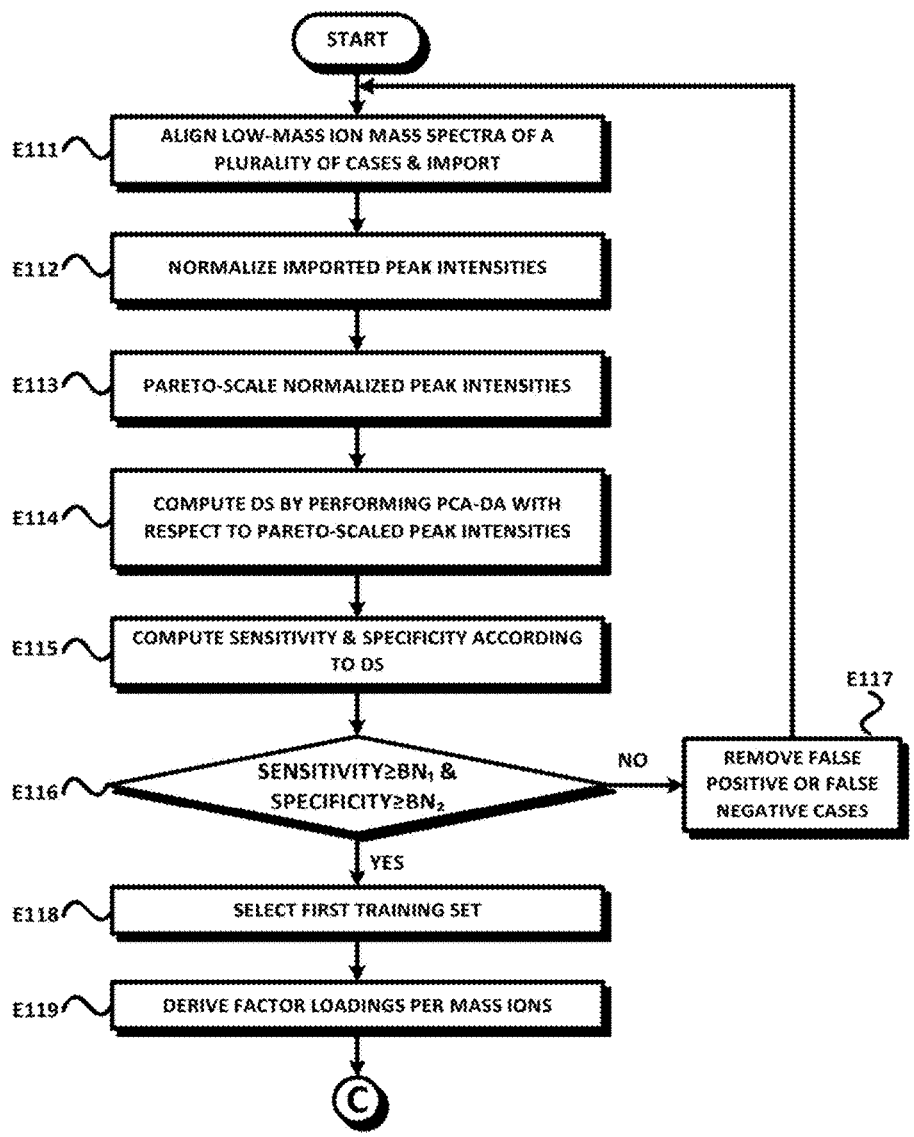

A method for selecting the first training set $C_0$ with the predetermined sensitivity and specificity will be explained below with reference to FIG. 27.

The first DS computing means 5200 aligned and imported the low-mass ion mass spectra of the BRC patient group and the normal control group of set $C_1$ (E111), normalized the imported peak intensities (E112), Pareto-scaled the normalized peak intensities (E113), and computed DS by performing biostatistical analysis with respect to the Pareto-scaled peak intensities (E114).

Among a variety of biostatistical analyzing methods that can be implemented to compute DS, in one embodiment, the PCA-DA was performed. Sensitivity and specificity were computed based on the DS (E115) and the result is shown in Table 219.

Next, sensitivity threshold $BN_1$ and specificity threshold $BN_2$ were set (E116), and false positive or false negative cases were excluded when the sensitivity or the specificity was less than the corresponding threshold (E117).

In one embodiment, both the sensitivity threshold $BN_1$ and the specificity threshold $BN_2$ were set to 1, to thus find the first training set $C_{01}$ with both the sensitivity and the specificity being 100%. That is, steps E111 to E115 were performed again with respect to the set from which 12 false positive cases and 12 false negative cases in Table 219 were excluded. The sensitivity and the specificity did not directly reach 100% when the steps E111 to E115 were repeated with respect to the set excluding the false positive and false negative cases. That is, the first training set $C_{01}$ with both the sensitivity and the specificity being 100% was found after the steps E111 to E117 were repeated predetermined number of times (E118).

The first type discriminant to discriminate BRC patient group from the normal controls reached the first training set $C_{01}$ when 15 false positive cases (7 CONT, 3 CRC, 2 GC, 3 NHL) were excluded, and the third type discriminant to discriminate BRC patient group from the patient groups with other types of cancer reached the first training set $C_{03}$ when 1 false positive case (1 GC) was excluded, with both the sensitivity and specificity reaching 100%.

The training set $C_{02}$ was used as is, i.e., without excluding cases, because the second type discriminant to distinguish BRC patient group from the normal controls already provides 100% sensitivity and specificity. Through this process, it is possible to derive factor loadings per mass ions which provide discrimination result with both 100% sensitivity and specificity (E119).

The series of the processes explained above may be performed at the factor loading computing means 5300.

(3-5) Implementing a Discriminant

The process of implementing the constructed discriminant on the sample of interest will be explained below.

First, MarkerView™ supports the function that can be used for the similar purpose. That is, it is possible to apply the PCA-DA on only the part of the imported sample data, and discriminate the rest samples using the discriminant constructed as a result. According to this function, it is possible to select only the first training set after the import of the first training set and the other samples for analysis so that only the first training set undergoes the PCA-DA to show how the samples for analysis are interpreted.

Meanwhile, the peak alignment function to align the peaks is performed in the import process of MarkerView™. Because there is no function to align the peaks of the samples of interest based on the first training set, the peak table (matrix of m/z rows and rows of peak intensities per samples) obtained when only the first training set is imported, does not match the first training set of the peak table which is generated when the first training set is imported together with the samples of interest. The peak intensity matrices are difference, and the m/z values corresponding to the same peak intensity column also do not always appear the same. Accordingly, in order to compute DS by implementing the discriminant constructed from the first training set on the samples of interest, a realignment operation to realign the peak table, generated when the first training set is imported together with the samples of interest, to the peak table generated when only the first training set is imported.

The misalignment becomes more serious, if several samples of interests are imported together with the first training set. Accordingly, in one embodiment, with respect to the entire samples of interest, one sample of interest is added to the first training set to be imported, realigned, normalized and Pareto-scaled.

The embodiment will be explained in greater detail below with reference to FIG. 28.

First, the low-mass ion mass spectra of the samples of interest were aligned with the first training set and imported (E211).

Meanwhile, since MarkerView™ in one embodiment does not support the function of aligning and importing the sample of interest to the first training set, as explained above, a program may be designed to realign the peak table generated after importing the low-mass ion mass spectrum of the sample of interest together with the first training set to the peak table which is generated after importing the first training set only, so that the low-mass ion mess spectrum of the sample of interest aligned with the first training set is extracted. However, it is more preferable that the sample of interest is directly aligned and imported to the first training set without having realigning process and this is implementable by designing a program.

Next, the imported peak intensities were normalized (E212), and the normalized peak intensities were Pareto-scaled (E213).

Next, discriminant score was computed using the Pareto-scaled peak intensities of the low-mass ions and the factor loadings per mass ions acquired by the PCA-DA (E214).

It is determined whether or not the computed DS exceeds a reference BS (E215), and if so, it is interpreted positive (E216), while it is interpreted negative if the computed DS is less than the reference BS (E217). In one embodiment, the reference BS may preferably be 0.

The series of processes explained above may be performed at the second aligning means 5500, the second DS computing means 5600 and a BRC determining means 5700.

Figure 29:
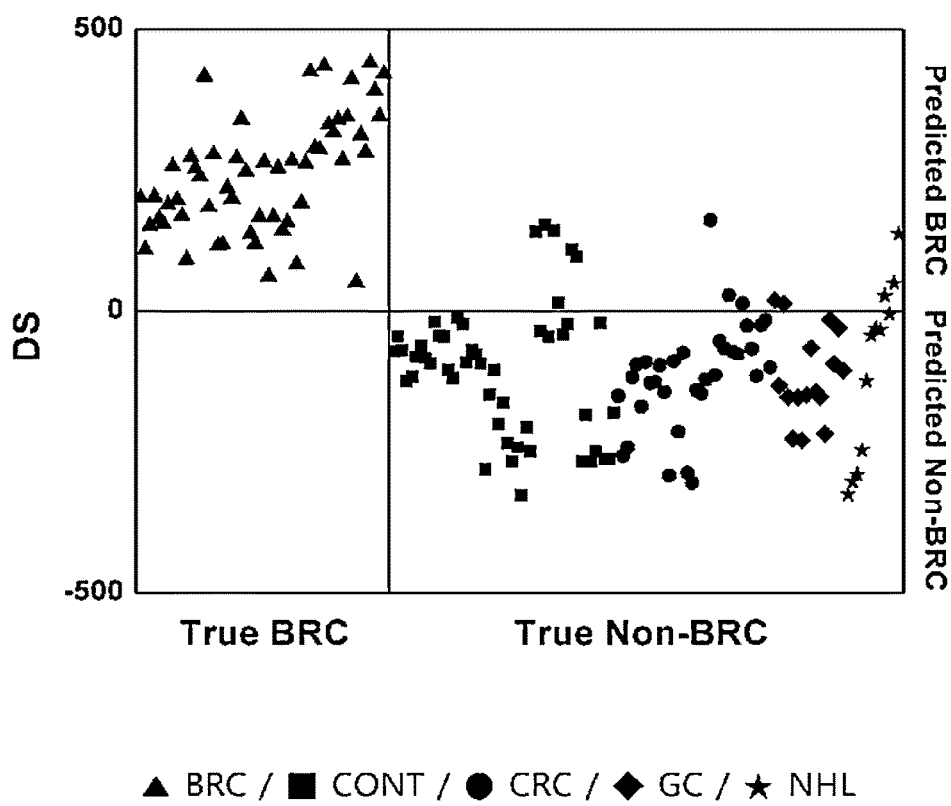
Figure 30:
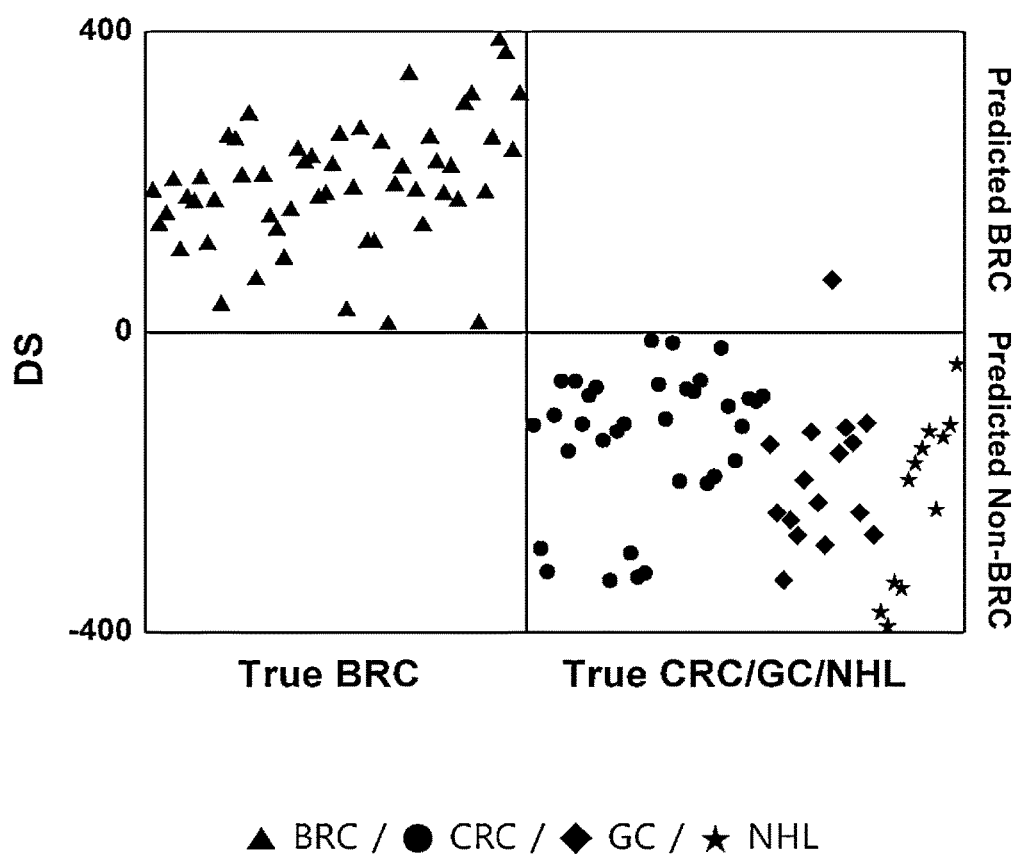

The DS was computed by applying factor loadings per mass ions computed at Clause (3-4) with respect to the 15 non-BRC patient samples which were excluded when constructing the first training set $C_{01}$ from the set $C_1$ to construct the first type discriminant, and the 1 GC patient sample which was excluded when constructing the first training set $C_{03}$ from the set $C_1$ to construct the third type discriminant Considering that the cases were excluded when constructing the first training sets $C_{01}$ and $C_{03}$, it was expected that the cases would be discriminated to be false positive or false negative, and they were determined to be the false positive or false negative cases as expected when the computation was done, except for one case of the normal control group related to the first type discriminant which was determined to be true negative. The result of discrimination of the set $C_1$ by applying the factor loadings per mass ions computed at Clause (3-4) is presented in FIGS. 29 and 30, in which FIG. 29 shows the result of the first type discriminant and FIG. 30 shows the result of the third discriminant.

(3-6) Constructing Preliminary Discriminant

Conventionally, DS is computed using the entire mass ions that are taken into consideration in the PCA-DA and the BRC patient was determined according to the computed DS. In one embodiment of the present invention, a preliminary discriminant is constructed, which uses only the mass ions that contribute considerably to the DS, in order to derive a discriminant with robust discrimination performance. As used herein, the term "preliminary discriminant" refers to an intermediate form of a discriminant which is obtained before the final discriminant is obtained, and the low-mass ions constructing the discriminant are the "preliminary candidate group" of the CRC-diagnosing low-mass ions to construct the final discriminant.

Figure 31:
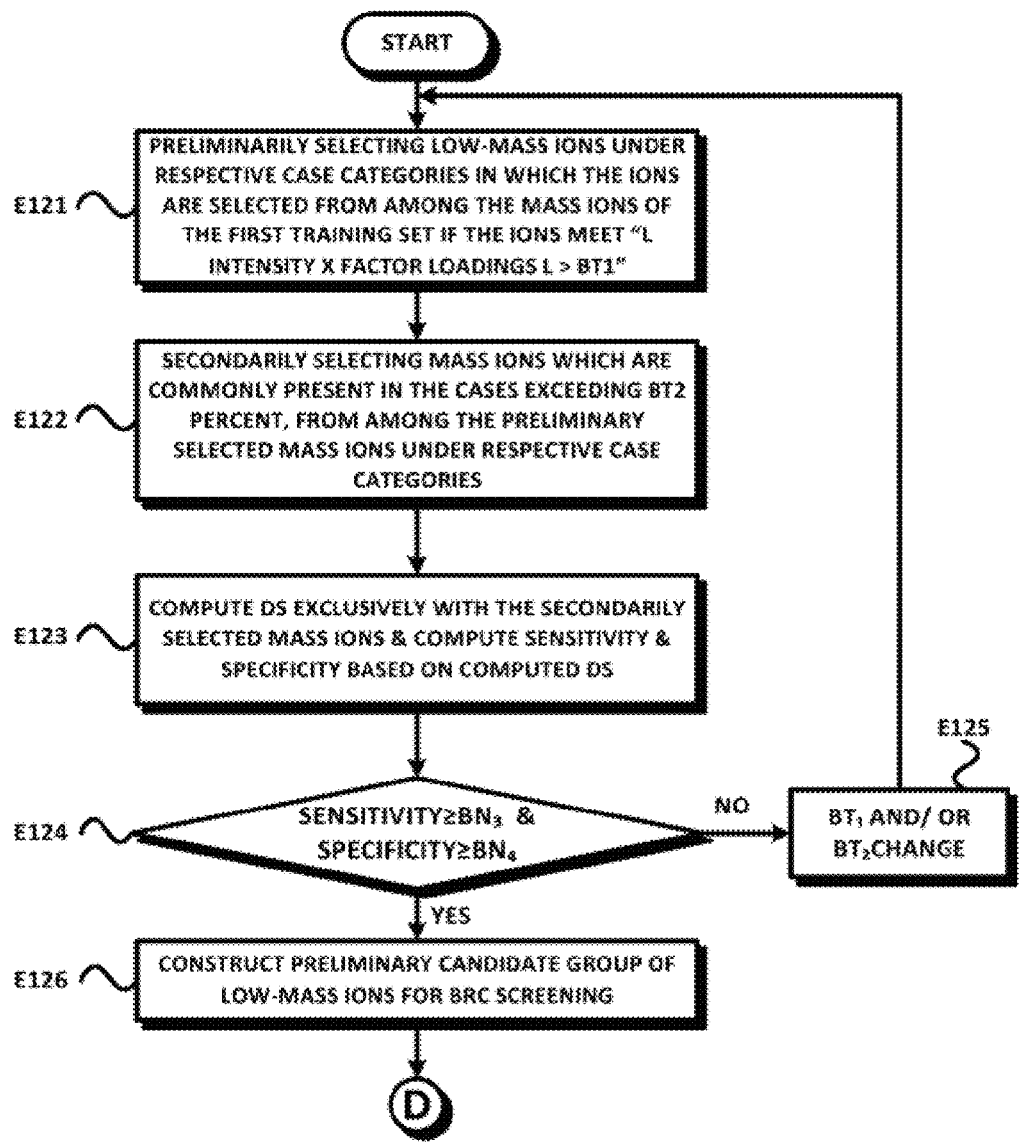

Through the process of FIG. 31, predetermined mass ions were selected, which give considerable influence on the DS, from among 10,000 mass ions. In one embodiment, 376 mass ions were selected by the first type discriminant, 353 mass ions were selected by the second discriminant, and 345 mass ions were selected by the third type discriminant.

As explained above with reference to Table 203, because the maximum number of the peaks under the import condition is set to 10,000 and sufficient samples are imported, the discriminant constructed by the PCA-DA of Marker-View™ consists of 10,000 terms. However, not all the 10,000 terms have the equal importance particularly in distinguishing BRC patients and non-BRC patients. Accordingly, the mass ions that give considerable influence on the DS were selected from among the 10,000 mass ions by two steps according to the process of FIG. 31. This particular step is employed to remove unnecessary mass ions in distinguishing BRC patients from non-BRC patients from the 10,000 mass ions.

The mass ions were preliminarily selected under corresponding case categories, if the absolute product obtained by multiplying the peak intensities by the factor loadings per mass ions exceeds the threshold $BT_1$ (E121). In one embodiment, the threshold $BT_1$ may preferably be 0.1.

Next, the mass ions were secondarily selected from among the preliminarily-selected mass ions under each case category, if the mass ions appear commonly in the cases exceeding the threshold percentage $BT_2$ (E122). In one embodiment, the threshold percentage $BT_2$ may preferably be 50. That is, take the second type discriminant for example, only the mass ions that appear commonly in at least 52 cases from among the 103 cases of the first training set were used to construct the preliminary discriminant.

The DS was again computed exclusively with the mass ions that were selected as explained above, and the sensitivity and the specificity were computed accordingly (E123). Again, the sensitivity threshold $BN_3$ and the specificity threshold $BN_4$ were set (E124), so that if the sensitivity or the specificity is less than the corresponding threshold, the threshold $BT_1$ used at step E121 and/or the threshold $BT_2$ used at step E122 was changed (E125) and the steps from E121 to E124 were repeated. In one embodiment, the sensitivity threshold $BN_3$ and the specificity threshold $BN_4$ may preferably be 0.9, respectively.

The preliminary candidate group of the BRC-diagnosing low-mass ions was constructed with the mass ions that were selected as explained above (E126), and in one embodiment, only 376 mass ions were selected by the first type discriminant from among the 10,000 mass ions, 353 mass ions were selected by the second type discriminant, or 345 mass ions were selected by the third type discriminant. Tables 221, 222, 223 provide the results of discriminating the first training sets $C_{01}$, $C_{02}$, $C_{03}$ with the first, second and third type preliminary discriminants, according to which the discrimination performance including the sensitivity and the specificity was slightly degraded from 100%, but still the result of computing with less than 4% of the total mass ions was certainly as good as the result obtained by using the entire mass ions.

Figure 32:
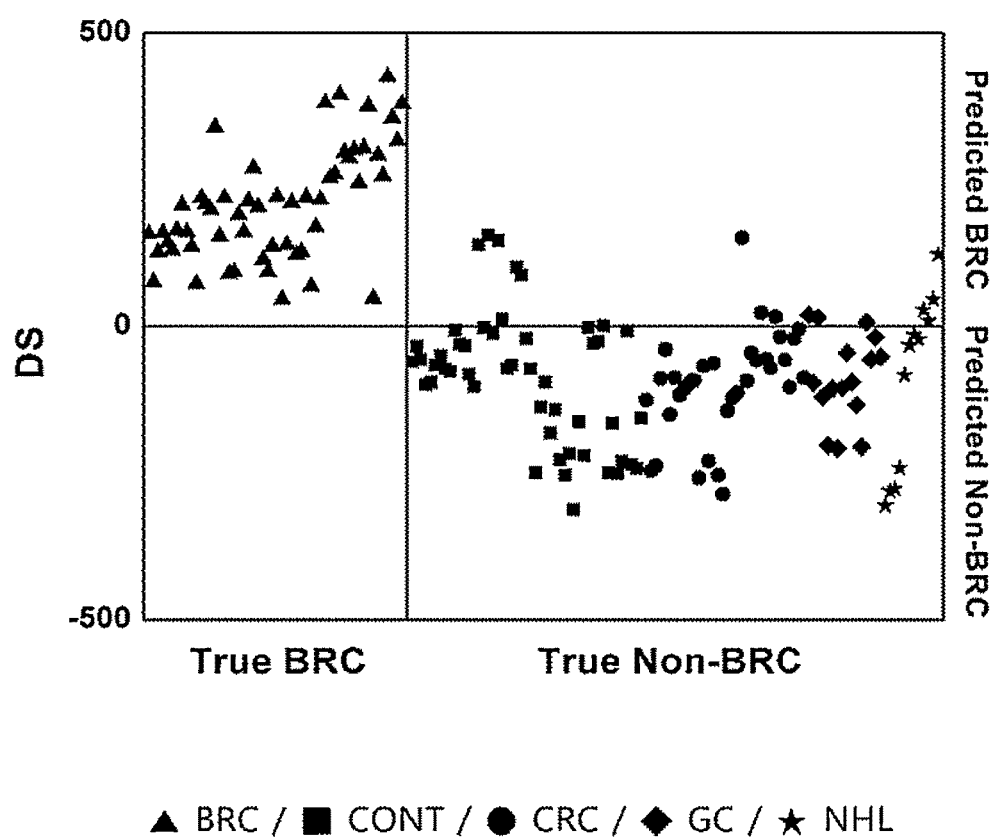
Figure 33:
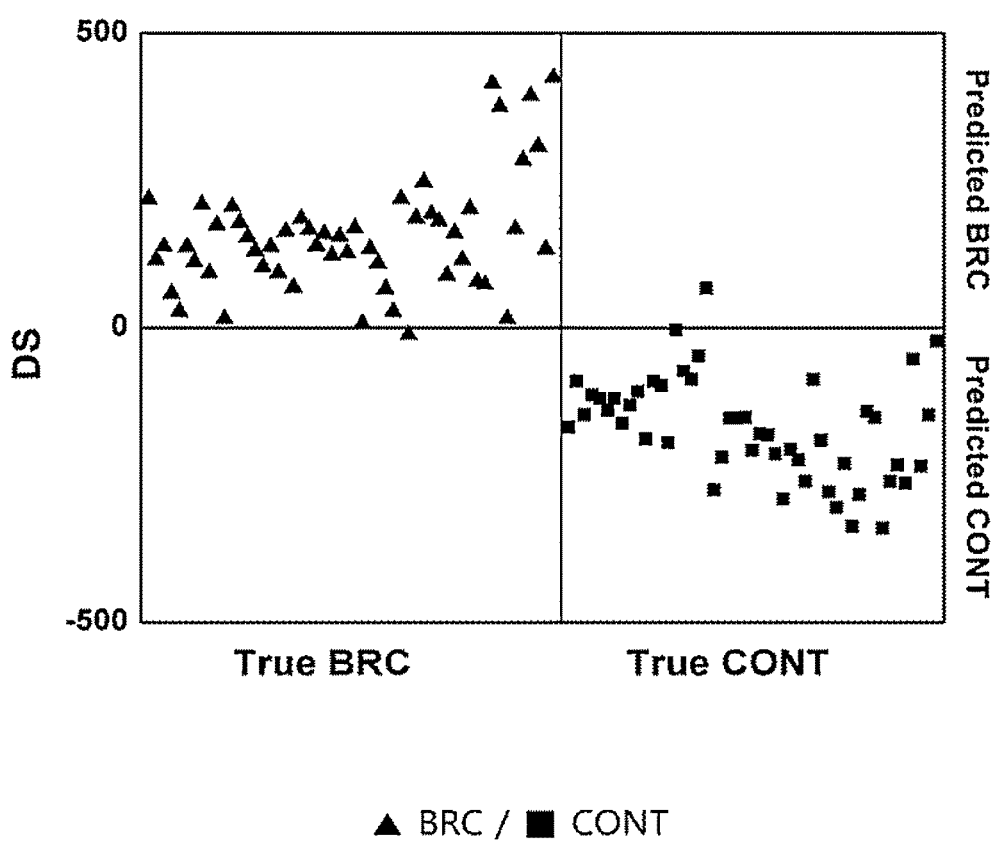
Figure 34:
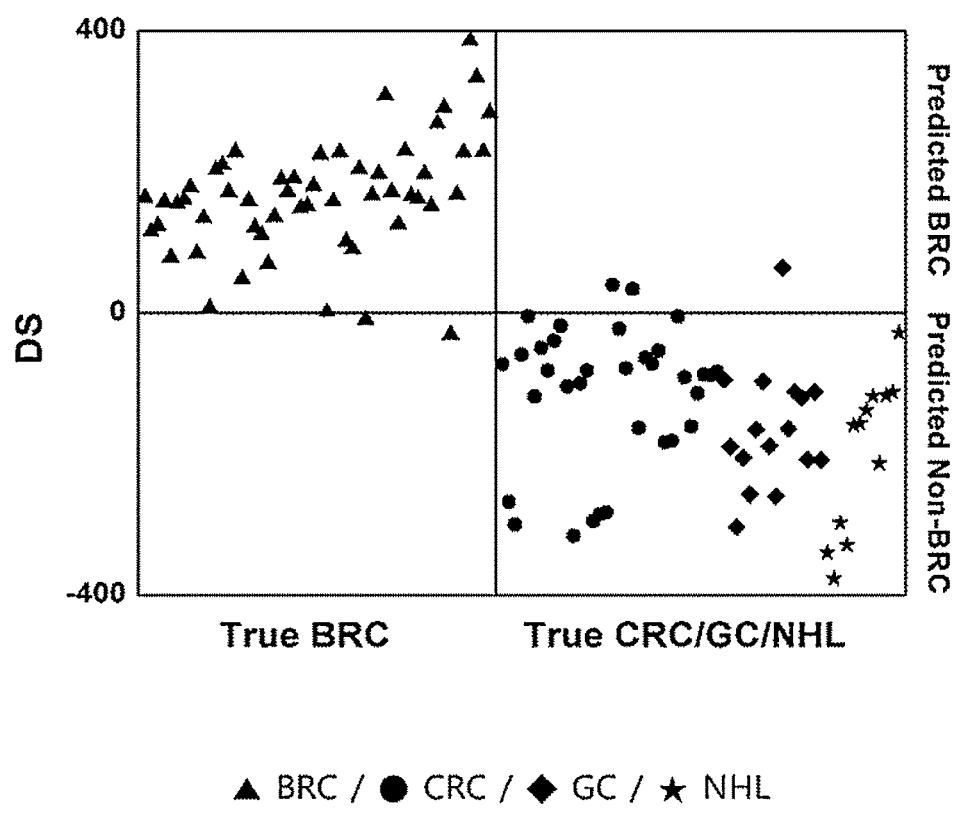

Further, FIGS. 32, 33, 34 provide the result of discriminating the set $C_1$ with the preliminary discriminant, in which FIG. 32 shows the result by the first type preliminary discriminant, FIG. 33 shows the result by the second type discriminant, and FIG. 34 shows the result by the third type discriminant. Compared to the sharp reduction in the number of mass ions used for the computation, the range of DS was not so influenced. This suggests that not all 10,000 mass ions are necessary to distinguish BRC patients from non-BRC patients.

TABLE 221

| Set $C_1$ | True BRC | True Non-BRC | | | |
|---|---|---|---|---|---|
| | | CONT | CRC | GC | NHL |
| Predicted BRC | 54 | 1 | 0 | 1 | 1 |
| Predicted Non-BRC | 0 | 41 | 31 | 13 | 8 |
| Sensitivity | | 100.0% | | | |
| Specificity | | 96.88% | | | |
| PPV | | 94.74% | | | |
| NPV | | 100.0% | | | |

TABLE 222

| Set $C_{02}$ | True BRC | True CONT |
|---|---|---|
| Predicted BRC | 53 | 1 |
| Predicted Non-BRC | 1 | 48 |
| Sensitivity | | 98.15% |
| Specificity | | 97.96% |
| PPV | | 98.15% |
| NPV | | 97.96% |

TABLE 223

| Set $C_{03}$ | True BRC | True Non-BRC | | |
|---|---|---|---|---|
| | | CRC | GC | NHL |
| Predicted BRC | 52 | 2 | 0 | 0 |
| Predicted Non-BRC | 2 | 32 | 15 | 12 |
| Sensitivity | | 96.30% | | |
| Specificity | | 96.72% | | |
| PPV | | 96.30% | | |
| NPV | | 96.72% | | |

The series of processes explained above may be performed at the BRC-diagnosing ion selecting means 5400 which includes the candidate ion set selecting means.

(3-7) Constructing a Final Discriminant

The mass ions were extracted from among the 10,000 mass ions imported in the process of constructing the preliminary discriminant, as those that contribute considerably to the numerical aspect of the DS. Considering that the selected mass ions include the mass ions that do not generate a problem in the first training set $C_0$, but can potentially deteriorate the discrimination performance in the discrimination with the mass spectrum that was re-measured with respect to the same BRC patient samples and non-BRC samples or in the discrimination of new BRC patient group and non-BRC patient group, additional step is necessary, which can actively remove the presence of such mass ions. The process of constructing a final discriminant includes such step before finally determining BRC-diagnosing low-mass ions.

To validate robustness of a discriminant, repeated measure experiment was conducted with respect to the set $C_1$ 5 times, and the repeated measure experiment was also performed 5 times with respect to the sets $C_2$ and D which were independent from the set $C_1$ and also independent from each other. It is hardly possible to confirm that the repeated measure of the mass spectrum is always conducted under the exactly same conditions in the processes like vaporization using laser beam, desorption, ionization, or the like, in addition to the process of freezing and thawing the serums and mixing the serums with methanol/chloroform to obtain extract, and it is also hard to rule out introduction of disturbances due to various causes. In other words, the DS with respect to the repeatedly-measured individual mass spectrum may have a predetermined deviation, and considering this, interpretation in one embodiment was made by computing an average DS with respect to the sample which was repeatedly measured 5 times.

Table 224 provides the result of discriminating the sets C and D with the discriminant of 10,000 terms as a result of the conventional technology, i.e., PCA-DA by MarkerView™, and Table 225 shows the result of discriminating the sets C and D with the first type preliminary discriminant with 376 terms, the second type preliminary discriminant with 353 terms, and the third type preliminary discriminant with 345 terms. Referring to the table, BRC LOME 1 (breast cancer low mass ion discriminant equation) refers to the first type discriminant, BRC LOME 2 refers to the second type discriminant, and BRC LOME 3 refers to the third type discriminant, and the following numbers indicate the number of low-mass ions included in the discriminant. Further, Table 226 shows the discrimination performance with respect to the validation set only, i.e., to the set D, in which the numbers in parenthesis refers to the discrimination performance when OVA patient group is excluded.

TABLE 224

| | BRC LOME 1-10000 | | | | | | BRC LOME 1-10000 | | | | | |
|---|---|---|---|---|---|---|---|---|---|---|---|---|
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 104 | 36 | 33 | 0 | 7 | Predicted BRC | 46 | 15 | 32 | 0 | 0 | 10 |
| Predicted Non-BRC | 4 | 59 | 30 | 31 | 12 | Predicted Non-BRC | 7 | 31 | 56 | 11 | 5 | 15 |

| | BRC LOME 2-10000 | | | | | | BRC LOME 2-10000 | | | | | |
|---|---|---|---|---|---|---|---|---|---|---|---|---|
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 100 | 54 | 35 | 1 | 5 | Predicted BRC | 46 | 25 | 52 | 0 | 0 | 1 |
| Predicted Non-BRC | 8 | 41 | 28 | 30 | 14 | Predicted Non-BRC | 7 | 21 | 36 | 11 | 5 | 24 |

| | BRC LOME 3-10000 | | | | | | BRC LOME 3-10000 | | | | | |
|---|---|---|---|---|---|---|---|---|---|---|---|---|
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 90 | 40 | 27 | 1 | 0 | Predicted BRC | 41 | 17 | 24 | 0 | 0 | 7 |
| Predicted Non-BRC | 18 | 55 | 36 | 30 | 19 | Predicted Non-BRC | 12 | 29 | 64 | 11 | 5 | 18 |

| | BRC LOMEs 2 & 3 | | | | | | BRC LOMEs 2 & 3 | | | | | |
|---|---|---|---|---|---|---|---|---|---|---|---|---|
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 88 | 35 | 26 | 0 | 0 | Predicted BRC | 35 | 15 | 22 | 0 | 0 | 1 |
| Predicted Non-BRC | 20 | 60 | 37 | 31 | 19 | Predicted Non-BRC | 18 | 31 | 66 | 11 | 5 | 24 |

TABLE 225

| | BRC LOME 1-376 | | | | | | BRC LOME 1-376 | | | | | |
|---|---|---|---|---|---|---|---|---|---|---|---|---|
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 104 | 35 | 33 | 0 | 7 | Predicted BRC | 45 | 14 | 33 | 0 | 0 | 10 |
| Predicted Non-BRC | 4 | 60 | 30 | 31 | 12 | Predicted Non-BRC | 8 | 32 | 55 | 11 | 5 | 15 |

| | BRC LOME 2-353 | | | | | | BRC LOME 2-353 | | | | | |
|---|---|---|---|---|---|---|---|---|---|---|---|---|
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 99 | 54 | 35 | 3 | 5 | Predicted BRC | 46 | 25 | 55 | 0 | 0 | 2 |
| Predicted Non-BRC | 9 | 41 | 28 | 28 | 14 | Predicted Non-BRC | 7 | 21 | 33 | 11 | 5 | 23 |

TABLE 225-continued

| | BRC LOME 3-345 | | | | | BRC LOME 3-345 | | | | | |
|---|---|---|---|---|---|---|---|---|---|---|---|
| | True | True Non-BRC | | | | True | True Non-BRC | | | | |
| Set C | BRC | CONT | CRC | GC | NHL | Set D | BRC | CONT | CRC | GC | NHL | OVC |
| Predicted BRC | 90 | 40 | 29 | 1 | 0 | Predicted BRC | 41 | 17 | 25 | 0 | 0 | 7 |
| Predicted Non-BRC | 18 | 55 | 34 | 30 | 19 | Predicted Non-BRC | 12 | 29 | 63 | 11 | 5 | 18 |

| | BRC LOMEs 2 & 3 | | | | | BRC LOMEs 2 & 3 | | | | | |
|---|---|---|---|---|---|---|---|---|---|---|---|
| | True | True Non-BRC | | | | True | True Non-BRC | | | | |
| Set C | BRC | CONT | CRC | GC | NHL | Set D | BRC | CONT | CRC | GC | NHL | OVC |
| Predicted BRC | 87 | 35 | 28 | 0 | 0 | Predicted BRC | 35 | 15 | 24 | 0 | 0 | 2 |
| Predicted Non-BRC | 21 | 60 | 35 | 31 | 19 | Predicted Non-BRC | 18 | 31 | 64 | 11 | 5 | 23 |

TABLE 226

| Set D | Sensitivity (%) | Specificity (%) | PPV (%) | NPV (%) |
|---|---|---|---|---|
| BRC LOME 1-10000 | 86.79 (86.79) | 67.43 (68.67) | 44.66 (49.46) | 94.40 (93.64) |
| BRC LOME 1-376 | 84.91 (84.91) | 67.43 (68.67) | 44.12 (48.91) | 93.65 (92.79) |
| BRC LOME 1-29 | 96.23 (96.23) | 91.43 (94.67) | 77.27 (86.44) | 98.77 (98.61) |
| BRC LOME 2-10000 & BRC LOME 3-10000 | 66.04 (66.04) | 78.29 (75.33) | 47.95 (48.61) | 88.39 (86.26) |
| BRC LOME 2-353 & BRC LOME 3-345 | 66.04 (66.04) | 76.57 (74.00) | 46.05 (47.30) | 88.16 (86.05) |
| BRC LOME 2-42 & BRC LOME 3-75 | 92.45 (92.45) | 96.57 (98.67) | 89.09 (96.08) | 97.69 (97.37) |

The discriminant consisting of 10,000 mass ions exhibits perfect discrimination performance with respect to the first training set $C_0$, but with reference to Table 226, the positive predictability was particularly low with respect to set D. All the first, second and third preliminary discriminants exhibited very good discrimination performance (Tables 122, 123) with respect to the first training set $C_0$, but the discrimination result with respect to set D was far from satisfaction.

Figure 35:
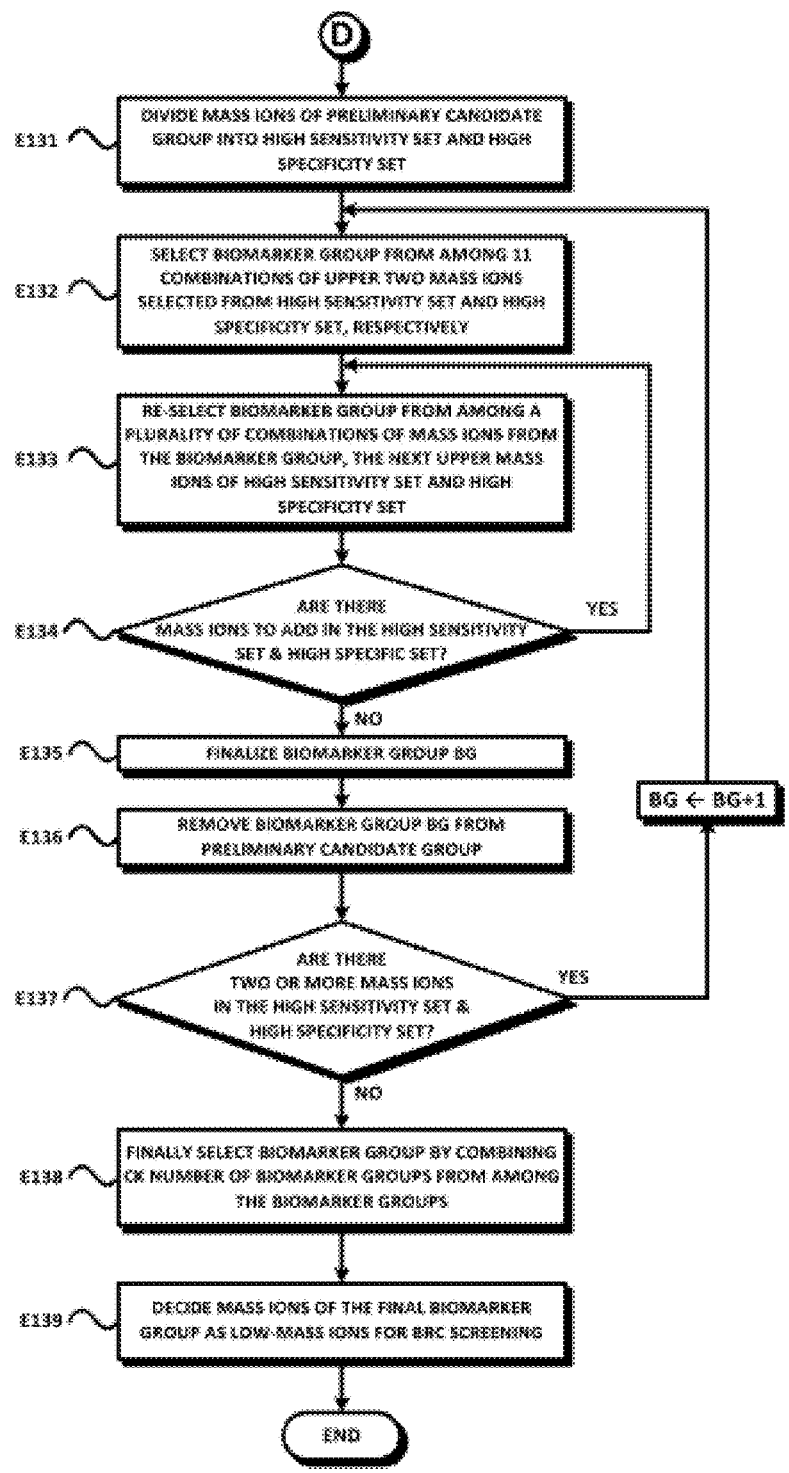

Accordingly, in one embodiment of the present invention, steps illustrated in FIG. 35 were performed to improve the preliminary discriminant to more robust discriminant.

First, the mass ions of the preliminary candidate group were divided into high sensitivity set and high specificity set (E131). As used herein, the mass ions of the high sensitivity set have higher sensitivity per mass ions than specificity, while the mass ions of the high specificity set have higher specificity per mass ions than sensitivity.

Next, the mass ions of the high sensitivity set and the mass ions of the high specificity set were sorted in a descending order $\{Sns_1, Sns_2, Sns_3 \ldots Sns_I\}$ $\{Spc_1, Spc_2, Spc_3 \ldots Spc_J\}$ in terms of the sum of the sensitivity and specificity per mass ions, and two top mass ions of the respective sets were taken $\{Sns_1, Sns_2, Sps_1, Spc_2\}$, and a biomarker group was selected with a combination of the best performance from among 11 combinations that are possibly made with the two or more mass ions of the four mass ions (E132).

The criteria to determine whether a combination has the best performance or not may be selected objectively and universally from among the following criteria which are listed in the order of importance:

Criterion 1) The combination with greater sum of sensitivity and specificity has better performance;

Criterion 2) The combination with less mass ions has better performance; and

Criterion 3) The combination with a greater difference between minimum DS of the true positive case and the maximum DS of true negative case has better performance.

Next, one more mass ion, i.e., the second top mass ion $\{Sns_3, Spc_3\}$ was additionally taken from each of the high sensitivity set and the high specificity, so that a set with the best performance was re-selected as a biomarker group from among the four sets {biomarker group}, {biomarker group, $Sns_3$}, {biomarker group, $Spc_3$}, {biomarker group, $Sns_3$, $Spc_3$} which are the combinations of the additionally-taken mass ions $\{Sns_3, Spc_3\}$ (E133).

The process repeated until the high sensitivity set and the high specificity set had no further mass ion to add (E134).

In other words, the process (E133) repeats as long as both the high sensitivity set and the high specificity set have mass ions to add, and when any of the high sensitivity set and the high specificity set has no further mass ion left to add, the next top mass ion $\{Sns_i$ or $Spc_j\}$ in the set having mass ions is additionally taken, so that a biomarker group is selected with a set of the best performance among the two sets {biomarker group}, {biomarker group, $Sns_i$ or $Spc_j$} which are combinations of the additionally-taken mass ion $\{Sns_i$ or $Spc_j\}$.

The process repeats as long as the high sensitivity set or the high specificity set is out of the mass ion, and the biomarker group that is selected when there is no mass ion left in the high sensitivity set and high specificity set becomes the biomarker group 1 (BG) (E135).

The biomarker group 1 (BG) was removed from the preliminary candidate group (E136), the high sensitivity set and the high specificity set were constructed with the remaining mass ions, and the above-explained process repeats. The process repeats until any of the high sensitivity set and the high specificity has less than two mass ions therein (E137).

BK number of biomarker groups were combined with the biomarker groups 1, 2, . . . which were obtained by the repeated process explained above, in the order of accuracy, to form a final biomarker group. As used herein, the "accuracy" refers to a proportion of true positive and true negative cases in the entire cases. In one embodiment, BK may preferably be 1, 2, or 3 (E138)

Accordingly, the mass ions of the final biomarker group were determined to be the BRC-diagnosing low-mass ions (E139).

The preliminary candidate group of the mass ions was selected from the set $C_1$, and more specifically, from the subset $C_0$, and to avoid overfitting problem, the set $C_2$ which was independent from the set $C_1$ was added to enlarge the training set when the final biomarker group was determined from the preliminary candidate group.

As a result of performing the process explained above with respect to the samples to distinguish BRC patient group from the non-BRC patient group, 29 mass ions were selected as the first type BRC-diagnosing low-mass ions. Further, as a result of performing the process explained above with respect to the samples to distinguish BRC patient group from the normal controls, 42 mass ions were selected as the second type BRC-diagnosing low-mass ions. Further, as a result of performing the process explained above with respect to the samples to distinguish BRC patient group from the patient groups with other types of cancers, 75 mass ions were selected as the third type BRC-diagnosing low-mass ions. The masses of the first, second and third type BRC-diagnosing low-mass ions are listed in Tables 227, 228 and 229. The low-mass ions explained above are referred to as the "first type BRC-diagnosing low-mass ions", the "second type CRC-diagnosing low-mass ions", and the "third type BRC-diagnosing low-mass ions", and the discriminant according to the present invention which is finally obtained using the same are referred to as the "first type BRC-diagnosing final discriminant", the "second type CRC-diagnosing final discriminant", and the "second type CRC-diagnosing final discriminant", respectively.

TABLE 227

| |
|---|
| 74.0937 |
| 74.1155 |
| 76.0728 |
| 136.1067 |
| 173.4872 |
| 193.0665 |
| 208.0565 |
| 212.0949 |
| 231.0726 |
| 258.1364 |
| 279.0841 |
| 280.0847 |
| 282.2777 |
| 313.2638 |
| 331.2024 |
| 332.3181 |
| 401.0588 |
| 427.3441 |
| 432.9954 |
| 452.2269 |
| 476.6038 |
| 490.3427 |
| 498.3237 |
| 499.3265 |
| 512.3145 |
| 562.3074 |
| 583.2323 |
| 584.2415 |
| 646.3851 |

TABLE 228

| | | | | | | |
|---|---|---|---|---|---|---|
| 38.9779 | 123.0821 | 225.1870 | 313.2618 | 424.3216 | 538.3428 | 610.3273 |
| 46.0647 | 130.1539 | 229.0005 | 332.3150 | 426.3389 | 540.3250 | 616.3286 |
| 74.1164 | 185.7723 | 231.0675 | 342.2482 | 428.1885 | 570.3234 | 618.3352 |
| 76.0733 | 191.1175 | 244.0962 | 368.2624 | 497.3194 | 580.3281 | 646.3959 |
| 97.0686 | 208.0530 | 281.0913 | 398.3034 | 513.3193 | 581.2310 | 725.3469 |
| 122.0777 | 212.0960 | 284.3205 | 416.0901 | 532.6918 | 581.3377 | 757.1117 |

TABLE 229

| | | | | | | |
|---|---|---|---|---|---|---|
| 38.9736 | 156.0412 | 228.0348 | 331.2036 | 478.8688 | 511.3367 | 583.2284 |
| 38.9892 | 172.3072 | 231.0726 | 332.3169 | 479.8724 | 518.8776 | 731.3330 |
| 44.0491 | 178.1330 | 234.0422 | 333.3233 | 480.3180 | 520.8826 | 733.3526 |
| 44.0656 | 182.0738 | 260.1013 | 337.1047 | 483.3301 | 534.2829 | 734.3563 |
| 74.0938 | 189.9525 | 279.0843 | 424.3272 | 487.3152 | 535.2882 | 735.3665 |
| 87.0991 | 192.1294 | 280.0849 | 426.3406 | 488.3287 | 542.8770 | 757.0995 |
| 104.1316 | 193.0660 | 282.2791 | 432.9948 | 488.6580 | 544.7878 | 757.3512 |
| 104.3161 | 196.0871 | 289.2960 | 433.9894 | 496.4331 | 544.8728 | 1465.5872 |
| 105.1091 | 212.3221 | 298.3425 | 446.0196 | 496.7718 | 546.3358 | 1466.5971 |
| 136.1021 | 217.0923 | 313.2630 | 454.3014 | 497.7764 | 559.2911 | |
| 155.1798 | 222.0231 | 316.3269 | 469.2924 | 502.8741 | 568.1146 | |

The series of the processes explained above may be performed at the BRC-diagnosing ion selecting means 5400 which includes the final ion set selecting means.

(3-8) Implementation of the Final Discriminant & Analysis

Figure 28:
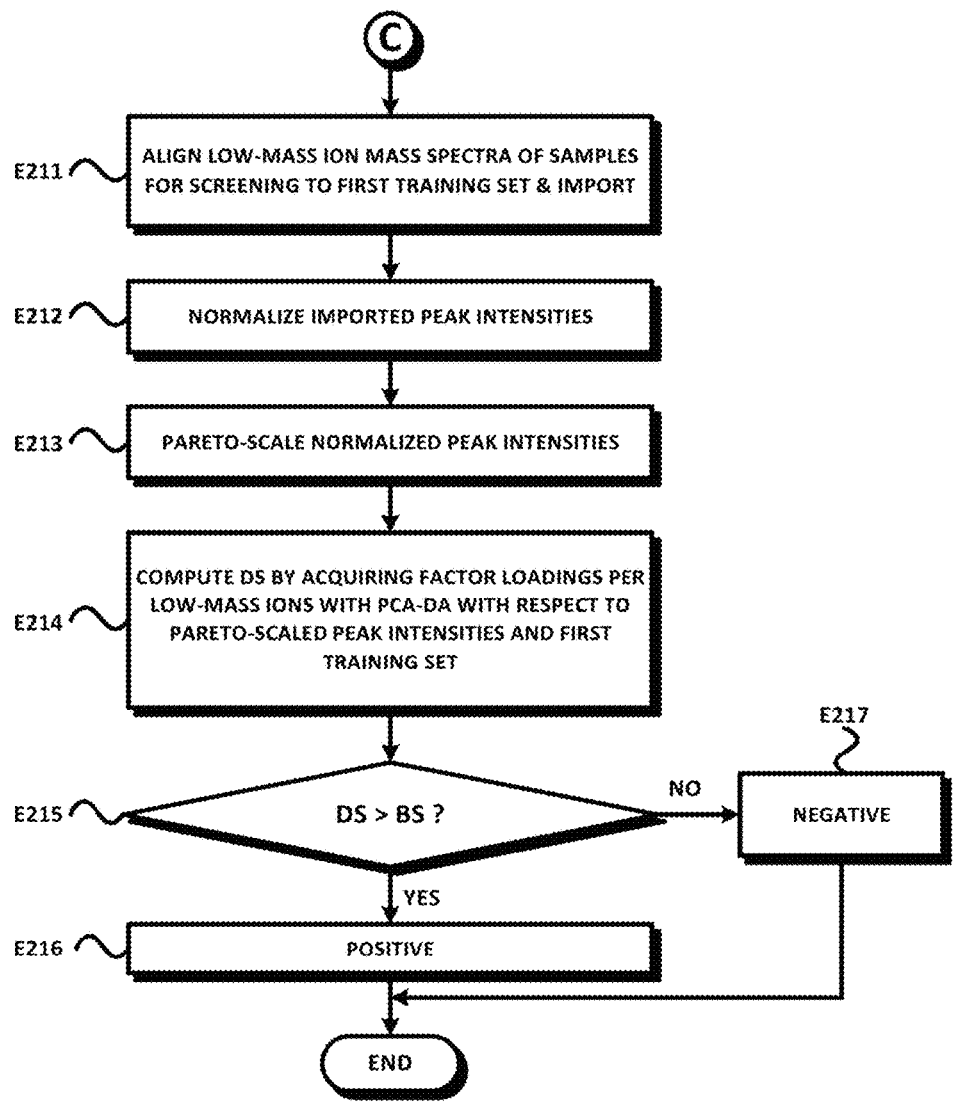

The interpretation is available when the first, second and third type BRC-diagnosing final discriminants using the first, second and third type BRC-diagnosing low-mass ions are implemented on the set D according to the method of FIG. 28.

Figure 36:
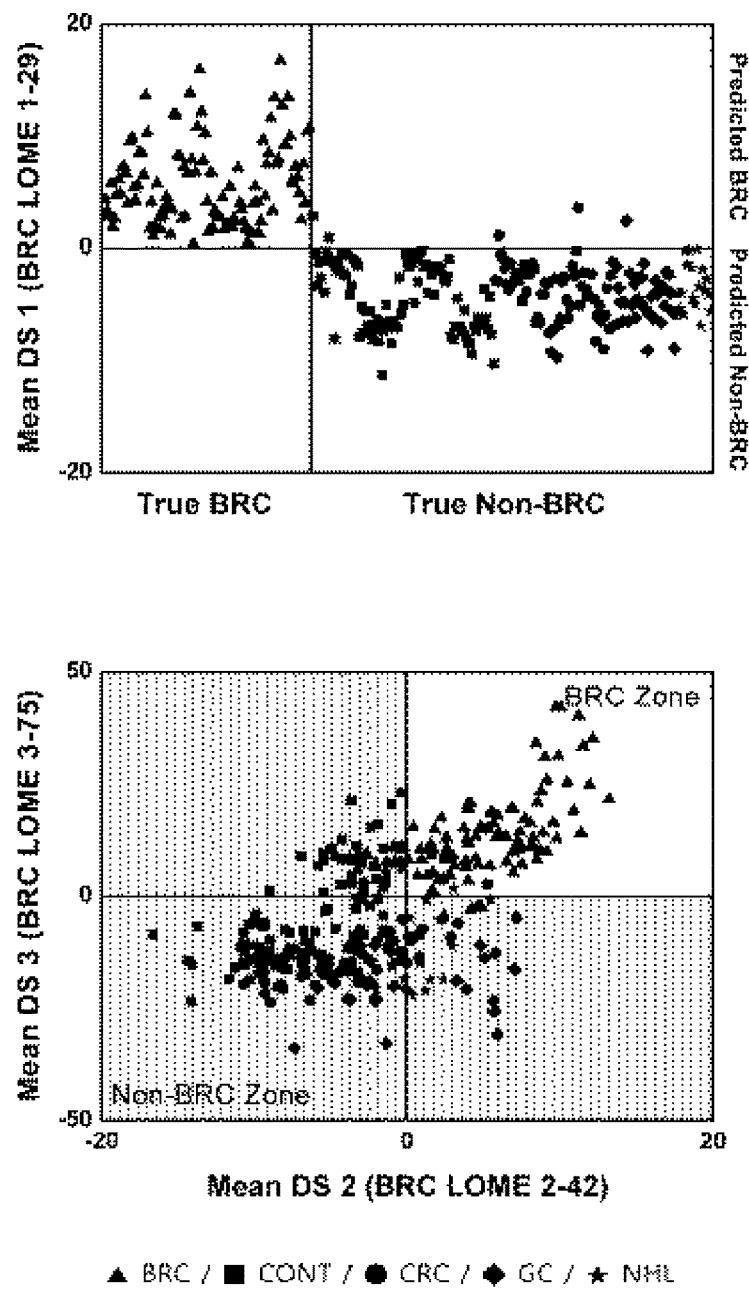
Figure 37:
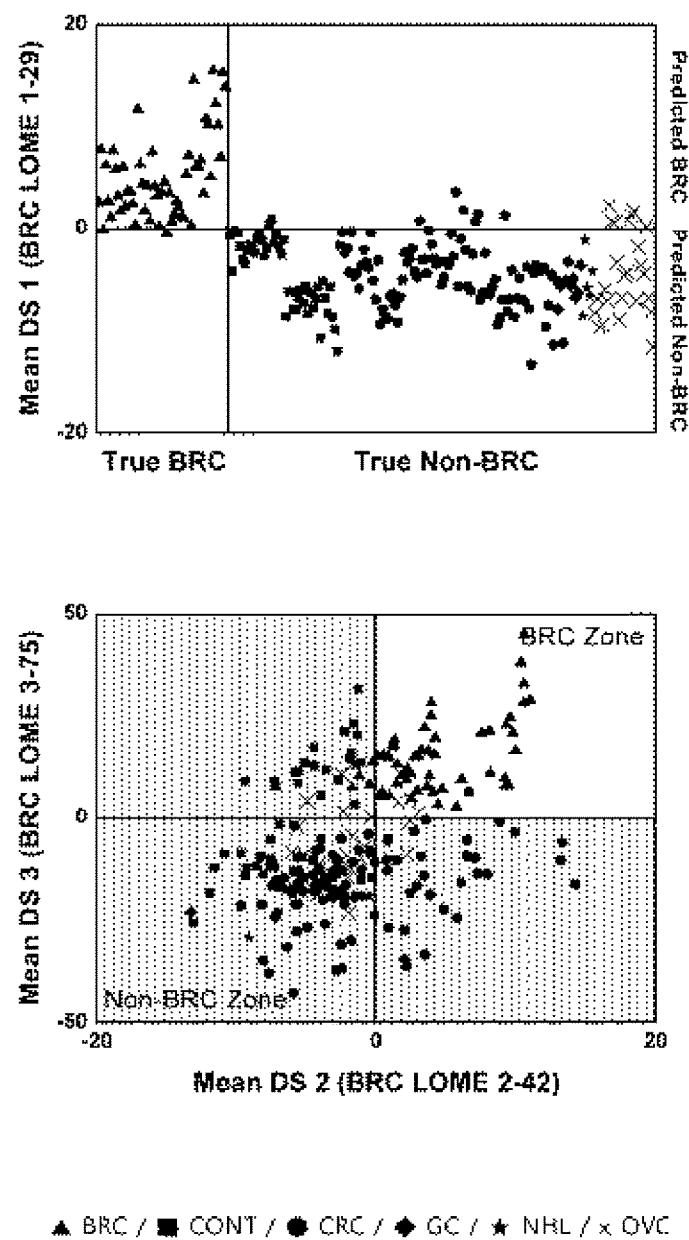

The result of interpretation obtained by the final discriminant is shown in FIGS. 36, 37 and Tables 226 and 230. FIGS.

36 and 37 illustrate the result of interpretation based on the average DS of the DS of five rounds, in which FIG. 36 shows the result of interpretation on set D and FIG. 37 shows the result of interpretation on set D.

TABLE 230

| | BRC LOME 1-29 | | | | | | BRC LOME 1-29 | | | | | |
|---|---|---|---|---|---|---|---|---|---|---|---|---|
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 108 | 2 | 2 | 1 | 0 | Predicted BRC | 51 | 2 | 6 | 0 | 0 | 7 |
| Predicted Non-BRC | 0 | 93 | 61 | 30 | 19 | Predicted Non-BRC | 2 | 44 | 82 | 11 | 5 | 18 |
| | BRC LOME 2-42 | | | | | | BRC LOME 2-42 | | | | | |
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 93 | 0 | 12 | 9 | 12 | Predicted BRC | 49 | 1 | 28 | 2 | 1 | 6 |
| Predicted Non-BRC | 15 | 95 | 51 | 22 | 7 | Predicted Non-BRC | 4 | 45 | 60 | 9 | 4 | 19 |
| | BRC LOME 3-75 | | | | | | BRC LOME 3-75 | | | | | |
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 106 | 31 | 1 | 1 | 1 | Predicted BRC | 53 | 22 | 1 | 0 | 0 | 8 |
| Predicted Non-BRC | 2 | 64 | 62 | 30 | 18 | Predicted Non-BRC | 0 | 24 | 87 | 11 | 5 | 17 |
| | BRC LOMEs 2 & 3 | | | | | | BRC LOMEs 2 & 3 | | | | | |
| | True | True Non-BRC | | | | | True | True Non-BRC | | | | |
| Set C | BRC | CONT | CRC | GC | NHL | Set D | BRC | CONT | CRC | GC | NHL | OVC |
| Predicted BRC | 91 | 0 | 1 | 0 | 1 | Predicted BRC | 49 | 1 | 1 | 0 | 0 | 4 |
| Predicted Non-BRC | 17 | 95 | 62 | 31 | 18 | Predicted Non-BRC | 4 | 45 | 87 | 11 | 5 | 21 |

Based on the discrimination performance of the validation set (D), compared to the result by the first type BRC-diagnosing final discriminant, the results by the second and third type BRC-diagnosing final discriminants were more accurate. When the second and third type BRC-diagnosing final discriminants were used, even with the OVC patient group included, which was excluded from the training set, all the sensitivity, specificity, positive predictability and negative predictability of set D exceeded 85%.

When the first type BRC-diagnosing final discriminant was used, the set D had 85% or above sensitivity, specificity, positive predictability and negative predictability only with respect to the set excluding OVC patient group. On the whole, the first type BRC-diagnosing final discriminant is considered to exhibit good discrimination result.

Accordingly, it is possible to discriminate the BRC patients from the non-BRC patients by analyzing the low-mass ion mass spectrum of the serum.

4. Example of an Apparatus for Screening Gastric Cancer (GC)

Figure 38:
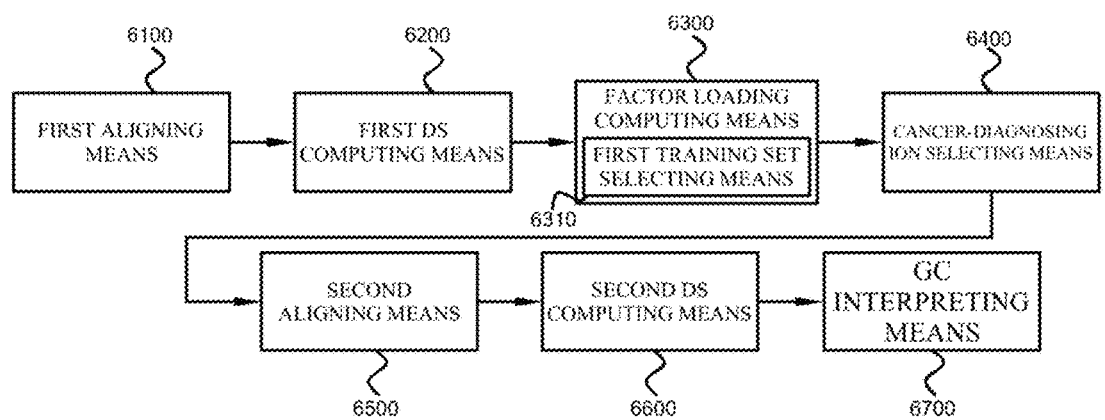

FIG. 38 is a detailed block diagram of the cancer diagnosing unit of FIG. 7 to diagnose GC according to an embodiment of the present invention.

Referring to FIG. 38, the cancer diagnosing unit according to one embodiment may include a first aligning means 6100 which aligns a low-mass ion mass spectrum of a candidate training set consisting of the GC patient and non-GC cases; a first DS computing means 6200 which computes DS by conducting biostatistical analysis with respect to the aligned mass spectrum; a factor loading computing means 6300 which computes sensitivity and specificity according to DS and selects a first training set based on the computed result, and computes factor loadings per low-mass ions; a GC diagnosing ion selecting means 6400 which selects low-mass ions for the purpose of diagnosing GC in terms of the discrimination performance from among the candidate low-mass ions that meet candidate condition; a second aligning means 6500 which aligns the low-mass ion mass spectrum of a biological sample of interest to the first training set; a second DS computing means 6600 which computes DS based on peak intensities of the low-mass ions of interest and the factor loadings; and a GC determining means 6700 which determines the subject of interest to be GC positive or negative depending on the DS. The GC diagnosing ion selecting means 6400 may divide the plurality of GC patient and non-GC cases into a first type discrimination case consisting of a plurality of GC patient cases and a plurality of normal cases, a second type discrimination case consisting of the plurality of GC patient cases and a plurality of cancer patient cases with cancers other than GC, a third type discrimination case consisting of the plurality of CRC patient cases and a plurality of BRC patient cases, and a fourth type discrimination case consisting of the plurality of GC patient cases and a plurality of non-Hodgkin lymphoma (NHL) patient cases, or alternatively, may divide the plurality of GC patient and non-GC patient cases into the first type discrimination cases and a fifth type discrimination cases consisting of the plurality of GC patient cases and the normal cases, and a plurality of CRC, BRC and NHN patient cases, and executed with respect to the first, second, third, fourth and fifth type discrimination cases, respectively, to divide the GC-diagnosing low-mass ions into first type GC diagnosing low-mass ions with respect to the first type discrimination case, second type GC-diagnosing low-mass ions with respect to the second type discrimination case, third type GC diagnosing low-mass ions with respect to the third type discrimination case, fourth type GC diagnosing low-mass ions with respect to the fourth type discrimination case, and fifth type GC diagnosing low-mass ions with respect to the fifth type discrimination case.

To the above-mentioned purpose, the low-mass ion detecting unit 1000 extracts mass spectrum of the low-mass ion by detecting peak intensity of the low-mass ions using mass spectrometer with respect to biological samples of a plurality of GC patient and non-GC cases.

The detailed components of the cancer diagnosing unit to diagnose the GC are identical to those of the apparatus for screening cancer explained above with reference to FIGS. 9 to 13. Accordingly, the like elements will not be explained in detail below for the sake of brevity.

Referring to FIG. 14, the apparatus for screening cancer according to one embodiment may be implemented in a hardware level, or alternatively, in a software level via program structure, and the example of implementation in the software level will be explained below with reference to the flowcharts accompanied hereto, to explain diagnosing GC with an apparatus for screening cancer according to an embodiment.

(4-1) Sample Preparation—Collecting Serums

Serums were collected from 49 BRC patients (Table 301), 84 normal controls (Table 302), 77 CRC patients (Table 305), 54 BRC patients (Table 306), and 24 non-Hodgkin lymphoma (NHL) patients (Table 307) and, respectively.

TABLE 305

| CRC | Sex | Age year | Stage | Location | Cell Type | CEA ng/mL |
|---|---|---|---|---|---|---|
| CRC-E1 | M | 77 | I | A-colon | AC | 1.8 |
| CRC-E2 | M | 50 | I | Rectum | AC | 1.9 |
| CRC-E3 | F | 47 | I | S-colon | AC | 0.7 |
| CRC-E4 | F | 82 | I | A-colon | AC | 1.1 |
| CRC-E5 | M | 59 | I | Rectum | AC | 1.9 |
| CRC-E6 | M | 73 | I | Rectum | AC | 3.6 |
| CRC-E7 | M | 71 | I | S-colon | AC | 3.6 |
| CRC-E8 | M | 71 | I | Rectum | AC | 9.8 |
| CRC-E9 | F | 47 | I | Rectum | AC | 3.9 |
| CRC-E10 | F | 54 | I | Rectum | AC | 1.6 |
| CRC-E11 | M | 73 | I | S-colon | AC | 7.1 |
| CRC-E12 | F | 74 | I | S-colon | AC | 2.3 |
| CRC-E13 | M | 75 | II | A-colon | AC | 2.1 |
| CRC-E14 | F | 81 | II | S-colon | AC | 4.1 |
| CRC-E15 | F | 76 | II | Rectum | AC | 25.3 |
| CRC-E16 | F | 71 | II | A-colon | AC | 1.6 |
| CRC-E17 | M | 72 | II | A-colon | AC | 3.8 |
| CRC-E18 | F | 82 | II | S-colon | AC | 1.8 |
| CRC-E19 | F | 68 | II | D-colon | AC | 1.7 |
| CRC-E20 | M | 71 | II | S-colon | AC | 3.6 |
| CRC-E21 | F | 67 | II | A-colon | AC | 1.9 |

TABLE 305-continued

| CRC | Sex | Age year | Stage | Location | Cell Type | CEA ng/mL |
|---|---|---|---|---|---|---|
| CRC-E22 | M | 45 | II | D-colon | MAC | 3.3 |
| CRC-E23 | M | 60 | II | S-colon | AC | 2.8 |
| CRC-E24 | M | 74 | II | S-colon | AC | 5.3 |
| CRC-E25 | M | 57 | II | Rectum | AC | 7.3 |
| CRC-E26 | F | 51 | II | Rectum | AC | 6.7 |
| CRC-E27 | M | 79 | II | S-colon | AC | 6.2 |
| CRC-E28 | F | 59 | II | A-colon | AC | 1 |
| CRC-E29 | M | 62 | II | S-colon | AC | — |
| CRC-E30 | M | 84 | II | S-colon | AC | 11.3 |
| CRC-E31 | M | 68 | II | Rectum | AC | 5.8 |
| CRC-E32 | M | 54 | II | A-colon | AC | 1.1 |
| CRC-E33 | F | 51 | II | D-colon | AC | 5.9 |
| CRC-E34 | F | 56 | III | S-colon | AC | 1.2 |
| CRC-E35 | M | 52 | III | S-colon | AC | 3.2 |
| CRC-E36 | F | 59 | III | S-colon | AC | 1.7 |
| CRC-E37 | F | 73 | III | S-colon | AC | 5.7 |
| CRC-E38 | M | 70 | III | S-colon | AC | 3.6 |
| CRC-E39 | M | 68 | III | A-colon | AC | 9.2 |
| CRC-E40 | F | 55 | III | Rectum | AC | 2.1 |
| CRC-E41 | F | 61 | III | A-colon | AC | 12.7 |
| CRC-E42 | M | 59 | III | S-colon | AC | 2.7 |
| CRC-E43 | M | 67 | III | Rectum | AC | 9.5 |
| CRC-E44 | M | 48 | III | S-colon | AC | 1.3 |
| CRC-E45 | M | 58 | III | Rectum | AC | 1.7 |
| CRC-E46 | F | 50 | III | S-colon | AC | 4.8 |
| CRC-E47 | F | 51 | III | S-colon | AC | 7 |
| CRC-E48 | F | 74 | III | T-colon | AC | 2.5 |
| CRC-E49 | M | 60 | III | Rectum | AC | 3.5 |
| CRC-E50 | M | 52 | III | S-colon | AC | 2.5 |
| CRC-E51 | M | 54 | III | A-colon | AC | 5.3 |
| CRC-E52 | M | 82 | III | S-colon | AC | 2.4 |
| CRC-E53 | M | 54 | III | S-colon | AC | 5.3 |
| CRC-E54 | F | 52 | III | S-colon | AC | 22.1 |
| CRC-E55 | M | 61 | III | Rectum | AC | 128.1 |
| CRC-E56 | F | 47 | III | S-colon | AC | 1.2 |
| CRC-E57 | M | 71 | III | A-colon | AC | 8.2 |
| CRC-E58 | M | 52 | III | S-colon | AC | 4.1 |
| CRC-E59 | F | 64 | III | S-colon | AC | 6.8 |
| CRC-E60 | F | 51 | III | S-colon | AC | 1.2 |
| CRC-E61 | M | 55 | III | A-colon | AC | 1.2 |
| CRC-E62 | M | 62 | III | Rectum | AC | 2.5 |
| CRC-E63 | M | 38 | III | Rectum | AC | 6.1 |
| CRC-E64 | F | 65 | III | D-colon | AC | 3.5 |
| CRC-E65 | M | 49 | III | S-colon, T-colon | AC | 3.8 |
| CRC-E66 | M | 66 | III | S-colon | AC | 10.7 |
| CRC-E67 | F | 54 | III | S-colon | AC | 8.8 |
| CRC-E68 | F | 70 | IV | Rectum | AC | 3.9 |
| CRC-E69 | M | 68 | IV | Rectum | AC | 6 |
| CRC-E70 | M | 53 | IV | Rectum | AC | 54.7 |
| CRC-E71 | F | 63 | IV | D-colon | AC | 12.3 |
| CRC-E72 | F | 63 | IV | A-colon | AC | 1.4 |
| CRC-E73 | M | 66 | IV | S-colon | AC | 6.4 |
| CRC-E74 | F | 50 | IV | Rectum | AC | 62 |
| CRC-E75 | M | 57 | IV | Rectum | AC | 6.4 |
| CRC-E76 | M | 57 | IV | S-colon | AC | 41.7 |
| CRC-E77 | M | 48 | IV | A-colon | AC | 59.4 |

AC: Adenocarcinoma
MAC: Mucinous adenocarcinoma

TABLE 306

| BRC | Sex | Age year | Node | ER | ER % | PR | PR % | HER2 | Tumor Size cm |
|---|---|---|---|---|---|---|---|---|---|
| BRC-E1 | F | 48 | — | 5 | 33-66% | 6 | 33-66% | 2 | — |
| BRC-E2 | F | 35 | — | 6 | 33-66% | 6 | 33-66% | 1 | — |
| BRC-E3 | F | 45 | pN1a | 5 | 33-66% | 5 | 33-66% | 0 | 1.5 |
| BRC-E4 | F | 61 | — | 0 | 0% | 0 | 0% | 2 | — |
| BRC-E5 | F | 70 | pN0(sn) | 0 | 0% | 0 | 0% | 1 | <0.1 |
| BRC-E6 | F | 58 | ypN0 | 3 | <10% | 3 | 10-33% | 3 | 0.5 |
| BRC-E7 | F | 49 | ypN0(i+) | 0 | 0% | 0 | 0% | 2 | 1.9 |
| BRC-E8 | F | 49 | ypN2a | 0 | 0% | 0 | 0% | 1 | 2.5 |
| BRC-E9 | F | 39 | pN1a | 6 | 33-66% | 7 | >66% | 1 | 2.2 |
| BRC-E10 | F | 48 | ypN2a | 6 | 33-66% | 4 | <10% | 3 | 5.8 |
| BRC-E11 | F | 39 | — | 0 | 0% | 0 | 0% | 1 | — |
| BRC-E12 | F | 56 | pN1a | 6 | 33-66% | 6 | 33-66% | 0 | 2.8 |
| BRC-E13 | F | 59 | pN0(sn) | 6 | 33-66% | 2 | <10% | 1 | 2.3 |
| BRC-E14 | F | 31 | pN1a | 5 | 33-66% | 4 | 10-33% | 1 | 2.2 |
| BRC-E15 | F | 46 | pN3a | 6 | 33-66% | 6 | 33-66% | 1 | 3.5 |
| BRC-E16 | F | 56 | — | 7 | >66% | 4 | 10-33% | 1 | — |
| BRC-E17 | F | 55 | — | 0 | 0% | 0 | 0% | 2 | — |
| BRC-E18 | F | 46 | pN0 | 0 | 0% | 0 | 0% | 0 | 1.5 |
| BRC-E19 | F | 60 | ypN0 | 0 | 0% | 0 | 0% | 3 | 1.9 |
| BRC-E20 | F | 49 | pN0(sn) | 5 | 33-66% | 2 | <10% | 2 | 1.5 |
| BRC-E21 | F | 55 | pN1mi | 0 | 0% | 0 | 0% | 3 | 1.8 |
| BRC-E22 | F | 65 | pN0 | 6 | 33-66% | 6 | 33-66% | 0 | 1.7 |
| BRC-E23 | F | 35 | ypN2a | 6 | 66% | 4 | 10-33% | 2 | 2.6 |
| BRC-E24 | F | 46 | pN1a | 6 | 33-66% | 6 | 33-66% | 3 | 2.5 |
| BRC-E25 | F | 45 | pN0(sn) | 6 | 33-66% | 6 | 33-66% | 1 | 0.8 |
| BRC-E26 | F | 42 | pN0(sn) | 3 | 10-33% | 6 | 33-66% | 0 | 1 |
| BRC-E27 | F | 58 | pN0(sn) | 6 | 33-66% | 6 | 33-66% | 1 | 1.5 |
| BRC-E28 | F | 62 | pN1a | 0 | 0% | 0 | 0% | 2 | 2.2 |
| BRC-E29 | F | 61 | — | 0 | 0% | 0 | 0% | 1 | — |
| BRC-E30 | F | 60 | — | — | — | — | — | — | — |
| BRC-E31 | F | 51 | — | — | — | — | — | — | — |
| BRC-E32 | F | 42 | pN0 | 7 | >66% | 7 | >66% | 2 | — |
| BRC-E33 | F | 43 | pN0(sn) | 3 | 10-33% | 4 | 10-33% | 0 | 2.3 |
| BRC-E34 | F | 60 | pN0(sn) | 0 | 0% | 0 | 0% | 1 | 2.3 |
| BRC-E35 | F | 61 | — | 6 | 33-66% | 0 | 0% | 2 | — |
| BRC-E36 | F | 61 | pN0(sn) | 0 | 0% | 2 | <10% | 2 | 1.8 |
| BRC-E37 | F | 49 | — | — | — | — | — | — | — |
| BRC-E38 | F | 45 | ypN0 | 0 | 0% | 0 | 0% | 0 | 0.9 |
| BRC-E39 | F | 59 | pN0 | 0 | 0% | 0 | 0% | 3 | 1.1 |
| BRC-E40 | F | 43 | pN1 | 0 | 0% | 0 | 0% | 0 | 1.5 |
| BRC-E41 | F | 46 | pN1 | 8 | 100% | 8 | 100% | 0 | 1.3 |
| BRC-E42 | F | 48 | pN0 | 6 | 50-60% | 5 | 10-20% | 3 | 1.3 |
| BRC-E43 | F | 39 | pN0 | 0 | 0% | 0 | 0% | 0 | 2.2 |
| BRC-E44 | F | 66 | pN0 | 8 | 95% | 8 | 95% | 0 | 1.7 |
| BRC-E45 | F | 39 | ypN0 | 0 | 0% | 0 | 0% | 0 | DCIS |
| BRC-E46 | F | 37 | pN0 | 7 | 70-80% | 8 | 80% | 3 | 1.5 |
| BRC-E47 | F | 64 | pN0 | 8 | 95% | 8 | 95% | 0 | 0.5 |
| BRC-E48 | F | 44 | ypN1 | 7 | 90% | 8 | 95% | 0 | 2 |
| BRC-E49 | F | 50 | pN2 | 8 | 95% | 8 | 100% | 0 | 1.1 |
| BRC-E50 | F | 47 | pN0 | 7 | 70% | 7 | 50-60% | 1 | 0.5 |
| BRC-E51 | F | 44 | pN1 | 8 | 90% | 8 | 95% | 1 | 0.6 |
| BRC-E52 | F | 50 | pN0 | 0 | 0% | 0 | 0% | 2 | 2.2 |
| BRC-E53 | F | 53 | pN0 | 7 | 95% | 8 | 95% | 0 | 1.1 |
| BRC-E54 | F | 65 | pN0 | 8 | 95% | 7 | 40% | 0 | 1.5 |

TABLE 307

| NHL | Sex | Age year | Stage | Involved Site | Subtype | IPI |
|---|---|---|---|---|---|---|
| NHL-E1 | M | 44 | 1 | stomach | DLBL | 1 |
| NHL-E2 | M | 39 | 1 | nasal cavity | NK/T cell L | 1 |
| NHL-E3 | M | 41 | 1 | inguinal LN | ALCL | 0 |
| NHL-E4 | F | 49 | 1 | mandibular area | DLBL | 0 |
| NHL-E5 | F | 48 | 1 | neck, submandibular | DLBL | 0 |
| NHL-E6 | M | 63 | 2 | stomach | DLBL | 1 |
| NHL-E7 | M | 64 | 2 | stomach | DLBL | 2 |
| NHL-E8 | M | 52 | 2 | spleen, pancreatic LN | DLBL | 1 |
| NHL-E9 | M | 42 | 2 | multiple | DLBL | 2 |
| NHL-E10 | M | 54 | 2 | stomach | DLBL | 1 |
| NHL-E11 | F | 41 | 2 | stomach | DLBL | 1 |
| NHL-E12 | F | 66 | 2 | gum, submandibular | DLBL | 1 |
| NHL-E13 | M | 65 | 3 | multiple | DLBL | 3 |
| NHL-E14 | M | 65 | 3 | multiple | DLBL | 3 |
| NHL-E15 | M | 65 | 3 | multiple | Follicular L | 2 |
| NHL-E16 | M | 58 | 3 | multiple | DLBL | 2 |
| NHL-E17 | M | 40 | 4 | multiple | DLBL | 3 |
| NHL-E18 | F | 57 | 4 | multiple | DLBL | 3 |
| NHL-E19 | F | 24 | 4 | multiple | DLBL | 4 |
| NHL-E20 | M | 56 | 4 | multiple | DLBL | 3 |
| NHL-E21 | F | 76 | 4 | multiple | DLBL | 3 |
| NHL-E22 | F | 69 | 4 | multiple | Mantle cell L | 4 |
| NHL-E23 | F | 64 | 4 | multiple | DLBL | 5 |
| NHL-E24 | M | 44 | 4 | multiple | DLBL | 2 |

With respect to set $E_1$ consisting of 288 cases, subset $E_0$ was constructed into the first training set. The weightings (factor loadings) per mass ions were computed by the biostatistical analysis, and the preliminary discriminant was acquired. Further, the training set was enlarged to include the second training set $E_2$ consisting of the 48 GC patients of Table 308, 83 normal controls of Table 309, 175 CRC patients of Table 310, 54 BRC patients of Table 311 and 22 NHL patients of Table 312. That is, to analyze GC-diagnosing low-mass ions according to the method explained below with respect to the preliminary candidate groups of the low-mass ions constructing the preliminary discriminant, the set E, i.e., union of set $E_1$ and set $E_2$, which are independent from each other, was used as the training set.

TABLE 308

| GC | Sex | Age year | CEA ng/mL | Stage |
|---|---|---|---|---|
| GC-E50 | M | 32 | — | I |
| GC-E51 | M | 71 | 3.54 | I |
| GC-E52 | M | 56 | 2.83 | I |
| GC-E53 | F | 40 | — | I |
| GC-E54 | M | 62 | — | I |
| GC-E55 | M | 79 | — | I |
| GC-E56 | M | 81 | — | I |
| GC-E57 | M | 52 | — | I |
| GC-E58 | M | 53 | — | I |
| GC-E59 | M | 72 | — | II |
| GC-E60 | F | 49 | — | II |
| GC-E61 | M | 69 | — | II |
| GC-E62 | M | 72 | — | II |
| GC-E63 | F | 49 | — | II |
| GC-E64 | M | 62 | — | II |
| GC-E65 | M | 67 | — | II |
| GC-E66 | F | 64 | — | II |
| GC-E67 | F | 40 | — | II |
| GC-E68 | M | 53 | 1 | III |
| GC-E69 | M | 42 | 0.69 | III |
| GC-E70 | M | 81 | — | III |
| GC-E71 | M | 70 | 1.26 | III |
| GC-E72 | F | 81 | — | III |
| GC-E73 | F | 36 | — | III |
| GC-E74 | M | 46 | — | III |
| GC-E75 | M | 62 | — | III |
| GC-E76 | M | 51 | — | III |
| GC-E77 | F | 42 | <0.4 | IV |
| GC-E78 | M | 49 | 104.73 | IV |
| GC-E79 | M | 65 | 1.69 | IV |
| GC-E80 | F | 57 | 6.98 | IV |
| GC-E81 | M | 55 | 2.03 | IV |
| GC-E82 | F | 51 | 0.51 | IV |
| GC-E83 | M | 63 | 27.18 | IV |
| GC-E84 | M | 51 | 1.93 | IV |
| GC-E85 | M | 64 | 2.41 | IV |
| GC-E86 | M | 62 | 2.72 | IV |
| GC-E87 | F | 40 | 0.64 | IV |
| GC-E88 | M | 66 | 11.68 | IV |
| GC-E89 | M | 51 | 5.6 | IV |
| GC-E90 | M | 66 | 1.22 | IV |
| GC-E91 | M | 70 | — | IV |
| GC-E92 | F | 71 | — | IV |
| GC-E93 | F | 52 | — | IV |
| GC-E94 | M | 68 | — | IV |
| GC-E95 | M | 68 | — | IV |
| GC-E96 | F | 33 | — | IV |
| GC-E97 | M | 31 | — | IV |

TABLE 309

| Control | Sex | Age year | CEA ng/mL |
|---|---|---|---|
| CONT-E85 | F | 67 | 1.5 |
| CONT-E86 | F | 45 | 0.6 |
| CONT-E87 | M | 30 | 1 |
| CONT-E88 | M | 55 | 1.2 |
| CONT-E89 | M | 54 | 2.1 |
| CONT-E90 | M | 69 | 2.8 |
| CONT-E91 | M | 53 | 1.8 |
| CONT-E92 | F | 47 | 1.7 |
| CONT-E93 | M | 53 | 3.2 |
| CONT-E94 | F | 49 | 1.4 |
| CONT-E95 | M | 62 | 1.7 |
| CONT-E96 | M | 31 | 2.3 |
| CONT-E97 | M | 40 | 0.8 |
| CONT-E98 | F | 49 | 1.4 |
| CONT-E99 | F | 33 | 1.7 |
| CONT-E100 | M | 51 | 3.4 |
| CONT-E101 | M | 52 | 2 |
| CONT-E102 | F | 66 | 1.3 |
| CONT-E103 | F | 65 | 1.4 |
| CONT-E104 | M | 50 | 1.4 |
| CONT-E105 | M | 54 | 1.3 |
| CONT-E106 | M | 68 | 1.6 |
| CONT-E107 | M | 59 | 2.5 |
| CONT-E108 | F | 51 | 2.1 |
| CONT-E109 | F | 39 | 0.8 |
| CONT-E110 | F | 50 | 1.9 |
| CONT-E111 | F | 64 | 2.9 |
| CONT-E112 | F | 52 | 1.9 |
| CONT-E113 | F | 37 | 2.1 |
| CONT-E114 | F | 49 | 2.6 |
| CONT-E115 | F | 30 | <0.5 |
| CONT-E116 | F | 49 | 2.1 |
| CONT-E117 | F | 38 | 0.6 |
| CONT-E118 | F | 59 | 1.6 |
| CONT-E119 | F | 41 | 1.8 |
| CONT-E120 | F | 48 | 1.2 |
| CONT-E121 | F | 39 | 0.5 |
| CONT-E122 | F | 51 | 1.1 |
| CONT-E123 | F | 44 | 1.5 |
| CONT-E124 | F | 38 | 1.5 |
| CONT-E125 | F | 48 | 1.9 |
| CONT-E126 | F | 70 | 4.8 |
| CONT-E127 | F | 38 | 2.8 |
| CONT-E128 | F | 50 | 1.1 |
| CONT-E129 | F | 54 | 1.8 |
| CONT-E130 | F | 58 | 3.1 |
| CONT-E131 | M | 65 | 2.8 |
| CONT-E132 | M | 66 | 0.8 |
| CONT-E133 | F | 54 | 1.6 |
| CONT-E134 | M | 50 | 1.9 |
| CONT-E135 | F | 60 | 1.1 |
| CONT-E136 | F | 55 | 8.8 |
| CONT-E137 | M | 62 | 0.9 |
| CONT-E138 | M | 65 | 2.3 |
| CONT-E139 | M | 52 | 2.4 |
| CONT-E140 | F | 64 | 1.7 |
| CONT-E141 | M | 57 | 0.8 |
| CONT-E142 | F | 54 | <0.5 |
| CONT-E143 | F | 59 | 0.8 |
| CONT-E144 | F | 65 | 1.6 |
| CONT-E145 | F | 68 | 1.6 |
| CONT-E146 | F | 51 | 1.7 |
| CONT-E147 | F | 62 | 1.3 |
| CONT-E148 | F | 63 | 1.6 |
| CONT-E149 | F | 60 | 1.9 |
| CONT-E150 | F | 68 | 1.4 |
| CONT-E151 | F | 62 | 1.9 |
| CONT-E152 | F | 68 | 5.6 |
| CONT-E153 | M | 63 | 4.5 |
| CONT-E154 | M | 50 | 2.1 |
| CONT-E155 | F | 53 | 2.3 |
| CONT-E156 | M | 60 | 3.3 |
| CONT-E157 | M | 64 | 1.8 |
| CONT-E158 | F | 63 | 1.1 |
| CONT-E159 | M | 53 | 2 |
| CONT-E160 | F | 51 | 2 |
| CONT-E161 | F | 42 | — |
| CONT-E162 | M | 41 | — |
| CONT-E163 | M | 40 | — |

TABLE 309-continued

| Control | Sex | Age year | CEA ng/mL |
|---|---|---|---|
| CONT-E164 | M | 51 | — |
| CONT-E165 | F | 59 | — |
| CONT-E166 | F | 57 | — |
| CONT-E167 | M | 47 | — |

TABLE 310

| CRC | Sex | Age year | Stage | Location | Cell Type | CEA ng/mL |
|---|---|---|---|---|---|---|
| CRC-E78 | M | 50 | I | S-colon | AC | 2.5 |
| CRC-E79 | M | 56 | I | S-colon | AC | 7.3 |
| CRC-E80 | M | 61 | I | Rectum | AC | 7.7 |
| CRC-E81 | F | 78 | I | Rectum | AC | 2.6 |
| CRC-E82 | M | 64 | I | S-colon | AC | 1.8 |
| CRC-E83 | F | 50 | I | Rectum | AC | 1.6 |
| CRC-E84 | F | 59 | I | Rectum | AC | 1.6 |
| CRC-E85 | M | 71 | I | Rectum | AC | 83.7 |
| CRC-E86 | M | 59 | I | S-colon | AC | 3 |
| CRC-E87 | M | 64 | I | Rectum | AC | 2.5 |
| CRC-E88 | M | 49 | I | Rectum | AC | 6.6 |
| CRC-E89 | F | 65 | II | S-colon | AC | 2.1 |
| CRC-E90 | M | 77 | II | A-colon | AC | 1.5 |
| CRC-E91 | M | 71 | II | D-colon | AC | 4.1 |
| CRC-E92 | F | 66 | II | Rectum | AC | 4.3 |
| CRC-E93 | F | 49 | II | A-colon | AC | 1.6 |
| CRC-E94 | F | 79 | II | A-colon | AC | 2.9 |
| CRC-E95 | M | 69 | II | S-colon | AC | 4.2 |
| CRC-E96 | M | 66 | II | S-colon | AC | 12 |
| CRC-E97 | M | 74 | II | A-colon | AC | 1.5 |
| CRC-E98 | M | 69 | II | T-colon | AC | 1.2 |
| CRC-E99 | M | 43 | II | S-colon | AC | 2.2 |
| CRC-E100 | F | 67 | II | A-colon | AC | 1.4 |
| CRC-E101 | M | 72 | II | A-colon | AC | 4.9 |
| CRC-E102 | F | 69 | II | S-colon, A-colon | AC | 5.1 |
| CRC-E103 | M | 39 | II | S-colon | AC | 2.9 |
| CRC-E104 | M | 54 | II | Rectum | AC | 4.6 |
| CRC-E105 | M | 58 | II | S-colon | AC | 2.9 |
| CRC-E106 | M | 65 | II | S-colon | AC | 1.7 |
| CRC-E107 | F | 52 | II | S-colon | AC | <0.5 |
| CRC-E108 | F | 76 | II | S-colon | AC | 2.2 |
| CRC-E109 | M | 51 | II | S-colon | ASC | 8.6 |
| CRC-E110 | F | 79 | III | Rectum | AC | 14.1 |
| CRC-E111 | F | 44 | III | S-colon | AC | 1.4 |
| CRC-E112 | M | 66 | III | Rectum | AC | 1.2 |
| CRC-E113 | M | 53 | III | A-colon | AC | 4.2 |
| CRC-E114 | M | 64 | III | T-colon | AC | 1.8 |
| CRC-E115 | F | 42 | III | S-colon | AC | 0.8 |
| CRC-E116 | M | 49 | III | Rectum | AC | 2.7 |
| CRC-E117 | M | 68 | III | Rectum | AC | 3.9 |
| CRC-E118 | M | 51 | III | S-colon | AC | 5.2 |
| CRC-E119 | M | 64 | III | Rectum | AC | 7.7 |
| CRC-E120 | M | 42 | III | S-colon | AC | 2.8 |
| CRC-E121 | F | 43 | III | A-colon | AC | 4.7 |
| CRC-E122 | M | 66 | III | S-colon | AC | 9.1 |
| CRC-E123 | M | 37 | III | Rectum | AC | 3.7 |
| CRC-E124 | F | 81 | III | Rectum | AC | 8.4 |
| CRC-E125 | F | 73 | III | S-colon | AC | 1.7 |
| CRC-E126 | M | 54 | III | Rectum | AC | 6.4 |
| CRC-E127 | F | 58 | III | Rectum | AC | 21.3 |
| CRC-E128 | F | 42 | III | Rectum | AC | 0.7 |
| CRC-E129 | M | 62 | III | S-colon | AC | 10.8 |
| CRC-E130 | F | 60 | III | S-colon, A-colon | AC | 28.5 |
| CRC-E131 | F | 73 | III | Rectum | AC | 3.7 |
| CRC-E132 | F | 54 | III | D-colon | AC | 1122.2 |
| CRC-E133 | F | 60 | III | A-colon | AC | 30.4 |
| CRC-E134 | M | 43 | III | A-colon | MAC | 77.6 |
| CRC-E135 | F | 69 | III | Rectum | AC | 1 |
| CRC-E136 | M | 72 | III | A-colon | AC | 2.4 |
| CRC-E137 | F | 52 | III | S-colon | AC | 9.2 |
| CRC-E138 | M | 52 | III | S-colon | AC | 3.2 |
| CRC-E139 | F | 55 | III | Rectum | AC | 0.9 |

TABLE 310-continued

| CRC | Sex | Age year | Stage | Location | Cell Type | CEA ng/mL |
|---|---|---|---|---|---|---|
| CRC-E140 | M | 77 | III | S-colon | AC | 2.5 |
| CRC-E141 | F | 47 | III | S-colon | AC | 1.5 |
| CRC-E142 | M | 48 | III | S-colon | AC | 1.7 |
| CRC-E143 | F | 72 | IV | A-colon | AC | 73.4 |
| CRC-E144 | F | 69 | IV | A-colon | AC | 49 |
| CRC-E145 | M | 75 | IV | S-colon | AC | 16.7 |
| CRC-E146 | M | 72 | IV | Rectum | SC | 8.2 |
| CRC-E147 | M | 73 | IV | Rectum | AC | 52.2 |
| CRC-E148 | M | 54 | IV | A-colon | AC | 2 |
| CRC-E149 | M | 67 | IV | Rectum | AC | 16.2 |
| CRC-E150 | F | 66 | IV | S-colon | AC | 18.5 |
| CRC-E151 | F | 78 | IV | A-colon | AC | 12.6 |
| CRC-E152 | F | 54 | IV | S-colon | AC | 27.9 |
| CRC-E153 | M | 70 | II | Rectum | AC | 1.3 |
| CRC-E154 | M | 55 | II | Rectum | AC | 22 |
| CRC-E155 | M | 62 | II | Rectum | AC | 6.1 |
| CRC-E156 | M | 64 | III | Rectum | AC | 4.8 |
| CRC-E157 | M | 62 | IV | Rectum | AC | 25.3 |
| CRC-E158 | M | 51 | III | Rectum | AC | 149.3 |
| CRC-E159 | F | 45 | II | Rectum | AC | 2.7 |
| CRC-E160 | F | 49 | II | Rectum | AC | 2.1 |
| CRC-E161 | F | 45 | 0 | Rectum | AC | 0.9 |
| CRC-E162 | M | 62 | III | Rectum | AC | 2.4 |
| CRC-E163 | M | 54 | 0 | Rectum | AC | 6.9 |
| CRC-E164 | M | 45 | 0 | Rectum | AC | 7.4 |
| CRC-E165 | F | 54 | 0 | Rectum | AC | 3.6 |
| CRC-E166 | M | 69 | II | Rectum | AC | 24 |
| CRC-E167 | M | 51 | I | Rectum | AC | 2.7 |
| CRC-E168 | M | 45 | I | Rectum | AC | 3.2 |
| CRC-E169 | M | 67 | I | Rectum | AC | 2.9 |
| CRC-E170 | M | 60 | I | Rectum | AC | 1.5 |
| CRC-E171 | M | 49 | 0 | Rectum | AC | 0.8 |
| CRC-E172 | M | 71 | I | Rectum | AC | 9.8 |
| CRC-E173 | M | 62 | III | Rectum | AC | 2.5 |
| CRC-E174 | M | 54 | II | Rectum | AC | 4.6 |
| CRC-E175 | M | 56 | II | Rectum | AC | 3 |
| CRC-E176 | F | 71 | III | Rectum | AC | 6.7 |
| CRC-E177 | M | 73 | 0 | Rectum | AC | 61.5 |
| CRC-E178 | F | 50 | III | Rectum | AC | 2.2 |
| CRC-E179 | F | 49 | 0 | Rectum | AC | 1.6 |
| CRC-E180 | F | 42 | III | Rectum | AC | 9.9 |
| CRC-E181 | M | 61 | III | Rectum | AC | 68.1 |
| CRC-E182 | F | 72 | II | Rectum | AC | 8 |
| CRC-E183 | F | 69 | III | Rectum | AC | 11.3 |
| CRC-E184 | M | 58 | II | Rectum | AC | 5.3 |
| CRC-E185 | M | 56 | I | Rectum | AC | 24.8 |
| CRC-E186 | M | 72 | III | Rectum | AC | 1.4 |
| CRC-E187 | M | 62 | III | Rectum | AC | 1.6 |
| CRC-E188 | M | 55 | II | Rectum | AC | 2.4 |
| CRC-E189 | F | 71 | III | Rectum | AC | 1.3 |
| CRC-E190 | M | 59 | III | Rectum | AC | 2.8 |
| CRC-E191 | M | 52 | II | Rectum | AC | 4 |
| CRC-E192 | M | 47 | III | Rectum | AC | 2.3 |
| CRC-E193 | M | 58 | II | Rectum | AC | 1.1 |
| CRC-E194 | M | 60 | 0 | Rectum | AC | 2 |
| CRC-E195 | M | 64 | I | Rectum | AC | 2 |
| CRC-E196 | M | 41 | III | Rectum | AC | 1.6 |
| CRC-E197 | M | 48 | I | Rectum | AC | 0.8 |
| CRC-E198 | M | 58 | II | Rectum | AC | 1.1 |
| CRC-E199 | M | 61 | I | Rectum | AC | 2.6 |
| CRC-E200 | M | 63 | I | Rectum | AC | 1.3 |
| CRC-E201 | F | 52 | II | Rectum | AC | 1.6 |
| CRC-E202 | M | 53 | II | Rectum | AC | 2 |
| CRC-E203 | M | 64 | I | Rectum | AC | 2 |
| CRC-E204 | M | 73 | II | Rectum | AC | 5.6 |
| CRC-E205 | M | 41 | III | Rectum | AC | 1.6 |
| CRC-E206 | M | 57 | III | Rectum | AC | 2 |
| CRC-E207 | M | 48 | I | Rectum | AC | 0.8 |
| CRC-E208 | M | 72 | III | Rectum | AC | 6.1 |
| CRC-E209 | F | 67 | 0 | Rectum | AC | 4.4 |
| CRC-E210 | F | 66 | II | Rectum | AC | 4.8 |
| CRC-E211 | M | 47 | III | S-colon | AC | 3.7 |
| CRC-E212 | M | 40 | III | A-colon | AC | 1.2 |
| CRC-E213 | M | 55 | II | D-colon | AC | 6 |
| CRC-E214 | F | 73 | I | D-colon, T-colon | AC | 2 |
| CRC-E215 | F | 69 | I | A-colon | AC | 5 |

TABLE 310-continued

| CRC | Sex | Age year | Stage | Location | Cell Type | CEA ng/mL |
|---|---|---|---|---|---|---|
| CRC-E216 | F | 69 | I | A-colon | AC | 5.7 |
| CRC-E217 | F | 74 | II | D-colon | AC | 12.5 |
| CRC-E218 | M | 61 | II | S-colon | MAC | 1.9 |
| CRC-E219 | M | 37 | III | Rectum | AC | 6 |
| CRC-E220 | M | 60 | III | S-colon | AC | 5.4 |
| CRC-E221 | M | 70 | II | S-colon | AC | 2.6 |
| CRC-E222 | M | 68 | III | Rectum | AC | 13.2 |
| CRC-E223 | M | 73 | I | Rectum | AC | 1.7 |
| CRC-E224 | M | 82 | III | T-colon | AC | 2.1 |
| CRC-E225 | F | 75 | II | Rectum | AC | 0.9 |
| CRC-E226 | F | 57 | I | A-colon | AC | 1.5 |
| CRC-E227 | F | 62 | III | S-colon | AC | 4.4 |
| CRC-E228 | M | 73 | II | Rectum | AC | 15.5 |
| CRC-E229 | M | 59 | I | S-colon | AC | 1.1 |
| CRC-E230 | F | 74 | III | Rectum | AC | 31 |
| CRC-E231 | F | 70 | I | A-colon | AC | 2.5 |
| CRC-E232 | M | 74 | II | S-colon | AC | 15.4 |
| CRC-E233 | M | 69 | II | Rectum | AC | 2.1 |
| CRC-E234 | M | 61 | II | A-colon, T-colon | AC | 2.3 |

TABLE 310-continued

| CRC | Sex | Age year | Stage | Location | Cell Type | CEA ng/mL |
|---|---|---|---|---|---|---|
| CRC-E235 | M | 73 | I | Rectum | AC | 1.9 |
| CRC-E236 | M | 64 | I | Rectum | AC | 2.8 |
| CRC-E237 | M | 69 | II | D-colon | AC | 5 |
| CRC-E238 | M | 58 | III | Rectum | AC | 1.6 |
| CRC-E239 | M | 73 | II | T-colon | AC | 2.6 |
| CRC-E240 | M | 70 | II | A-colon | AC | 20.8 |
| CRC-E241 | M | 56 | IV | Rectum | AC | 29.9 |
| CRC-E242 | F | 70 | II | A-colon | AC | 5.9 |
| CRC-E243 | M | 71 | III | S-colon | AC | 110.1 |
| CRC-E244 | M | 47 | III | Rectum | AC | 13.7 |
| CRC-E245 | M | 61 | III | Rectum | AC | 2.8 |
| CRC-E246 | F | 77 | II | S-colon | AC | 1.5 |
| CRC-E247 | F | 62 | III | Rectum | AC | 13.7 |
| CRC-E248 | M | 61 | II | S-colon | AC | 2.3 |
| CRC-E249 | M | 66 | II | S-colon | AC | 1.7 |
| CRC-E250 | M | 64 | III | A-colon | AC | 1 |
| CRC-E251 | M | 69 | II | S-colon | AC | 23 |
| CRC-E252 | M | 66 | 0 | Rectum | AC | 58.4 |

ASC: Adenosquamous carcinoma

TABLE 311

| BRC | Sex | Age year | Node | ER | ER % | PR | PR % | HER2 | Tumor Size cm |
|---|---|---|---|---|---|---|---|---|---|
| BRC-E55 | F | 44 | pN0 | 6 | 33-66% | 7 | >66% | 1 | 1.2 |
| BRC-E56 | F | 72 | pN0(sn) | 0 | 0% | 0 | 0% | 0 | 1.8 |
| BRC-E57 | F | 48 | pN0(sn) | 5 | 33-66% | 4 | 10-33% | 1 | 0.8 |
| BRC-E58 | F | 44 | pN0 | 5 | 33-66% | 7 | >66% | 1 | 2 |
| BRC-E59 | F | 41 | pN2a | 5 | 33-66% | 6 | 33-66% | 1 | 4 |
| BRC-E60 | F | 58 | pN0 | 6 | 33-66% | 0 | 0% | 2 | <0.1 |
| BRC-E61 | F | 42 | — | 5 | 33-66% | 6 | 33-66% | 2 | — |
| BRC-E62 | F | 44 | pN1a | 4 | 10-33% | 2 | <10% | 2 | 5.5 |
| BRC-E63 | F | 62 | pN0(sn) | 7 | >66% | 0 | 0% | 0 | 2 |
| BRC-E64 | F | 47 | pN0 | 6 | 33-66% | 6 | 33-66% | 2 | 2.4 |
| BRC-E65 | F | 52 | pN1a | 6 | 33-66% | 0 | 0% | 3 | 1.8 |
| BRC-E66 | F | 44 | pN0(sn) | 6 | 33-66% | 0 | 0% | 0 | 2 |
| BRC-E67 | F | 49 | pN0(sn) | 2 | <10% | 2 | <10% | 3 | 0.4 |
| BRC-E68 | F | 46 | pN0(sn) | 6 | 33-66% | 5 | 33-66% | 1 | 0.7 |
| BRC-E69 | F | 58 | pN0(sn) | 7 | >66% | 5 | 33-66% | 1 | 2.3 |
| BRC-E70 | F | 64 | pN1a | 6 | 33-66% | 7 | >66% | 1 | 2 |
| BRC-E71 | F | 47 | — | 6 | 33-66% | 6 | 33-66% | 2 | — |
| BRC-E72 | F | 74 | pN1a | 6 | 33-66% | 6 | 33-66% | 1 | 1.8 |
| BRC-E73 | F | 64 | pN0(sn) | 0 | 0% | 0 | 0% | 1 | 2.2 |
| BRC-E74 | F | 40 | ypN1a | 6 | 33-66% | 6 | 33-66% | 1 | 3.5 |
| BRC-E75 | F | 43 | pN0 | 6 | 33-66% | 6 | 33-66% | 2 | 2.5 |
| BRC-E76 | F | 43 | ypN0 | 0 | 0% | 0 | 0% | 2 | — |
| BRC-E77 | F | 42 | pN0 | 0 | 0% | 0 | 0% | 0 | 2.3 |
| BRC-E78 | F | 37 | pN0(i+) | 6 | 33-66% | 6 | 33-66% | 1 | 1 |
| BRC-E79 | F | 50 | pN1a | 6 | 33-66% | 6 | 33-66% | 1 | 1 |
| BRC-E80 | F | 57 | pN0(sn) | 6 | 33-66% | 96 | 33-66% | 1 | 1.4 |
| BRC-E81 | F | 38 | ypN0 | 0 | 0% | 0 | 0% | 1 | 2 |
| BRC-E82 | F | 67 | — | 6 | 33-66% | 2 | <10% | 1 | — |
| BRC-E83 | F | 42 | pN0(sn) | 6 | 33-66% | 6 | 33-66% | 2 | 0.5 |
| BRC-E84 | F | 46 | pN0(sn) | 6 | 33-66% | 6 | 33-66% | 1 | 1 |
| BRC-E85 | F | 48 | pN2a | 4 | 10-33% | 4 | 10-33% | 3 | 2.5 |
| BRC-E86 | F | 58 | pN0 | 2 | <10% | 0 | 0 | 1 | 0.5 |
| BRC-E87 | F | 53 | pN0(sn) | 0 | 0% | 0 | 0% | 3 | <0.1 |
| BRC-E88 | F | 56 | — | 0 | 0% | 0 | 0% | 0 | — |
| BRC-E89 | F | 45 | pN0(sn) | 6 | 33-66% | 6 | 33-66% | 2 | <0.1 |
| BRC-E90 | F | 59 | pN0(sn) | 5 | 33-66% | 0 | 0% | 2 | 1.4 |
| BRC-E91 | F | 40 | ypN1a | 2 | <10% | 0 | 0% | 0 | 0.3 |
| BRC-E92 | F | 39 | pN1 | 7 | >95% | 3 | <10% | 0 | 2.2 |
| BRC-E93 | F | 54 | pN0(i+) | 7 | 95% | 5 | 10-30% | 1 | 1.7 |
| BRC-E94 | F | 48 | pN3a | 7 | 90% | 8 | 90% | 0 | 3.2 |
| BRC-E95 | F | 54 | pN0 | 0 | 0% | 0 | 0% | 0 | 3 |
| BRC-E96 | F | 43 | pN0 | 7 | 50-60% | 7 | 50-60% | 3 | 2.3 |
| BRC-E97 | F | 61 | pN0 | 8 | 95% | 8 | 95% | 0 | 1.6 |
| BRC-E98 | F | 54 | — | 0 | 0% | 0 | 0% | 3 | — |
| BRC-E99 | F | 46 | pN0 | 7 | 80% | 8 | 95% | 0 | 2.2 |
| BRC-E100 | F | 61 | pN0(i + 0) | 7 | >95% | 0 | 0% | 0 | 4 |
| BRC-E101 | F | 53 | pN0 | 7 | 80% | 5 | 25% | 0 | 0.6 |
| BRC-E102 | F | 49 | pN0 | 3 | 20% | 7 | 60% | 0 | 0.3 |
| BRC-E103 | F | 57 | pN0 | 0 | 0% | 0 | 0% | 0 | 0.8 |

TABLE 311-continued

| BRC | Sex | Age year | Node | ER | ER % | PR | PR % | HER2 | Tumor Size cm |
|---|---|---|---|---|---|---|---|---|---|
| BRC-E104 | F | 68 | pN0 | 0 | 0% | 3 | 1% | 3 | 1.2 |
| BRC-E105 | F | 58 | pN0 | 8 | 95% | 4 | 40% | 0 | 0.8 |
| BRC-E106 | F | 40 | — | 8 | 95% | 8 | 95% | 0 | — |
| BRC-E107 | F | 29 | pN0 | 8 | 95% | 8 | 95% | 1 | 1.2 |
| BRC-E108 | F | 40 | — | — | — | — | — | — | — |

TABLE 312

| NHL | Sex | Age year | Stage | Involved Site | Subtype | IPI |
|---|---|---|---|---|---|---|
| NHL-E25 | F | 56 | 1 | breast | DLBL | 0 |
| NHL-E26 | F | 38 | 1 | stomach | DLBL | 0 |
| NHL-E27 | F | 73 | 1 | nasal cavity | DLBL | 2 |
| NHL-E28 | F | 48 | 1 | breast | DLBL | 1 |
| NHL-E29 | F | 72 | 1 | stomach | DLBL | 2 |
| NHL-E30 | M | 44 | 2 | cervical LN, tonsil | DLBL | 0 |
| NHL-E31 | F | 38 | 2 | tonsil, neck LN | DLBL | 0 |
| NHL-E32 | M | 70 | 2 | neck area LN | DLBL | 1 |
| NHL-E33 | M | 80 | 2 | stomach | PTCL | 1 |
| NHL-E34 | F | 61 | 2 | stomach | DLBL | 3 |
| NHL-E35 | F | 76 | 2 | stomach | DLBL | 1 |
| NHL-E36 | M | 67 | 3 | multiple | Burkitt's L | 3 |
| NHL-E37 | F | 73 | 3 | multiple | DLBL | 2 |
| NHL-E38 | M | 49 | 3 | multiple | DLBL | 3 |
| NHL-E39 | F | 69 | 3 | multiple | ATCL | 3 |
| NHL-E40 | M | 71 | 4 | multiple | Mantle cell L | 3 |
| NHL-E41 | F | 38 | 4 | multiple | DLBL | 3 |
| NHL-E42 | F | 70 | 4 | multiple | DLBL | 3 |
| NHL-E43 | M | 25 | 4 | multiple | NK/T cell L | 3 |
| NHL-E44 | M | 48 | 4 | multiple | DLBL | 3 |
| NHL-E45 | M | 67 | 4 | multiple | MZBCL | 2 |
| NHL-E46 | M | 24 | 4 | multiple | DLBL | 3 |

Further, validation set was constructed with set E and set F consisting of 44 GC patients of Table 313, 81 normal controls of Table 314, 168 CRC patients of Table 315, 53 BRC patients of Table 316, 20 NHL patents of Table 317, and 25 ovarian cancer (OVC) patients of Table 318. The OVC patients were not reflected at all when obtaining weighting per mass ions or investigating GC-diagnosing low-mass ions, and included to see how these particular patient group IS discriminated with the discriminant constructed according to the present invention.

TABLE 313

| GC | Sex | Age year | CEA ng/mL | Stage |
|---|---|---|---|---|
| GC-F1 | F | 62 | — | I |
| GC-F2 | M | 52 | 1.86 | I |
| GC-F3 | F | 64 | 4.16 | I |
| GC-F4 | M | 67 | — | I |
| GC-F5 | M | 61 | — | I |
| GC-F6 | F | 77 | — | I |
| GC-F7 | F | 74 | — | I |
| GC-F8 | F | 81 | — | I |
| GC-F9 | F | 55 | — | I |
| GC-F10 | M | 69 | 21.71 | II |
| GC-F11 | M | 59 | — | II |
| GC-F12 | M | 64 | — | II |
| GC-F13 | M | 68 | — | II |
| GC-F14 | M | 54 | — | II |
| GC-F15 | F | 52 | — | II |
| GC-F16 | M | 59 | — | II |
| GC-F17 | F | 81 | — | II |
| GC-F18 | F | 68 | 5.56 | III |
| GC-F19 | M | 48 | 1.44 | III |
| GC-F20 | F | 80 | — | III |
| GC-F21 | M | 46 | 1.68 | III |
| GC-F22 | M | 42 | — | III |
| GC-F23 | M | 81 | — | III |
| GC-F24 | F | 81 | — | III |
| GC-F25 | M | 70 | — | III |
| GC-F26 | M | 51 | — | III |
| GC-F27 | M | 71 | 8.46 | IV |
| GC-F28 | M | 46 | 2.67 | IV |
| GC-F29 | M | 68 | 24.93 | IV |
| GC-F30 | M | 68 | 3.23 | IV |
| GC-F31 | M | 57 | 41.32 | IV |
| GC-F32 | M | 71 | 2.8 | IV |
| GC-F33 | F | 43 | 1.62 | IV |
| GC-F34 | M | 58 | 6.6 | IV |
| GC-F35 | M | 73 | — | IV |
| GC-F36 | M | 61 | 10.41 | IV |
| GC-F37 | M | 66 | — | IV |
| GC-F38 | F | 57 | 2.46 | IV |
| GC-F39 | M | 52 | — | IV |
| GC-F40 | M | 59 | — | IV |
| GC-F41 | M | 56 | — | IV |
| GC-F42 | M | 82 | — | IV |
| GC-F43 | F | 52 | — | IV |
| GC-F44 | M | 82 | — | IV |

TABLE 314

| Control | Sex | Age year | CEA ng/mL |
|---|---|---|---|
| CONT-F1 | M | 49 | 1.2 |
| CONT-F2 | F | 38 | 0.9 |
| CONT-F3 | F | 44 | — |
| CONT-F4 | M | 52 | — |
| CONT-F5 | F | 45 | — |
| CONT-F6 | F | 54 | — |
| CONT-F7 | F | 51 | 3.1 |
| CONT-F8 | M | 54 | 6.4 |
| CONT-F9 | M | 46 | 1.1 |
| CONT-F10 | M | 47 | 1.8 |
| CONT-F11 | M | 49 | 1.7 |
| CONT-F12 | F | 55 | <0.5 |
| CONT-F13 | M | 46 | 3.7 |
| CONT-F14 | F | 46 | <0.5 |
| CONT-F15 | M | 34 | 1.7 |
| CONT-F16 | M | 53 | 2.9 |
| CONT-F17 | M | 45 | 3.7 |
| CONT-F18 | M | 47 | 4.5 |
| CONT-F19 | F | 34 | 0.6 |
| CONT-F20 | F | 58 | 1.5 |
| CONT-F21 | F | 54 | — |
| CONT-F22 | M | 35 | 1.8 |
| CONT-F23 | M | 49 | 1.4 |
| CONT-F24 | M | 48 | 3.2 |
| CONT-F25 | F | 34 | <0.5 |
| CONT-F26 | M | 45 | 4.4 |
| CONT-F27 | M | 52 | — |
| CONT-F28 | F | 44 | — |
| CONT-F29 | M | 58 | — |
| CONT-F30 | M | 45 | 4.3 |
| CONT-F31 | M | 61 | 1.4 |

TABLE 314-continued

| Control | Sex | Age year | CEA ng/mL |
|---|---|---|---|
| CONT-F32 | M | 42 | 2.7 |
| CONT-F33 | M | 48 | 3 |
| CONT-F34 | M | 53 | 1.9 |
| CONT-F35 | F | 54 | 2.3 |
| CONT-F36 | F | 39 | 1.3 |
| CONT-F37 | F | 55 | 1.3 |
| CONT-F38 | M | 53 | — |
| CONT-F39 | F | 45 | — |
| CONT-F40 | F | 63 | — |
| CONT-F41 | F | 51 | — |
| CONT-F42 | M | 51 | — |
| CONT-F43 | F | 52 | — |
| CONT-F44 | F | 52 | — |
| CONT-F45 | M | 57 | 3.3 |
| CONT-F46 | M | 61 | 2.8 |
| CONT-F47 | F | 68 | 1.4 |
| CONT-F48 | F | 52 | 1.5 |
| CONT-F49 | M | 60 | 4.6 |
| CONT-F50 | M | 55 | 2.2 |
| CONT-F51 | M | 55 | 1.8 |
| CONT-F52 | M | 56 | 2.2 |
| CONT-F53 | F | 63 | 1.8 |
| CONT-F54 | F | 65 | 1.1 |
| CONT-F55 | F | 55 | 4.8 |
| CONT-F56 | M | 63 | 2.6 |
| CONT-F57 | F | 52 | 4.1 |
| CONT-F58 | M | 51 | 4 |
| CONT-F59 | M | 59 | 2 |
| CONT-F60 | M | 68 | 4.6 |
| CONT-F61 | M | 50 | 5 |
| CONT-F62 | F | 64 | <0.5 |
| CONT-F63 | F | 63 | 2.2 |
| CONT-F64 | M | 64 | 1.7 |
| CONT-F65 | M | 51 | 2.3 |
| CONT-F66 | F | 62 | 1.1 |
| CONT-F67 | M | 54 | 2.5 |
| CONT-F68 | F | 53 | 0.7 |
| CONT-F69 | F | 65 | 3.8 |
| CONT-F70 | F | 64 | 1.5 |
| CONT-F71 | F | 53 | 1 |
| CONT-F72 | M | 50 | 1.1 |
| CONT-F73 | F | 66 | 1.7 |
| CONT-F74 | F | 50 | 1.9 |
| CONT-F75 | M | 61 | 1.5 |
| CONT-F76 | M | 81 | — |
| CONT-F77 | F | 53 | — |
| CONT-F78 | M | 75 | — |
| CONT-F79 | F | 44 | — |
| CONT-F80 | M | 42 | — |
| CONT-F81 | M | 62 | — |

TABLE 315

| CRC | Sex | Age year | Stage | Location | Cell Type | CEA ng/mL |
|---|---|---|---|---|---|---|
| CRC-F1 | M | 73 | I | Rectum | AC | 1.9 |
| CRC-F2 | M | 65 | I | S-colon | AC | 14 |
| CRC-F3 | M | 72 | I | S-colon | AC | 4.6 |
| CRC-F4 | M | 82 | I | Rectum | AC | 3.2 |
| CRC-F5 | M | 77 | I | D-colon | AC | 6.4 |
| CRC-F6 | M | 78 | I | Rectum | AC | 2.7 |
| CRC-F7 | F | 46 | I | S-colon | AC | 1.4 |
| CRC-F8 | M | 61 | I | Rectum | AC | 1.4 |
| CRC-F9 | M | 43 | I | Rectum | AC | 0.5 |
| CRC-F10 | M | 53 | I | Rectum | AC | 3.5 |
| CRC-F11 | F | 67 | II | A-colon | AC | 7.3 |
| CRC-F12 | F | 75 | II | Rectum | AC | 12.6 |
| CRC-F13 | M | 68 | II | D-colon | AC | 4.7 |
| CRC-F14 | F | 60 | II | S-colon | AC | 3.3 |
| CRC-F15 | M | 74 | II | S-colon | AC | 9 |
| CRC-F16 | M | 63 | II | D-colon | AC | 4.9 |
| CRC-F17 | F | 66 | II | S-colon | AC | 4.2 |
| CRC-F18 | M | 48 | II | Rectum | AC | 28.4 |
| CRC-F19 | M | 68 | II | S-colon | AC | 2.3 |
| CRC-F20 | M | 48 | II | S-colon | AC | 4.8 |
| CRC-F21 | F | 81 | II | S-colon | AC | 2.4 |
| CRC-F22 | M | 56 | II | A-colon | AC | 34.6 |
| CRC-F23 | M | 56 | II | Rectum | AC | 3 |
| CRC-F24 | F | 77 | II | Rectum | AC | 6.2 |
| CRC-F25 | M | 44 | II | T-colon | AC | 1.8 |
| CRC-F26 | F | 82 | II | A-colon | AC | 2.8 |
| CRC-F27 | M | 67 | II | A-colon | AC | 20.1 |
| CRC-F28 | M | 72 | II | A-colon | AC | 3.4 |
| CRC-F29 | M | 59 | II | S-colon | AC | 2.1 |
| CRC-F30 | F | 50 | III | D-colon | AC | 6.4 |
| CRC-F31 | M | 56 | III | S-colon | AC | 7.3 |
| CRC-F32 | F | 58 | III | S-colon | AC | 2.1 |
| CRC-F33 | M | 71 | III | Rectum | AC | 16.5 |
| CRC-F34 | M | 66 | III | S-colon | AC | 689.8 |
| CRC-F35 | M | 65 | III | D-colon | AC | 3.4 |
| CRC-F36 | F | 65 | III | S-colon | MAC | 2.7 |
| CRC-F37 | F | 51 | III | Rectum | AC | 1.4 |
| CRC-F38 | M | 58 | III | S-colon | AC | 2.8 |
| CRC-F39 | F | 48 | III | A-colon | AC | 0.9 |
| CRC-F40 | M | 71 | III | S-colon | AC | 6 |
| CRC-F41 | M | 68 | III | A-colon | AC | 2.7 |
| CRC-F42 | F | 54 | III | A-colon | AC | 1.7 |
| CRC-F43 | F | 49 | III | S-colon | AC | 1 |
| CRC-F44 | F | 63 | III | A-colon | AC | 58.2 |
| CRC-F45 | M | 74 | III | A-colon | AC | 2.8 |
| CRC-F46 | F | 54 | III | T-colon | AC | 2.2 |
| CRC-F47 | M | 68 | III | Rectum | AC | 22.5 |
| CRC-F48 | M | 66 | III | Rectum | MAC | 1.2 |
| CRC-F49 | F | 70 | III | S-colon | MAC | 36 |
| CRC-F50 | M | 64 | III | A-colon | AC | 2.2 |
| CRC-F51 | F | 54 | III | Rectum | AC | 5.5 |
| CRC-F52 | M | 53 | III | Rectum | AC | 1.4 |
| CRC-F53 | M | 81 | III | A-colon | MAC | 10.9 |
| CRC-F54 | F | 52 | III | A-colon | AC | 1.2 |
| CRC-F55 | F | 71 | III | A-colon | AC | 2.8 |
| CRC-F56 | M | 84 | III | Rectum | AC | 15 |
| CRC-F57 | F | 33 | III | D-colon | AC | 4.7 |
| CRC-F58 | F | 68 | III | Rectum | AC | 3.3 |
| CRC-F59 | M | 69 | III | Rectum | AC | 3.5 |
| CRC-F60 | F | 61 | III | A-colon | AC | 2.8 |
| CRC-F61 | M | 73 | III | Rectum | AC | 11.1 |
| CRC-F62 | M | 64 | III | D-colon | AC | 8.2 |
| CRC-F63 | F | 54 | IV | S-colon | AC | 29.8 |
| CRC-F64 | M | 43 | IV | Rectum | AC | 36.4 |
| CRC-F65 | F | 52 | IV | A-colon | MAC | 9 |
| CRC-F66 | M | 48 | IV | S-colon | AC | 15.9 |
| CRC-F67 | M | 62 | IV | Rectum | AC | 6.3 |
| CRC-F68 | M | 69 | IV | A-colon | AC | 33.5 |
| CRC-F69 | M | 78 | IV | Rectum | AC | 4.1 |
| CRC-F70 | M | 38 | IV | Rectum | AC | 2.1 |
| CRC-F71 | M | 74 | II | Rectum | AC | 7.9 |
| CRC-F72 | F | 59 | III | Rectum | AC | 1.4 |
| CRC-F73 | M | 56 | I | Rectum | AC | 2.6 |
| CRC-F74 | M | 69 | II | Rectum | AC | 14 |
| CRC-F75 | M | 58 | II | Rectum | AC | 10.2 |
| CRC-F76 | F | 75 | II | Rectum | AC | 2.4 |
| CRC-F77 | M | 47 | II | Rectum | AC | 3.2 |
| CRC-F78 | F | 68 | II | Rectum | AC | 0.7 |
| CRC-F79 | M | 52 | III | Rectum | AC | 2.9 |
| CRC-F80 | M | 68 | I | Rectum | AC | 7 |
| CRC-F81 | M | 51 | II | Rectum | AC | 1.4 |
| CRC-F82 | M | 66 | 0 | Rectum | AC | 1.2 |
| CRC-F83 | M | 74 | 0 | Rectum | AC | 4.5 |
| CRC-F84 | M | 43 | II | Rectum | AC | 12.3 |
| CRC-F85 | M | 68 | III | Rectum | AC | 2.5 |
| CRC-F86 | M | 68 | III | Rectum | AC | 19.4 |
| CRC-F87 | F | 56 | I | Rectum | AC | 2.3 |
| CRC-F88 | M | 63 | 0 | Rectum | AC | 1.3 |
| CRC-F89 | M | 65 | II | Rectum | AC | 2.1 |
| CRC-F90 | M | 60 | II | Rectum | AC | 4.6 |
| CRC-F91 | M | 51 | II | Rectum | AC | 1.3 |
| CRC-F92 | M | 44 | 0 | Rectum | AC | 2.2 |
| CRC-F93 | M | 61 | II | Rectum | AC | 2 |
| CRC-F94 | M | 57 | III | Rectum | AC | 2.2 |
| CRC-F95 | M | 41 | II | Rectum | AC | 3.1 |

TABLE 315-continued

| CRC | Sex | Age year | Stage | Location | Cell Type | CEA ng/mL |
|---|---|---|---|---|---|---|
| CRC-F96 | M | 50 | I | Rectum | AC | 4.9 |
| CRC-F97 | F | 56 | III | Rectum | AC | 1 |
| CRC-F98 | M | 54 | III | Rectum | AC | 1.7 |
| CRC-F99 | F | 69 | I | Rectum | AC | 1.5 |
| CRC-F100 | M | 54 | I | Rectum | AC | 2.6 |
| CRC-F101 | M | 61 | II | Rectum | AC | 3.7 |
| CRC-F102 | M | 72 | III | Rectum | AC | 3 |
| CRC-F103 | F | 71 | III | Rectum | AC | 1.8 |
| CRC-F104 | M | 54 | II | Rectum | AC | 3 |
| CRC-F105 | M | 77 | II | Rectum | AC | 1.6 |
| CRC-F106 | M | 67 | III | Rectum | AC | 1.1 |
| CRC-F107 | M | 59 | II | Rectum | AC | 7.2 |
| CRC-F108 | M | 56 | III | Rectum | AC | 9 |
| CRC-F109 | F | 51 | I | Rectum | AC | 1.5 |
| CRC-F110 | F | 67 | III | Rectum | AC | 3.4 |
| CRC-F111 | F | 76 | III | Rectum | AC | 1 |
| CRC-F112 | F | 38 | III | Rectum | AC | 0.7 |
| CRC-F113 | M | 53 | II | Rectum | AC | 3.3 |
| CRC-F114 | M | 58 | III | Rectum | AC | 1.6 |
| CRC-F115 | M | 69 | III | Rectum | AC | 6.4 |
| CRC-F116 | F | 60 | I | Rectum | AC | 1.2 |
| CRC-F117 | M | 52 | II | Rectum | AC | 4 |
| CRC-F118 | M | 59 | III | Rectum | AC | 2.8 |
| CRC-F119 | F | 56 | III | Rectum | AC | 2.3 |
| CRC-F120 | F | 68 | I | Rectum | AC | 2 |
| CRC-F121 | M | 65 | I | Rectum | AC | 1.6 |
| CRC-F122 | M | 33 | II | Rectum | AC | 1.9 |
| CRC-F123 | M | 61 | III | Rectum | AC | 3.2 |
| CRC-F124 | F | 41 | III | Rectum | AC | 1.5 |
| CRC-F125 | M | 61 | I | Rectum | AC | 1.6 |
| CRC-F126 | F | 34 | III | Rectum | AC | 5.2 |
| CRC-F127 | M | 47 | III | Rectum | AC | 2.3 |
| CRC-F128 | F | 61 | III | A-colon | AC | 30.4 |
| CRC-F129 | M | 71 | IV | A-colon | AC | 33.5 |
| CRC-F130 | M | 44 | III | A-colon | MAC | 77.6 |
| CRC-F131 | F | 71 | III | Rectum | AC | 1 |
| CRC-F132 | M | 59 | II | S-colon | AC | 2.9 |
| CRC-F133 | M | 79 | IV | Rectum | AC | 4.1 |
| CRC-F134 | M | 66 | II | S-colon | AC | 1.7 |
| CRC-F135 | M | 78 | III | S-colon | AC | 2.5 |
| CRC-F136 | F | 53 | II | S-colon | AC | 1.3 |
| CRC-F137 | M | 50 | III | S-colon | AC | 1.7 |
| CRC-F138 | F | 77 | II | S-colon | AC | 2.2 |
| CRC-F139 | M | 53 | II | S-colon | ASC | 8.6 |
| CRC-F140 | M | 63 | I | Rectum | AC | 1.4 |
| CRC-F141 | F | 71 | III | S-colon | MAC | 36 |
| CRC-F142 | F | 79 | II | Rectum | AC | 6.2 |
| CRC-F143 | M | 83 | III | A-colon | MAC | 10.9 |
| CRC-F144 | F | 53 | III | A-colon | AC | 1.2 |
| CRC-F145 | F | 72 | III | A-colon | AC | 2.8 |
| CRC-F146 | F | 34 | III | D-colon | AC | 4.7 |
| CRC-F147 | M | 70 | III | Rectum | AC | 3.5 |
| CRC-F148 | F | 62 | III | A-colon | AC | 2.8 |
| CRC-F149 | M | 45 | II | T-colon | AC | 1.8 |
| CRC-F150 | F | 84 | II | A-colon | AC | 2.8 |
| CRC-F151 | M | 74 | III | Rectum | AC | 11.1 |
| CRC-F152 | M | 65 | III | D-colon | AC | 8.2 |
| CRC-F153 | M | 69 | II | A-colon | AC | 20.1 |
| CRC-F154 | M | 73 | II | A-colon | AC | 2.3 |
| CRC-F155 | M | 61 | II | S-colon | AC | 2.1 |
| CRC-F156 | F | 71 | II | S-colon | AC | 15.3 |
| CRC-F157 | F | 56 | I | S-colon | AC | 0.7 |
| CRC-F158 | F | 70 | II | S-colon | AC | 1.4 |
| CRC-F159 | F | 62 | III | Rectum | AC | 235.4 |
| CRC-F160 | M | 61 | III | S-colon | AC | 11.2 |
| CRC-F161 | F | 52 | III | S-colon | AC | 6.4 |
| CRC-F162 | M | 62 | II | S-colon | AC | 4.9 |
| CRC-F163 | F | 61 | III | T-colon | AC | 13.9 |
| CRC-F164 | F | 88 | II | A-colon | AC | 3 |
| CRC-F165 | M | 73 | II | S-colon | AC | 16.5 |
| CRC-F166 | M | 69 | III | A-colon | AC | 1.7 |
| CRC-F167 | M | 71 | III | A-colon | MAC | 2.4 |
| CRC-F168 | F | 45 | 0 | Rectum | AC | — |

TABLE 316

| BRC | Sex | Age year | Node | ER | ER % | PR | PR % | HER2 | Tumor Size cm |
|---|---|---|---|---|---|---|---|---|---|
| BRC-F1 | F | 34 | pN0(sn) | 2 | <10% | 0 | 0% | 2 | 2 |
| BRC-F2 | F | 69 | — | 6 | 33-66% | 6 | 33-66% | 1 | — |
| BRC-F3 | F | 52 | — | — | — | — | — | — | — |
| BRC-F4 | F | 67 | — | — | — | — | — | — | — |
| BRC-F5 | F | 61 | — | 6 | 33-66% | 2 | <10% | 0 | — |
| BRC-F6 | F | 38 | pN1a | 6 | 33-66% | 5 | 33-66% | 1 | — |
| BRC-F7 | F | 60 | pN0 | 6 | 33-66% | 3 | 10-33% | 1 | 1 |
| BRC-F8 | F | 55 | pN2a | 5 | 33-66% | 0 | 0% | 2 | 2.2 |
| BRC-F9 | F | 46 | ypN0 | 5 | 33-66% | 2 | <10% | 1 | 1.5 |
| BRC-F10 | F | 67 | pN0 | 6 | 33-66% | 6 | 33-66% | 1 | 2.8 |
| BRC-F11 | F | 46 | pN1a | 6 | 33-66% | 6 | 33-66% | 2 | 0.7 |
| BRC-F12 | F | 39 | pN1mi | 6 | 33-66% | 6 | 33-66% | 2 | 2.5 |
| BRC-F13 | F | 50 | pN0(sn) | 4 | 10-33% | 5 | 33-66% | 0 | 1 |
| BRC-F14 | F | 31 | pN1mi(sn) | 6 | 33-66% | 6 | 33-66% | 1 | 1 |
| BRC-F15 | F | 46 | pN0 | 6 | 33-66% | 7 | >66% | 1 | 1.2 |
| BRC-F16 | F | 44 | pN0(sn) | 6 | 33-66% | 7 | >66% | 1 | 2.5 |
| BRC-F17 | F | 40 | pN0 | 0 | 0% | 0 | 0% | 0 | — |
| BRC-F18 | F | 40 | — | 6 | 33-66% | 6 | 33-66% | 1 | — |
| BRC-F19 | F | 56 | — | 7 | >66% | 0 | 0 | 0 | 0.6 |
| BRC-F20 | F | 48 | pN1a | 0 | 0% | 0 | 0% | 0 | 3 |
| BRC-F21 | F | 39 | pN0(sn) | 6 | 33-66% | 6 | 33-66% | 1 | 3.5 |
| BRC-F22 | F | 40 | ypN1a | 6 | 33-66% | 4 | 10-33% | 2 | 3 |
| BRC-F23 | F | 48 | pN0(sn) | 6 | 33-66% | 6 | 33-66% | 0 | 2.5 |
| BRC-F24 | F | 59 | — | 7 | >66% | 2 | <10% | 1 | — |
| BRC-F25 | F | 46 | — | 0 | 0% | 0 | 0% | 2 | — |
| BRC-F26 | F | 37 | pN3a | 6 | 33-66% | 6 | 33-66% | 2 | 0.6 |
| BRC-F27 | F | 38 | pN0(sn) | 6 | 33-66% | 6 | 33-66% | 2 | 0.3 |
| BRC-F28 | F | 66 | pN1a | 6 | 33-66% | 6 | 33-66% | 0 | 1.5 |
| BRC-F29 | F | 58 | pN0(sn) | 0 | 0% | 0 | 0% | 2 | 1.7 |
| BRC-F30 | F | 42 | pN3a | 5 | 33-66% | 6 | 33-66% | 0 | 1.8 |
| BRC-F31 | F | 52 | pN0 | 6 | 33-66% | 6 | 33-66% | 0 | 0.7 |
| BRC-F32 | F | 46 | pN0(sn) | 0 | 0% | 2 | <10% | 1 | 1.5 |

TABLE 316-continued

| BRC | Sex | Age year | Node | ER | ER % | PR | PR % | HER2 | Tumor Size cm |
|---|---|---|---|---|---|---|---|---|---|
| BRC-F33 | F | 42 | pN0(sn) | 4 | 10-33% | 6 | 33-66% | 1 | 0.6 |
| BRC-F34 | F | 48 | — | — | — | — | — | — | — |
| BRC-F35 | F | 47 | pN0 | 6 | 33-66% | 2 | <10% | 2 | 3 |
| BRC-F36 | F | 59 | pN1a | 6 | 33-66% | 4 | 10-33% | 1 | 1.8 |
| BRC-F37 | F | 56 | — | 0 | 0% | 0 | 0% | 3 | — |
| BRC-F38 | F | 61 | pN0(i + 0) | 7 | >95% | 0 | 0% | 0 | 4 |
| BRC-F39 | F | 40 | — | 8 | 95% | 8 | 95% | 0 | — |
| BRC-F40 | F | 43 | pN0 | 0 | 0% | 0 | 0% | 3 | 0.7 |
| BRC-F41 | F | 59 | pN0 | 8 | 95% | 8 | 95% | 0 | 1.2 |
| BRC-F42 | F | 45 | PN2 | 7 | 95% | 8 | 95% | 1 | 2.1 |
| BRC-F43 | F | 55 | pN0 | 0 | 0% | 0 | 0% | 3 | 1.8 |
| BRC-F44 | F | 52 | pN0 | 7 | 80-90% | 8 | 80-90% | 0 | 0.3 |
| BRC-F45 | F | 59 | pN0 | 8 | 95% | 5 | 2~3% | 1 | 1.3 |
| BRC-F46 | F | 39 | — | 7 | >95% | 7 | 70-80% | 0 | — |
| BRC-F47 | F | 39 | pN0 | 0 | 0% | 0 | 0% | 3 | 1.1 |
| BRC-F48 | F | 40 | pN0 | 5 | 50-60% | 5 | 20-30% | 0 | 0.8 |
| BRC-F49 | F | 46 | pN0 | 7 | 95% | 8 | 95% | 0 | 4.9 |
| BRC-F50 | F | 51 | pN0 | 0 | <1% | 0 | 0% | 0 | 0.9 |
| BRC-F51 | F | 61 | pN0 | 7 | 90% | 8 | 90% | 0 | 1.3 |
| BRC-F52 | F | 48 | pN0 | 0 | 0% | 0 | 0% | 0 | 0.6 |
| BRC-F53 | p | 47 | pN0 | 8 | >95% | 8 | 95% | 0 | 0.7 |

TABLE 317

| NHL | Sex | Age year | Stage | Involved Site | Subtype | IPI |
|---|---|---|---|---|---|---|
| NHL-F1 | F | 41 | 1 | 0 | DLBL | 0 |
| NHL-F2 | M | 73 | 1 | nasal cavity | DLBL | 1 |
| NHL-F3 | M | 79 | 1 | nasal cavity | malignant L | 2 |
| NHL-F4 | M | 37 | 1 | cervical LN | DLBL | 0 |
| NHL-F5 | F | 39 | 2 | tonsil, neck LN | DLBL | 0 |
| NHL-F6 | M | 31 | 2 | neck | DLBL | 0 |
| NHL-F7 | M | 46 | 2 | nasopharynx, tonsil | DLBL | 0 |
| NHL-F8 | M | 72 | 2 | stomach | DLBL | 1 |
| NHL-F9 | M | 34 | 2 | neck, SCN | DLBL | 1 |
| NHL-F10 | M | 70 | 2 | stomach | DLBL | 1 |
| NHL-F11 | M | 52 | 3 | multiple | DLBL | 2 |
| NHL-F12 | M | 52 | 3 | multiple | DLBL | 2 |
| NHL-F13 | M | 67 | 4 | multiple | DLBL | 2 |
| NHL-F14 | M | 73 | 4 | tibia, leg(skin) | DLBL | 3 |
| NHL-F15 | F | 48 | 4 | multiple | DLBL | 3 |
| NHL-F16 | M | 38 | 4 | multiple | Hodgkin L | — |
| NHL-F17 | M | 70 | 4 | multiple | DLBL | 3 |
| NHL-F18 | M | 64 | 4 | multiple | DLBL | 4 |
| NHL-F19 | M | 25 | 4 | multiple | PTCL | 2 |
| NHL-F20 | M | 71 | — | stomach | r/o Lymphoma | — |

TABLE 318

| OVC | Age year | Histology | Stage |
|---|---|---|---|
| OVC-F1 | 56 | IIIc | Clear cell carcinoma |
| OVC-F2 | 52 | IIa | Endometrioid adenocarcinoma |
| OVC-F3 | 63 | IV | Papillary serous adenocarcinoma |
| OVC-F4 | 55 | Ia | Malignant Brenner tumor |
| OVC-F5 | 47 | IIIc | Papillary serous adenocarcinoma |
| OVC-F6 | 50 | Ic | Clear cell carcinoma |
| OVC-F7 | 68 | Ib | Serous adenocarcinoma |
| OVC-F8 | 74 | IIIc | Papillary serous adenocarcinoma |
| OVC-F9 | 43 | Ic | Mucinous adenocarcinoma |
| OVC-F10 | 44 | IIIc | Papillary serous adenocarcinoma |
| OVC-F11 | 54 | IIIc | Papillary serous adenocarcinoma |
| OVC-F12 | 55 | IV | Serous adenocarcinoma |
| OVC-F13 | 72 | IIIc | Serous adenocarcinoma |
| OVC-F14 | 58 | IIIc | Mucinous adenocarcinoma |
| OVC-F15 | 44 | IIIc | Papillary serous adenocarcinoma |
| OVC-F16 | 57 | IV | Serous adenocarcinoma |
| OVC-F17 | 54 | IIIc | Papillary serous adenocarcinoma |
| OVC-F18 | 73 | IIIc | Serous adenocarcinoma |
| OVC-F19 | 47 | IIIc | Papillary serous adenocarcinoma |
| OVC-F20 | 40 | Ic | Papillary serous adenocarcinoma |
| OVC-F21 | 74 | IIb | Transitional cell carcinoma |
| OVC-F22 | 65 | IIIc | Papillary serous adenocarcinoma |
| OVC-F23 | 47 | IV | Serous adenocarcinoma |
| OVC-F24 | 58 | IIc | Serous adenocarcinoma |
| OVC-F25 | 57 | Ib | Mixed cell adenocarcinoma |

(4-2) Sample Preparation—Preparing Serum and Measuring Mass Spectrum

4× volume of methanol/chloroform (2:1, v/v) was mixed with 250 serum violently and incubated at room temperature for 10 min. The mixture was centrifuged at 4° C., 10 min, 6000×g. The supernatant was completely dried for 1 h in the concentrator, and dissolved in the vortexer in 30 µl of 50% acetonitrile/0.1% trifluoroacetic acid (TFA).

Methanol/chloroform extract was mixed with a-cyano-4-hydroxycinnamic acid solution in 50% acetonitrile/0.1% TFA (1:12, v/v), and 1 µl mixture was placed on MALDI-target plate. The mass spectra of the serum extracts from the BRC patients and normal subjects were measured using the Proteomics Analyzer (Applied Biosystems, Foster City, Calif., USA).

The mass spectrum data for one sample is extracted based on the average of spectrum which was repeatedly measured 20 times. The mass region of the entire individual samples was adjusted so that the maximum mass was set at approximately 2500 m/z. To minimize experimental error, various factors including focus mass, laser intensity, target plate, data acquisition time were taken into consideration.

The focus mass and the laser intensity were fixed at preferable levels, i.e., 500 m/z and 5000, respectively. In addition to the fixed focus mass and the laser intensity, the entire samples were repeatedly measured at least five times under viewpoint of other extraction and other data collection. The set $C_1$, from which weightings per mass ions were computed, was measured one more time.

Accordingly, the low-mass ion detecting means 6000 extracted the low-mass ion mass spectrum from the serum sample via the processes explained above, using the MALDI-TOF.

(4-3) Discrimination Strategy

In order for the constructed discriminant to be GC specific, the discriminant is required to discriminate the GC patient group from not only the normal control, but also the patient groups with other cancer types. In one embodiment, the patient groups with other cancer types include CRC patients, BRC patients and NHL patients. Table 319 provides the result of implementing the conventional PCA-DA to investigate whether one discriminant can discriminate the GC patient group from the non-GC group (normal controls, CRC patient group, BRC patient group and NHL patient group). The specificity of the NHL patient group was as low as 25.00%, and this reveals the fact that one discriminant cannot discriminate the GC patient group from the non-GC groups.

TABLE 319

| Set $E_1$ | True GC | True Non-GC | | | |
|---|---|---|---|---|---|
| | | CONT | CRC | BRC | NHL |
| Predicted GC | 48 | 4 | 13 | 8 | 18 |
| Predicted Non-GC | 1 | 80 | 64 | 46 | 6 |
| Sensitivity | | | | 97.96% | |
| Specificity | | CONT | | 95.24% | |
| | | CRC | | 83.12% | |
| | | BRC | | 85.19% | |
| | | NHL | | 25.00% | |

Figure 6:
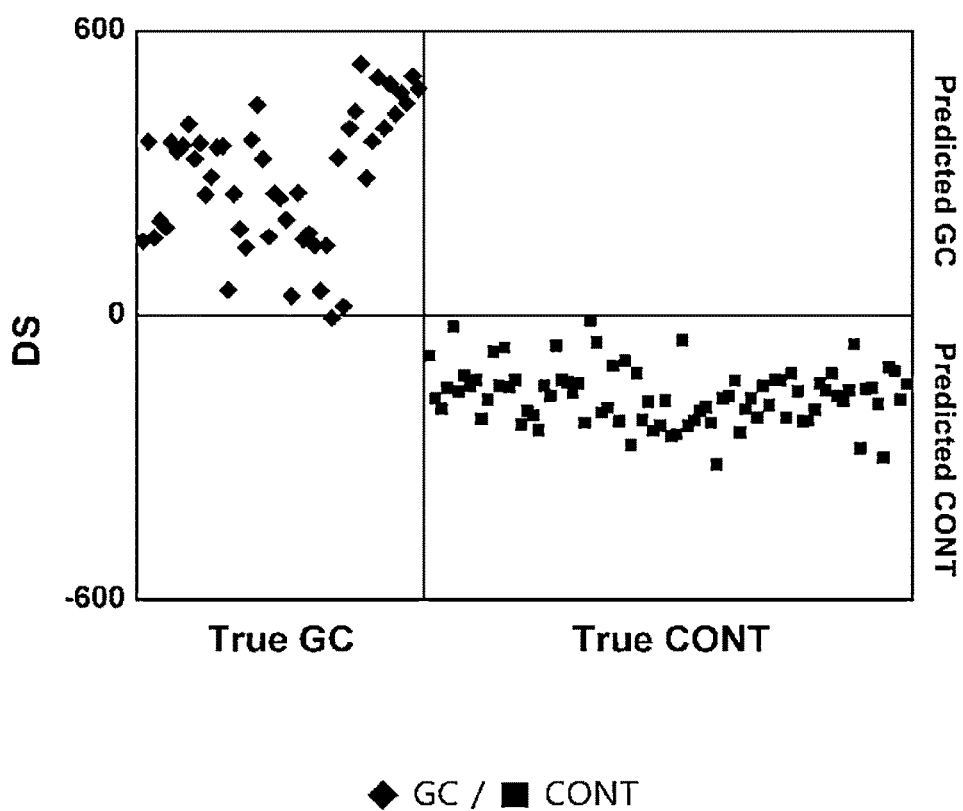

Referring to FIG. 6 and Table 304, considering the excellent discrimination result of the GC patient group from the normal controls, it was also investigated if the GC patient group was discriminated from the patient groups with other cancer types, and the result is provided by Tables 320 to 322.

TABLE 320

| Set $E_1$ | True GC | True CRC |
|---|---|---|
| Predicted GC | 46 | 1 |
| Predicted CRC | 3 | 76 |
| Sensitivity | | 93.88% |
| Specificity | | 98.70% |
| PPV | | 97.87% |
| NPV | | 96.20% |

TABLE 321

| Set $E_1$ | True GC | True BRC |
|---|---|---|
| Predicted GC | 46 | 1 |
| Predicted BRC | 3 | 53 |
| Sensitivity | | 93.88% |
| Specificity | | 98.15% |
| PPV | | 97.87% |
| NPV | | 94.64% |

TABLE 322

| Set $E_1$ | True GC | True NHL |
|---|---|---|
| Predicted GC | 49 | 0 |
| Predicted NHL | 0 | 24 |
| Sensitivity | | 100.0% |
| Specificity | | 100.0% |
| PPV | | 100.0% |
| NPV | | 100.0% |

Accordingly, discriminating the GC patient group from the non-GC patient groups may implement four discriminants consisting of a first type discriminant to discriminate GC patient group from normal controls, a second type discriminant to discriminate the GC patient group from the CRC patient group, a third type discriminant to discriminate the GC patient group from BRC patient group, and a fourth type discriminant to discriminate the GC patient group from the NHL patient group, in which the GC patient is determined if all of the four discriminant indicate GC, while the non-GC patient is determined if any of the four discriminants indicates non-GC patient.

Considering the requirement that GC be determined based on all the discriminants will inevitably compromise the sensitivity as the number of discriminants increases, the number of discriminants may be reduced. Table 323 shows GC patient group and the normal controls distinguished from the patient groups with other types of cancers, which generally exhibits good discrimination result. Accordingly, to distinguish the GC patient group from the non-GC patient group, it is possible to combine this discriminant with the first type discriminant to distinguish the GC patient group and the normal controls from the patient groups with other types of cancers, and then distinguish the GC patient group from the normal controls. The discriminant to distinguish the GC patient group and the normal control from the patient groups with the other types of cancers will be referred to as a fifth type discriminant. It is possible to implement four discriminants or alternatively, to implement two discriminants, and these examples will be explained below.

TABLE 323

| Set $E_1$ | True GC/CONT | | True CRC/BRC/NHL | | |
|---|---|---|---|---|---|
| | GC | CONT | CRC | BRC | NHL |
| Predicted GC/CONT | 44 | 80 | 10 | 0 | 0 |
| Predicted CRC/BRC/NHL | 5 | 4 | 67 | 54 | 24 |
| Sensitivity | GC | | | 89.80% | |
| | CONT | | | 95.24% | |
| Specificity | CRC | | | 87.01% | |
| | BRC | | | 100.0% | |
| | NHL | | | 100.0% | |

(4-4) Selecting First Training Set $E_0$ and Computing Weightings Per Mass Ions

Although the result of discrimination of Tables 304, 320, 321, 323 are good, the sensitivity and the specificity are not always 100%. In one embodiment of the present invention, the first training set $E_0$ with predetermined sensitivity and specificity is selected, and weightings per mass ions of the first training set $E_0$ were computed, in which the predetermined sensitivity and specificity were both 100%.

Figure 39:
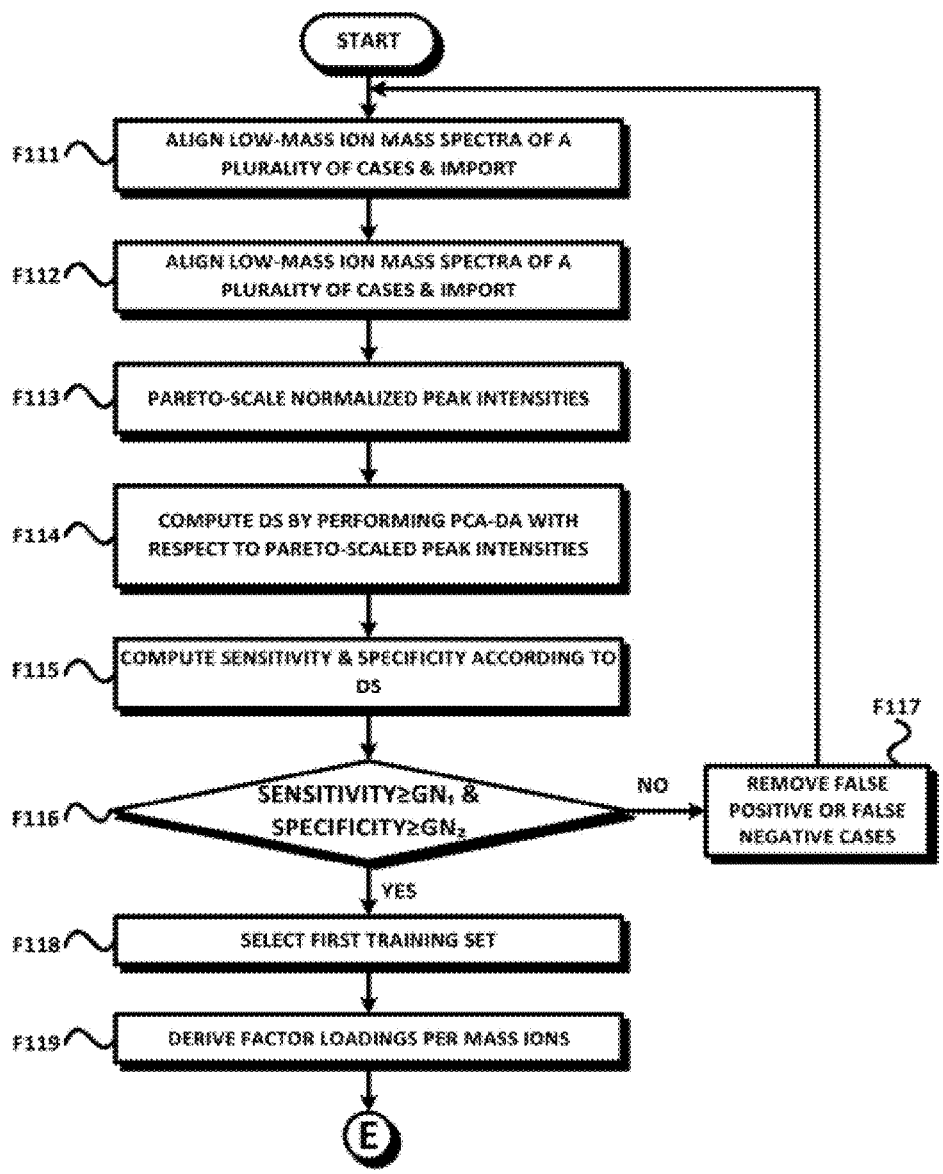

A method for selecting the first training set $E_0$ with the predetermined sensitivity and specificity will be explained below with reference to FIG. 39.

The first DS computing means 6200 aligned and imported the low-mass ion mass spectra of the GC patient group and the normal control group of set $E_1$ (F111), normalized the imported peak intensities (E112), Pareto-scaled the normalized peak intensities (F113), and computed DS by performing biostatistical analysis with respect to the Pareto-scaled peak intensities (F114).

Among a variety of biostatistical analyzing methods that can be implemented to compute DS, in one embodiment, the PCA-DA was performed. Sensitivity and specificity were computed based on the DS (F115) and the result is shown in Table 304.

Next, sensitivity threshold $GN_1$ and specificity threshold $GN_2$ were set (F116), and false positive or false negative cases were excluded when the sensitivity or the specificity was less than the corresponding threshold (F117).

In one embodiment, both the sensitivity threshold $GN_1$ and the specificity threshold $GN_2$ were set to 1, to thus find the first training set $E_{01}$ with both the sensitivity and the specificity being 100%. That is, steps F111 to F115 were performed again with respect to the set from which one false negative case in Table 304 were excluded. It was thus confirmed that the first type discriminant directly achieved 100% of sensitivity and specificity, but considering that the sensitivity and the specificity did not directly reach 100% when the steps F111 to F115 were repeated with respect to the set excluding the false negative case, the first training set $E_{01}$ with both the sensitivity and the specificity being 100% was found after the steps F111 to F117 were repeated predetermined number of times (F118).

The first type discriminant to discriminate GC patient group from the normal controls reached the first training set $E_{01}$ when 1 false negative case was excluded, the second type discriminant to discriminate GC patient group from the CRC patient group reached the first training set $E_{01}$ when 4 false negative cases and 2 false positive cases were excluded, the third type discriminant to discriminate GC patient group from the BRC patient groups reached the first training set $E_{03}$ when 4 false negative cases and 1 false positive case were excluded, and the fifth type discriminant to discriminate the GC patient group and the normal control from the patient groups with the other types of cancers reached the first training set $E_{05}$ when 11 false negative cases (5 GC and 6 CONT) and 21 false positive cases (20 CRC, 1 BRC) were excluded, with both the sensitivity and specificity of each first training set reaching 100%.

Since the fourth type discriminant to discriminate the GC patient group from the NHL patient group already has 100% sensitivity and specificity as indicated in Table 322, the corresponding cases were used as they area for the first training set $E_{04}$. Through this process, it is possible to derive factor loadings per mass ions which provide discrimination result with both 100% sensitivity and specificity (F119).

The series of the processes explained above may be performed at the factor loading computing means 6300.

(4-5) Implementing a Discriminant

The process of implementing the constructed discriminant on the sample of interest will be explained below.

First, MarkerView™ supports the function that can be used for the similar purpose. That is, it is possible to apply the PCA-DA on only the part of the imported sample data, and discriminate the rest samples using the discriminant constructed as a result. According to this function, it is possible to select only the first training set after the import of the first training set and the other samples for analysis so that only the first training set undergoes the PCA-DA to show how the samples for analysis are interpreted.

Meanwhile, the peak alignment function to align the peaks is performed in the import process of MarkerView™. Because there is no function to align the peaks of the samples of interest based on the first training set, the peak table (matrix of m/z rows and rows of peak intensities per samples) obtained when only the first training set is imported, does not match the first training set of the peak table which is generated when the first training set is imported together with the samples of interest. The peak intensity matrices are difference, and the m/z values corresponding to the same peak intensity column also do not always appear the same. Accordingly, in order to compute DS by implementing the discriminant constructed from the first training set on the samples of interest, a realignment operation to realign the peak table, generated when the first training set is imported together with the samples of interest, to the peak table generated when only the first training set is imported.

The misalignment becomes more serious, if several samples of interests are imported together with the first training set. Accordingly, in one embodiment, with respect to the entire samples of interest, one sample of interest is added to the first training set to be imported, realigned, normalized and Pareto-scaled.

The embodiment will be explained in greater detail below with reference to FIG. 40.

First, the low-mass ion mass spectra of the samples of interest were aligned with the first training set and imported (F211).

Meanwhile, since MarkerView™ in one embodiment does not support the function of aligning and importing the sample of interest to the first training set, as explained above, a program may be designed to realign the peak table generated after importing the low-mass ion mass spectrum of the sample of interest together with the first training set to the peak table which is generated after importing the first training set only, so that the low-mass ion mess spectrum of the sample of interest aligned with the first training set is extracted. However, it is more preferable that the sample of interest is directly aligned and imported to the first training set without having realigning process and this is implementable by designing a program.

Next, the imported peak intensities were normalized (F212), and the normalized peak intensities were Pareto-scaled (F213).

Next, discriminant score was computed using the Pareto-scaled peak intensities of the low-mass ions and the factor loadings per mass ions acquired by the PCA-DA (F214).

It is determined whether or not the computed DS exceeds a reference GS (F215), and if so, it is interpreted positive (F216), while it is interpreted negative if the computed DS is less than the reference GS (F217). In one embodiment, the reference GS may preferably be 0.

The series of processes explained above may be performed at the second aligning means 6500, the second DS computing means 6600 and a GC determining means 6700.

Figure 41:
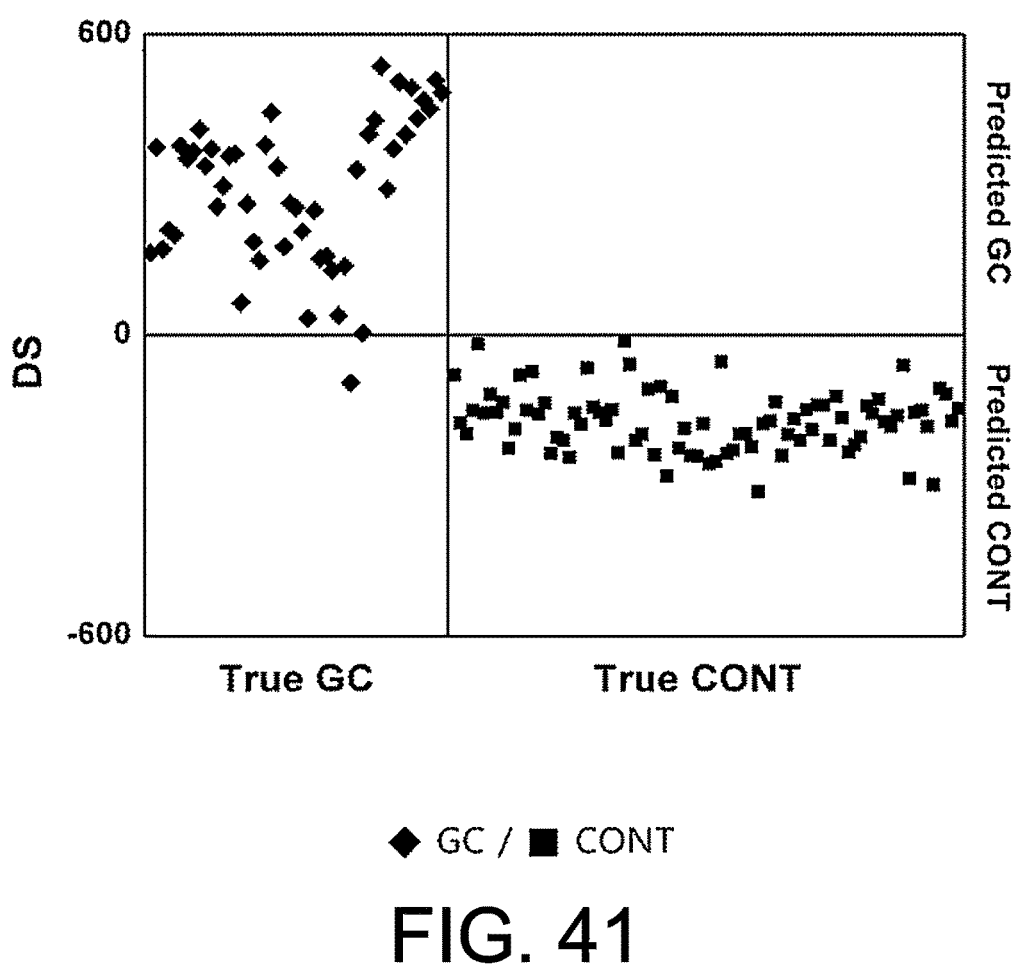
Figure 42:
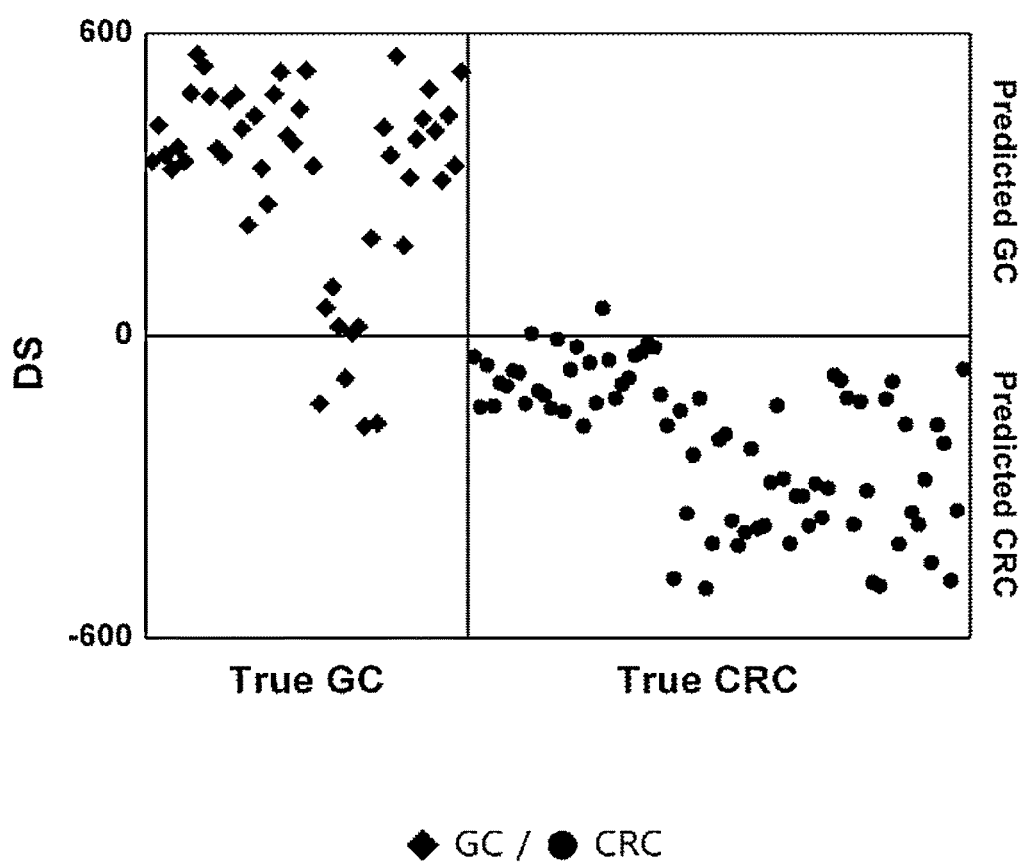
Figure 43:
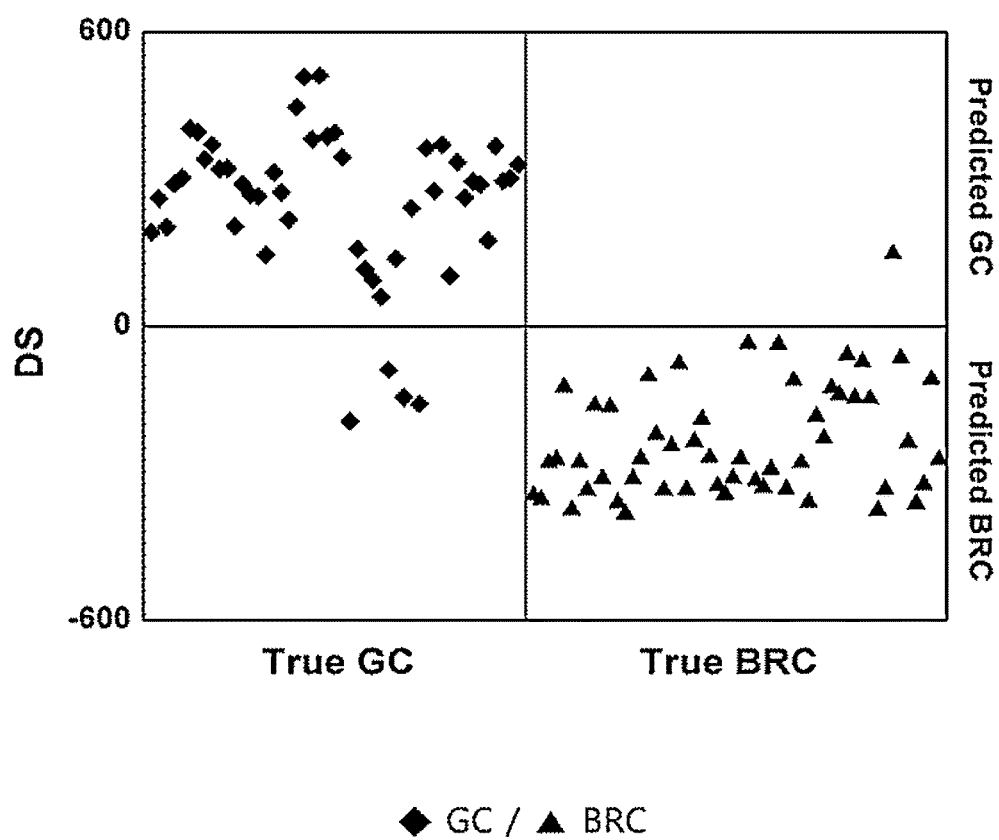
Figure 44:
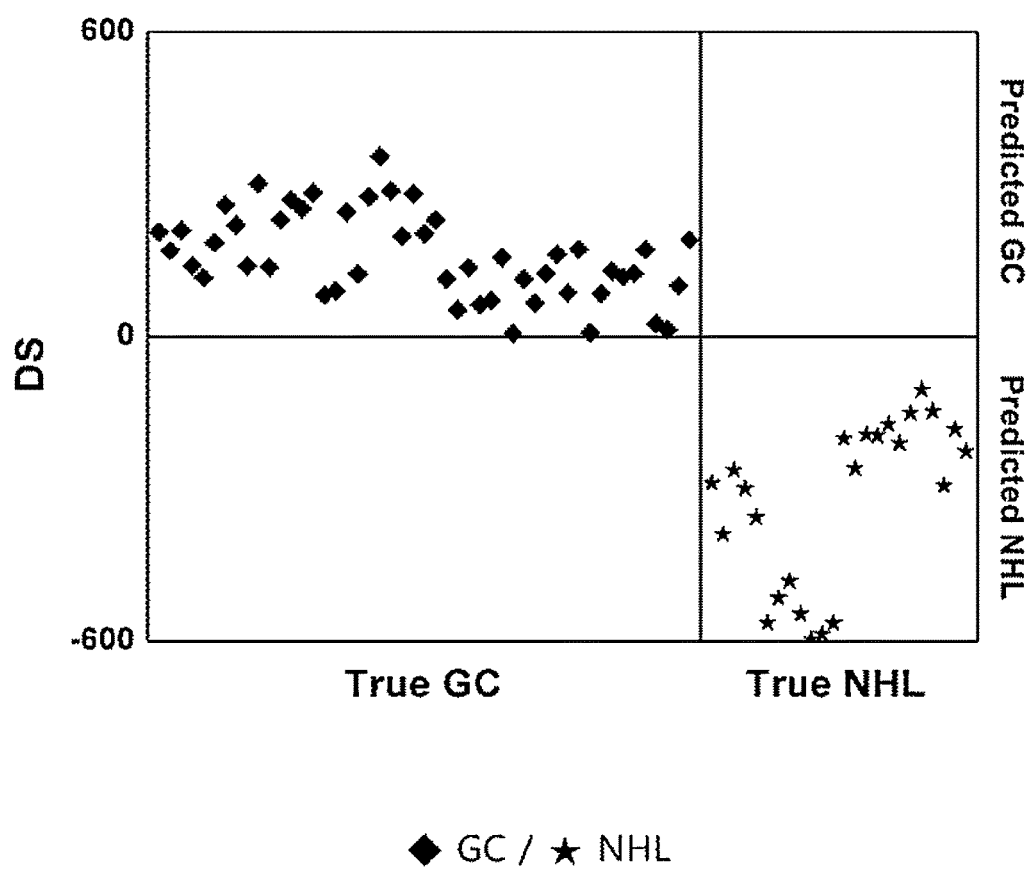
Figure 45:
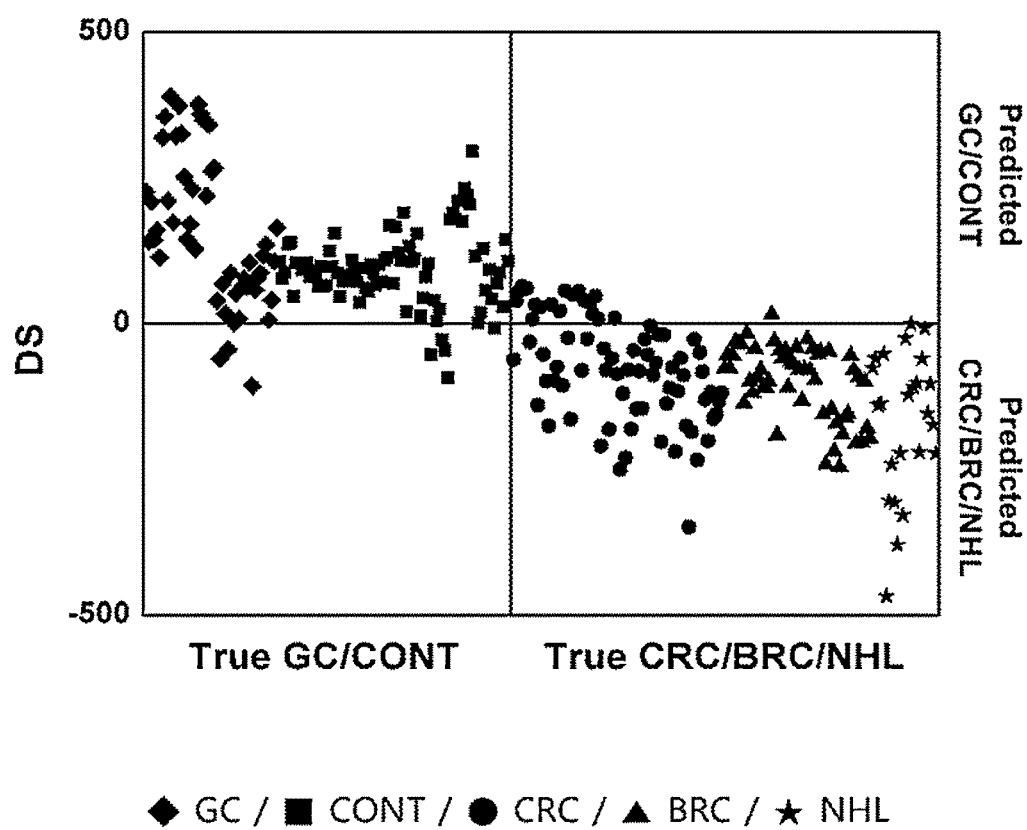

The DS was computed by applying factor loadings per mass ions computed at Clause (4-4) with respect to the 1 GC patient sample which was excluded when constructing the first training set $E_{01}$ from the set $E_1$ to construct the first type discriminant, 4 GC patient samples and 2 CRC patient samples which were excluded when constructing the first training set $E_{02}$ from the set $E_1$ to construct the second type discriminant, 4 GC patient samples and 1 BRC patient sample which were excluded when constructing the first training set $E_{03}$ from the set $E_1$ to construct the third type discriminant, and 5 GC patient samples, 6 normal control samples, 20 CRC patient samples, and 1 BRC patient sample which were excluded when constructing the first training set $E_{05}$ from the set $E_1$ to construct the fifth type discriminant Considering that the cases were excluded when constructing the first training sets $E_{01}$, $E_{02}$, $E_{03}$ and $E_{05}$, it was expected that the cases would be discriminated to be false positive or false negative, they were determined to be the false positive or false negative cases as expected when the computation was done, except for two cases from the GC patient group and one case from the normal control group related to the fifth type discriminant which were determined to be true positive. The result of discrimination of the set $E_1$ by applying the factor loadings per mass ions computed at Clause (4-4) is presented in FIGS. 41 to 45, in which FIG. 41 shows the result of the first type discriminant, FIG. 42 shows the result of the second discriminant, FIG. 43 shows the result of the third discriminant, FIG. 44 shows the result of the fourth discriminant, and FIG. 45 shows the result of the fifth discriminant.

(4-6) Constructing Preliminary Discriminant

Conventionally, DS is computed using the entire mass ions that are taken into consideration in the PCA-DA and the GC patient was determined according to the computed DS. In one embodiment of the present invention, a preliminary discriminant is constructed, which uses only the mass ions that contribute considerably to the DS, in order to derive a discriminant with robust discrimination performance. As used herein, the term "preliminary discriminant" refers to an intermediate form of a discriminant which is obtained before the final discriminant is obtained, and the low-mass ions constructing the discriminant are the "preliminary candidate group" of the GC-diagnosing low-mass ions to construct the final discriminant.

Figure 46:
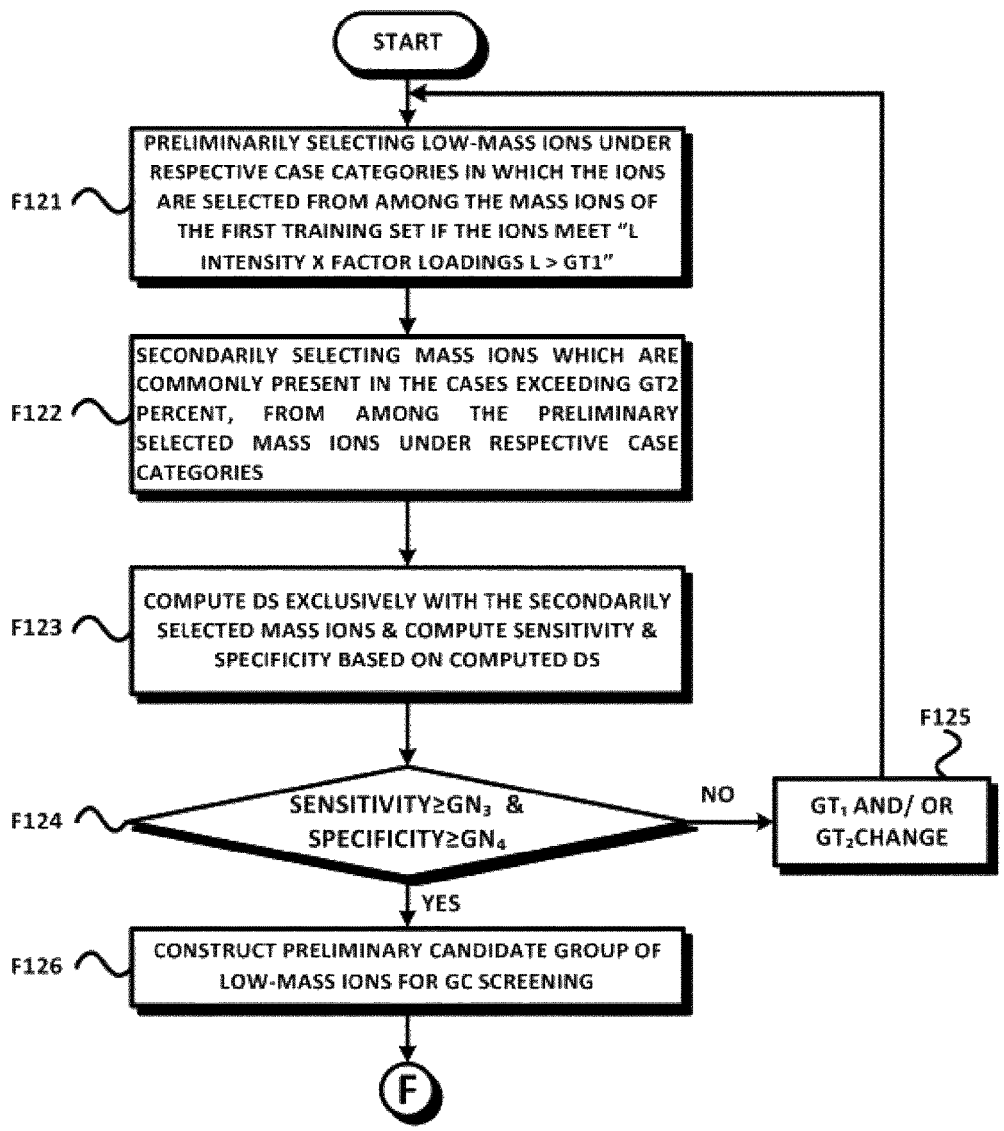

Through the process of FIG. 46, predetermined mass ions were selected, which give considerable influence on the DS, from among 10,000 mass ions. In one embodiment, 299 mass ions were selected by the first type discriminant, 351 mass ions were selected by the second discriminant, 384 mass ions were selected by the third discriminant, 348 mass ions were selected by the fourth discriminant, and 383 mass ions were selected by the fifth type discriminant.

As explained above with reference to Table 303, because the maximum number of the peaks under the import condition is set to 10,000 and sufficient samples are imported, the discriminant constructed by the PCA-DA of Marker-View™ consists of 10,000 terms. However, not all the 10,000 terms have the equal importance particularly in distinguishing GC patients and non-GC patients. Accordingly, the mass ions that give considerable influence on the DS were selected from among the 10,000 mass ions by two steps according to the process of FIG. 46. This particular step is employed to remove unnecessary mass ions in distinguishing GC patients from non-GC patients from the 10,000 mass ions.

The mass ions were preliminarily selected under corresponding case categories, if the absolute product obtained by multiplying the peak intensities by the factor loadings per mass ions exceeds the threshold $GT_1$ (F121). In one embodiment, the threshold $GT_1$ may preferably be 0.1.

Next, the mass ions were secondarily selected from among the preliminarily-selected mass ions under each case category, if the mass ions appear commonly in the cases exceeding the threshold percentage $GT_2$ (F122). In one embodiment, the threshold percentage $GT_2$ may preferably be 50. That is, take the fourth type discriminant for example, only the mass ions that appear commonly in at least 37 cases from among the 73 cases of the first training set were used to construct the preliminary discriminant.

The DS was again computed exclusively with the mass ions that were selected as explained above, and the sensitivity and the specificity were computed accordingly (F123). Again, the sensitivity threshold $GN_3$ and the specificity threshold $GN_4$ were set (F124), so that if the sensitivity or the specificity is less than the corresponding threshold, the threshold $GT_1$ used at step F121 and/or the threshold $GT_2$ used at step F122 was changed (F125) and the steps from F121 to F124 were repeated. In one embodiment, the sensitivity threshold $GN_3$ and the specificity threshold $GN_4$ may preferably be 0.9, respectively.

The preliminary candidate group of the GC-diagnosing low-mass ions was constructed with the mass ions that were selected as explained above (F126), and in one embodiment, only 299 mass ions were selected by the first type discriminant from among the 10,000 mass ions, 351 mass ions were selected by the second type discriminant, 384 mass ions were selected by the third type discriminant, 348 mass ions were selected by the fourth type discriminant, and 383 mass ions were selected by the fifth type discriminant, Tables 324 to 328 provide the results of discriminating the first training sets $E_{01}$ to $E_{05}$ with the first, second, third, fourth and fifth type preliminary discriminants, according to which the discrimination performance including the sensitivity and the specificity was slightly degraded from 100%, but still the result of computing with less than 4% of the total mass ions was certainly as good as the result obtained by using the entire mass ions.

Figure 47:
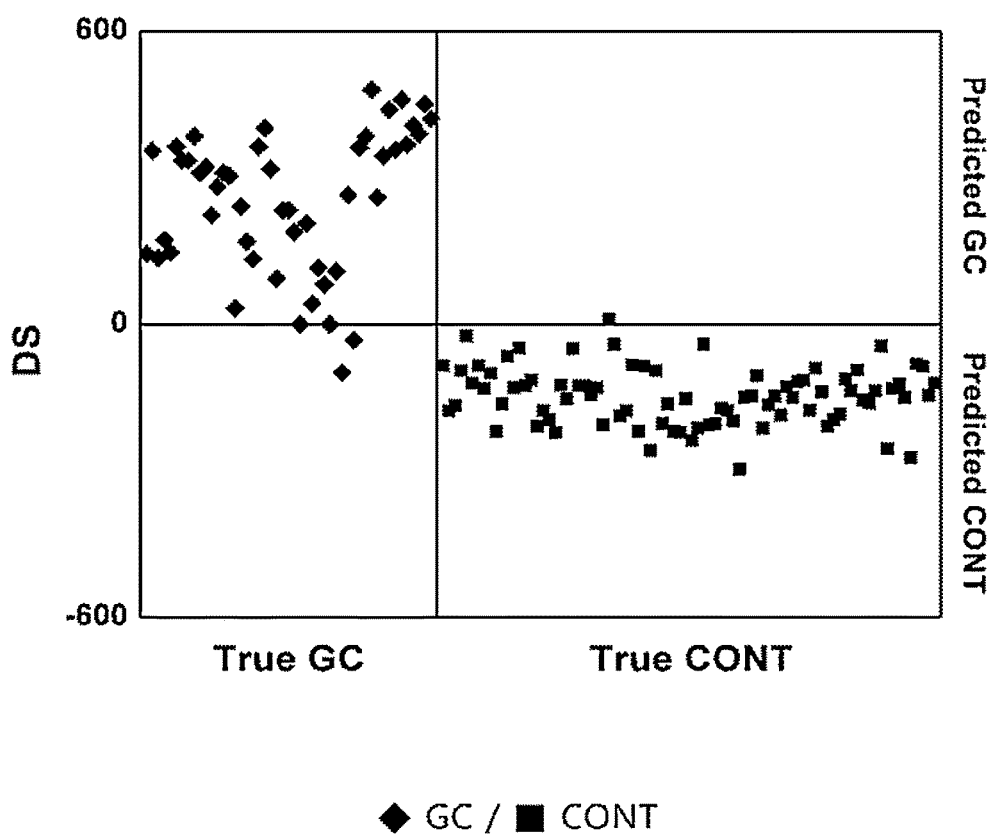
Figure 48:
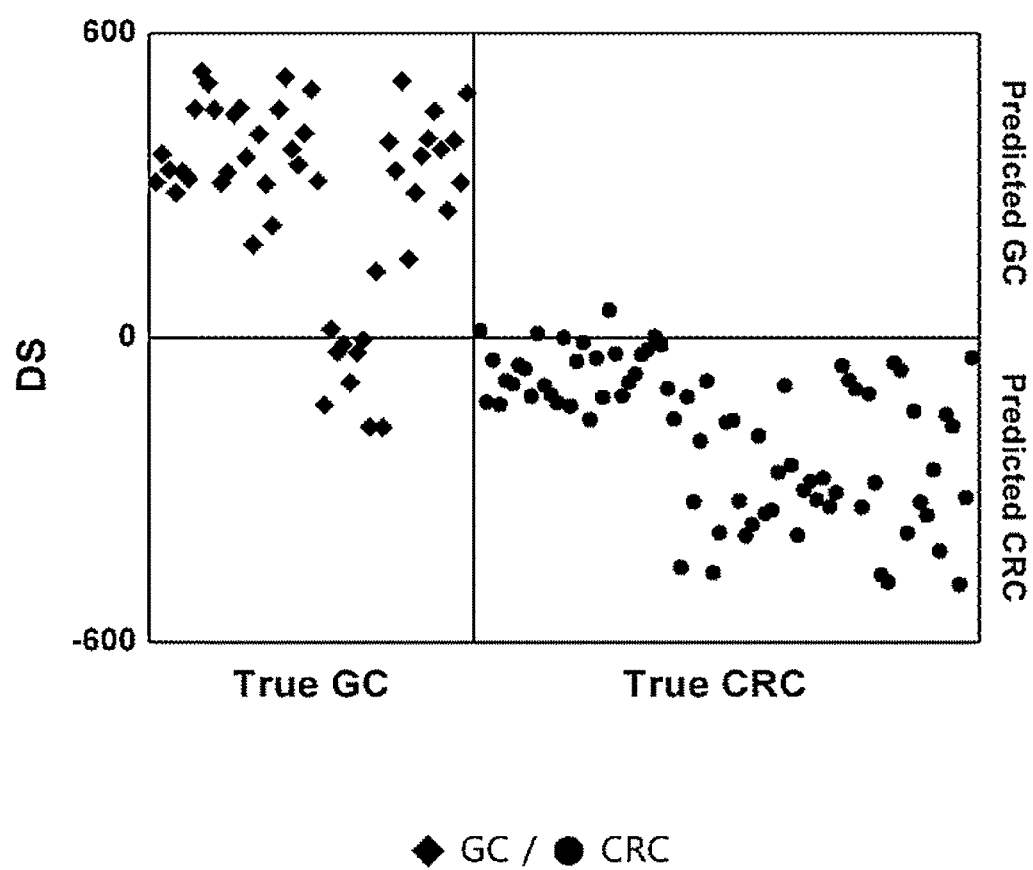
Figure 49:
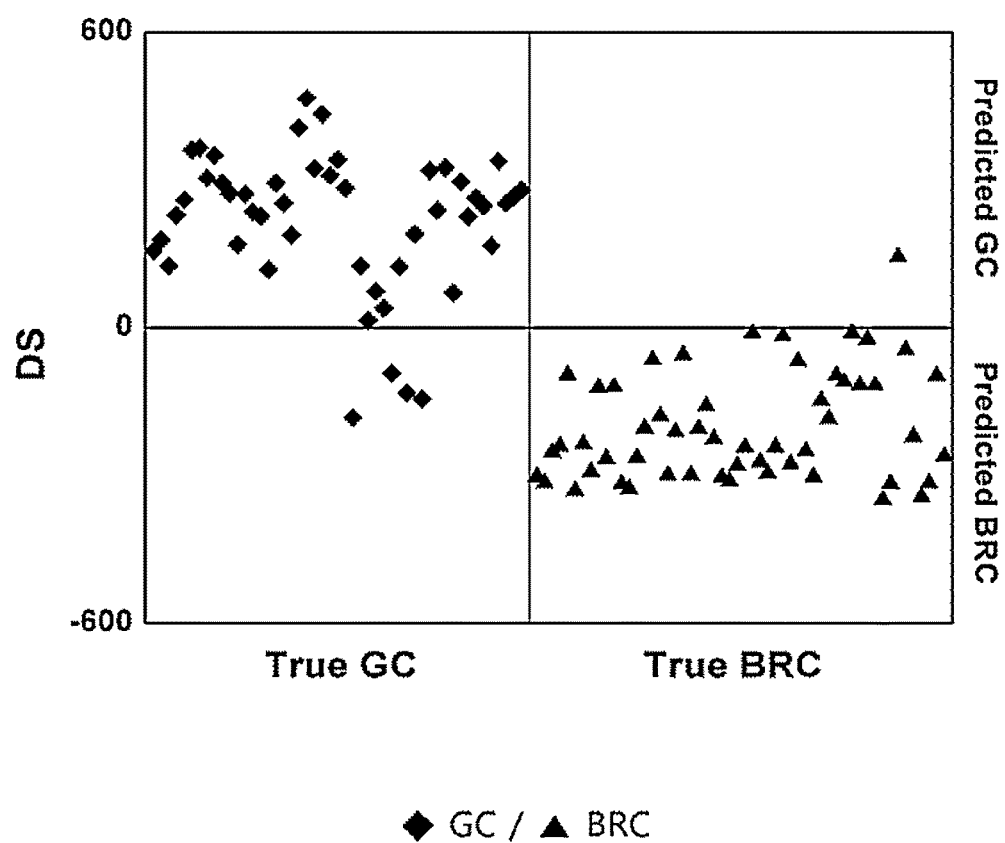
Figure 50:
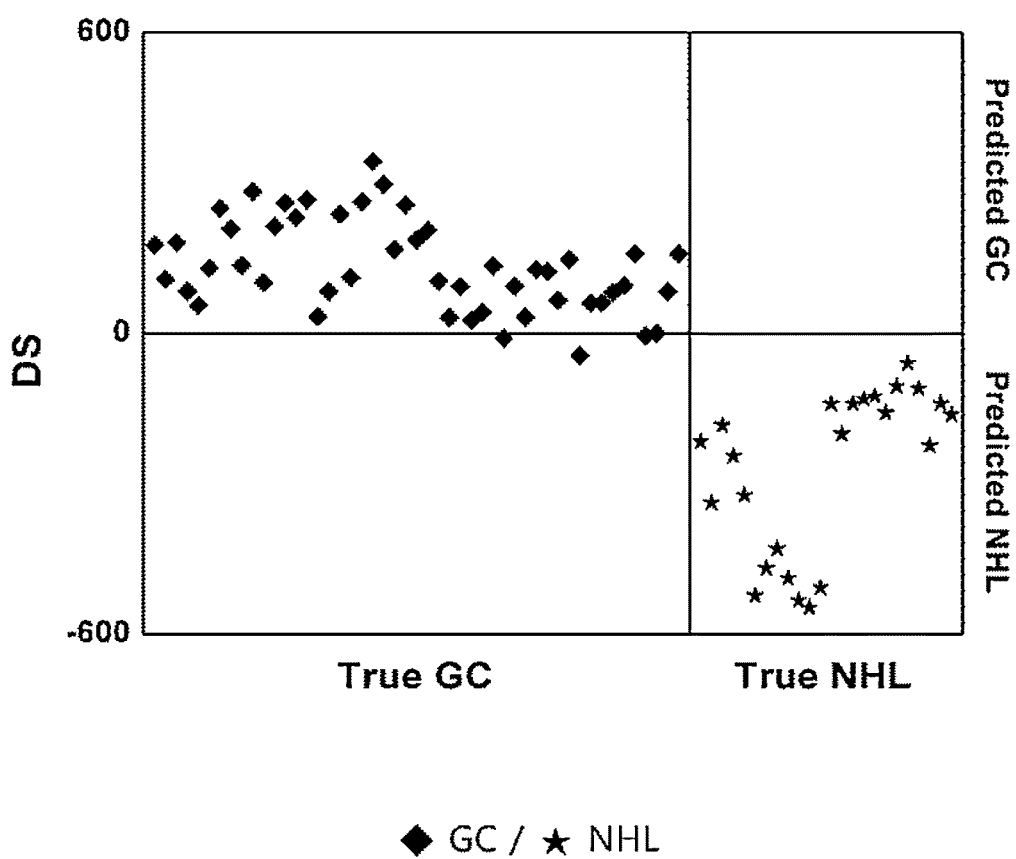
Figure 51:
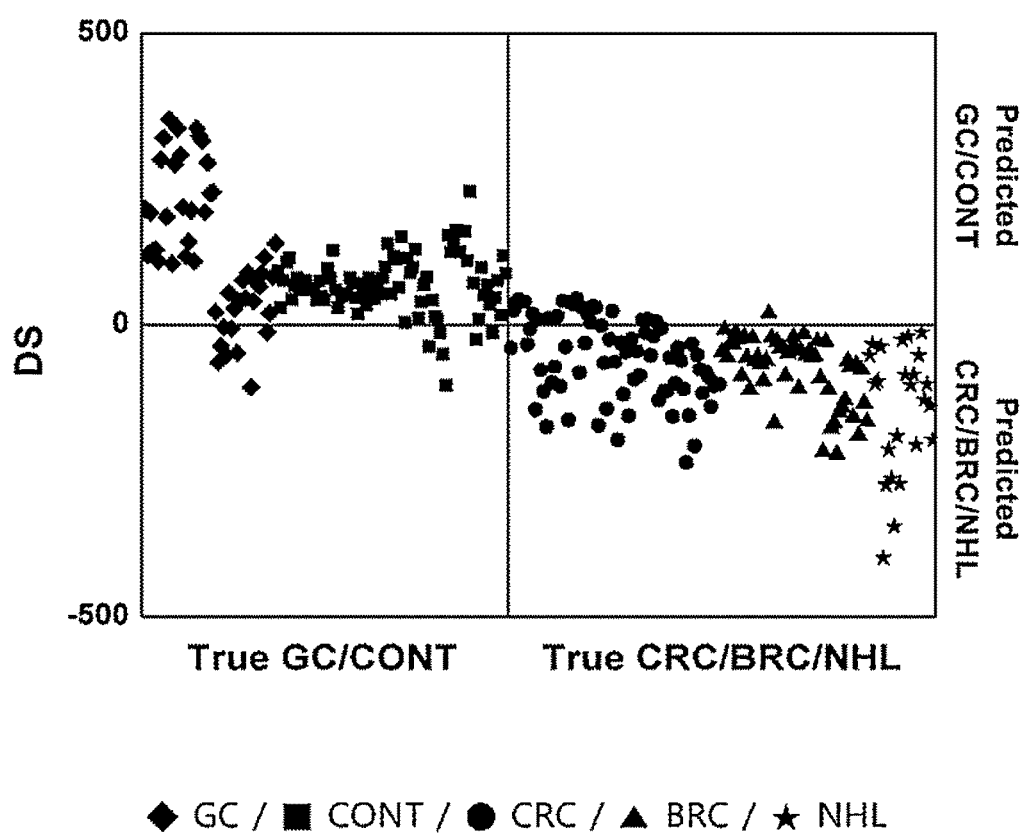

Further, FIGS. 47 to 51 provide the result of discriminating the set $E_1$ with the preliminary discriminant, in which FIG. 47 shows the result by the first type preliminary discriminant, FIG. 48 shows the result by the second type discriminant, FIG. 49 shows the result by the third type discriminant, FIG. 50 shows the result by the fourth type discriminant, and FIG. 51 shows the result by the fifth type discriminant Compared to the sharp reduction in the number of mass ions used for the computation, the range of DS was not so influenced. This suggests that not all 10,000 mass ions are necessary to distinguish GC patients from non-GC patients.

TABLE 324

| Set $E_{01}$ | True GC | True CONT |
|---|---|---|
| Predicted GC | 46 | 1 |
| Predicted CONT | 2 | 83 |
| Sensitivity | | 95.83% |
| Specificity | | 98.81% |
| PPV | | 97.87% |
| NPV | | 97.65% |

TABLE 325

| Set $E_{02}$ | True GC | True CRC |
|---|---|---|
| Predicted GC | 41 | 2 |
| Predicted CRC | 4 | 73 |

| | |
|---|---|
| Sensitivity | 91.11% |
| Specificity | 97.33% |
| PPV | 95.35% |
| NPV | 94.81% |

TABLE 326

| Set $E_{03}$ | True GC | True BRC |
|---|---|---|
| Predicted GC | 45 | 0 |
| Predicted BRC | 0 | 53 |

| | |
|---|---|
| Sensitivity | 100.0% |
| Specificity | 100.0% |
| PPV | 100.0% |
| NPV | 100.0% |

TABLE 327

| Set $E_{04}$ | True GC | True NHL |
|---|---|---|
| Predicted GC | 46 | 0 |
| Predicted NHL | 3 | 24 |

| | |
|---|---|
| Sensitivity | 93.88% |
| Specificity | 100.0% |
| PPV | 100.0% |
| NPV | 88.89% |

TABLE 328

| | True GC/CONT | | True CRC/BRC/NHL | | |
|---|---|---|---|---|---|
| Set $E_{05}$ | GC | CONT | CRC | BRC | NHL |
| Predicted GC/CONT | 41 | 77 | 3 | 0 | 0 |
| Predicted CRC/BRC/NHL | 3 | 1 | 54 | 53 | 24 |

| | |
|---|---|
| Sensitivity | 96.72% |
| Specificity | 97.76% |

TABLE 328-continued

| | |
|---|---|
| PPV | 97.52% |
| NPV | 97.04% |

The series of processes explained above may be performed at the GC-diagnosing ion selecting means 6400 which includes the candidate ion set selecting means.

(4-7) Constructing a Final Discriminant

The mass ions were extracted from among the 10,000 mass ions imported in the process of constructing the preliminary discriminant, as those that contribute considerably to the numerical aspect of the DS. Considering that the selected mass ions include the mass ions that do not generate a problem in the first training set $E_0$, but can potentially deteriorate the discrimination performance in the discrimination with the mass spectrum that was re-measured with respect to the same GC patient samples and non-GC samples or in the discrimination of new GC patient group and non-GC patient group, additional step is necessary, which can actively remove the presence of such mass ions. The process of constructing a final discriminant includes such step before finally determining GC-diagnosing low-mass ions.

To validate robustness of a discriminant, repeated measure experiment was conducted with respect to the set $E_1$ 5 times, and the repeated measure experiment was also performed 5 times with respect to the sets $E_2$ and F which were independent from the set $E_1$ and also independent from each other. It is hardly possible to confirm that the repeated measure of the mass spectrum is always conducted under the exactly same conditions in the processes like vaporization using laser beam, desorption, ionization, or the like, in addition to the process of freezing and thawing the serums and mixing the serums with methanol/chloroform to obtain extract, and it is also hard to rule out introduction of disturbances due to various causes. In other words, the DS with respect to the repeatedly-measured individual mass spectrum may have a predetermined deviation, and considering this, interpretation in one embodiment was made by computing an average DS with respect to the sample which was repeatedly measured 5 times.

Table 329 provides the result of discriminating the sets E and F with the discriminant of 10,000 terms as a result of the conventional technology, i.e., PCA-DA by MarkerView™, and Table 330 shows the result of discriminating the sets E and F with the first type preliminary discriminant with 299 terms, the second type preliminary discriminant with 351 terms, the third type preliminary discriminant with 384 terms, the fourth type preliminary discriminant with 348 terms, and the fifth type preliminary discriminant with 383 terms.

Referring to the table, GC LOME 1 to 5 (gastric cancer low mass ion discriminant equation) refers to the first to fifth type discriminants, and the following numbers indicate the number of low-mass ions included in the discriminant. Further, Table 331 shows the discrimination performance with respect to the validation set only, i.e., to the set F.

TABLE 329

| GC LOME 1-10000 | | | | | | GC LOME 1-10000 | | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 88 | 9 | 86 | 38 | 46 | Predicted GC | 36 | 5 | 68 | 21 | 20 | 20 |

TABLE 329-continued

| | | | | | | | | | | | |
|---|---|---|---|---|---|---|---|---|---|---|---|
| Predicted Non-GC | 9 | 158 | 166 | 70 | 0 | Predicted Non-GC | 8 | 76 | 100 | 32 | 0 | 5 |

GC LOME 2-10000

| | True GC | True Non-GC | | | | | True GC | True Non-GC | | | | |
|---|---|---|---|---|---|---|---|---|---|---|---|---|
| Set E | GC | CONT | CRC | BRC | NHL | Set F | GC | CONT | CRC | BRC | NHL | OVC |
| Predicted GC | 81 | 13 | 76 | 29 | 43 | Predicted GC | 35 | 10 | 66 | 15 | 18 | 21 |
| Predicted Non-GC | 16 | 154 | 176 | 79 | 3 | Predicted Non-GC | 9 | 71 | 102 | 38 | 2 | 4 |

GC LOME 3-10000

| Set E | GC | CONT | CRC | BRC | NHL | Set F | GC | CONT | CRC | BRC | NHL | OVC |
|---|---|---|---|---|---|---|---|---|---|---|---|---|
| Predicted GC | 88 | 32 | 77 | 19 | 31 | Predicted GC | 37 | 16 | 45 | 15 | 15 | 18 |
| Predicted Non-GC | 9 | 135 | 175 | 89 | 15 | Predicted Non-GC | 7 | 65 | 123 | 38 | 5 | 7 |

GC LOME 4-10000

| Set E | GC | CONT | CRC | BRC | NHL | Set F | GC | CONT | CRC | BRC | NHL | OVC |
|---|---|---|---|---|---|---|---|---|---|---|---|---|
| Predicted GC | 67 | 146 | 151 | 38 | 0 | Predicted GC | 32 | 69 | 86 | 11 | 0 | 11 |
| Predicted Non-GC | 30 | 21 | 101 | 70 | 46 | Predicted Non-GC | 12 | 12 | 82 | 42 | 20 | 14 |

GC LOME 5-10000

| Set E | GC | CONT | CRC | BRC | NHL | Set F | GC | CONT | CRC | BRC | NHL | OVC |
|---|---|---|---|---|---|---|---|---|---|---|---|---|
| Predicted GC | 60 | 137 | 87 | 0 | 2 | Predicted GC | 30 | 36 | 58 | 2 | 1 | 8 |
| Predicted Non-GC | 37 | 30 | 165 | 108 | 44 | Predicted Non-GC | 14 | 45 | 110 | 51 | 19 | 17 |

GC LOMEs 1, 2, 3 & 4

| Set E | GC | CONT | CRC | BRC | NHL | Set F | GC | CONT | CRC | BRC | NHL | OVC |
|---|---|---|---|---|---|---|---|---|---|---|---|---|
| Predicted GC | 54 | 0 | 4 | 0 | 0 | Predicted GC | 23 | 0 | 4 | 0 | 0 | 6 |
| Predicted Non-GC | 43 | 167 | 248 | 108 | 46 | Predicted Non-GC | 21 | 81 | 164 | 53 | 20 | 19 |

GC LOMEs 1 & 5

| Set E | GC | CONT | CRC | BRC | NHL | Set F | GC | CONT | CRC | BRC | NHL | OVC |
|---|---|---|---|---|---|---|---|---|---|---|---|---|
| Predicted GC | 54 | 5 | 17 | 0 | 2 | Predicted GC | 24 | 3 | 20 | 0 | 1 | 4 |
| Predicted Non-GC | 43 | 162 | 235 | 108 | 44 | Predicted Non-GC | 20 | 78 | 148 | 53 | 19 | 21 |

TABLE 330

| | GC LOME 1-299 | | | | | | GC LOME 1-299 | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 87 | 9 | 84 | 38 | 46 | Predicted GC | 36 | 8 | 65 | 21 | 20 | 20 |
| Predicted Non-GC | 10 | 158 | 168 | 70 | 0 | Predicted Non-GC | 8 | 73 | 103 | 32 | 0 | 5 |

| | GC LOME 2-351 | | | | | | GC LOME 2-351 | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 78 | 12 | 73 | 29 | 42 | Predicted GC | 35 | 10 | 63 | 15 | 18 | 21 |
| Predicted Non-GC | 19 | 155 | 179 | 79 | 4 | Predicted Non-GC | 9 | 71 | 105 | 38 | 2 | 4 |

| | GC LOME 3-384 | | | | | | GC LOME 3-384 | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 87 | 29 | 75 | 18 | 34 | Predicted GC | 37 | 16 | 43 | 14 | 15 | 19 |
| Predicted Non-GC | 10 | 138 | 177 | 90 | 12 | Predicted Non-GC | 7 | 65 | 125 | 39 | 5 | 6 |

| | GC LOME 4-348 | | | | | | GC LOME 4-348 | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 68 | 146 | 152 | 40 | 0 | Predicted GC | 32 | 67 | 84 | 10 | 0 | 12 |
| Predicted Non-GC | 29 | 21 | 100 | 68 | 46 | Predicted Non-GC | 12 | 14 | 84 | 43 | 20 | 13 |

| | GC LOME 5-383 | | | | | | GC LOME 5-383 | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 56 | 134 | 84 | 2 | 1 | Predicted GC | 29 | 35 | 59 | 1 | 1 | 6 |
| Predicted Non-GC | 41 | 33 | 168 | 106 | 45 | Predicted Non-GC | 15 | 46 | 109 | 52 | 19 | 19 |

| | GC LOMEs 1, 2, 3 & 4 | | | | | | GC LOMEs 1, 2, 3 & 4 | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 54 | 0 | 4 | 0 | 0 | Predicted GC | 23 | 0 | 5 | 0 | 0 | 7 |
| Predicted Non-GC | 43 | 167 | 248 | 108 | 46 | Predicted Non-GC | 21 | 81 | 163 | 53 | 20 | 18 |

| | GC LOMEs 1 & 5 | | | | | | GC LOMEs 1 & 5 | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 52 | 4 | 13 | 0 | 1 | Predicted GC | 23 | 5 | 18 | 0 | 1 | 4 |
| Predicted Non-GC | 45 | 163 | 239 | 108 | 45 | Predicted Non-GC | 21 | 76 | 150 | 53 | 19 | 21 |

TABLE 331

| Set F | Sensitivity (%) | Specificity (%) | PPV (%) | NPV (%) |
|---|---|---|---|---|
| GC LOME 1-10000, GC LOME 2-10000, GC LOME 3-10000 & GC LOME 4-10000 | 52.27 | 97.12 | 69.70 | 94.13 |
| GC LOME 1-299, GC LOME 2-351, GC LOME 3-384 & GC LOME 4-348 | 52.27 | 96.54 | 65.71 | 94.10 |
| GC LOME 1-14, GC LOME 2-36, GC LOME 3-50 & GC LOME 4-46 | 93.18 | 98.85 | 91.11 | 99.13 |
| GC LOME 1-10000 & GC LOME 5-10000 | 54.55 | 91.93 | 46.15 | 94.10 |
| GC LOME 1-299 & GC LOME 5-383 | 52.27 | 91.93 | 45.10 | 93.82 |
| GC LOME 1-14 & GC LOME 5-55 | 79.55 | 98.56 | 87.50 | 97.44 |

The discriminant consisting of 10,000 mass ions exhibits perfect discrimination performance with respect to the first training set $E_0$, but with reference to Table 331, the positive predictability was particularly low with respect to set F. All the first, second, third, fourth and fifth preliminary discriminants exhibited generally good discrimination performance (Tables 324 to 328) with respect to the first training set $E_0$, but the discrimination result with respect to set F was far from satisfaction.

Figure 52:
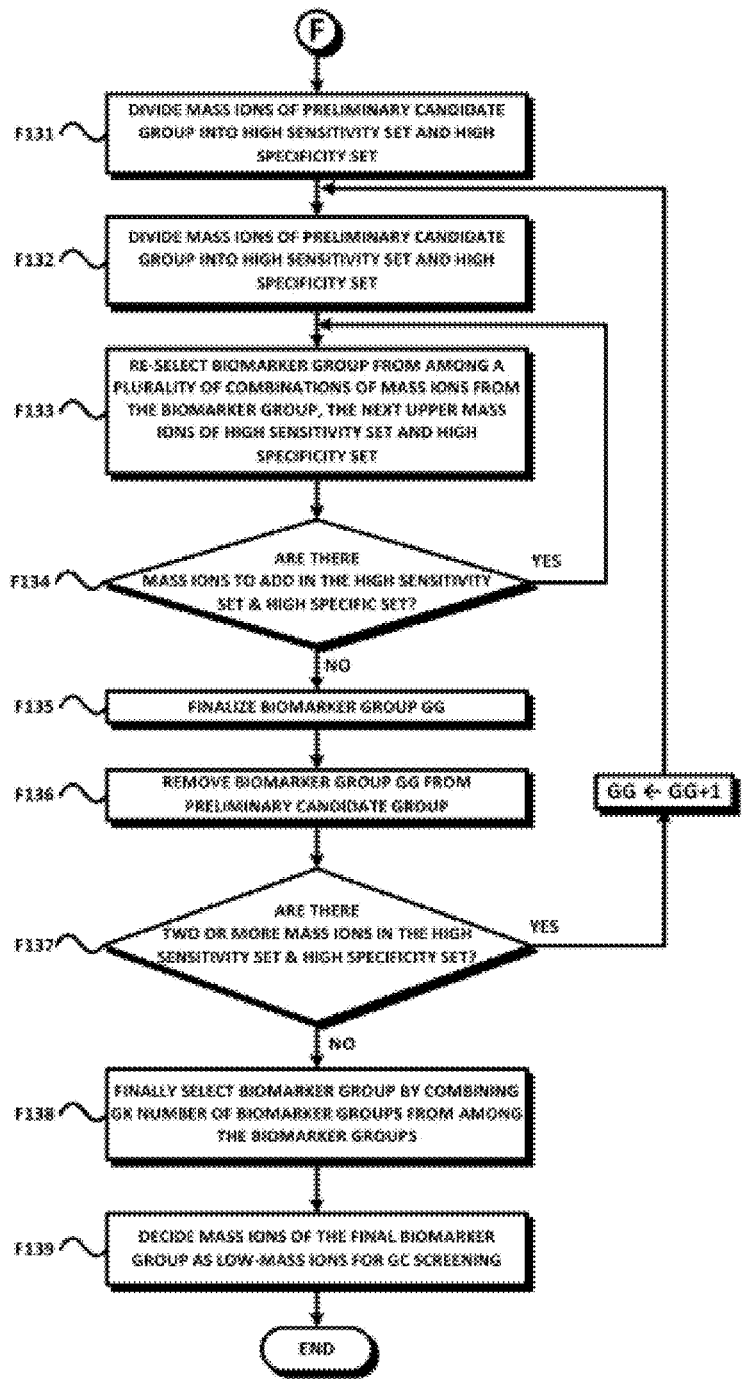

Accordingly, in one embodiment of the present invention, steps illustrated in FIG. 52 were performed to improve the preliminary discriminant to more robust discriminant First, the mass ions of the preliminary candidate group were divided into high sensitivity set and high specificity set (F131). As used herein, the mass ions of the high sensitivity set have higher sensitivity per mass ions than specificity, while the mass ions of the high specificity set have higher specificity per mass ions than sensitivity.

Next, the mass ions of the high sensitivity set and the mass ions of the high specificity set were sorted in a descending order $\{Sns_1, Sns_2, Sns_3 \ldots Sns_I\}$ $\{Spc_1, Spc_2, Spc_3 \ldots Spc_J\}$ in terms of the sum of the sensitivity and specificity per mass ions, and two top mass ions of the respective sets were taken $\{Sns_1, Sns_2, Spc_1, Spc_2\}$, and a biomarker group was selected with a combination of the best performance from among 11 combinations that are possibly made with the two or more mass ions of the four mass ions (F132).

The criteria to determine whether a combination has the best performance or not may be selected objectively and universally from among the following criteria which are listed in the order of importance:

Criterion 1) The combination with greater sum of sensitivity and specificity has better performance;

Criterion 2) The combination with less mass ions has better performance; and

Criterion 3) The combination with a greater difference between minimum DS of the true positive case and the maximum DS of true negative case has better performance.

Next, one more mass ion, i.e., the second top mass ion $\{Sns_3, Spc_3\}$ was additionally taken from each of the high sensitivity set and the high specificity, so that a set with the best performance was re-selected as a biomarker group from among the four sets {biomarker group}, {biomarker group, $Sns_3$}, {biomarker group, $Spc_3$}, {biomarker group, $Sns_3$, $Spc_3$} which are the combinations of the additionally-taken mass ions $\{Sns_3, Spc_3\}$ (F133).

The process repeated until the high sensitivity set and the high specificity set had no further mass ion to add (F134).

In other words, the process (F133) repeats as long as both the high sensitivity set and the high specificity set have mass ions to add, and when any of the high sensitivity set and the high specificity set has no further mass ion left to add, the next top mass ion $\{Sns_i$ or $Spc_j\}$ in the set having mass ions is additionally taken, so that a biomarker group is selected with a set of the best performance among the two sets {biomarker group}, {biomarker group, $Sns_i$ or $Spc_j$} which are combinations of the additionally-taken mass ion $\{Sns_i$ or $Spc_j\}$.

The process repeats as long as the high sensitivity set or the high specificity set is out of the mass ion, and the biomarker group that is selected when there is no mass ion left in the high sensitivity set and high specificity set becomes the biomarker group 1 (GG) (F135).

The biomarker group 1 (GG) was removed from the preliminary candidate group (F136), the high sensitivity set and the high specificity set were constructed with the remaining mass ions, and the above-explained process repeats. The process repeats until any of the high sensitivity set and the high specificity has less than two mass ions therein (F137).

GK number of biomarker groups were combined with the biomarker groups 1, 2, . . . which were obtained by the repeated process explained above, in the order of accuracy, to form a final biomarker group. As used herein, the "accuracy" refers to a proportion of true positive and true negative cases in the entire cases. In one embodiment, GK may preferably be 1, 2, or 3 (F138)

Accordingly, the mass ions of the final biomarker group were determined to be the BRC-diagnosing low-mass ions (F139).

The preliminary candidate group of the mass ions was selected from the set $E_1$, and more specifically, from the subset $E_0$, and to avoid overfitting problem, the set $E_2$ which was independent from the set $E_1$ was added to enlarge the training set when the final biomarker group was determined from the preliminary candidate group.

As a result of performing the process explained above with respect to the samples to distinguish GC patient group from the normal control group, 14 mass ions were selected as the first type GC-diagnosing low-mass ions. Further, as a result of performing the process explained above with respect to the samples to distinguish GC patient group from the CRC patient group, 36 mass ions were selected as the second type GC-diagnosing low-mass ions. Further, as a result of performing the process explained above with respect to the samples to distinguish GC patient group from the BRC patient group, 50 mass ions were selected as the third type GC-diagnosing low-mass ions. Further, as a result of performing the process explained above with respect to the samples to distinguish GC patient group from the NHL patient group, 46 mass ions were selected as the fourth type GC-diagnosing low-mass ions. Further, as a result of performing the process explained above with respect to the samples to distinguish GC patient group from the cancer patient group with other types of cancers, 55 mass ions were selected as the fifth type GC-diagnosing low-mass ions.

The masses of the first to fifth type GC-diagnosing low-mass ions are listed in Tables 332 to 336. The low-mass ions explained above are referred to as the "first type GC-diagnosing low-mass ions", "second type GC-diagnosing low-mass ions", "third type GC-diagnosing low-mass ions", "fourth type GC-diagnosing low-mass ions", and "fifth type GC-diagnosing low-mass ions", and the discriminants according to the present invention which is finally obtained using the same are referred to as the "first type GC-diagnosing final discriminant", "second type GC-diagnosing final discriminant", "third type GC-diagnosing final discriminant", "fourth type GC-diagnosing final discriminant", and "fifth type GC-diagnosing final discriminant", respectively.

TABLE 332

| | | | | | | |
|---|---|---|---|---|---|---|
| 22.9851 | 123.0842 | 324.1365 | 488.6538 | 526.3426 | 576.2893 | 616.1397 |
| 87.0959 | 314.2151 | 366.2424 | 490.3374 | 532.3719 | 606.2658 | 1466.5612 |

TABLE 333

| | | | | | | |
|---|---|---|---|---|---|---|
| 18.0260 | 137.0721 | 207.0729 | 401.0680 | 489.3564 | 528.3633 | 585.2726 |
| 22.9830 | 144.1092 | 265.2034 | 431.9882 | 489.5293 | 535.2970 | 587.2805 |
| 38.9752 | 156.0171 | 356.1278 | 442.3197 | 490.2775 | 553.3205 | 710.3687 |
| 72.0788 | 172.3740 | 380.1643 | 445.0278 | 490.3586 | 557.4392 | 946.4028 |
| 86.1216 | 172.6583 | 381.0949 | 458.3228 | 525.3611 | 584.2675 | 1466.6433 |
| 122.0584 | | | | | | |

TABLE 334

| | | | | | | |
|---|---|---|---|---|---|---|
| 22.9852 | 184.1123 | 299.3423 | 430.3313 | 487.3295 | 534.2973 | 580.3417 |
| 74.0764 | 212.1032 | 314.2316 | 432.9929 | 488.3316 | 535.3013 | 583.2274 |
| 104.1387 | 217.9461 | 338.1143 | 456.2963 | 490.3400 | 537.3199 | 584.2345 |
| 105.1157 | 226.0798 | 377.0710 | 459.2425 | 496.8846 | 550.3255 | 584.3355 |
| 106.0555 | 228.0046 | 387.9830 | 480.3312 | 506.9148 | 560.3121 | 585.2423 |
| 148.0788 | 284.3291 | 426.3417 | 481.3399 | 509.3577 | 562.3203 | 600.3366 |
| 173.4924 | 299.1308 | 427.3321 | 482.3368 | 532.3532 | 574.3090 | 616.1446 |
| 176.1198 | | | | | | |

TABLE 335

| | | | | | | |
|---|---|---|---|---|---|---|
| 18.0264 | 112.0850 | 176.1298 | 213.0575 | 274.0827 | 430.3169 | 491.3348 |
| 22.9798 | 123.0738 | 178.1388 | 229.0033 | 284.3265 | 434.2556 | 532.2725 |
| 23.0539 | 129.0710 | 179.1466 | 232.0822 | 314.2277 | 456.3015 | 534.2841 |
| 38.9638 | 155.1762 | 192.1245 | 234.0749 | 326.3916 | 459.2257 | 569.3303 |
| 38.9937 | 164.0701 | 201.2036 | 235.0331 | 383.0532 | 460.9913 | |
| 46.0666 | 165.0955 | 204.1077 | 240.0907 | 417.0381 | 489.3314 | |
| 86.1328 | 175.1219 | 212.3577 | 251.9799 | 429.3172 | 490.3361 | |

TABLE 336

| | | | | | | |
|---|---|---|---|---|---|---|
| 38.9674 | 190.1141 | 267.9562 | 368.2644 | 443.2100 | 548.3441 | 684.3511 |
| 76.0758 | 193.0672 | 289.2849 | 369.2702 | 445.0283 | 552.3114 | 708.3570 |
| 123.0414 | 215.0444 | 295.1666 | 370.2806 | 498.3276 | 553.3178 | 711.3711 |
| 156.0432 | 228.0389 | 301.1386 | 371.2848 | 510.2755 | 571.3341 | 723.3455 |
| 163.1135 | 230.0004 | 315.2230 | 396.0400 | 511.3414 | 573.2402 | 725.3580 |
| 164.0712 | 256.3291 | 330.2485 | 412.1977 | 513.3220 | 584.2661 | 726.3760 |
| 184.1062 | 257.2950 | 342.2497 | 428.1904 | 530.3908 | 666.3899 | 741.3357 |
| 184.1375 | 265.9579 | 346.2809 | 442.3155 | 532.2863 | 683.3451 | |

The series of processes explained above may be performed at the GC-diagnosing ion selecting means 6400 which includes the candidate ion set selecting means.

(4-8) Implementation of the Final Discriminant & Analysis

Figure 40:
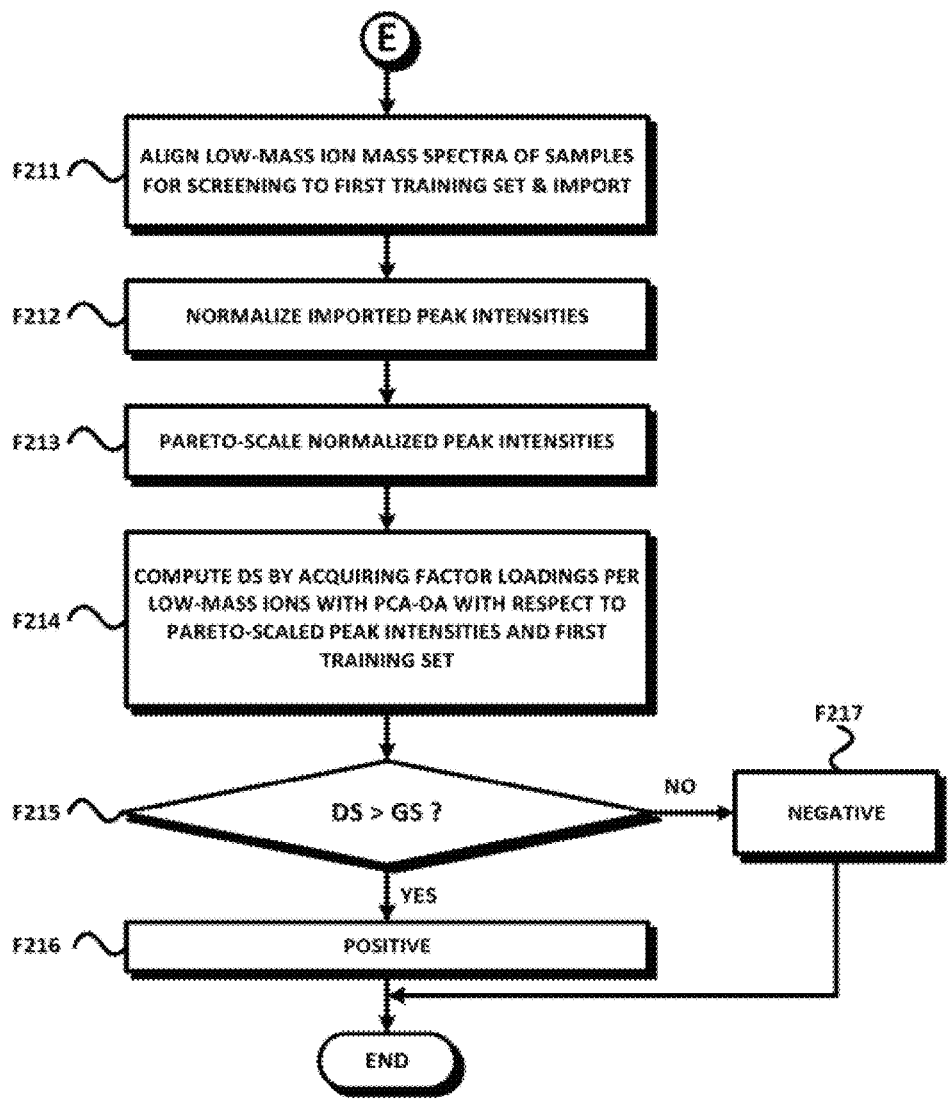

The interpretation is available when the first to fourth type, or first and fifth type GC-diagnosing final discriminants using the first to fifth type, or first and fifth type GC-diagnosing low-mass ions are implemented on the set F according to the method of FIG. 40.

Figure 53:
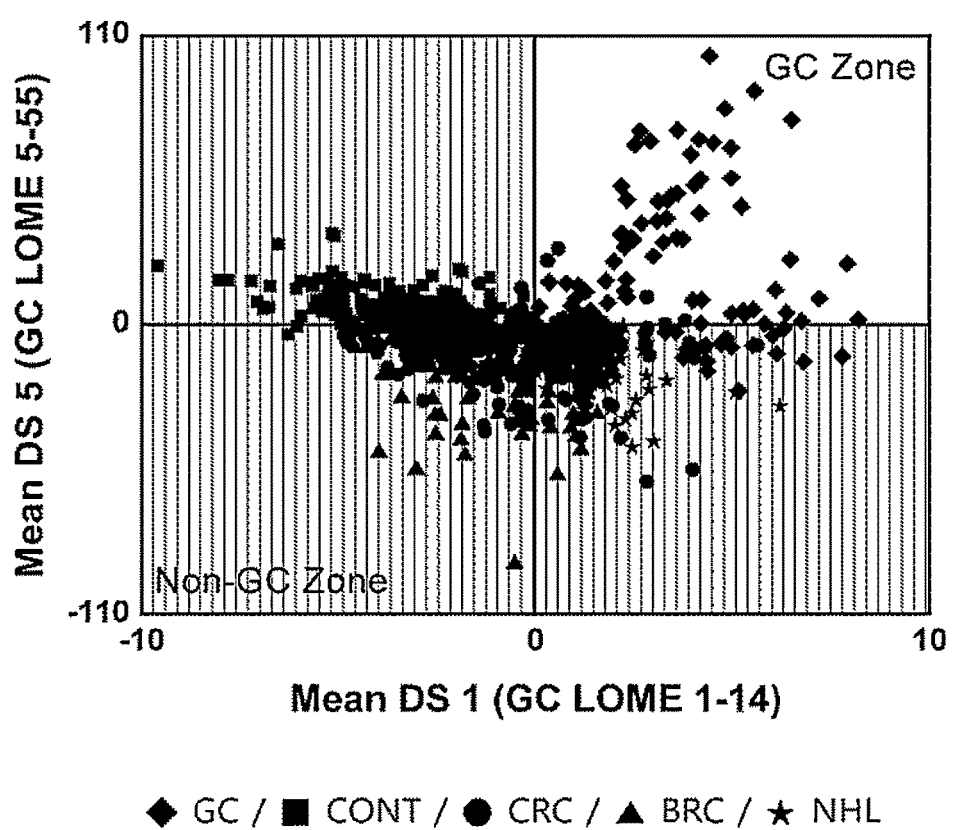
Figure 54:
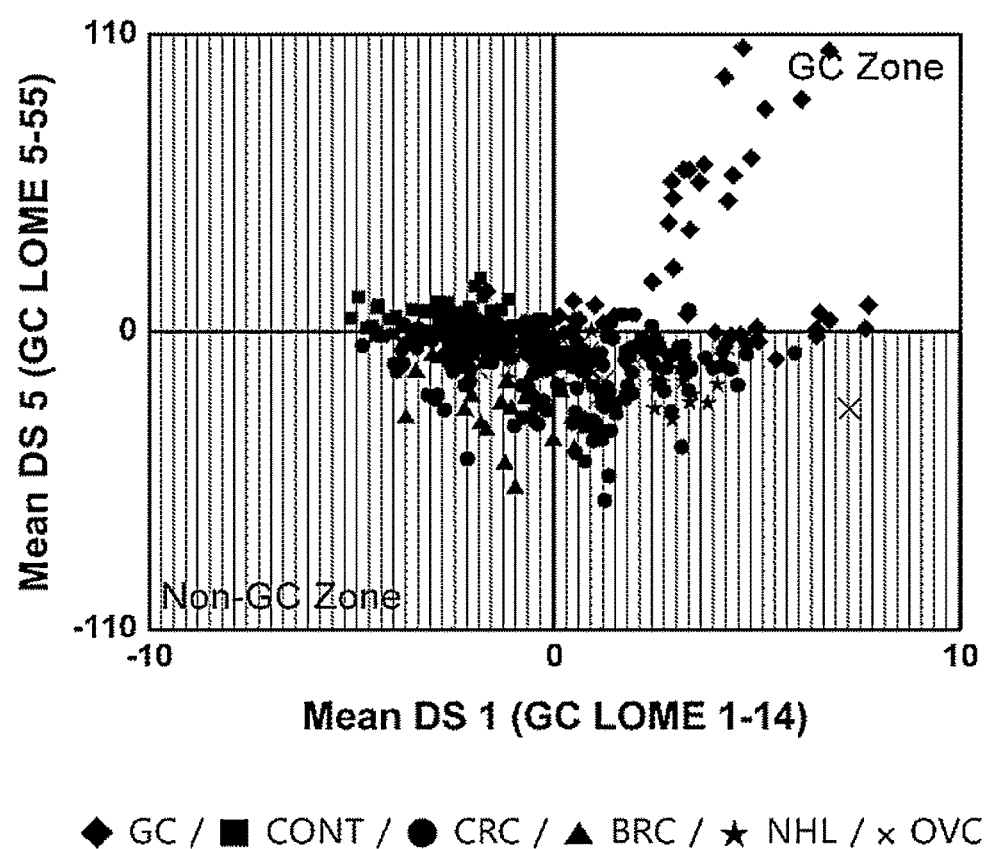

The result of interpretation obtained by the final discriminant is shown in FIGS. 53 and 54 and Tables 331 and 337. FIGS. 53 and 54 illustrate the result of interpretation based on the average DS of the DS of five rounds, in which FIG. 53 shows the result of interpretation on set F and FIG. 54 shows the result of interpretation on set F. Since the three-dimensional representation is necessary when the first to fourth GC-diagnosing final discriminants are used, illustration thereof is omitted, while the example of using the first and fifth GC-diagnosing final discriminants is illustrated in the accompanying drawing.

TABLE 337

| | GC LOME 1-14 | | | | | | GC LOME 1-14 | | | | | |
|---|---|---|---|---|---|---|---|---|---|---|---|---|
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 95 | 0 | 107 | 13 | 43 | Predicted GC | 42 | 0 | 92 | 5 | 19 | 14 |
| Predicted Non-GC | 2 | 167 | 145 | 95 | 3 | Predicted Non-GC | 2 | 81 | 76 | 48 | 1 | 11 |
| | GC LOME 2-36 | | | | | | GC LOME 2-36 | | | | | |
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 93 | 9 | 7 | 5 | 22 | Predicted GC | 42 | 12 | 9 | 3 | 8 | 14 |
| Predicted Non-GC | 4 | 158 | 245 | 103 | 24 | Predicted Non-GC | 2 | 69 | 159 | 50 | 12 | 11 |
| | GC LOME 3-50 | | | | | | GC LOME 3-50 | | | | | |
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 96 | 79 | 133 | 1 | 24 | Predicted GC | 44 | 35 | 111 | 0 | 13 | 15 |
| Predicted Non-GC | 1 | 88 | 119 | 107 | 22 | Predicted Non-GC | 0 | 46 | 57 | 53 | 7 | 10 |
| | GC LOME 4-46 | | | | | | GC LOME 4-46 | | | | | |
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 95 | 145 | 164 | 30 | 0 | Predicted GC | 44 | 70 | 100 | 6 | 0 | 3 |
| Predicted Non-GC | 2 | 22 | 88 | 78 | 46 | Predicted Non-GC | 0 | 11 | 68 | 47 | 20 | 22 |
| | GC LOME 5-55 | | | | | | GC LOME 5-55 | | | | | |
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 70 | 153 | 28 | 7 | 1 | Predicted GC | 37 | 60 | 12 | 3 | 1 | 0 |
| Predicted Non-GC | 27 | 14 | 224 | 101 | 45 | Predicted Non-GC | 7 | 21 | 156 | 50 | 19 | 25 |
| | GC LOMEs 1, 2, 3 & 4 | | | | | | GC LOMEs 1, 2, 3 & 4 | | | | | |
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 89 | 0 | 5 | 0 | 0 | Predicted GC | 41 | 0 | 4 | 0 | 0 | 0 |
| Predicted Non-GC | 8 | 167 | 247 | 108 | 46 | Predicted Non-GC | 3 | 81 | 164 | 53 | 20 | 25 |
| | GC LOMEs 1 & 5 | | | | | | GC LOMEs 1 & 5 | | | | | |
| | True | True Non-GC | | | | | True | True Non-GC | | | | |
| Set E | GC | CONT | CRC | BRC | NHL | Set F | GC | CONT | CRC | BRC | NHL | OVC |
| Predicted GC | 69 | 0 | 12 | 0 | 1 | Predicted GC | 35 | 0 | 4 | 0 | 1 | 0 |
| Predicted Non-GC | 28 | 167 | 240 | 108 | 45 | Predicted Non-GC | 9 | 81 | 164 | 53 | 19 | 25 |

Based on the discrimination performance of the validation set (F), compared to the result by the first and fifth type GC-diagnosing final discriminants, the results by the first to fifth type GC-diagnosing final discriminants were more accurate. While the increased number of discriminants is generally accompanied with the reduction in the sensitivity, considering that the third and fourth discriminants show 100% sensitivity as explained in the example, from a viewpoint of the degradation of sensitivity, it is almost like when there are indeed two discriminants. In other words, the sensitivity is not severely influenced according to the number of discriminants.

When the second and third type BRC-diagnosing final discriminants were used, even with the OVC patient group included, which was excluded from the training set, all the sensitivity, specificity, positive predictability and negative predictability of set D exceeded 85%.

When the first to fifth type GC-diagnosing final discriminant were used, the set F had 90% or above sensitivity, specificity, positive predictability and negative predictability. When the first and fifth type GC-diagnosing final discriminant were used, the set F had approximately 80% or above sensitivity, specificity, positive predictability and negative predictability. On the whole, the first and fifth type GC-diagnosing final discriminants are also considered to exhibit good discrimination result.

Accordingly, it is possible to discriminate the GC patients from the non-GC patients by analyzing the low-mass ion mass spectrum of the serum.

The embodiment of the present invention is easily expanded to construct a discriminant to distinguish a specific cancer patient group other than CRC, BRC or GC patient groups from the normal control groups by the similar processes explained above. Further, those skilled in the art would be easily able to appreciate that it is possible to expand the embodiment of the present invention to screening of not only cancers, but also other disease types.

What is claimed is:

1. A system for cancer diagnosis from a biological sample, the biological sample having been prepared by chemical extraction of a biological material, comprising:
    a low-mass ion detector which detects low-mass ion mass spectra of the biological sample;
    a processor that receives the low-mass ion mass spectra and performs an algorithmic analysis of the low-mass ion mass spectra to arrive at a cancer diagnosis; wherein
    the processor is configured to align the low-mass ion mass spectra of patients with cancer and non-cancer subjects on a candidate training set;
    the processor is configured to compute a discriminate score by performing biostatistical analysis with respect to the mass spectra as aligned;
    the processor is configured to determine the sensitivity and specificity according to the discriminant score, determine a first training set by the sensitivity and specificity, and compute factor loadings based on the first training set;
    the processor is configured to determine the discriminant score by normalizing the peak intensities of the low-mass ion spectra of the candidate training set, scaling the normalized peak intensities, and computing the discriminant score by performing the biostatistical analysis with respect to the scaled peak intensities and the factor leadings;
    and the processor is configured to determine the cancer diagnosis to be cancer positive or negative depending on the discriminant score; and
    a display unit which display cancer diagnosis information on the discriminant score.

2. The system of claim 1, wherein the processor is configured to perform the scaling by Pareto scaling.

3. The system of claim 1, wherein the processor is configured to determine the discriminant score biostatistical analysis using a principal component analysis-based linear discriminant analysis (PCA-DA).

4. The system of claim 3, wherein the processor is configured to determine the discriminant score using both the factor loadings acquired by the PCA-DA and the scaled peak intensities.

5. The system of claim 1, wherein the processor is configured to determine the first training set with the patients with cancer and the non-cancer subjects, if the result of the biostatistical analysis indicates that the sensitivity equals to or is greater than a threshold (N1), and the specificity equals to or is greater than a threshold (N2).

6. The system of claim 5, wherein the thresholds (N1, N2) are 1, respectively.

7. The system of claim 1, wherein the processor is configured to perform the scaling by Pareto scaling.

8. The system of claim 1, wherein the processor is configured to compute the discriminant score based on the scaled peak intensities of the low-mass ions for cancer diagnosis and the associated factor loadings.

9. The system of claim 1, wherein the processor is configured to determine the subject for cancer screening to be cancer positive or negative depending on the discriminant score, in which the processor is configured to determine cancer positive if the discriminant score of the subject for cancer screening is greater than the threshold (S), or determines cancer negative if the discriminant score of the subject for cancer screening is less than the threshold (S).

10. The system of claim 9, wherein the threshold(S) is 0.

11. The system of claim 9, wherein the processor is configured to determine the cancer information of the subject for cancer screening based on an average of a plurality of the discriminant scores which are computed with respect to a plurality of low-mass ion mass spectra obtained as a result of repeatedly measuring the biological sample for cancer screening.

12. The system of claim 1, wherein the
    processor is configured to select a candidate ion set with candidate low-mass ions that meet a condition for candidate from the first training set; and
    the processor is configured to select a final ion set with low-mass ions for cancer diagnosis based on individual or combinational discriminating performance of the candidate low-mass ions of the candidate ion set.

13. The system of claim 12, wherein the processor is configured to select first low-mass ions for each training case, if a product of multiplying the peak intensity of each low-mass ion by the associated factor loading is greater than a threshold (T1).

14. The system of claim 13, wherein the threshold (T1) is 0.1.

15. The system of claim 13, wherein the processor is configured to select the candidate ion set with second low-mass ions present commonly in cases above a threshold percent (T2) from among the first low-mass ions.

16. The system of claim 15, wherein the threshold (T2) is 50.

17. The system of claim 15, wherein the
    processor is configured to compute a discriminant score, indicative of whether each of the training cases is cancer positive or negative using the second low-mass ions, and compute sensitivity and specificity according to the discriminant score; and the processor is configured to select a final candidate ion set by changing at least one from among the thresholds (T1, T2) if the sensitivity is less than a threshold (N3) or the specificity is less than a threshold (N4).

18. The system of claim 17, wherein the thresholds (N3,N4) are 0.9, respectively.

19. The system of claim 12, wherein a criterion to evaluate the discriminating performance comprises a first criterion according to which a low-mass ion is selected if a sum of the sensitivity and the specificity thereof equals to or is greater than a threshold, or a combination of the candidate low-mass ions is selected if a sum of the sensitivity and the specificity thereof is greater than any other combinations in a comparison group.

20. The system of claim 12, wherein a criterion to evaluate the discriminating performance comprises a second criterion according to which a combination of a least number of low-mass ions is selected from among the combinations of the candidate low-mass ions in a comparison group.

21. The system of claim 12, wherein a criterion to evaluate the discriminating performance comprises a third criterion according to which a combination of the candidate low-mass ions is selected, if a difference between the lowest discriminant score of true positive cases and the highest discriminant score of true negative cases thereof is greater than any other combinations in a comparison group, wherein the discriminant score is computed based on the scaled peak intensities of the candidate low-mass ions and the associated factor loadings, and indicative of cancer positive or negative.

22. The system of claim 12, wherein the processor is configured to select the final ion set by ion classifying the candidate low-mass ions into a high sensitivity set $\{Sns_1, Sns_2, Sns_3 \ Sns_I\}$ which includes a high sensitivity low-mass ions with sensitivity exceeding the specificity and arranges the high sensitivity low-mass ions in a descending order of the sum of the sensitivity and the specificity, and a high specificity set $\{Spc_1, Spc_2, Spc_3 \ldots Spc_J\}$ which includes a high specificity low-mass ions and arranges the high specificity low-mass ions in a descending order of the sum of the sensitivity and the specificity;

the A processor is configured to select a biomarker group with a combination selected from candidate combinations of two or more low-mass ions from L upper high sensitivity low-mass ions $\{Sns_1, Sns_2, Sns_3 \ Sns_L\}$ and L upper high specificity low-mass ions $\{Spc_1, Spc_2, Spc_3 \ldots Spc_L\}$, if the combination meets one or more of the first, second and third criteria for evaluating the discriminating performance;

the B processor is configured to re-select the group of low-mass ions with a combination selected from among the group of low-mass ions and candidate combinations in which one or more low-mass ions from M next upper high sensitivity low-mass ions and M next upper high specificity low-mass ions are added to the group of low-mass ions, if the combination meets one or more of the first, second and third criteria; and the C processor is configured to select a final group of low-mass ions after repeating the re-selecting until there are no next upper low-mass ions left in the high sensitivity set or the high specificity set.

23. The system of claim 22, wherein the final ion set by selecting additional groups of low-mass ions by repeating the A, B and C processes to select the group of low-mass ions with respect to the candidate ion set excluding the final group of low-mass ions finalized by the final group of low-mass ions selecting module, until there are less than L low-mass ions left in the high sensitivity set or the high specificity set; and the processor is configured to select the final ion set as a combination of low-mass ions of top K groups of low-mass ions in terms of accuracy from among the group of low-mass ions and the additional groups of low-mass ions.

24. The system of claim 23, wherein L is 2, M is 1, K is 1, 2 or 3.

25. The system of claim 12, wherein the processor is configured to select the final ion set using a training set enlarged by adding a second training set, independent of the first training set, to the first training set.

26. The system of claim 1, wherein the patients with cancer comprise CRC patients with colorectal cancer, BCR patients with breast cancer, GC patients with gastric cancer, or patients with other types of cancer.

* * * * *